(12) United States Patent
Bartolozzi et al.

(10) Patent No.: US 8,916,576 B2
(45) Date of Patent: *Dec. 23, 2014

(54) PHARMACOKINETICALLY IMPROVED COMPOUNDS

(71) Applicant: Surface Logix, Inc., Brighton, MA (US)

(72) Inventors: Alessandra Bartolozzi, Norwalk, CT (US); Stewart Campbell, Framingham, MA (US); Hope Foudoulakis, Framingham, MA (US); Brian Kirk, Sudbury, MA (US); Siya Ram, Winchester, MA (US); Paul Sweetnam, Marblehead, MA (US); Hemalatha Seshadri, Waltham, MA (US)

(73) Assignee: Surface Logix, Inc., Brighton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/715,644

(22) Filed: Dec. 14, 2012

(65) Prior Publication Data

US 2013/0131047 A1    May 23, 2013

Related U.S. Application Data

(63) Continuation of application No. 11/887,218, filed as application No. PCT/US2006/011271 on Mar. 27, 2006, now Pat. No. 8,357,693.

(60) Provisional application No. 60/665,165, filed on Mar. 25, 2005.

(51) Int. Cl.
| | |
|---|---|
| *A01N 43/54* | (2006.01) |
| *A61K 31/517* | (2006.01) |
| *C07D 403/14* | (2006.01) |
| *C07D 413/14* | (2006.01) |
| *C07D 405/14* | (2006.01) |
| *C07D 401/14* | (2006.01) |
| *C07D 403/12* | (2006.01) |
| *B82Y 30/00* | (2011.01) |

(52) U.S. Cl.
CPC ............ *C07D 413/14* (2013.01); *C07D 403/14* (2013.01); *C07D 405/14* (2013.01); *C07D 401/14* (2013.01); *C07D 403/12* (2013.01); *B82Y 30/00* (2013.01)
USPC .................... 514/266.23; 514/266.2; 544/284

(58) Field of Classification Search
USPC ........................... 514/266.23, 266.2; 544/284
See application file for complete search history.

(56) References Cited

U.S. PATENT DOCUMENTS

| | | | |
|---|---|---|---|
| 6,218,410 B1 | 4/2001 | Uehata et al. | |
| 6,924,292 B2 * | 8/2005 | Kawano et al. | 514/291 |
| 2003/0087919 A1 | 5/2003 | Nagarathnam et al. | |
| 2003/0125344 A1 | 7/2003 | Nagarathnam et al. | |
| 2003/0220357 A1 | 11/2003 | Bankston et al. | |
| 2005/0014783 A1 | 1/2005 | Dole et al. | |

FOREIGN PATENT DOCUMENTS

| | | |
|---|---|---|
| RU | 2 206 321 C2 | 6/2003 |
| RU | 2003/103606 A | 8/2004 |
| RU | 2003/104284 A | 8/2004 |
| WO | 02/48676 A3 | 6/2002 |
| WO | 02/076976 A2 | 10/2002 |
| WO | WO 02076976 A2 * | 10/2002 |
| WO | 03/012392 A2 | 2/2003 |
| WO | 03/018854 A3 | 3/2003 |
| WO | 03/054515 A2 | 7/2003 |

OTHER PUBLICATIONS

B.K. Mueller et al.,4 Nature Reviews Drug Discovery, 387-398 (2005).*
T. Murata et al., 35 Journal of Hepatology, 474-481 (2001).*
Y. Rikitake et al., 36 Stroke, 2251-2257 (2005).*
Greene et al. "Protective Groups in Organic Synthesis." 2nd ed., Wiley-Interscience, 1991.
Greene et al. "Protective Groups in Organic Synthesis." 3rd ed., Wiley-Interscience, 1999.
Chapman et al. "Surveying for Surfaces that Resist the Adsorption of Proteins." J. Am. Chem. Soc., 2000, 122:8303-8304.
Ostuni et al. "A Survey of Structure-Property Relationships of Surfaces that Resist the Adsorption of Protein." Langmuir, 2001, 17:5605-5620.
Holmlin et al. "Zwitterionic SAMs that Resist Nonspecific Adsorption of Protein from Aqueous Buffer." Langmuir, 2001, 17:2841-2850.
Ostuni et al. "Self-Assembled Monolayers that Resist the Adsorption of Proteins and the Adhesion of Bacterial and Mammalian Cells." Langmuir, 2001, 17:6336-6343.
Sasaki et al. "Transcellular Transport of Organic Anions Across a Double-Transfected Madin-Darby Canine Kidney II Cell Monolayer Expressing Both Human Organic Anion—Transporting Polypeptide (OATP2/SLC21A6) and Multidrug Resistance-Associated Protein 2 (MRP2/ABCC2)." Journal of Biological Chemistry, Feb. 22, 2002, vol. 277, No. 8, pp. 6497-6503.
Berge et al. "Pharmaceutical Salts." Journal of Pharmaceutical Sciences, Jan. 1977, vol. 66, No. 1, pp. 1-19.
Grampton et al. "Applied Animal Nutrition." 2nd ed., W.H. Freedman and Company, 1969.
Church, "Livestock Feeds and Feeding." O & B Books, 1977.
Dordunoo et al., "Preformulation Studies on Solid Dispersions Containing Triamterene or Temazepam in Polyethylene Glycols or Gelucire 44/4 for Liquid Filling of Hard Gelatin Capsules." Drug Development and Industrial Pharmacy, 1991, vol. 17, No. 12, pp. 1685-1713.
Sheen et al. "Bioavailability of a Poorly Water-Soluble Drug from Tablet and Solid Dispersion in Humans." Journal of Pharmaceutical Sciences, Jul. 1991, vol. 80, No. 7, pp. 712-714.

(Continued)

*Primary Examiner* — James O Wilson
*Assistant Examiner* — Alexander R Pagano
(74) *Attorney, Agent, or Firm* — Kenyon & Kenyon LLP

(57) ABSTRACT

The present invention relates to inhibitors of ROCK1 and ROCK2 and methods of modulating the pharmacokinetic and/or pharmacodynamic properties of such compounds. Also provided are methods of inhibiting ROCK1 and or ROCK2 that are useful for the treatment of disease.

33 Claims, 10 Drawing Sheets

(56) References Cited

OTHER PUBLICATIONS

Kuhn et al. "A Novel, High-Performance Random Array Platform for Quantitative Gene Expression Profiling." Genome Research, 2004, vol. 14, No. 11, pp. 2347-2356.

Ashburner et al. "Gene Ontology" Tool for the Unification of Biology. Nature Genetics, May 2000; vol. 25, No. 1, pp. 25-92.
Wikipedia, "Rho-associated protein kinase", Apr. 4, 2011, pp. 1-6, http://en.wikipedia.org/wiki/Rho-associated_protein_kinase.

* cited by examiner

US 8,916,576 B2

PHARMACOKINETICALLY IMPROVED COMPOUNDS

CROSS REFERENCE TO RELATED APPLICATIONS

This application is a continuation of U.S. Ser. No. 11/887,218, filed Mar. 14, 2008, now U.S. Pat. No. 8,357,693, which is a 371 national stage application of International Application No. PCT/US06/11271, filed Mar. 27, 2006, and claims priority to Provisional Application 60/665,165, filed Mar. 25, 2005, the contents of which applications are hereby incorporated by reference in their entireties.

BACKGROUND OF THE INVENTION

The development of a new pharmaceutical agent requires careful optimization of the chemical and biological properties of a lead compound. For example, a successful drug candidate must be safe and effective for its intended use. Further, the compound must possess desired pharmacokinetic and pharmacodynamic profiles. This arduous development process usually requires extensive experimentation. In many cases, the process for determining the optimal compound can often require preparation of thousands of structurally similar compounds.

Among the properties that can limit the utility of a potential pharmaceutical agent the degree to which the compound is complexed to proteins in vivo. If a high percentage of the compound present in vivo is non-specifically bound, for example by components of blood and blood plasma, this leaves only a very small amount of free compound available to tissue to perform its therapeutic function. Thus, binding of the compound to various proteins and other plasma components may require an unacceptably large dosage of compound to achieve the desired therapeutic effect.

Traditional approaches have sought to alter pharmacokinetic properties.

The Rho-associated kinase is a key intracellular regulator of cytoskeletal dynamics and cell motility. Rho-kinase regulates a number of downstream targets of RhoA through phosphorylation, including, for example, myosin light chain, the myosin light chain phosphatase binding subunit and LIM-kinase 2. In smooth muscle cells Rho-kinase mediates calcium sensitization and smooth muscle contraction. Inhibition of Rho-kinase blocks 5-HT and phenylephrine agonist induced muscle contraction. When introduced into non-smooth muscle cells, Rho kinase induces stress fiber formation and is required for the cellular transformation mediated by RhoA. Rho kinase participates in a variety of cellular processes, including but not limited to Na/H exchange transport system activation, stress fiber formation, adducin activation. Rho kinase is involved in physiological processes such as vasoconstriction, bronchial smooth muscle constriction, vascular smooth muscle and endothelial cell proliferation, platelet aggregation, and others.

Inhibition of Rho-kinase activity in animal models has demonstrated a number of benefits of Rho-kinase inhibitors for the treatment of human diseases. These include models of cardiovascular diseases such as hypertension, atherosclerosis, restenosis, cardiac hypertrophy, ocular hypertension, cerebral ischemia, cerebral vasospasm, penile erectile dysfunction, central nervous system disorders such as neuronal degeneration and spinal cord injury, and in neoplasias where inhibition of Rho-kinase activity has been shown to inhibit tumor cell growth and metastasis, angiogenesis, arterial thrombotic disorders such as platelet aggregation and leukocyte aggregation, asthma, regulation of intraocular pressure, and bone resorption. The inhibition of Rho-kinase activity in patients has benefits for controlling cerebral vasospasms and ischemia following subarachnoid hemorrhage.

In mammals, Rho-kinase consists of two isoforms, ROCK1 (ROCKβ; p160-ROCK) and ROCK2 (ROCKα). ROCK1 and ROCK2 are differentially expressed and regulated in specific tissues. For example, ROCK1 is ubiquitously expressed at relatively high levels, whereas ROCK2 is preferentially expressed in cardiac and brain tissues and in a developmental stage specific manner. ROCK1 is a substrate for cleavage by caspase-3 during apoptosis, whereas ROCK2 is not. Smooth muscle specific basic calponin is phosphorylated only by ROCK2.

Further, the physiological roles of the proteins appear to be distinct. For example, a recent study comparing the ROCK1/+ haploinsufficient mice with wild type littermates indicated that ROCK1 is critical for the development of cardiac fibrosis, but not hypertrophy, in response to various pathological conditions and suggest that signaling pathways leading to the hypertrophic and profibrotic response of the heart are distinct. However, the lack of inhibitors specific for ROCK1 or ROCK2 has impeded their respective roles to otherwise be distinguished.

Accordingly, there is a need for improved ROCK specific kinase inhibitors, including kinase inhibitors that specifically inhibit ROCK1 or ROCK2.

SUMMARY OF THE INVENTION

The present invention relates to compounds having the formula I

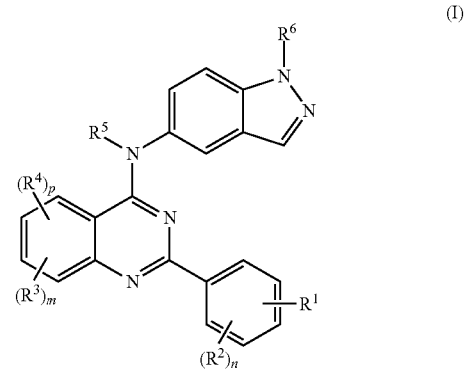

or pharmaceutically acceptable salt or hydrate thereof, wherein:

$R^1$ is selected from the group consisting of aryl, —$(CH_2)_y$—$NR^{13}R^{14}$, —X—$R^{12}$, —O—$(CH_2)_y$—$CO_2R^{12}$, —O—$(CH_2)_y$—, —C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_n$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-NR$^{16}$R$^{17}$, —CO$_2$R$^{18}$, —O—(CH$_2$)$_x$—CO$_2$R$^{18}$, and —C(=O)NR$^{16}$R$^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^4$ is selected from —(CH$_2$)$_a$—NR$^{43}$R$^{44}$, —Y—R$^{42}$, —O—(CH$_2$)$_a$—CO$_2$R$^{42}$, —O—(CH$_2$)$_a$—C(=O)NR$^{43}$R$^{44}$, —O—(CH$_2$)$_a$-heteroaryl, —O—(CH$_2$)$_a$-cycloalkyl, —O—C(=O)—(CH$_2$)$_c$—NR$^{43}$R$^{44}$, —O—(CH$_2$)$_a$—NR$^{43}$R$^{44}$, —NH—C(=O)—(CH$_2$)$_a$—NR$^{43}$R$^{44}$, —NH—C(=O)—Y—R$^{45}$, —NH—C(=O)—(CH$_2$)$_a$—NR$^{43}$R$^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-C(=O)NR$^{46}$R$^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-C(=O)NR$^{46}$R$^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-NR$^{46}$R$^{47}$, —CO$_2$R$^{48}$, —O—(CH$_2$)$_b$—CO$_2$R$^{48}$, and —C(=O)NR$^{46}$R$^{47}$, $R^{46}$ and $R^{47}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{46}$ and $R^{47}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

a is selected from 0 to 6;
b is selected from 0 to 6;
c is selected from 2 to 6;

$R^5$ is selected from the group consisting of H, $C_1$-$C_6$ alkyl, —(CH$_2$)$_d$—C(=O)—NR$^{53}$R$^{54}$, —C(=O)—(CH$_2$)$_d$—NR$^{53}$R$^{54}$, —C(=O)—X—R$^{55}$, and —C(=O)—(CH$_2$)$_d$—NR$^{53}$R$^{54}$;

$R^{53}$ and $R^{54}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{56}$R$^{57}$, —($C_1$-$C_6$ alkyl)-C(=O)NR$^{56}$R$^{57}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{53}$ and $R^{54}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

$R^{55}$ is selected from the group consisting of H, aryl, —($C_1$-$C_6$ alkyl)-O—($C_1$-$C_6$ alkyl), —($C_1$-$C_6$ alkyl)-$NR^{56}R^{57}$, —$CO_2R^{58}$, —O—$(CH_2)_e$—$CO_2R^{58}$, and —C(=O)$NR^{56}R^{57}$, $R^{56}$ and $R^{57}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{56}$ and $R^{57}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{58}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

d is selected from 0 to 6;

e is selected from 0 to 6;

$R^6$ is selected from the group consisting of H, $C_1$-$C_6$ alkyl, —$(CH_2)_r$—C(=O)—$NR^{63}R^{64}$, —C(=O)—$(CH_2)_r$—$NR^{63}R^{64}$, —C(=O)—X—$R^{65}$, and —C(=O)—$(CH_2)_r$—$NR^{63}R^{64}$;

$R^{63}$ and $R^{64}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-C(=O)$NR^{66}R^{67}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{63}$ and $R^{64}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

$R^{65}$ is selected from the group consisting of H, aryl, —($C_1$-$C_6$ alkyl)-O—($C_1$-$C_6$ alkyl), —($C_1$-$C_6$ alkyl)-$NR^{66}R^{67}$, —$CO_2R^{68}$, —O—$(CH_2)_s$—$CO_2R^{68}$, and —C(=O)$NR^{66}R^{67}$, $R^{66}$ and $R^{67}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{66}$ and $R^{67}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{68}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

r is selected from 0 to 6;

s is selected from 0 to 6;

n is selected from 0 to 4;

m is selected from 0 to 3; and p is selected from 0 and 1.

The present invention includes pharmaceutical compositions comprising the compounds of the invention and a pharmaceutically acceptable carrier and/or diluents.

The present invention includes pharmaceutical compositions comprising a substantially pure compound of the invention, or a pharmaceutically acceptable salt, stereoisomer, or hydrate thereof, and a pharmaceutically acceptable excipient and/or diluents.

DETAILED DESCRIPTION

Figure 1:
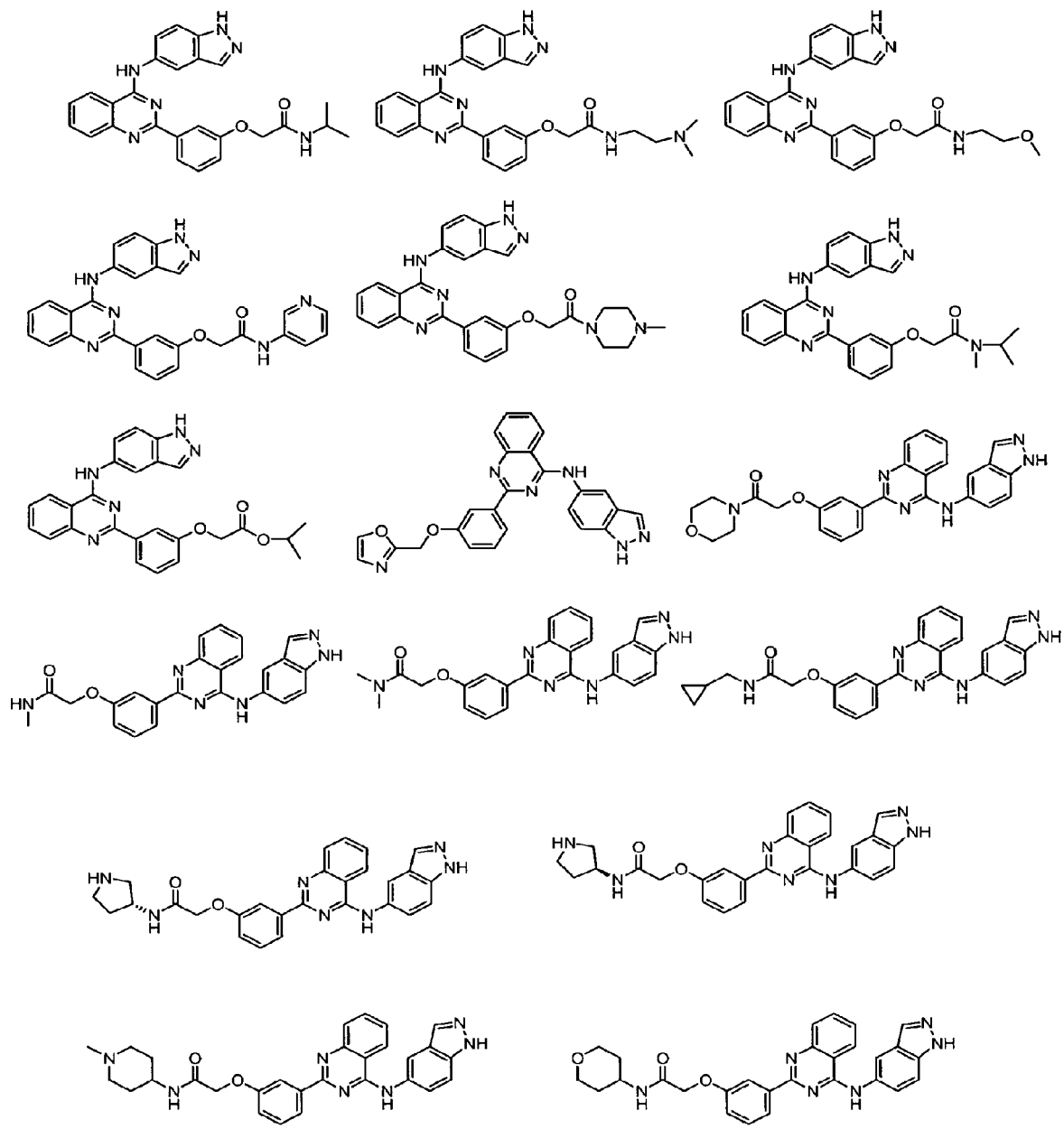
FIG. 1 shows various compounds that represent embodiment of the present invention.
Figure 2:
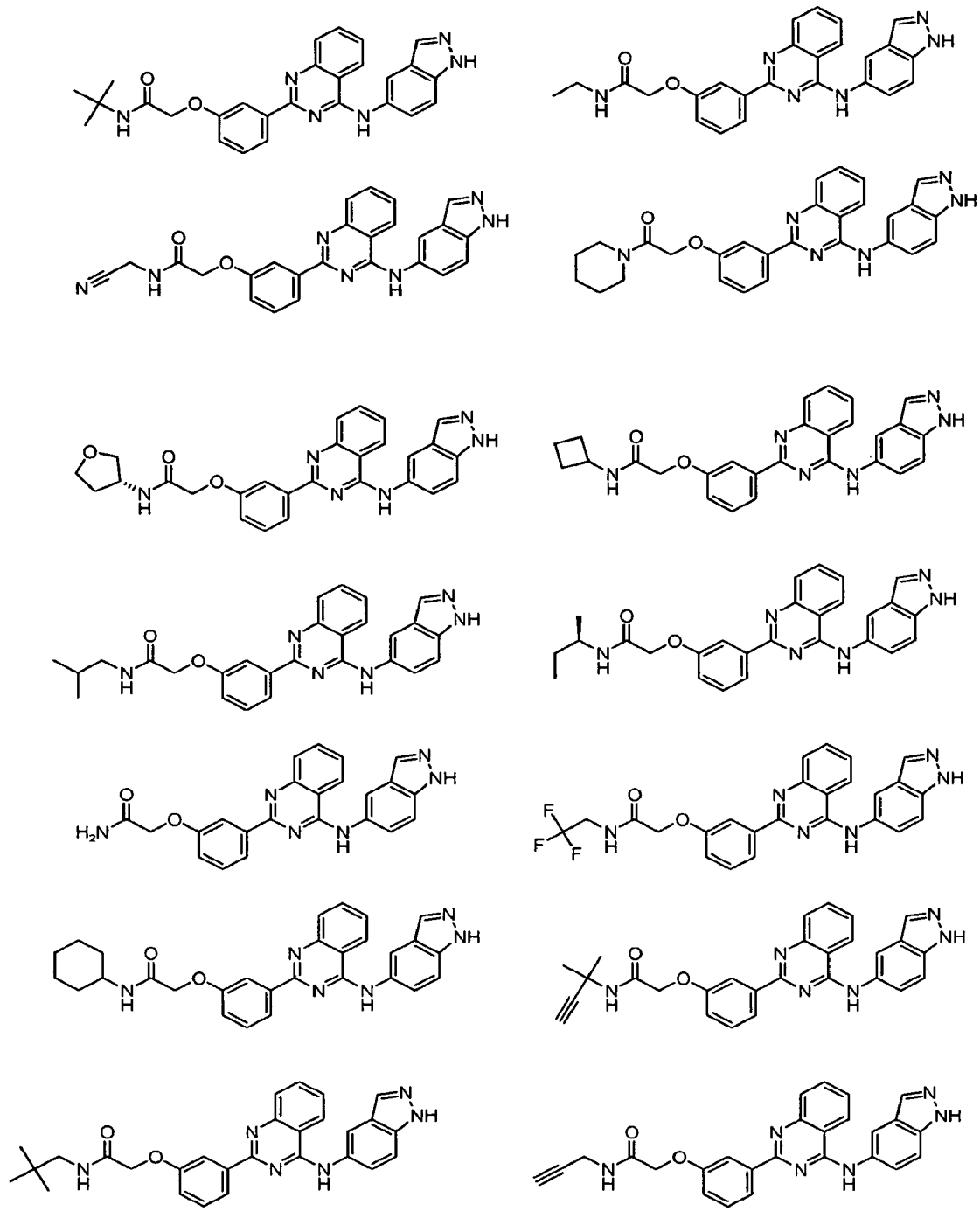
FIG. 2 shows various compounds that represent embodiment of the present invention.
Figure 3:
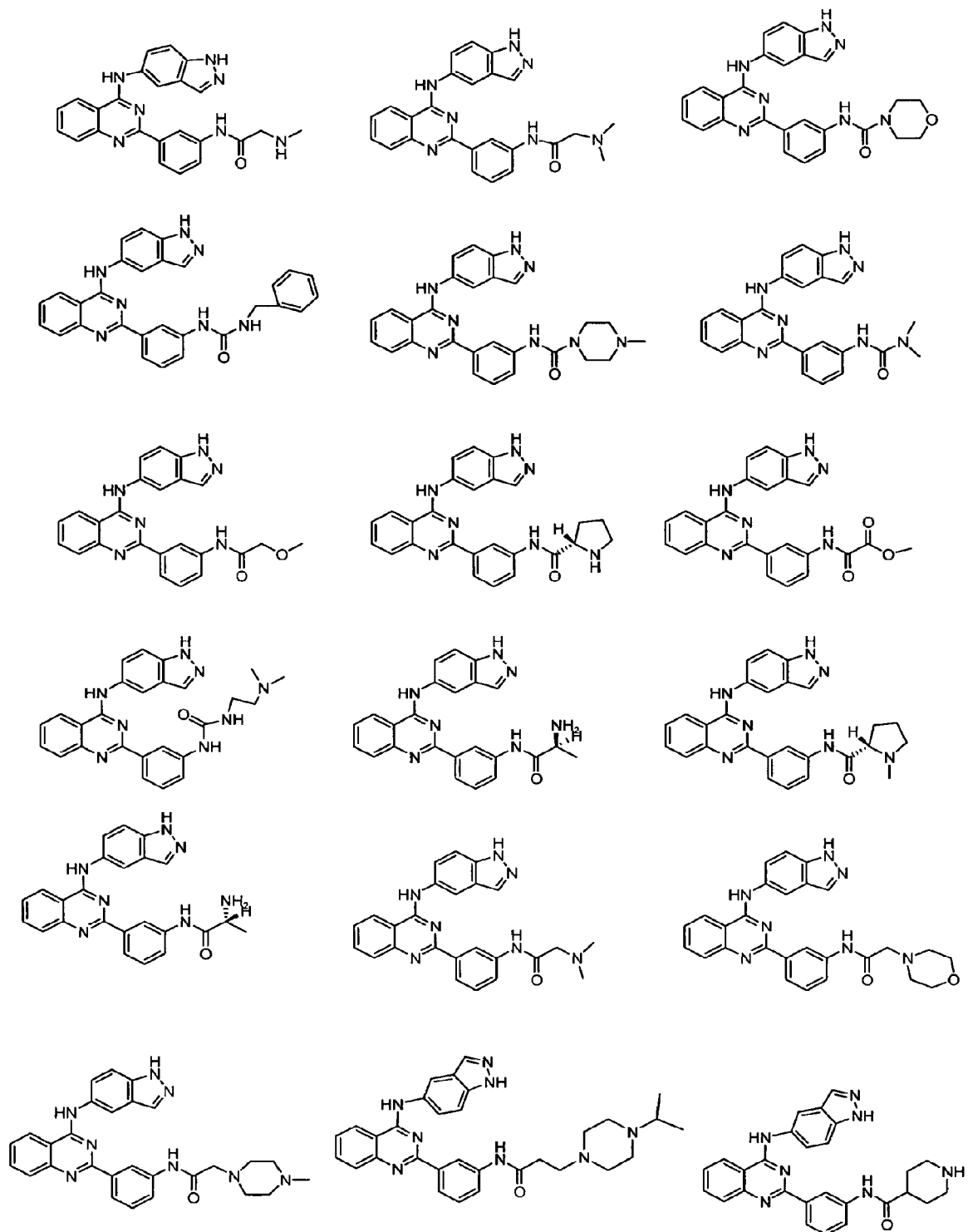
FIG. 3 shows various compounds that represent embodiment of the present invention.
Figure 4:
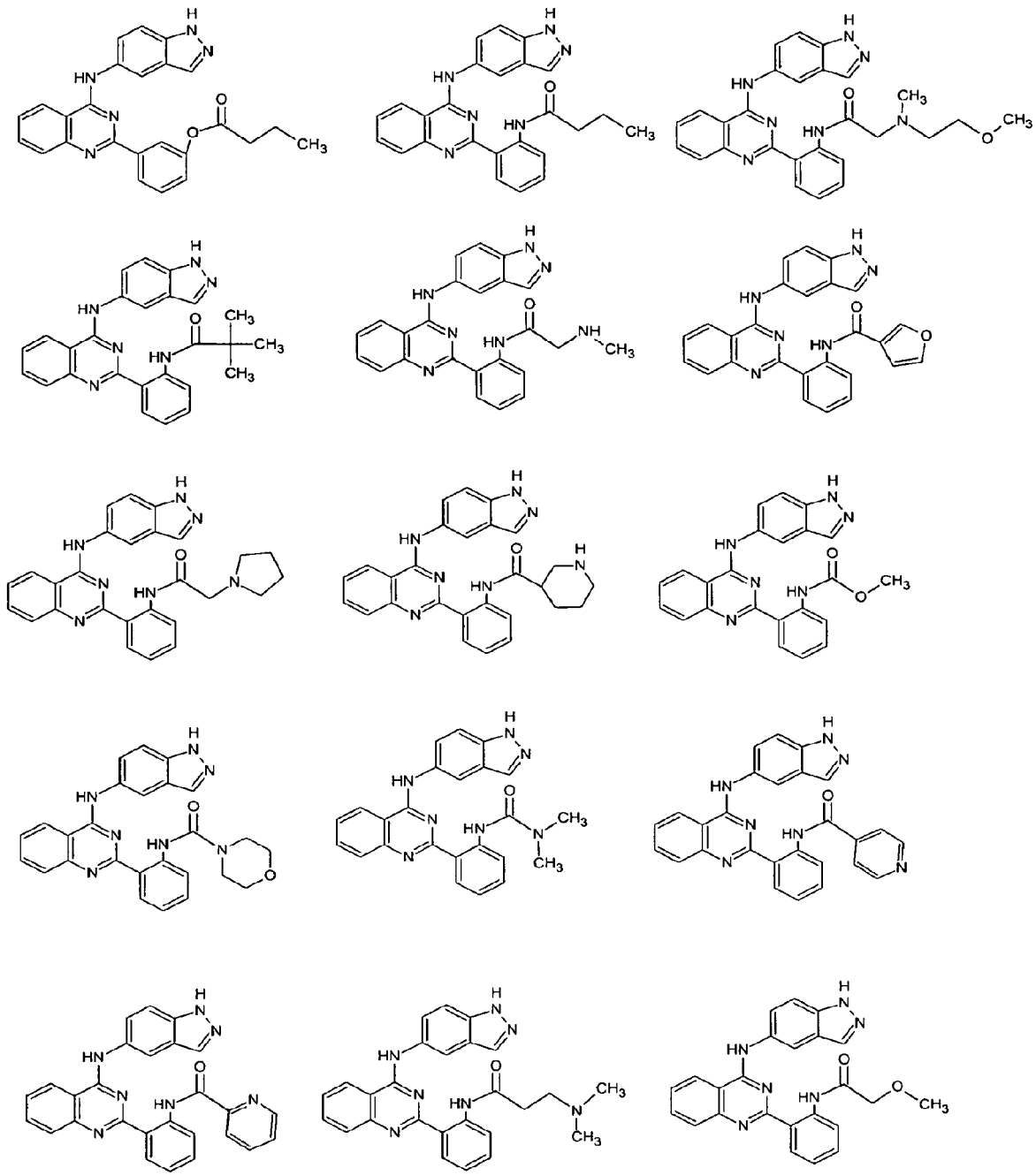
FIG. 4 shows various compounds that represent embodiment of the present invention.
Figure 5:
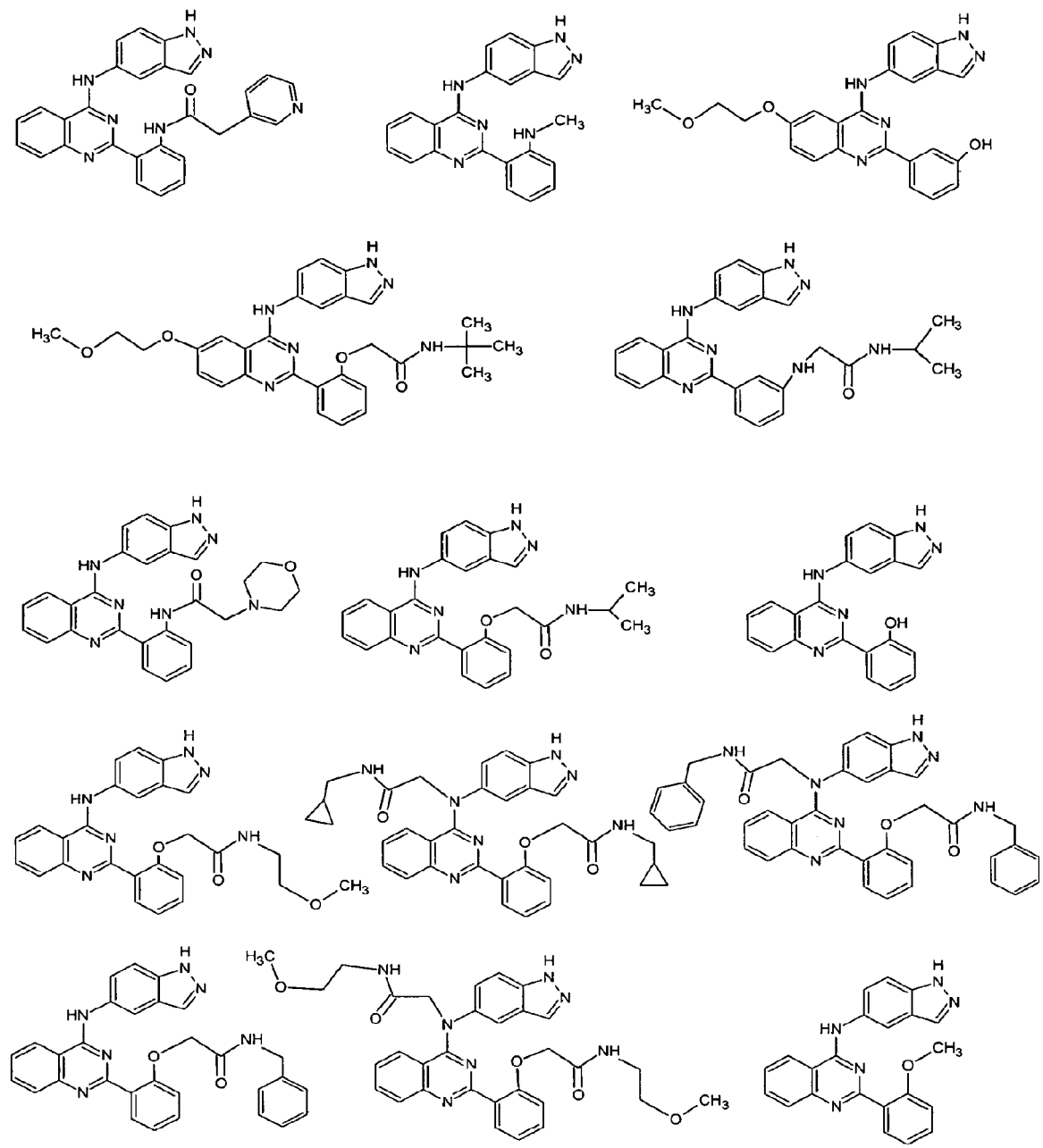
FIG. 5 shows various compounds that represent embodiment of the present invention.
Figure 6:
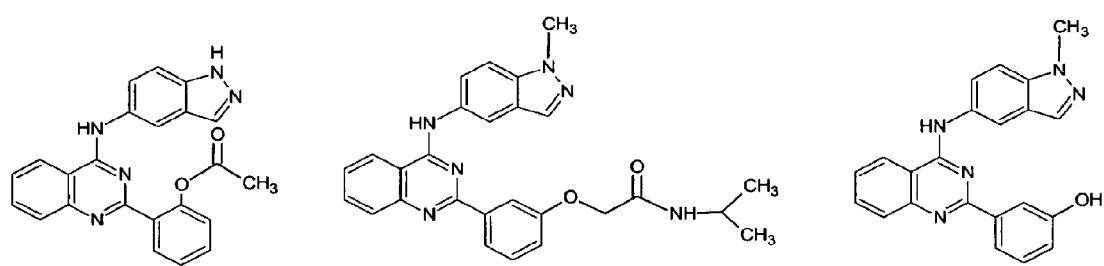
FIG. 6 shows various compounds that represent embodiment of the present invention.
Figure 7:
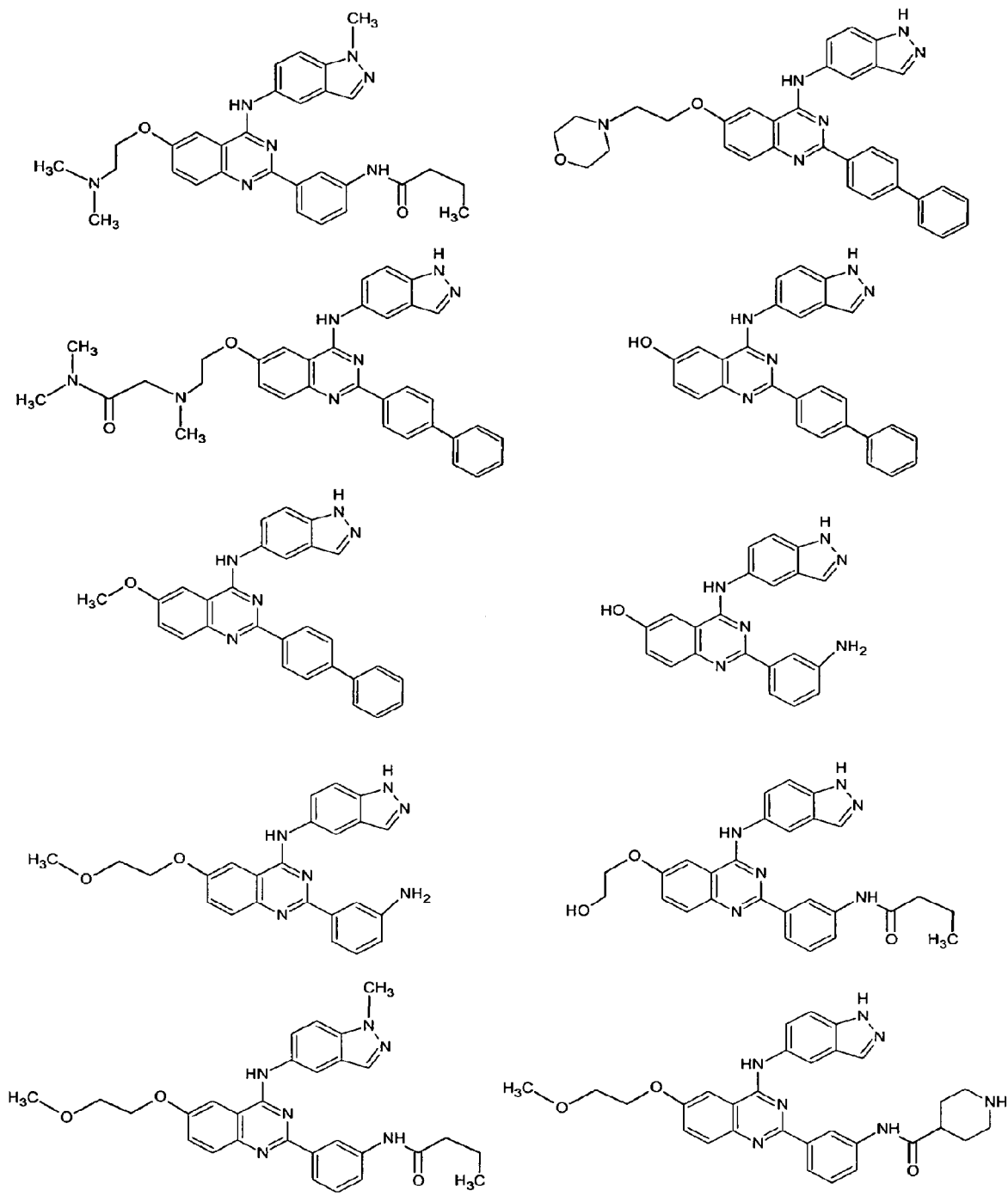
FIG. 7 shows various compounds that represent embodiment of the present invention.
Figure 8:
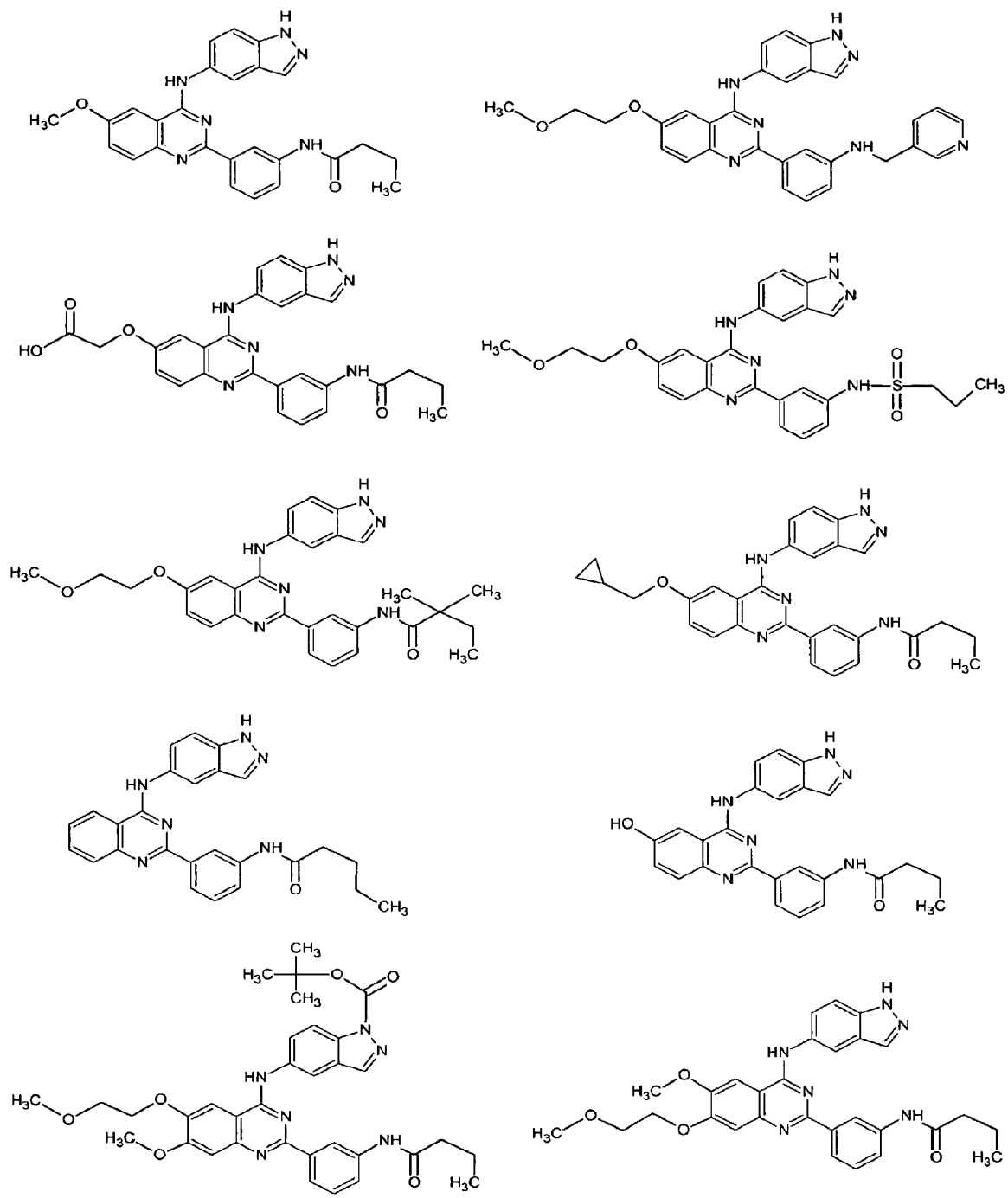
FIG. 8 shows various compounds that represent embodiment of the present invention.
Figure 9:
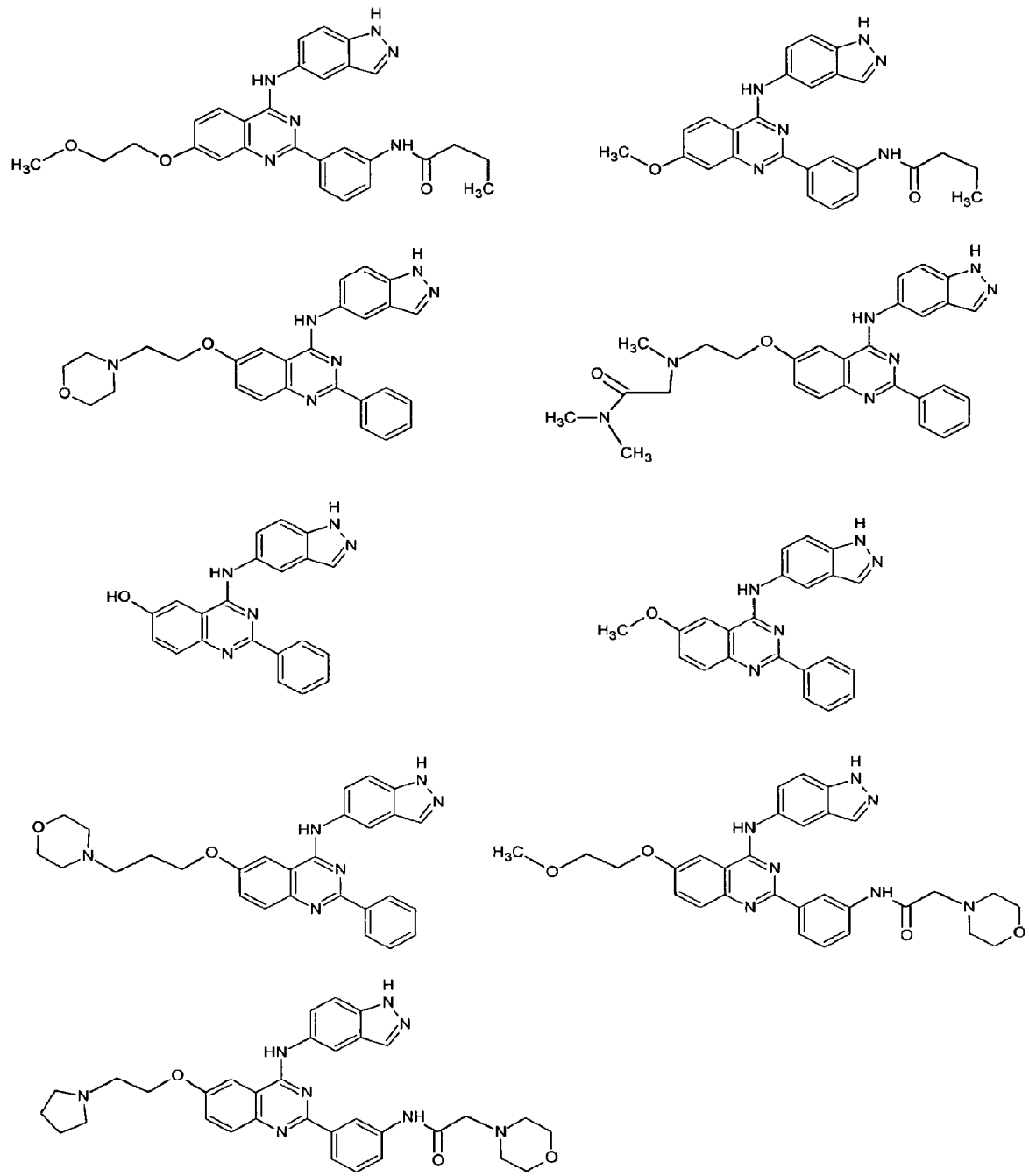
FIG. 9 shows various compounds that represent embodiment of the present invention.
Figure 10:
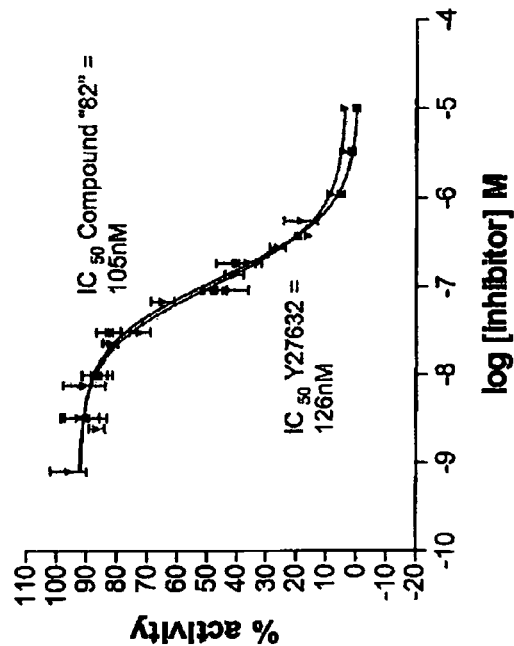
FIG. 10 depicts the specific inhibition of ROCK2 by the compound of Example 82. Inhibition is compared to Y27632, which inhibits both ROCK1 and ROCK2, as well as PKC.
Figure 10:
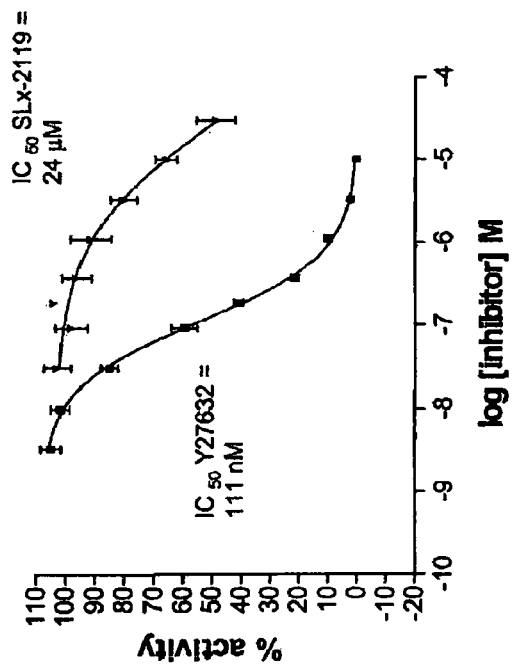

The present invention relates to compounds having the formula I

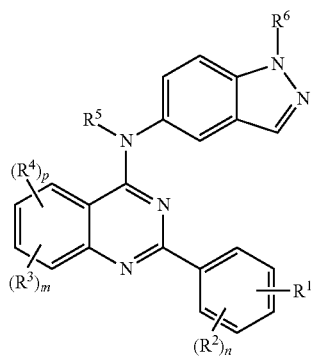

(I)

or pharmaceutically acceptable salt or hydrate thereof, wherein:

$R^1$ is selected from the group consisting of aryl, —$(CH_2)_y$—$NR^{13}R^{14}$, —X—$R^{12}$, —O—$(CH_2)_y$—$CO_2R^{12}$, —O—$(CH_2)_y$, —C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

each X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^4$ is selected from —$(CH_2)_a$—$NR^{43}R^{44}$, —Y—$R^{42}$, —O—$(CH_2)_a$—$CO_2R^{42}$, —O—$(CH_2)_a$—C(=O)$NR^{43}R^{44}$, —O—$(CH_2)_a$-heteroaryl, —O—$(CH_2)_a$-cycloalkyl, —O—C(=O)—$(CH_2)_a$—$NR^{43}R^{44}$, —O—$(CH_2)_c$—$NR^{43}R^{44}$, —NH—C(=O)—$(CH_2)_a$—$NR^{43}R^{44}$, —NH—C(=O)—Y—$R^{45}$, —NH—C(=O)—$(CH_2)_a$—$NR^{43}R^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-$NR^{46}R^{47}$, —$CO_2R^{48}$, —O—$(CH_2)_b$—$CO_2R^{48}$, and —C(=O)$NR^{46}R^{47}$, $R^{46}$ and $R^{47}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{46}$ and $R^{47}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

a is selected from 0 to 6;
b is selected from 0 to 6;
c is selected from 2 to 6;

$R^5$ is selected from the group consisting of H, $C_1$-$C_6$ alkyl, —$(CH_2)_d$—C(=O)—$NR^{53}R^{54}$, —C(=O)—$(CH_2)_d$—$NR^{53}R^{54}$, —C(=O)—X—$R^{55}$, and —C(=O)—$(CH_2)_d$—$NR^{53}R^{54}$;

$R^{53}$ and $R^{54}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-C(=O)$NR^{56}R^{57}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{53}$ and $R^{54}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

$R^{55}$ is selected from the group consisting of H, aryl, —($C_1$-$C_6$ alkyl)-O—($C_1$-$C_6$ alkyl), —($C_1$-$C_6$ alkyl)-$NR^{56}R^{57}$, —$CO_2R^{58}$, —O—$(CH_2)_e$—$CO_2R^{58}$, and —C(=O)$NR^{56}R^{57}$, $R^{56}$ and $R^{57}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{56}$ and $R^{57}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{58}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

d is selected from 0 to 6;
e is selected from 0 to 6;

$R^6$ is selected from the group consisting of H, $C_1$-$C_6$ alkyl, —$(CH_2)_r$—C(=O)—$NR^{63}R^{64}$, —C(=O)—$(CH_2)_r$—$NR^{63}R^{64}$, —C(=O)—X—$R^{65}$, and —C(=O)—$(CH_2)_r$—$NR^{63}R^{64}$;

$R^{63}$ and $R^{64}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-C(=O)$NR^{66}R^{67}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{63}$ and $R^{64}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

$R^{65}$ is selected from the group consisting of H, aryl, —($C_1$-$C_6$ alkyl)-O—($C_1$-$C_6$ alkyl), —($C_1$-$C_6$ alkyl)-$NR^{66}R^{67}$, —$CO_2R^{68}$, —O—$(CH_2)_s$—$CO_2R^{68}$, and —C(=O)$NR^{66}R^{67}$, $R^{66}$ and $R^{67}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{66}$ and $R^{67}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{68}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

r is selected from 0 to 6;
s is selected from 0 to 6;
n is selected from 0 to 4;
m is selected from 0 to 3; and
p is selected from 0 and 1.

In preferred embodiments of the invention, $R^1$ is selected to be —O—$(CH_2)_y$—C(=O)$NR^{13}R^{14}$ or —NH—C(=O)—$(CH_2)_y$—$NR^{13}R^{14}$.

In preferred embodiments of the invention, $R^4$ and $R^5$ are independently selected from H and alkyl, and in more preferably H.

In a preferred embodiment of the present invention, there is provided a compound of the formula II or III:

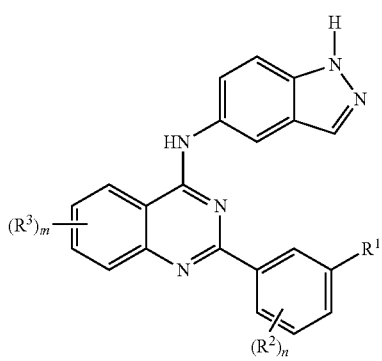

(II)

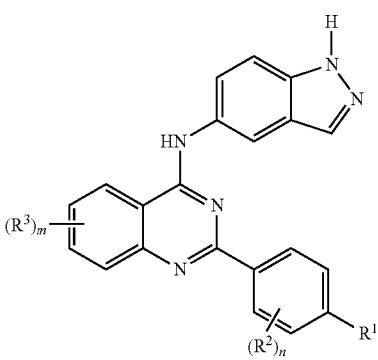

(III)

or pharmaceutically acceptable salt or hydrate thereof, wherein $R^1$, $R^2$, $R^3$, n and m are as for the compound of the formula I.

In a preferred embodiment of the invention, there in provided a compound of the formula IV,

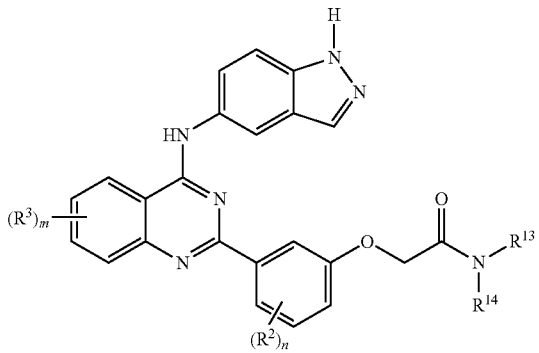

(IV)

or pharmaceutically acceptable salt or hydrate thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and
m is selected from 0 to 3.

In a preferred embodiments of the invention, there in provided a compound of the formula $IV_a$:

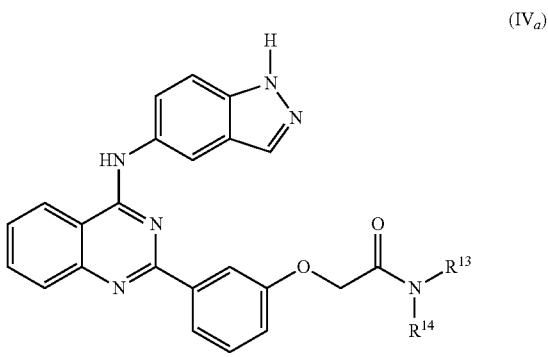

($IV_a$)

or pharmaceutically acceptable salt or hydrate thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl.

In a preferred embodiments of the invention, there in provided a compound of the formula V:

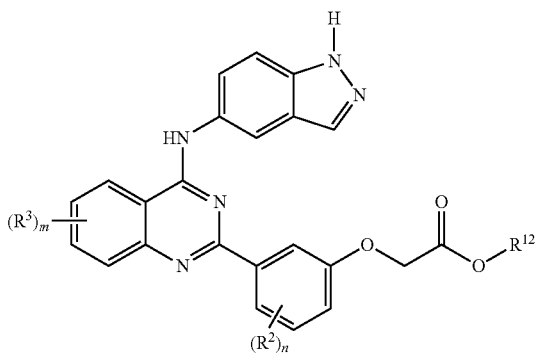

(V)

or pharmaceutically acceptable salt or hydrate thereof, wherein:

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and
m is selected from 0 to 3.

In a preferred embodiments of the invention, there in provided a compound of the formula $V_a$:

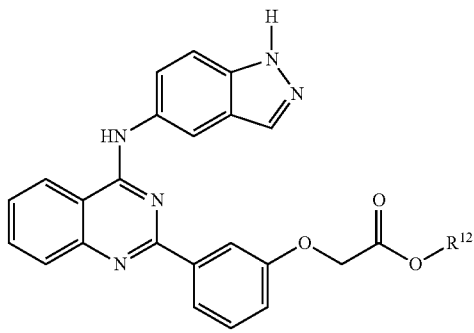

($V_a$)

or pharmaceutically acceptable salt or hydrate thereof, wherein:

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

In a preferred embodiments of the invention, there in provided a compound of the formula VI:

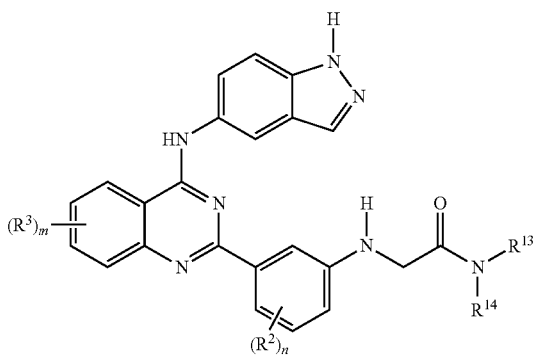

(VI)

or pharmaceutically acceptable salt or hydrate thereof, wherein:

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

R$^{16}$ and R$^{17}$ independently selected from the group consisting of H, C$_1$-C$_8$ alkyl, C$_2$-C$_8$ alkenyl, C$_1$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_1$-C$_6$ alkoxy, hydroxy, amino, cyano and C$_1$-C$_3$ perfluoro alkyl;

or R$^{16}$ and R$^{17}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, oxo, hydroxy, amino, cyano and C$_1$-C$_3$ perfluoro alkyl;

each R$^2$ is independently selected from the group consisting of lower alkyl, CN, halo, hydroxy, lower alkoxy, amino, and perfluoro lower alkyl;

each R$^3$ is independently selected from the group consisting of lower alkyl, CN, halo, hydroxy, lower alkoxy, amino, and perfluoro lower alkyl;

n is selected from 0 to 4; and m is selected from 0 to 3.

In a preferred embodiments of the invention, there in provided a compound of the formula VI$_a$:

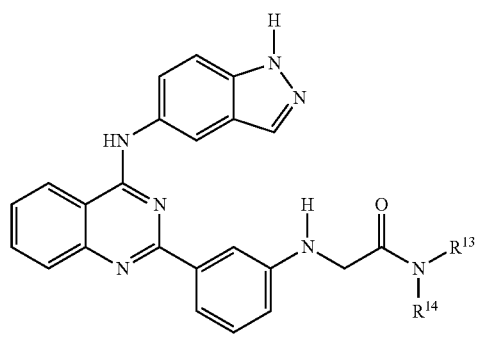

(VI$_a$)

or pharmaceutically acceptable salt or hydrate thereof, wherein:

R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), —(C$_1$-C$_6$ alkyl)-NR$^{16}$R$^{17}$, —(C$_1$-C$_6$ alkyl)-C(=O)NR$^{16}$R$^{17}$, aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_3$-C$_7$ cycloalkyl, C$_1$-C$_6$ alkoxy, hydroxy, amino, cyano and C$_1$-C$_3$ perfluoro alkyl;

or R$^{13}$ and R$^{14}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, C$_3$-C$_7$ cycloalkyl, oxo, hydroxy, amino, cyano and C$_1$-C$_3$ perfluoro alkyl;

R$^{16}$ and R$^{17}$ independently selected from the group consisting of H, C$_1$-C$_8$ alkyl, C$_2$-C$_8$ alkenyl, C$_1$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_1$-C$_6$ alkoxy, hydroxy, amino, cyano and C$_1$-C$_3$ perfluoro alkyl;

or R$^{16}$ and R$^{17}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, oxo, hydroxy, amino, cyano and C$_1$-C$_3$ perfluoro alkyl.

In a preferred embodiments of the invention, there in provided a compound of the formula VII:

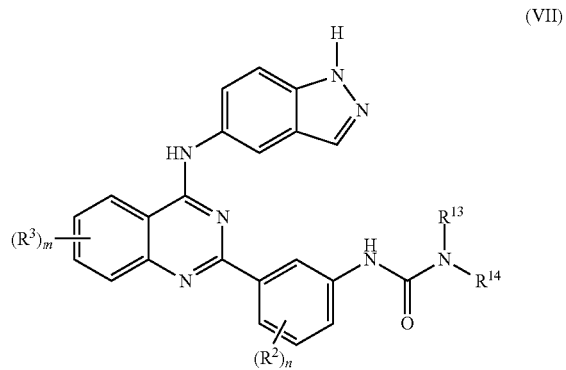

(VII)

or pharmaceutically acceptable salt or hydrate thereof, wherein:

R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), —(C$_1$-C$_6$ alkyl)-NR$^{16}$R$^{17}$, —(C$_1$-C$_6$ alkyl)-C(=O)NR$^{16}$R$^{17}$, aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_3$-C$_7$ cycloalkyl, C$_1$-C$_6$ alkoxy, hydroxy, amino, cyano and C$_1$-C$_3$ perfluoro alkyl;

or R$^{13}$ and R$^{14}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, oxo, hydroxy, amino, cyano and C$_1$-C$_3$ perfluoro alkyl;

R$^{16}$ and R$^{17}$ independently selected from the group consisting of H, C$_1$-C$_8$ alkyl, C$_2$-C$_8$ alkenyl, C$_1$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_1$-C$_6$ alkoxy, hydroxy, amino, cyano and C$_1$-C$_3$ perfluoro alkyl;

or R$^{16}$ and R$^{17}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, oxo, hydroxy, amino, cyano and C$_1$-C$_3$ perfluoro alkyl;

each R$^2$ is independently selected from the group consisting of lower alkyl, CN, halo, hydroxy, lower alkoxy, amino, and perfluoro lower alkyl;

each R³ is independently selected from the group consisting of lower alkyl, CN, halo, hydroxy, lower alkoxy, amino, and perfluoro lower alkyl;

n is selected from 0 to 4; and m is selected from 0 to 3.

In a preferred embodiments of the invention, there in provided a compound of the formula VIII$_a$:

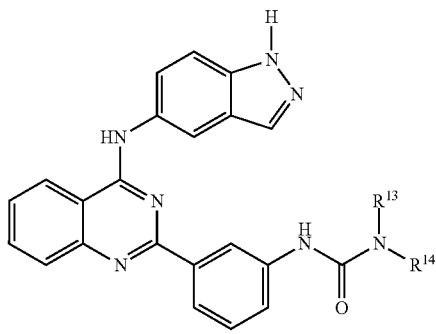

(VII$_a$)

or pharmaceutically acceptable salt or hydrate thereof, wherein:

R¹³ and R¹⁴ are independently selected from the group consisting of H, C₁-C₈ alkyl, C₂-C₈ alkenyl, C₂-C₈ alkynyl, —(C₁-C₆ alkyl)-O—(C₁-C₆ alkyl), —(C₁-C₆ alkyl)-NR¹⁶R¹⁷, —(C₁-C₆ alkyl)-C(=O)NR¹⁶R¹⁷, aryl, aralkyl, heteroaryl, C₃-C₇ cycloalkyl, a three to twelve membered heterocyclic ring containing up to 3 heteroatoms, each of which may be optionally substituted by from 1 to 3 substituents independently selected from halo, C₁-C₆ alkyl, C₁-C₆, alkenyl, C₃-C₇ cycloalkyl, C₁-C₆ alkoxy, hydroxy, amino, cyano and C₁-C₃ perfluoro alkyl;

or R¹³ and R¹⁴ may be taken together form a three to twelve membered heterocyclic ring having up to 3 heteroatoms which is optionally substituted by from 1 to 3 substituents independently selected from halo, C₁-C₆ alkyl, C₁-C₆, alkenyl, C₁-C₆ alkoxy, oxo, hydroxy, amino, cyano and C₁-C₃ perfluoro alkyl;

R¹⁶ and R¹⁷ independently selected from the group consisting of H, C₁-C₈ alkyl, C₂-C₈ alkenyl, C₁-C₈ alkynyl, —(C₁-C₆ alkyl)-O—(C₁-C₆ alkyl), aryl, aralkyl, heteroaryl, C₃-C₇ cycloalkyl, a three to twelve membered heterocyclic ring containing up to 3 heteroatoms, each of which may be optionally substituted by from 1 to 3 substituents independently selected from halo, C₁-C₆ alkyl, C₂-C₆, alkenyl, C₁-C₆ alkoxy, hydroxy, amino, cyano and C₁-C₃ perfluoro alkyl;

or R¹⁶ and R¹⁷ may be taken together form a three to twelve membered heterocyclic ring having up to 3 heteroatoms which is optionally substituted by from 1 to 3 substituents independently selected from halo, C₁-C₆ alkyl, C₂-C₆, alkenyl, C₁-C₆ alkoxy, oxo, hydroxy, amino, cyano and C₁-C₃ perfluoro alkyl.

In a preferred embodiments of the invention, there in provided a compound of the formula VIII:

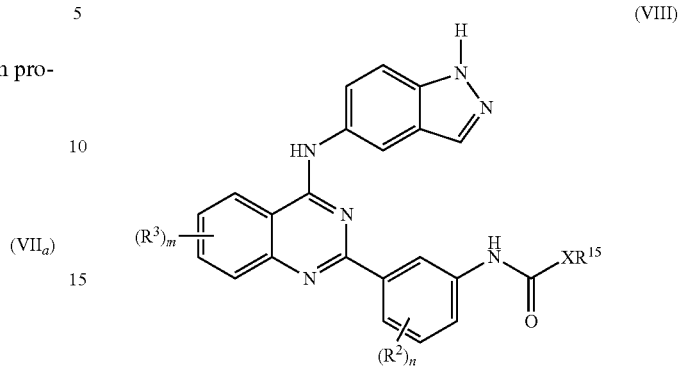

(VIII)

or pharmaceutically acceptable salt or hydrate thereof, wherein:

X is selected from a covalent bond, O, NH, and C₁-C₆ alkyl;

R¹⁵ is selected from the group consisting of H, aryl, heteroaryl, C₃-C₇ cycloalkyl, a three to twelve membered heterocyclic ring containing up to 3 heteroatoms, each of which may be optionally substituted by from 1 to 3 substituents independently selected from halo, C₁-C₆ alkyl, C₂-C₆, alkenyl, C₁-C₆ alkoxy, hydroxy, amino, cyano and C₁-C₃ perfluoro alkyl, or R¹⁵ is selected from —(C₁-C₆ alkyl)-O—(C₁-C₆ alkyl), —(C₁-C₆ alkyl)-NR¹⁶R¹⁷, —CO₂R¹⁸, —O—(CH₂)$_x$—CO₂R¹⁸, and —C(=O)NR¹⁶R¹⁷;

R¹⁶ and R¹⁷ independently selected from the group consisting of H, C₁-C₈ alkyl, C₂-C₈ alkenyl, C₁-C₈ alkynyl, —(C₁-C₆ alkyl)-O—(C₁-C₆ alkyl), aryl, aralkyl, heteroaryl, C₃-C₇ cycloalkyl, a three to twelve membered heterocyclic ring containing up to 3 heteroatoms, each of which may be optionally substituted by from 1 to 3 substituents independently selected from halo, C₁-C₆ alkyl, C₂-C₆, alkenyl, C₁-C₆ alkoxy, hydroxy, amino, cyano and C₁-C₃ perfluoro alkyl;

or R¹⁶ and R¹⁷ may be taken together form a three to twelve membered heterocyclic ring having up to 3 heteroatoms which is optionally substituted by from 1 to 3 substituents independently selected from halo, C₁-C₆ alkyl, C₂-C₆, alkenyl, C₁-C₆ alkoxy, oxo, hydroxy, amino, cyano and C₁-C₃ perfluoro alkyl;

R¹⁸ is selected from the group consisting of H, aryl, aralkyl, heteroaryl, C₁-C₆ alkyl, —(C₁-C₆ alkyl)-O—(C₁-C₆ alkyl), —(C₁-C₆ alkyl)-NR¹⁶R¹⁷, —(C₁-C₆ alkyl)-O—(C₁-C₆ alkyl)-O—(C$_r$ C₆ alkyl), each of which may be optionally substituted by from 1 to 3 substituents independently selected from halo, C₁-C₆ alkoxy, hydroxy, amino, cyano and C₁-C₃ perfluoroalkyl;

x is selected from 0 to 6, each R² is independently selected from the group consisting of lower alkyl, CN, halo, hydroxy, lower alkoxy, amino, and perfluoro lower alkyl;

each R³ is independently selected from the group consisting of lower alkyl, CN, halo, hydroxy, lower alkoxy, amino, and perfluoro lower alkyl;

n is selected from 0 to 4; and m is selected from 0 to 3.

In a preferred embodiments of the invention, there in provided a compound of the formula VIII$_a$:

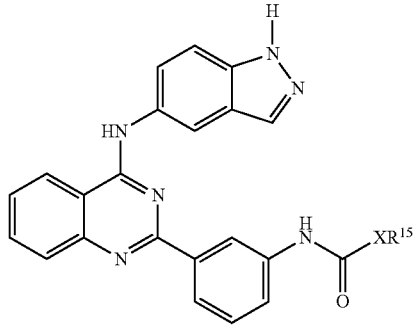

(VIII$_a$)

or pharmaceutically acceptable salt or hydrate thereof, wherein:

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—($CH_2$)$_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl; and x is selected from 0 to 6.

In a preferred embodiments of the invention, there in provided a compound of the formula IX:

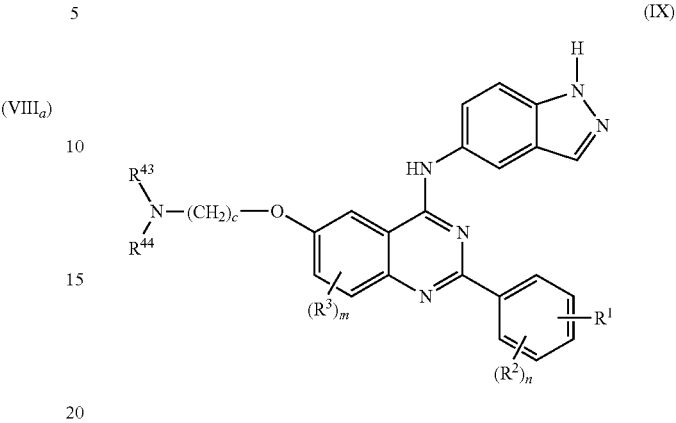

(IX)

or pharmaceutically acceptable salt or hydrate thereof, wherein:

$R^1$ is selected from the group consisting of aryl, —($CH_2$)$_y$—$NR^{13}R^{14}$, —X—$R^{12}$, —O—($CH_2$)$_y$—$CO_2R^{12}$, —O—($CH_2$)$_y$, —C(=O)$NR^{13}R^{14}$, —O—($CH_2$)$_y$-heteroaryl, —O—($CH_2$)$_y$-cycloalkyl, —O—C(=O)—($CH_2$)$_y$—$NR^{13}R^{14}$, —O—($CH_2$)$_z$—$NR^{13}R^{14}$, —NH—C(=O)—($CH_2$)$_y$—$NR^{13}R^{14}$, —NH—C(=O)—X—$R^{15}$, —NH—($CH_2$)$_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—($CH_2$)$_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^{43}$ and $R^{44}$ are independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{46}$ and $R^{47}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{46}$ and $R^{47}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

c is selected from 2 to 6;
n is selected from 0 to 4; and
m is selected from 0 to 3.

In a preferred embodiments of the invention, there in provided a compound of the formula X:

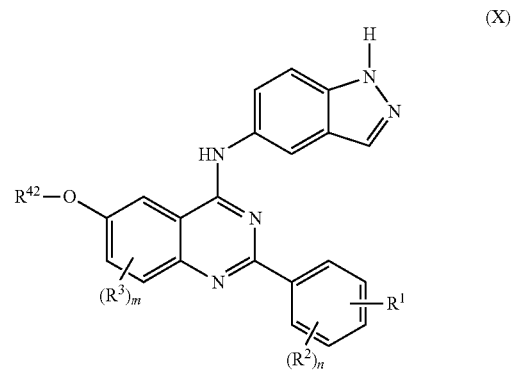

(X)

or pharmaceutically acceptable salt or hydrate thereof, wherein:

$R^1$ is selected from the group consisting of aryl, —$(CH_2)_y$—$NR^{13}R^{14}$, —X—$R^{12}$, —O—$(CH_2)_y$—$CO_2R^{12}$, —O—$(CH_2)_y$, —C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_x$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;

y is selected from 0 to 6;

z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{46}$ and $R^{47}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{46}$ and $R^{47}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

n is selected from 0 to 4; and m is selected from 0 to 3.

In a preferred embodiments of the invention, there in provided a compound of the formula XI:

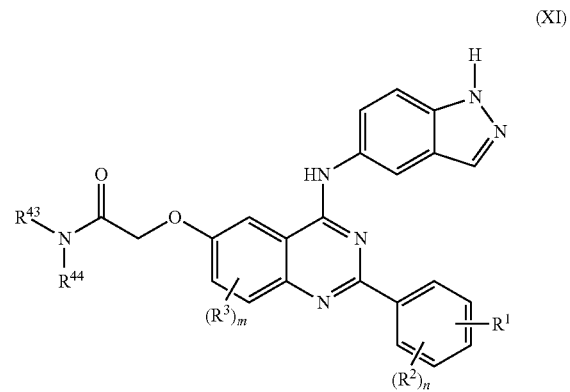

(XI)

or pharmaceutically acceptable salt or hydrate thereof, wherein:

$R^1$ is selected from the group consisting of aryl, —$(CH_2)_y$—$NR^{13}R^{14}$, —X—$R^{12}$, —O—$(CH_2)_y$—$CO_2R^{12}$, —O—$(CH_2)_y$, —C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

R$^{16}$ and R$^{17}$ independently selected from the group consisting of H, C$_1$-C$_8$ alkyl, C$_2$-C$_8$ alkenyl, C$_1$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_1$-C$_6$ alkoxy, hydroxy, amino, cyano and C$_1$-C$_3$ perfluoro alkyl;

or R$^{16}$ and R$^{17}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, oxo, hydroxy, amino, cyano and C$_1$-C$_3$ perfluoro alkyl;

R$^{18}$ is selected from the group consisting of H, aryl, aralkyl, heteroaryl, C$_1$-C$_6$ alkyl, —(C$_1$-C$_6$ alkyl)-O—(C$_1$-C$_6$ alkyl), —(C$_1$-C$_6$ alkyl)-NR$^{16}$R$^{17}$, —(C$_1$-C$_6$ alkyl)-O—(C$_1$-C$_6$ alkyl)-O—(C$_1$-C$_6$ alkyl), each of which may be optionally substituted by from 1 to 3 substituents independently selected from halo, C$_1$-C$_6$ alkoxy, hydroxy, amino, cyano and C$_1$-C$_3$ perfluoroalkyl;

x is selected from 0 to 6;
y is selected from 0 to 6;
z is selected from 2 to 6;

each R$^2$ is independently selected from the group consisting of lower alkyl, CN, halo, hydroxy, lower alkoxy, amino, and perfluoro lower alkyl;

each R$^3$ is independently selected from the group consisting of lower alkyl, CN, halo, hydroxy, lower alkoxy, amino, and perfluoro lower alkyl;

R$^{43}$ and R$^{44}$ are independently selected from the group consisting of H, C$_1$-C$_8$ alkyl, C$_2$-C$_8$ alkenyl, C$_1$-C$_8$ alkynyl, —(C$_1$-C$_6$ alkyl)-O—(C$_1$-C$_6$ alkyl), —(C$_1$-C$_6$ alkyl)-NR$^{46}$R$^{47}$, —(C$_1$-C$_6$ alkyl)-C(=O)NR$^{46}$R$^{47}$, aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_3$-C$_7$ cycloalkyl, C$_1$-C$_6$ alkoxy, hydroxy, amino, cyano and C$_1$-C$_3$ perfluoro alkyl;

or R$^{43}$ and R$^{44}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, oxo, hydroxy, amino, cyano and C$_1$-C$_3$ perfluoro alkyl;

R$^{46}$ and R$^{47}$ independently selected from the group consisting of H, C$_1$-C$_8$ alkyl, C$_2$-C$_8$ alkenyl, C$_1$-C$_8$ alkynyl, —(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_1$-C$_6$ alkoxy, hydroxy, amino, cyano and C$_1$-C$_3$ perfluoro alkyl;

or R$^{46}$ and R$^{47}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, oxo, hydroxy, amino, cyano and C$_1$-C$_3$ perfluoro alkyl;

R$^{48}$ is selected from the group consisting of H, aryl, aralkyl, heteroaryl, C$_1$-C$_6$ alkyl, —(C$_1$-C$_6$ alkyl)-O—(C$_1$-C$_6$ alkyl), —(C$_1$-C$_6$ alkyl)-NR$^{46}$R$^{47}$, —(C$_1$-C$_6$ alkyl)-O—(C$_1$-C$_6$ alkyl)-O—(C$_1$-C$_6$ alkyl), each of which may be optionally substituted by from 1 to 3 substituents independently selected from halo, C$_1$-C$_6$ alkoxy, hydroxy, amino, cyano and C$_1$-C$_3$ perfluoroalkyl;

n is selected from 0 to 4; and
m is selected from 0 to 3.

In a preferred embodiments of the invention, there in provided a compound of the formula XII:

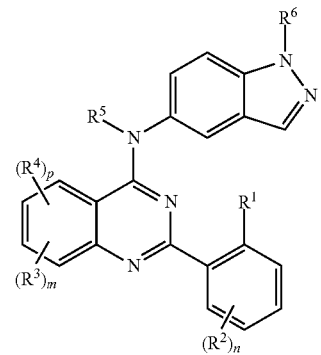

XII or pharmaceutically acceptable salt or hydrate thereof, wherein:

R$^1$ is selected from the group consisting of aryl, —(CH$_2$)$_y$—NR$^{13}$R$^{14}$, —X—R$^{12}$, —O—(CH$_2$)$_y$—CO$_2$R$^{12}$, —O—(CH$_2$)$_y$, —C(=O)NR$^{13}$R$^{14}$, —O—(CH$_2$)$_y$-heteroaryl, —O—(CH$_2$)$_y$-cycloalkyl, —O—C(=O)—(CH$_2$)$_y$—NR$^{13}$R$^{14}$, —O—(CH$_2$)$_z$—NR$^{13}$R$^{14}$, —NH—C(=O)—(CH$_2$)$_y$—NR$^{13}$R$^{14}$, —NH—C(=O)—X—R$^{15}$, —NH—(CH$_2$)$_y$—NR$^{13}$R$^{14}$;

R$^{12}$ is selected from the group consisting of C$_1$-C$_6$ alkyl, —(C$_1$-C$_6$ alkyl)-O—(C$_1$-C$_6$ alkyl), —(C$_1$-C$_6$ alkyl)-NR$^{16}$R$^{17}$, —(C$_1$-C$_6$ alkyl)-C(=O)NR$^{16}$R$^{17}$, —(C$_1$-C$_6$ alkyl)-O—(C$_1$-C$_6$ alkyl)-O—(C$_1$-C$_6$ alkyl), aryl, aralkyl, heteroaryl, C$_3$-C$_7$ cycloalkyl, a three to twelve membered heterocyclic ring containing up to 3 heteroatoms, each of which may be optionally substituted at one or more carbon atoms by from 1 to 3 substituents independently selected from halo, C$_1$-C$_6$ alkoxy, hydroxy, amino, cyano and C$_1$-C$_3$ perfluoro alkyl;

R$^{13}$ and R$^{14}$ are independently selected from the group consisting of H, C$_1$-C$_8$ alkyl, C$_2$-C$_8$ alkenyl, C$_2$-C$_8$ alkynyl, —(C$_1$-C$_6$ alkyl)-O—(C$_1$-C$_6$ alkyl), —(C$_1$-C$_6$ alkyl)-NR$^{16}$R$^{17}$, —(C$_1$-C$_6$ alkyl)-C(=O)NR$^{16}$R$^{17}$, aryl, aralkyl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, C$_2$-C$_6$, alkenyl, C$_3$-C$_7$ cycloalkyl, C$_1$-C$_6$ alkoxy, hydroxy, amino, cyano and C$_1$-C$_3$ perfluoro alkyl;

or R$^{13}$ and R$^{14}$ may be taken together form a three to twelve membered heterocyclic ring having up to 3 heteroatoms which is optionally substituted by from 1 to 3 substituents independently selected from halo, C$_1$-C$_6$ alkyl, C$_2$-C$_6$, alkenyl, C$_1$-C$_6$ alkoxy, C$_3$-C$_7$ cycloalkyl, oxo, hydroxy, amino, cyano and C$_1$-C$_3$ perfluoro alkyl;

X is selected from a covalent bond, O, NH, and C$_1$-C$_6$ alkyl;

R$^{15}$ is selected from the group consisting of H, aryl, heteroaryl, C$_3$-C$_7$ cycloalkyl, a three to twelve membered heterocyclic ring containing up to 3 heteroatoms, each of which may be optionally substituted by from 1 to 3 substituents independently selected from halo, C$_1$-C$_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-NR$^{16}$R$^{17}$, —CO$_2$R$^{18}$, —O—(CH$_2$)$_x$—CO$_2$R$^{18}$, and —C(=O)NR$^{16}$R$^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^4$ is selected from —(CH$_2$)$_a$—NR$^{43}$R$^{44}$, —Y—R$^{42}$, —O—(CH$_2$)$_a$—CO$_2$R$^{42}$, —O—(CH$_2$)$_a$—C(=O)NR$^{43}$R$^{44}$, —O—(CH$_2$)$_a$-heteroaryl, —O—(CH$_2$)$_a$-cycloalkyl, —O—C(=O)—(CH$_2$)$_a$—NR$^{43}$R$^{44}$, —O—(CH$_2$)$_c$—NR$^{43}$R$^{44}$, —NH—C(=O)—(CH$_2$)$_a$—NR$^{43}$R$^{44}$, —NH—C(=O)—Y—R$^{45}$, —NH—C(=O)—(CH$_2$)$_a$—NR$^{43}$R$^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-C(=O)NR$^{46}$R$^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-C(=O)NR$^{46}$R$^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-NR$^{46}$R$^{47}$, —CO$_2$R$^{48}$, —O—(CH$_2$)$_b$—CO$_2$R$^{48}$, and —C(=O)NR$^{46}$R$^{47}$, $R^{46}$ and $R^{47}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{46}$ and $R^{47}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

a is selected from 0 to 6;
b is selected from 0 to 6;
c is selected from 2 to 6;

$R^5$ is selected from the group consisting of H, $C_1$-$C_6$ alkyl, —(CH$_2$)$_d$—C(=O)—NR$^{53}$R$^{54}$, —C(=O)—(CH$_2$)$_d$—NR$^{53}$R$^{54}$, —C(=O)—X—R$^{55}$, and —C(=O)—(CH$_2$)$_d$—NR$^{53}$R$^{54}$;

$R^{53}$ and $R^{54}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{56}$R$^{57}$, —($C_1$-$C_6$ alkyl)-C(=O)NR$^{56}$R$^{57}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{53}$ and $R^{54}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

$R^{55}$ is selected from the group consisting of H, aryl, —($C_1$-$C_6$ alkyl)-O—($C_1$-$C_6$ alkyl), —($C_1$-$C_6$ alkyl)-NR$^{56}$R$^{57}$, —CO$_2$R$^{58}$, —O—(CH$_2$)$_e$—CO$_2$R$^{58}$, and —C(=O)NR$^{56}$R$^{57}$, $R^{56}$ and $R^{57}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{56}$ and $R^{57}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{58}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{56}$R$^{57}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

d is selected from 0 to 6;

e is selected from 0 to 6;

$R^6$ is selected from the group consisting of H, $C_1$-$C_6$ alkyl, —(CH$_2$)$_r$—C(=O)—NR$^{63}$R$^{64}$, —C(=O)—(CH$_2$)$_r$—NR$^{63}$R$^{64}$, —C(=O)—X—R$^{65}$, and —C(=O)—(CH$_2$)$_r$—NR$^{63}$R$^{64}$;

$R^{63}$ and $R^{64}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{66}$R$^{67}$, —($C_1$-$C_6$ alkyl)-C(=O)NR$^{66}$R$^{67}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{63}$ and $R^{64}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

$R^{65}$ is selected from the group consisting of H, aryl, —($C_1$-$C_6$ alkyl)-O—($C_1$-$C_6$ alkyl), —($C_1$-$C_6$ alkyl)-NR$^{66}$R$^{67}$, —CO$_2$R$^{68}$, —O—(CH$_2$)$_s$—CO$_2$R$^{68}$, and —C(=O)NR$^{66}$R$^{67}$, $R^{66}$ and $R^{67}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{66}$ and $R^{67}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{68}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{66}$R$^{67}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

r is selected from 0 to 6;

s is selected from 0 to 6;

n is selected from 0 to 4;

m is selected from 0 to 3; and p is selected from 0 and 1.

In a preferred embodiments of the invention, there in provided a compound of the formula XII$_a$:

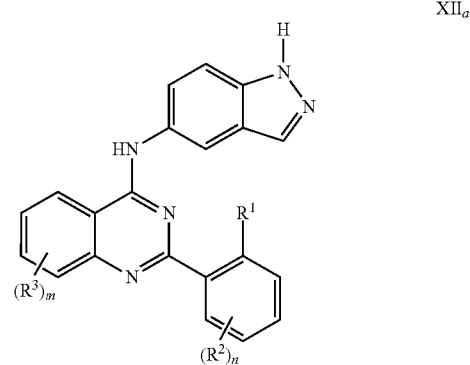

XII$_a$ or pharmaceutically acceptable salt or hydrate thereof, wherein:

$R^1$ is selected from the group consisting of aryl, —(CH$_2$)$_y$—NR$^{13}$R$^{14}$, —X—R$^{12}$, —O—(CH$_2$)$_y$—CO$_2$R$^{12}$, —O—(CH$_2$)$_y$—C(=O)NR$^{13}$R$^{14}$, —O—(CH$_2$)$_y$-heteroaryl, —O—(CH$_2$)$_y$-cycloalkyl, —O—C(=O)—(CH$_2$)$_y$—NR$^{13}$R$^{14}$, —O—(CH$_2$)$_z$—NR$^{13}$R$^{14}$, —NH—C(=O)—(CH$_2$)$_y$—NR$^{13}$R$^{14}$, —NH—C(=O)—X—R$^{15}$, —NH—(CH$_2$)$_y$—NR$^{13}$R$^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and
m is selected from 0 to 3.

In further preferred embodiments of the invention, there in provided a compound of the formula $XII_a$, wherein $R^1$ is selected from —$NR^{13}R^{14}$, —NH—$R^{12}$, —NH—C(=O)—$(CH_2)_y$—$NR^{13}R^{14}$, —NH—C(=O)—X—$R^{15}$, and —NH—$(CH_2)_y$—$NR^{13}R^{14}$.

In a preferred embodiments of the invention, there in provided a compound of the formula $XII_b$:

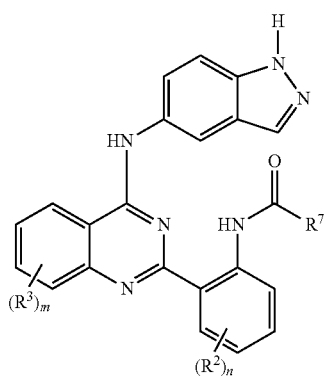

$XII_b$ or pharmaceutically acceptable salt or hydrate thereof, wherein:

$R^7$ is selected from the group consisting of —$(CH_2)_y$—$NR^{13}R^{14}$, and X—$R^{15}$;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together form a three to twelve membered heterocyclic ring having up to 3 heteroatoms which is optionally substituted by from 1 to 3 substituents independently selected from halo, $C_1$-$C_6$ alkyl, $C_2$-$C_6$, alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$, alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ independently selected from the group consisting of H, $C_1$-$C_8$ alkyl, $C_2$-$C_8$ alkenyl, $C_1$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_1$-$C_6$, alkenyl, $C_1$-$C_6$ alkoxy, hydroxy, amino, cyano and $C_1$-$C_3$ perfluoro alkyl;

or $R^{16}$ and $R^{17}$ may be taken together form a three to twelve membered heterocyclic ring having up to 3 heteroatoms which is optionally substituted by from 1 to 3 substituents independently selected from halo, $C_1$-$C_6$ alkyl, $C_1$-$C_6$, alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and
m is selected from 0 to 3.

Preferred compounds according to the present invention include:

2-(3-(4-(1H-indazol-5-ylamino)quinazolin-2-yl)phenoxy)-N-isopropylacetamide,
2-(3-(4-(1H-indazol-5-ylamino)quinazolin-2-yl)phenoxy)-N-(2-methoxyethyl)acetamide,
2-(3-(4-(1H-indazol-5-ylamino)quinazolin-2-yl)phenoxy)-N-(pyridin-3-yl)acetamide,
2-(3-(4-(1H-indazol-5-ylamino)quinazolin-2-yl)phenoxy)-1-(4-methylpiperazin-1-yl)ethanone,
2-(3-(4-(1H-indazol-5-ylamino)quinazolin-2-yl)phenoxy)-1-morpholinoethanone,
2-(3-(4-(1H-indazol-5-ylamino)quinazolin-2-yl)phenoxy)-N-methylacetamide,
2-(3-(4-(1H-indazol-5-ylamino)quinazolin-2-yl)phenoxy)-N—(R)-pyrrolidin-3-yl)acetamide,
2-(3-(4-(1H-indazol-5-ylamino)quinazolin-2-yl)phenoxy)-N—((S)-pyrrolidin-3-yl)acetamide,
2-(3-(4-(1H-indazol-5-ylamino)quinazolin-2-yl)phenoxy)-N—((R)-tetrahydrofuran-3-yl)acetamide,
2-(3-(4-(1H-indazol-5-ylamino)quinazolin-2-yl)phenoxy)-1-(piperidin-1-yl)ethanone,
2-(3-(4-(1H-indazol-5-ylamino)quinazolin-2-yl)phenoxy)-N-tert-butylacetamide,
2-(3-(4-(1H-indazol-5-ylamino)quinazolin-2-yl)phenoxy)-N-ethylacetamide,
2-(3-(4-(1H-indazol-5-ylamino)quinazolin-2-yl)phenoxy)-N-(cyanomethyl)acetamide,
2-(3-(4-(1H-indazol-5-ylamino)quinazolin-2-yl)phenoxy)-N-cyclobutylacetamide,
2-(3-(4-(1H-indazol-5-ylamino)quinazolin-2-yl)phenoxy)-N-isobutylacetamide,
2-(3-(4-(1H-indazol-5-ylamino)quinazolin-2-yl)phenoxy)-N-(2,2,2-trifluoroethyl)acetamide,
2-(3-(4-(1H-indazol-5-ylamino)quinazolin-2-yl)phenoxy)-N-cyclohexylacetamide,
2-(3-(4-(1H-indazol-5-ylamino)quinazolin-2-yl)phenoxy)-N-neopentylacetamide,
2-(3-(4-(1H-indazol-5-ylamino)quinazolin-2-yl)phenoxy)-N-(prop-2-ynyl)acetamide,
N-(3-(4-(1H-indazol-5-ylamino)quinazolin-2-yl)phenyl)-4-methylpiperazine-1-carboxamide,
3-(3-(4-(1H-indazol-5-ylamino)quinazolin-2-yl)phenyl)-1,1-dimethylurea,
N-(3-(4-(1H-indazol-5-ylamino)quinazolin-2-yl)phenyl)-2-methoxyacetamide,
methyl 2-(3-(4-(1H-indazol-5-ylamino)quinazolin-2-yl)phenylamino)-2-oxoacetate,
1-(3-(4-(1H-indazol-5-ylamino)quinazolin-2-yl)phenyl)-3-(2-(dimethylamino)ethyl)urea,
N-(3-(4-(1H-indazol-5-ylamino)quinazolin-2-yl)phenyl)-2-morpholinoacetamide,
N-(3-(4-(1H-indazol-5-ylamino)quinazolin-2-yl)phenyl)-3-(4-isopropylpiperazin-1-yl)propanamide,
N-(3-(4-(1H-indazol-5-ylamino)quinazolin-2-yl)phenyl)piperidine-4-carboxamide,
2-(3-fluoro-4-(phenyl)phenyl)-N-(1H-indazol-5-yl)-7-methoxy-6-(2-(4-methylpiperazin-1-yl)ethoxy)quinazolin-4-amine,
6-(2-(dimethylamino)ethoxy)-2-(3-fluoro-4-(phenyl)phenyl)-N-(1H-indazol-5-yl)-7-methoxyquinazolin-4-amine,
2-(3-fluoro-4-(phenyl)phenyl)-N-(1H-indazol-5-yl)-7-methoxy-6-(2-(pyrrolidin-1-yl)ethoxy)quinazolin-4-amine,
2-(4-(1H-indazol-5-ylamino)-2-[(3-phenyl)phenyl]-7-methoxyquinazolin-6-yloxy)-1-(4-methylpiperazin-1-yl)ethanone,
2-[(3-(phenyl)phenyl)-N-(1H-indazol-5-yl)-7-methoxy-6-(2-methoxyethoxy)quinazolin-4-amine,
6-(2-(dimethylamino)ethoxy)-N-(1H-indazol-5-yl)-7-methoxy-2-(3-(phenyl)phenyl)quinazolin-4-amine,
2-[(3-phenyl)phenyl]-N-(1H-indazol-5-yl)-7-methoxy-6-(2-(pyrrolidin-1-yl)ethoxy)quinazolin-4-amine,
2-((2-(4-(1H-indazol-5-ylamino)-2-[(3-phenyl)phenyl]-7-methoxyquinazolin-6-yloxy)ethyl)(methyl)amino)-N,N-dimethylacetamide,
2-[(3-phenyl)phenyl)-N-(1H-indazol-5-yl)-7-methoxy-6-(2-(4-methylpiperazin-1-yl)ethoxy)quinazolin-4-amine,
2-[(3-phenyl)phenyl)-N-(1H-indazol-5-yl)-7-methoxy-6-(2-morpholinoethoxy)quinazolin-4-amine,
2-[(3-phenyl)phenyl)-N-(1H-indazol-5-yl)-7-methoxy-6-(2-(4-methyl-1,4-diazepan-1-yl)ethoxy)quinazolin-4-amine,
N-(3-(4-(1H-indazol-5-ylamino)-6-(2-(dimethylamino)ethoxy)quinazolin-2-yl)phenyl)nicotinamide,
N-(3-(4-(1H-indazol-5-ylamino)-6-(2-methoxyethoxy)quinazolin-2-yl)phenyl)nicotinamide,
N-(3-(4-(1H-indazol-5-ylamino)-6-(2-(dimethylamino)ethoxy)quinazolin-2-yl)phenyl)butyramide,
N-(3-(4-(1H-indazol-5-ylamino)-6-(3-(dimethylamino)propoxy)quinazolin-2-yl)phenyl)butyramide,
N-(3-(4-(1H-indazol-5-ylamino)-7-methoxy-6-(3-morpholinopropoxy)quinazolin-2-yl)phenyl)butyramide,
N-(3-(4-(1H-indazol-5-ylamino)-7-methoxy-6-(3-morpholinopropoxy)quinazolin-2-yl)phenyl)isonicotinamide,
N-(3-(4-(1H-indazol-5-ylamino)-7-methoxy-6-(3-morpholinopropoxy)quinazolin-2-yl)phenyl)nicotinamide,
N-(3-(4-(1H-Indazol-5-ylamino)-7-methoxy-6-(2-(pyrrolidin-1-yl)ethoxy)quinazolin-2-yl)phenyl)-2-morpholinoacetamide,
N-(3-(4-(1H-indazol-5-ylamino)-6-(2-(dimethylamino)ethoxy)-7-methoxyquinazolin-2-yl)phenyl)butyramide,
N-(3-(4-(1H-indazol-5-ylamino)-6-(2-(dimethylamino)-2-oxoethoxy)-7-methoxyquinazolin-2-yl)phenyl)nicotinamide,
N-(3-(4-(1H-Indazol-5-ylamino)-6-(2-(dimethylamino)ethoxy)-7-methoxyquinazolin-2-yl)phenyl)nicotinamide,
N-(3-(4-(1H-Indazol-5-ylamino)-7-methoxy-6-(2-methoxyethoxy)quinazolin-2-yl)phenyl)nicotinamide,
N-(3-(4-(1H-indazol-5-ylamino)-7-methoxy-6-(2-methoxyethoxy)quinazolin-2-yl)phenyl)-2-morpholinoacetamide,
2-(3-(4-(1H-indazol-5-ylamino)-7-methoxy-6-(2-methoxyethoxy)quinazolin-2-yl)phenoxy)-N-isopropylacetamide,
N-(3-(4-(1H-Indazol-5-ylamino)-6-(2-(pyrrolidin-1-yl)ethoxy)quinazolin-2-yl)phenyl)butyramide,
N-(3-(4-(1H-indazol-5-ylamino)-6-(2-(piperidin-1-yl)ethoxy)quinazolin-2-yl)phenyl)butyramide,
N-(3-(4-(1H-indazol-5-ylamino)-6-(2-methoxyethoxy)quinazolin-2-yl)phenyl)butyramide,
N-(3-(4-(1H-indazol-5-ylamino)-6-(2-((2-methoxyethyl)(methyl)amino)ethoxy)-quinazolin-2-yl)phenyl)butyramide,
N-(3-(4-(1H-indazol-5-ylamino)-6-(2-(4-methylpiperazin-1-yl)ethoxy)quinazolin-2-yl)phenyl)butyramide,
N-(3-(4-(1H-indazol-5-ylamino)-6-(2-(2-oxopyrrolidin-1-yl)ethoxy)quinazolin-2-yl)phenyl)butyramide,
N-(3-(4-(1H-indazol-5-ylamino)-6-(2-(3-hydroxypyrrolidin-1-yl)ethoxy)quinazolin-2-yl)phenyl)butyramide,
N-(3-(4-(1H-indazol-5-ylamino)-7-methoxy-6-(2-(2-oxopyrrolidin-1-yl)ethoxy)quinazolin-2-yl)phenyl)butyramide,
N-(3-(4-(1H-indazol-5-ylamino)-7-methoxy-6-(2-methoxyethoxy)quinazolin-2-yl)phenyl)butyramide,
N-(3-(4-(1H-indazol-5-ylamino)-7-methoxy-6-(2-(4-methylpiperazin-1-yl)ethoxy)quinazolin-2-yl)phenyl)butyramide, and N-(3-(4-(1H-indazol-5-ylamino)-6-(2-((S)-3-(dimethylamino)pyrrolidin-1-yl)ethoxy)-7-methoxyquinazolin-2-yl)phenyl)butyramide.

It is believed that the $R^1$ and/or the $R^4$ group modulates the pharmacokinetic and/or pharmacodynamic profile of the compound and may result in improved pharmacokinetic properties compared to the unmodified, i.e., parent compound. In certain embodiments, the active agent has improved physicochemical properties, pharmacokinetics, metabolism, or toxicity profile. In a preferred embodiment, the active agent has superior solubility, lower $IC_{50}$, and/or is substantially less protein bound in vivo compared to the compound lacking the $R^1$ residue.

Preferably, the compounds of the invention include but are not limited to inhibitors and activators of proteins and enzymes. Specifically, the compounds of the present invention may modulate the function of Rho-Kinase. The compounds of the invention may be useful in the treatment of cancer, neuronal degeneration (peripheral or central), spinal cord injury, erectile dysfunction, atherosclerosis, hypertension, cerebral vasospasm, cerebral ischemia, restenosis, asthma, glaucoma, asthma, osteoporosis, fibrotic disease (liver and kidney), Kidney dialysis (epithelial stability), and neuronal degeneration inflammation.

The term "heteroatom" as used herein means an atom of any element other than carbon or hydrogen. Preferred heteroatoms are boron, nitrogen, oxygen, phosphorus, sulfur and selenium. Most preferred are nitrogen or oxygen.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to six carbons, and more preferably from one to four carbon atoms. Likewise, "lower alkenyl" and "lower alkynyl" have similar chain lengths. Preferred alkyl groups are lower alkyls. In preferred embodiments, a substituent designated herein as alkyl is a lower alkyl.

The term "cycloalkyl" refers to saturated, carbocyclic groups having from 3 to 7 carbons in the ring. Preferred cycloalkyl groups include cyclopropyl, cyclobutyl, cyclopentyl and cyclohexyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" or "halo" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

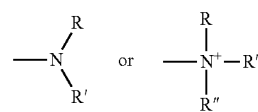

wherein R, R' and R" each independently represent a group permitted by the rules of valence, preferably H, alkyl, alkenyl, alkynyl, aralkyl, aryl, and heterocyclic groups.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term lower alkoxy refers to an alkoxy group having from 1 to 6 carbon atoms.

The term "oxo" as used herein refers to an oxygen atom that has a double bond to a carbon.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

As used herein, the definition of each expression, e.g. alkyl, m, n, R, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

In addition, if, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover.

The compounds of the invention may be prepared according to the following synthetic schemes:

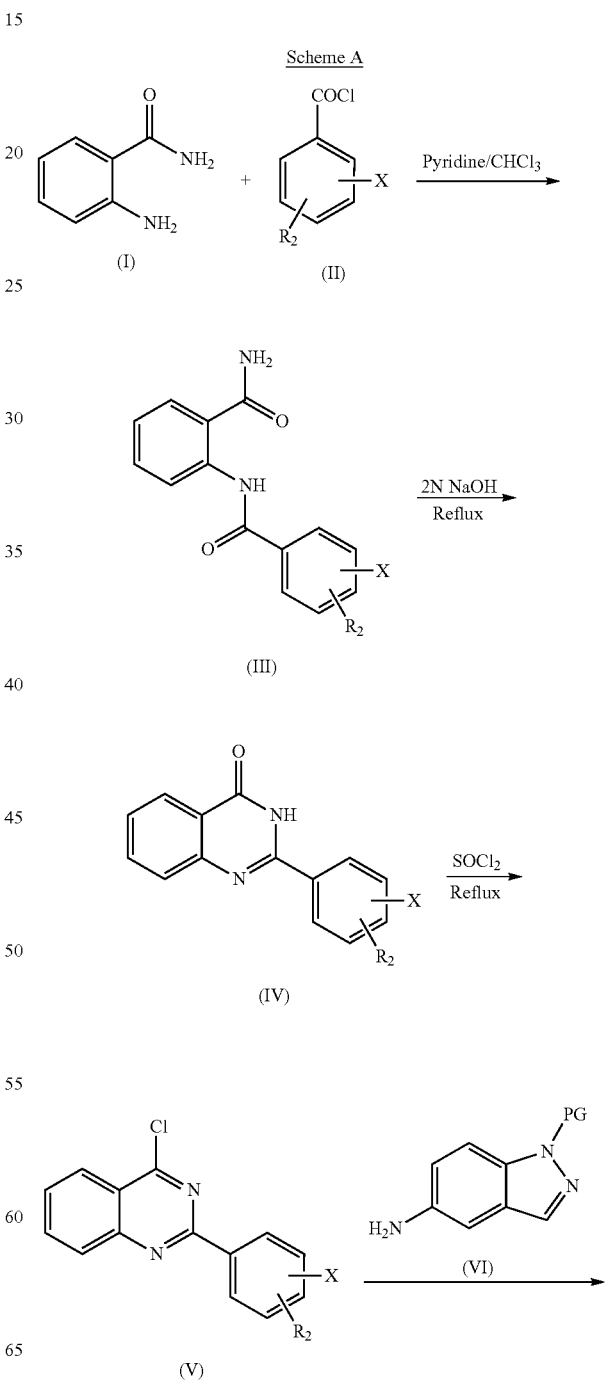

-continued

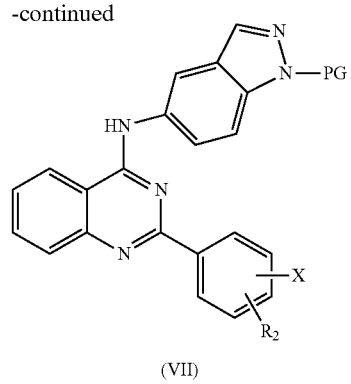

(VII)

-continued

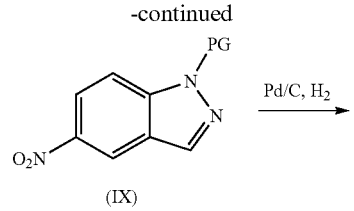

(IX)

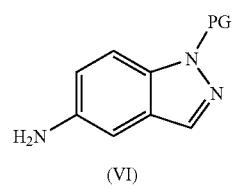

(VI)

The general intermediate of formula (VII) may be prepared as illustrated in Scheme A. As illustrated in Scheme A, anthralamide (2-aminobenzamide (I)) is coupled with an appropriately substituted acid chloride of formula (II) in the presence of a base such as pyridine to give the benzamide (III). The reaction is run in an aprotic solvent such as chloroform (CHCl$_3$) at a temperature of −20 to 50° C., preferably at room temperature for 1-24 hours, preferably for 6 hours. Alternatively the benzamide (III) may be formed by treatment of the anthralamide (2-aminobenzamide (I)) with the benzoic acid in the presence of a coupling agent. Suitable coupling agents include N-cyclohexyl-N'-(4-diethylaminocyclohexyl)-carbodiimide (DCC), 1-(3-dimethylaminopropyl)-3-ethylcarbodiimide (EDC) and bromotripyrrolidino phosphonium hexafluorophosphate (PyBroP®), benzotriazole1-1yl-oxy-tris-pyrrolidino phosphonium hexafluorophosphate (PyBOP®) with suitable additives if necessary which include 1-hydroxybenzotriazole (HOBt) and 3-hydroxy-4-oxo-3,4-dihydro-1,2,3-benzotriazine.

Cyclodehydration of compound (III) is carried out under refluxing basic aqueous conditions using sodium hydroxide (NaOH) as base, though other bases such as potassium hydroxide (KOH) may also be used. The reaction of compound (III) is carried out at the reflux temperature of the mixture for about 1-24 hours, preferably about 4 hours. When X=OMe (compound VII) it may be necessary to exchange phenol protecting groups. This can be achieved via methods known to those skilled in the art.

The compound (IV) is aromatized to the chloroquinazoline (V) by treatment with thionyl chloride (SOCl$_2$) with catalytic dimethylformamide (DMF). The reaction mixture is heated to reflux for 1-6 hours preferably 4 hours. Alternatively phosphorous oxy trichloride (POCl$_3$) or oxalyl chloride can be used instead of SOCl$_2$ to effect this transformation.

The chloroquinazoline is reacted with an appropriately protected 5-amino indazole (VI) to give the amino quinazoline (VII). The reaction is carried out in iso-propanol at 95° C. for a reaction time of 30 minutes to 2 hours.

Scheme B (VIII)

The protected indazole (VI) can be prepared as depicted in Scheme B. 5-Nitro-indazole is appropriately protected via methods known to those skilled in the art, preferably with a tert-butoxy carbonyl group. The nitro group is the reduced to the amino group via hydrogenation using a metal catalyst such as Pd/C in an inert solvent such as methanol (MeOH), 1,2 dimethoxethane (DME), ethanol (EtOH) or acetic acid (AcOH) or a combination of solvents preferably in a combination of MeOH and DME. The reaction can be carried out under balloon pressure or under a pressure of 20-50 pounds per square inch (p.s.i.).

Scheme C (VII), X = OH (XI)

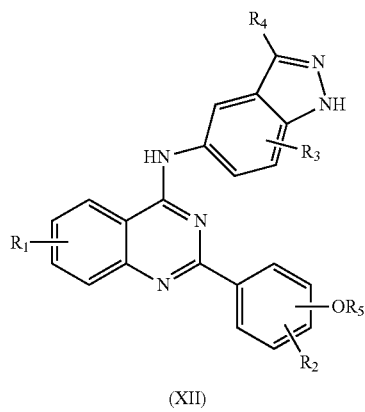

(XII)

X = OH

Compounds of formula (XII) can be synthesized as depicted in scheme C. Compound (VII) can undergo selective deprotection of the O-protecting group functionality to give compound (VII) where X=OH. This can be done by a variety of methods, which are well known to those skilled in the art. The phenol (VII) is then alkylated with an electrophile of formula (X) in the presence of a base such as potassium carbonate ($K_2CO_3$), potassium tert-butoxide ($KO^tBu$), sodium hydride (NaH), sodium hexamethylsilazide (NaHMDs) or potassium hexamethylsilazide (KHMDS) preferably $K_2CO_3$ to give the ether (XI). The reaction is run in an inert solvent such as DMF at a temperature of 20-100° C., preferably at 30-40° C. The electrophile (X) can be either a chloride (Y=Cl), bromide, (Y=Br), iodide (Y=I) or other suitable leaving group though it is preferred to use a bromide. Additives such as sodium iodide (NaI) or potassium iodide (KI) may be optionally added to the reaction.

Scheme D

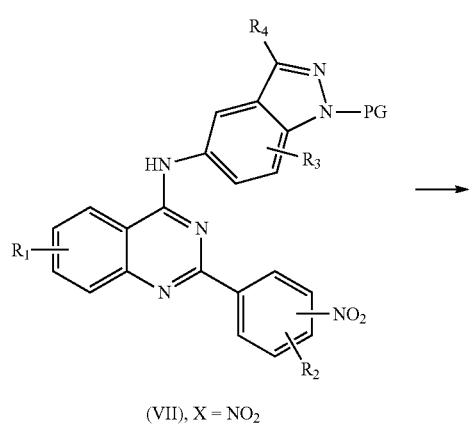

(VII), X = $NO_2$

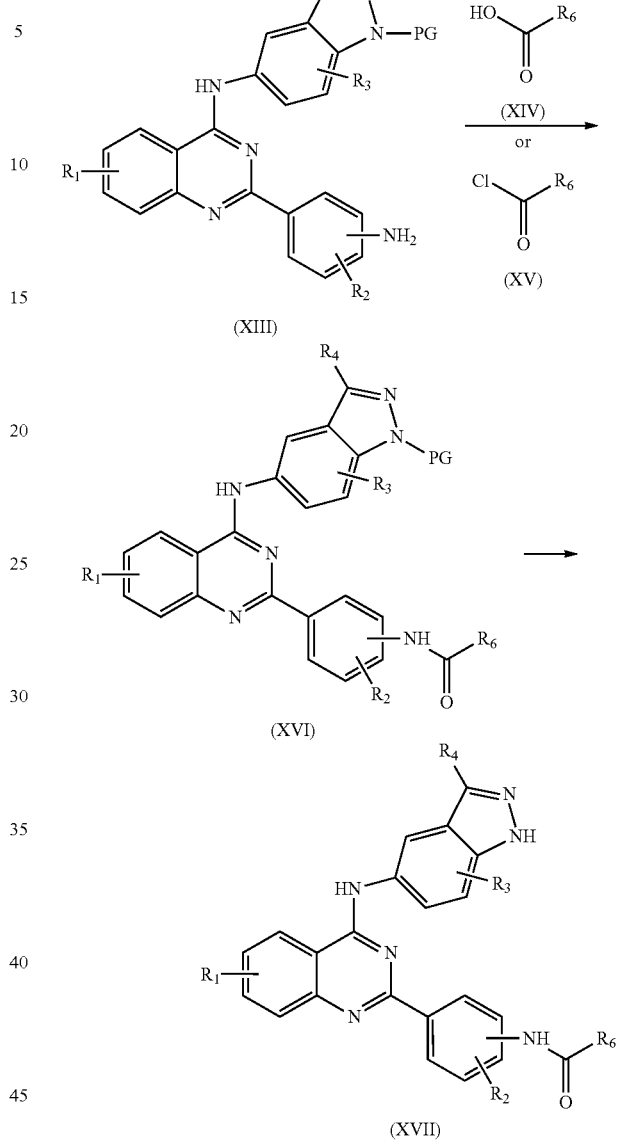

Compounds of formula (XVII) may be synthesized as depicted in Scheme D. A compound of formula (VII) where X=$NO_2$, may be reduced to the anilino compound (XIII) via catalytic hydrogenation in an inert solvent or mixture of solvents such as EtOH, MeOH, THF or DME preferably a mixture of MeOH and DME. The transformation is effected by use of a metal catalyst such as palladium on carbon (Pd/C). The compound of formula (XIII) can be treated with, preferably at room temperature, with a carboxylic acid of formula (XIV) in the presence of a coupling agent (e.g., PyBOP, PyBrOP, dicyclohexylcarbodiimide (DCC), 1-(3'-dimethylaminopropyl)-3-ethylcarbodiimide (EDC), or 1-propanephosphonic acid cyclic anhydride (PPAA)) and a suitable base (e.g., triethylamine, DMAP, or N-methylmorpholine (NMO)) in a solvent such as dichloromethane, chloroform, or dimethylformamide. Optionally, agents such as HOBt maybe added to the reaction. Alternatively the compound of formula (XVI) may be synthesized via treatment with an acid chloride of formula (XV) in the presence a tertiary amine base such as triethylamine or DMAP to give an amide of formula (XVI). The acid chlorides of formula (XV) are commercially available or can be prepared from carboxylic acids by procedures known to those skilled in the art. If necessary the indazole protecting group can be removed at this point to reveal the final compounds (XVII) via methods known to those skilled in the art.

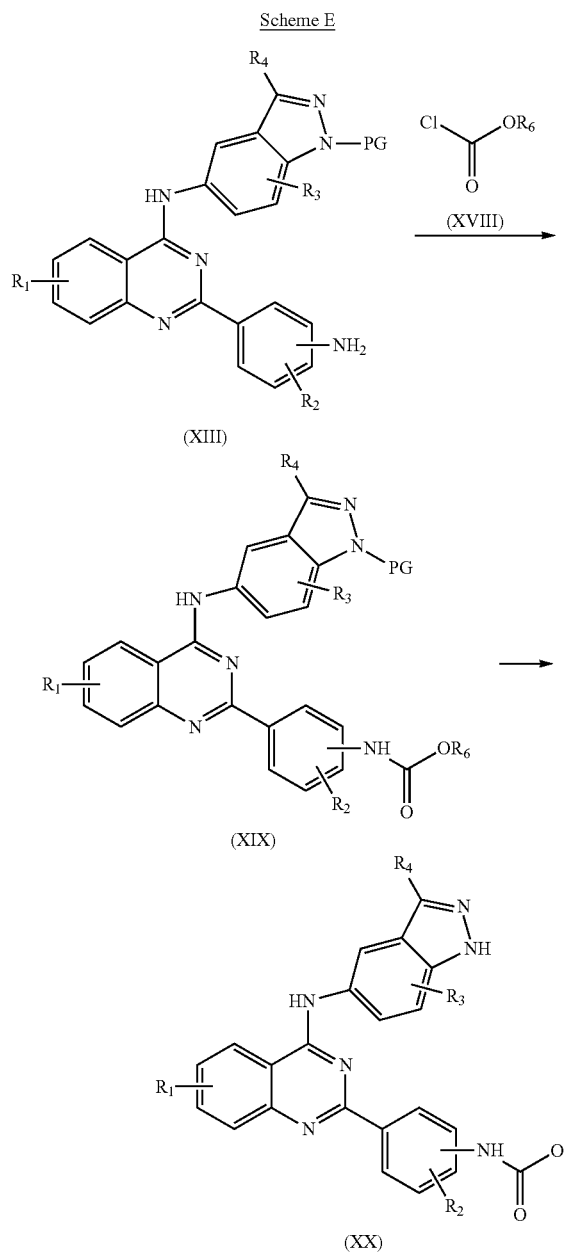

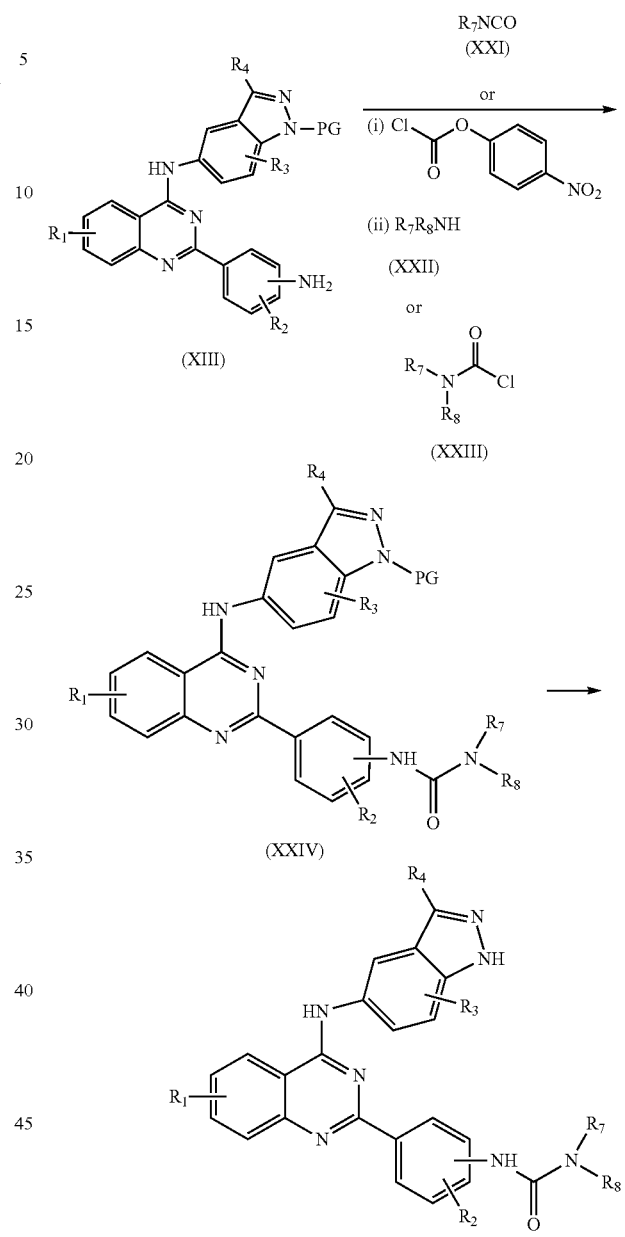

Compounds of formula (XX) can be prepared by reacting the amines of formula (XIII) with a chloroformate of formula (XVI) in the presence of a base such as triethylamine, DMAP, NMO, or sodium hydrogen carbonate in a suitable solvent such as dichloromethane, chloroform, aqueous or anhydrous tetrahydrofuran, or dimethylformamide or in a combination of such solvents. The reaction can be run at 0 to 60° C., though room temperature is preferred. If required the indazole protecting group may be removed to give compound of formula (XX) by methods known to those skilled in the art.

Ureas of formula (XXV) may be synthesized as depicted in Scheme F. Treatment of an aniline of formula (XIII) with an isocyanate of formula (XXI) in an inert solvent such as $CH_2Cl_2$ in the presence of an amine base such as $Et_3N$, DIEA or NMO to give the urea of formula (XXIV) where $R_8$ is a hydrogen. Alternatively, anilines of formula (XIII) may be treated with 4-nitrophenyl carbonochloridate followed by the sequential addition of an amine of formula (XXII). The reaction is run in an inert solvent such as THF, DMF or $CH_2Cl_2$ in the presence of an amine base such as $Et_3N$, DIEA or NMO. Another option of the synthesis of the ureas of formula (XXIV) is to treat the anilines of formula (XIII) with a carbamoyl chloride of formula (XXIII) in the presence of a base such as $Et_3N$, DIEA or NMO. If appropriate protecting groups (e.g. indazole) may be removed by methods known to those skilled in the art.

Scheme G

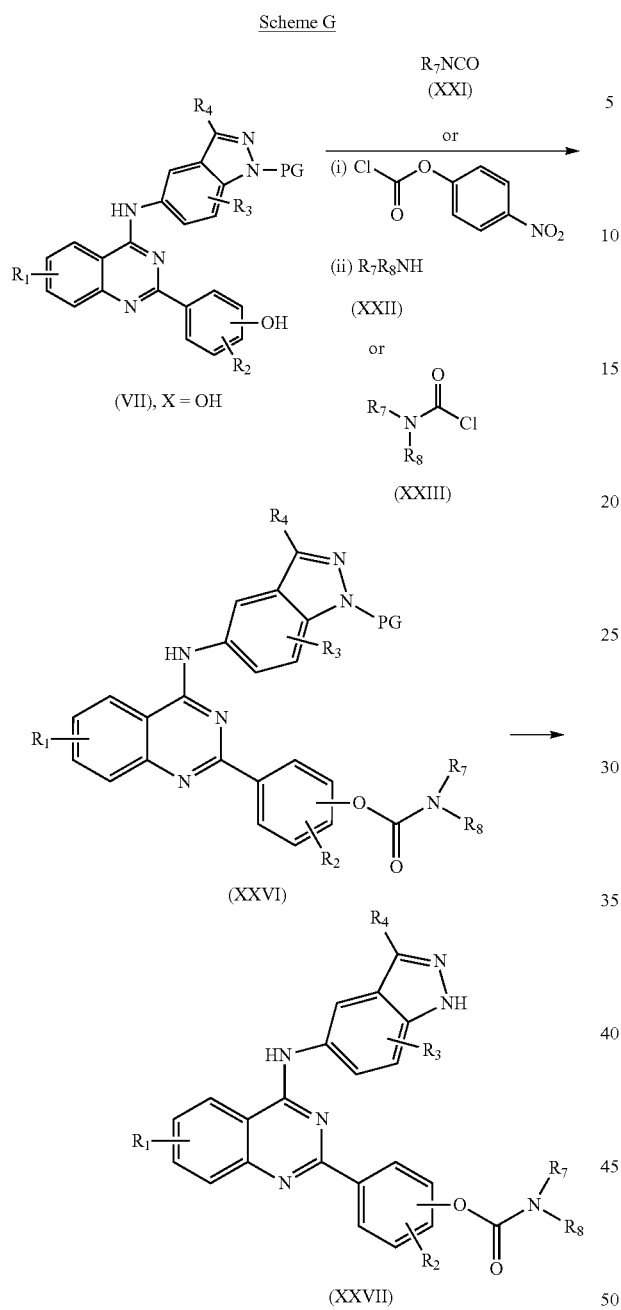

Scheme H

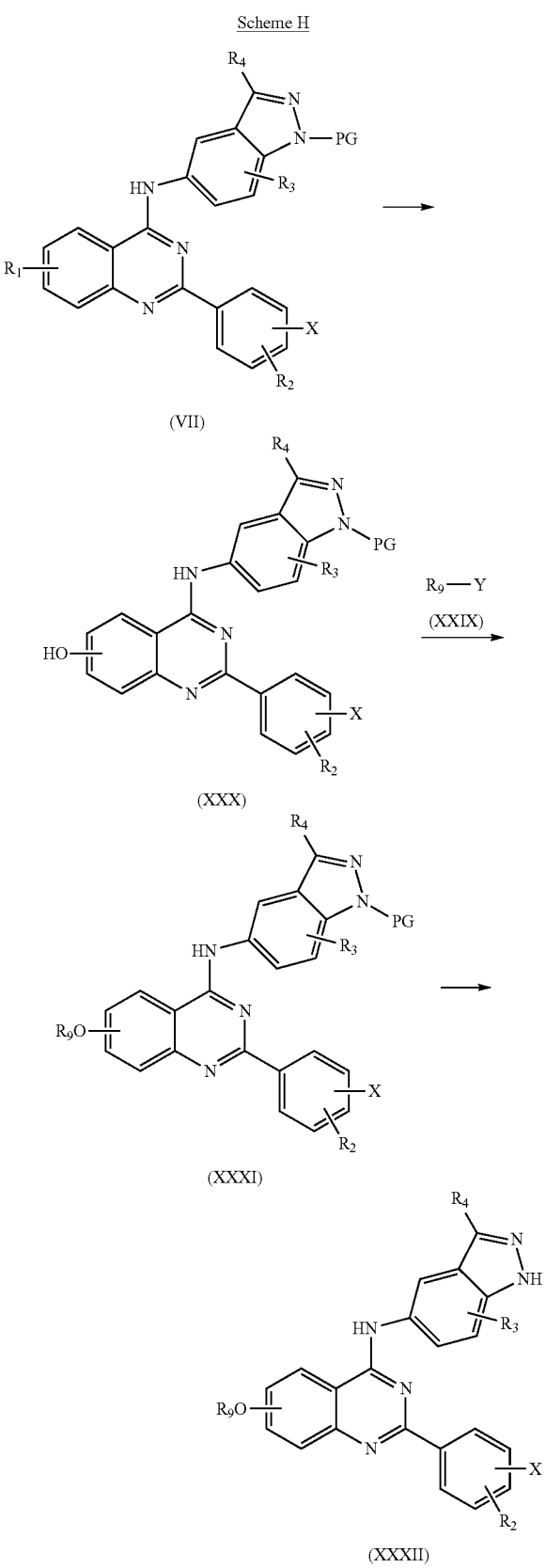

Carbamates of formula (XXVII) may be synthesized as depicted in Scheme G. Treatment of a phenol of formula (VII) where X=OH with an isocyanate of formula (XXII) in an inert solvent such as $CH_2Cl_2$ in the presence of an amine base such as $Et_3N$, DIEA or NMO. Alternatively, phenols of formula (VII) where X=OH) may be treated with 4-nitrophenyl carbonochloridate followed by the sequential addition of an amine of formula (XXII). The reaction is run in an inert solvent such as THF, DMF or $CH_2Cl_2$ in the presence of an amine base such as $Et_3N$, DIEA or NMO. Another option of the synthesis of the carbamates of formula (XXVI) is to treat the phenols of formula (VII) where X=OH) with a carbamoyl chloride of formula (XXIII) in the presence of a base such as $Et_3N$, DIEA or NMO. If appropriate protecting groups (e.g. indazole) may be removed by methods known to those skilled in the art to give the final compounds (XXVII).

Compounds of general formula (XXXIII) can be synthesized as depicted in Scheme H. Compound (VII) can undergo selective deprotection of the O-protecting group ($R_1$) functionality to give compound (XXX). This can be done by a variety of methods, which are well known to those skilled in the art. The phenol (XXX) is then alkylated with an electrophile of formula (XXIX) in the presence of a base such as potassium carbonate ($K_2CO_3$), potassium tert-butoxide ($KO^tBu$), sodium hydride (NaH), sodium hexamethylsilazide (NaHMDs) or potassium hexamethylsilazide (KHMDS) preferably $K_2CO_3$ to give the ether (XXXI). The reaction is run in an inert solvent such as DMF at a temperature of 20-100° C., preferably at 85° C. The electrophile (XXIX) can be either a chloride (Y=Cl), bromide, (Y=Br), iodide (Y=I) or other suitable leaving group though it is preferred to use a bromide. Additives such as sodium iodide (NaI) or potassium iodide (KI) may be optionally added to the reaction.

Deprotection of the indazole protecting group, which is well known by those skilled in the art, gives the desired compounds (XXXII).

Practitioners of the art will recognize that subsequent modification of $R_9$ may be necessary and can be performed as depicted in scheme I-J.

In Scheme I the chloro compounds of formula (XXXI) where $R_9$ is Z—Cl and Z is an appropriate linker is heated in the presence of an amine of formula (XXXIII) in a suitable solvent such as DMSO or DMF to give the amine containing compounds (XXXIV). Additives such as NaI or KI may be optionally added to the reaction. If appropriate protecting groups may be removed at this point by methods known to those skilled in the art.

Scheme I

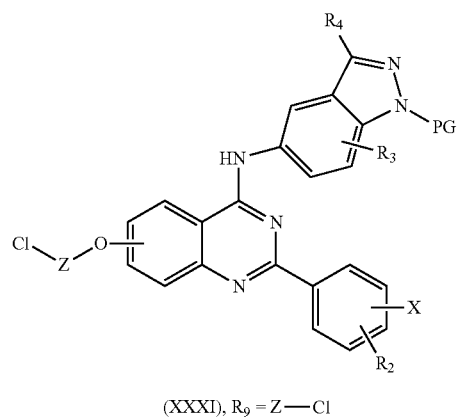

Scheme J

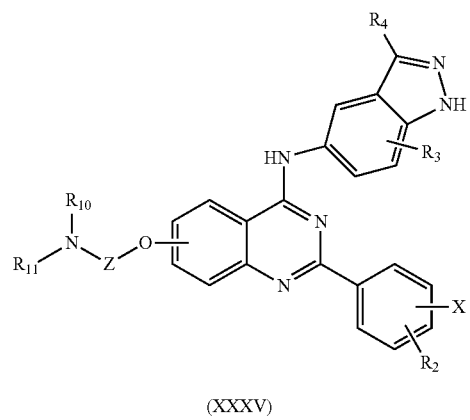

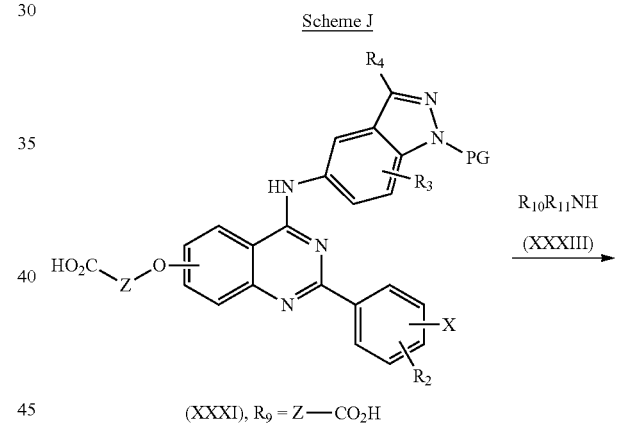

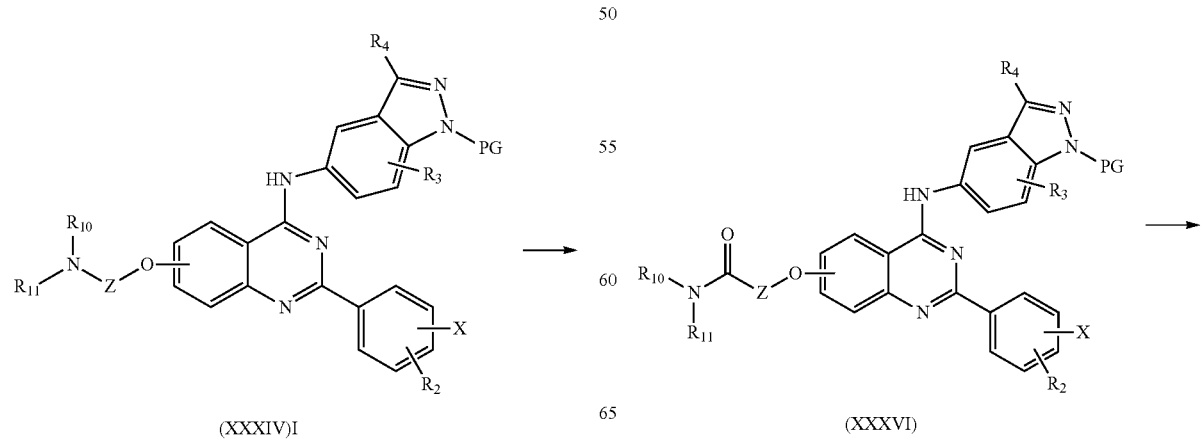

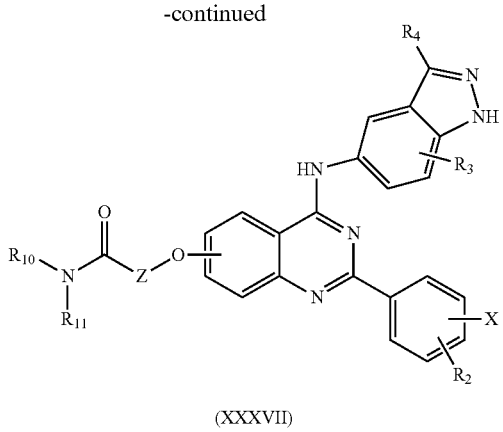

(XXXVII)

In scheme J the acid compounds of formula (XXXI) where $R_9$ is Z—$CO_2$H and Z is an appropriate linker is treated with an amine of formula (XXXIII) preferably at room temperature, in the presence of a coupling agent (e.g., PyBOP, PyBrOP®, dicyclohexylcarbodiimide (DCC), 1-(3'-dimethylaminopropyl)-3-ethylcarbodiimide (EDC), or 1-propanephosphonic acid cyclic anhydride (PPAA)) and a suitable base (e.g., triethylamine, DMAP, or N-methylmorpholine (NMO)) in a solvent such as dichloromethane, chloroform, or dimethylformamide to give the amides of formula (XXXVI). Optionally, agents such as HOBt maybe added to the reaction. If appropriate protecting groups may be removed at this point by methods known to those skilled in the art to give the product compounds of formula (XXXVII).

Practitioners of the art will also recognize that the order of certain steps in the above schemes (A-L) may be altered. Further, certain conditions such as solvent, temperature, etc. may be adjusted as would be recognized by the ordinarily skilled practitioner.

Reactive groups not involved in the above process steps can be protected with standard protecting groups during the reactions and removed by standard procedures (T. W. Greene & P. G. M. Wuts, Protecting Groups in Organic Synthesis, Third Edition, Wiley-Interscience) known to those of ordinary skill in the art. Presently preferred protecting groups include methyl, benzyl, acetate and tetrahydropyranyl for the hydroxyl moiety, and BOC, CBz, trifluoroacetamide and benzyl for the amino moiety, methyl, ethyl, tert-butyl and benzyl esters for the carboxylic acid moiety. The preferred protecting groups for the indazole moiety are BOC, CBz, trifluoroacetamide and benzyl.

The modification of protein binding is based on surface technology, i.e. the preparation and screening of surfaces for their ability to resist adsorption of proteins from solution. Surfaces which are resistant to adsorption of proteins from solution are known to one of skill in the art as "protein resistant" surfaces. Functional groups may be screened to identify the group(s) present in protein resistant surfaces, as described in e.g., Chapman et al. Surveying for Surfaces that Resist the Adsorption of Proteins, J. Am. Chem. Soc. 2000, 122:8303-8304; Ostuni et al. A Survey of Structure-Property Relationships of Surfaces that Resist the Adsorption of Protein, Langmuir 2001, 17:5605-5620; Holmlin, et al. Zwitterionic SAMs that Resist Nonspecific Adsorption of Protein from Aqueous Buffer, Langmuir 2001, 17:2841-2850; and Ostuni et al. Self-Assembled Monolayers that Resist the Adsorption of Proteins and the Adhesion of Bacterial and Mammalian Cells, Langmuir 2001, 17:6336-6343.

In general, protein binding is assessed by measuring the capacity of molecules of the invention to bind to one or more human serum components or mimics thereof. In one embodiment, suitable functional residues may be identified by screening of surfaces comprising such residues for their ability to resist adsorption of serum components, including, but not limited to serum proteins, and preferably human serum proteins. Candidate residues can be screened directly by attaching them to a solid support and testing the support for protein resistance. Alternatively, candidate residues are incorporated into, or linked to molecules of pharmaceutical interest. Such compounds may be synthesized on a solid support, or bound to a solid support after synthesis. In a non-limiting example of a direct binding assay, immobilized candidate functional residues or molecules incorporating such residues are tested for their ability to bind serum components. The serum components can be labeled with a signaling moiety for detection, or a labeled secondary reagent that binds to such serum components can be used.

Surfaces which are resistant to adsorption of proteins from solution are known as "protein resistant" surfaces. Functional groups may be screened to identify the group(s) present in protein resistant surfaces, as described in e.g., Chapman et al. Surveying for Surfaces that Resist the Adsorption of Proteins, J. Am. Chem. Soc. 2000, 122:8303-8304; Ostuni et al. A Survey of Structure-Property Relationships of Surfaces that Resist the Adsorption of Protein, Langmuir 2001, 17:5605-5620; Holmlin, et al. Zwitterionic SAMs that Resist Nonspecific Adsorption of Protein from Aqueous Buffer, Langmuir 2001, 17:2841-2850; and Ostuni et al. Self-Assembled Monolayers that Resist the Adsorption of Proteins and the Adhesion of Bacterial and Mammalian Cells, Langmuir 2001, 17:6336-6343.

Upon identification of a functional residue which provides such protein resistance, one of skill in the art will readily determine a suitable chemical skeleton or backbone of a known biologically or chemically active compound to which the functional residue may be attached by either substitution of functional group of the active compound or by replacement of a nonessential functional group of the active compound. For example, as discussed above, the presence of a piperazine group on a compound will indicate that such group may be either replaced or substituted with an functional residue. One of skill in the art, e.g. a medicinal chemist, will recognize other suitable groups on known active compounds which may be replaced or substituted with at least one functional residue. Accordingly, a combinatorial library of compounds, may be generated as described infra, wherein the compounds are modified compounds comprising a conjugate of an active site of the compound (an essential backbone of a compound having a particular desired activity), e.g. compound A and at least one functional residue attached thereto, wherein each conjugate has a different functional residue attached thereto, e.g. residues having formula C, wherein each R group is selected from the various groups described herein. Accordingly, a library may be used to screen a plurality of different functional residues for improved pharmacokinetic and/or pharmacodynamic properties including non-specific protein binding of the modified compound.

In preferred embodiments, the solid support itself is chosen or modified to minimize its interaction with the serum components. Examples of such supports and assay systems are described in International Application WO 02/48676, WO 03/12392, WO 03/18854, WO 03/54515, herein incorporated by reference. Alternatively, the molecules of the invention may be mixed with one or more serum components in liquid phase, and the amount of unbound molecules determined.

A direct binding analysis can also be preformed in liquid phase. For example, test compounds can be mixed with one or more serum components in liquid phase, and the unbound molecules determined.

In an example of a preferred embodiment, molecules having reduced protein binding are identified as follows: a self-assembled monolayer of thiol molecules terminated with anhydride groups is formed at a gold surface. A set of small molecules with amine groups at one end, and groups that are designed to resist binding to albumin, for example, at the other end are then attached to the surface via reaction between the amine and anhydride. The set of molecules are spotted onto spatially distinct regions on the gold surface to create an array of molecules that might resist protein binding. This array is then exposed to a solution containing albumin that is fluorescently labeled. After a suitable incubation period, the gold surface is washed and scanned on a fluorescent scanner. The immobilized chemical groups that bound to albumin will be identified by the presence of a fluorescent signal; groups that resist albumin binding will have low fluorescence in that part of the array. If a fluorescent protein is not available then antibodies against the protein of interest in combination with fluorescent secondary antibodies can be used to detect protein binding to the chemical groups. If an antibody is not available then a labeless detection method such as surface plasmon resonance (SPR) or MALDI mass spectrometry can be used to identify the presence of the protein at individual elements in the array. SPR also has the advantage of providing kinetic information on the binding of protein to the chemical groups.

The use of this system is not limited to albumin; any protein of pharmacokinetic interest can be tested for binding potential. For example, blood proteins that bind small molecules, such as $\alpha$-acid glycoprotein (AAG, AGP) and lipoproteins, could be exposed to the array and protein binding detected.

In an embodiment of the invention, chemical groups can be identified that resist binding to P-glycoprotein (PGP) and therefore have the potential to reduce efflux when appended to a small molecule therapeutic. This is particularly important for development of anti-cancer drugs provide effective treatment where multiple drug resistance (MDR) has developed.

The method could also be used to identify chemical groups that resist binding to proteins such as thrombin, anti-thrombin, and Factor Xa and therefore have the potential to control coagulation.

This method would also be useful for identifying groups that improve therapeutics that are designed as supplemental or replacement therapies where protein binding and PK properties are very important, e.g., hormones and their binding proteins, and steroids and their binding proteins such as testosterone and sex hormone binding globulin (SHBG).

The following describes a surface-based method for identifying groups that can improve the solubility of small molecules. A self-assembled monolayer of thiol molecules terminated with maleimide groups is formed at a gold surface. A set of small molecules with thiol groups at one end, and groups that are hydrophilic at the other end are then attached to the surface via reaction between the thiol and maleimide. The set of molecules are spotted onto spatially distinct regions on the gold surface to create an array of molecules that might increase the solubility of a small molecule. Droplets of both polar (e.g., water) and hydrophobic (e.g., octanol) liquids are then placed onto each element of the array. The contact angles of the two liquids on each element are then measured at each element of the array using a goniometer. Alternatively, the wettability of a particular liquid at a surface presenting a chemical group can be determined by measuring the area of the surface covered by a droplet when viewed from above (high contact angle will yield droplets of small area; low contact angles cover greater areas). The contact angle of a liquid on a surface presenting a chemical group is inversely proportional to the miscibility of that chemical group with that liquid (solvent). For example, a chemical group for which water has a high contact angle when it is presented at the surface, such as methyl ($CH_3$), has low miscibility with water, i.e., it will tend to reduce the solubility of a small molecule. Conversely, a chemical group for which water has a low contact angle when it is presented at the surface, such as carboxyl (COOH), has high miscibility with water, i.e., it will tend to increase the solubility of a small molecule. Sets of chemical groups can therefore be screened rapidly using contact angles on surfaces to identify groups that improve solubility or reduce hydrophilicity. This approach can be used to evaluate the effect on solubility of chemical groups used according to the invention.

A common parameter for the ability of a small molecule to cross the lipid membrane of a cell is logP where P is the partition coefficient of the compound between octanol and water. The relative contact angle of a surface presenting chemical groups for octanol and water therefore offers a rapid, empirical method for ranking large sets of chemical groups for their potential effect on the logP of a compound.

The pH dependence of the solubility of small molecules can be addressed in this method by measuring the contact angles of solutions at different pHs. The parameter equivalent to logP in this case is logD, where D is the distribution coefficient, defined as the ratio of the sum of the concentrations of all species of the compound in octanol to the sum of the concentrations of all species of the compound in water at various pHs. Contact angles measured at different pHs therefore offer the possibility of an equivalent measure to logD.

It will also be useful to screen candidate compounds for their capacity to be actively transported across cell membranes and cells, or for their resistance to such transport. For example, it is well known that pharmaceutically useful anti-cancer molecules may be limited in their effectiveness due to active transport out of target tumor cells. Similarly, monolayers of brain capillary endothelial cells have been observed to unidirectionally transport vincristine from basal side to apical side, effectively preventing the anti-cancer agent from entering the central nervous system. In some instances, chemical groups of value will, in addition to reducing non-specific protein binding, improve pharmcokinetics by enhancing passive or active transport towards their site of action, and/or inhibiting transport from the site of action.

The brain is one of the most difficult tissues for small molecules to penetrate. The neurovascular junctions are tight and contain very few active transporters that are mostly responsible for clearing small molecules out of the brain. The paracellular route (between cell junctions) is not available to small molecules, but only the transcellular route is (through cell membranes). Classically, molecules to target the brain, such as benzodiazepines, are hydrophobic to allow them to penetrate cell membranes. The instant invention is compatible with the search for chemical groups that confer protein resistant and alleviate the common problem of excessive protein binding associated with molecules such as the benzodiazepines; this requires high dosing to account for the large percentage of binding to serum proteins. The approaches described earlier for the identification of binders of PGP will be of help to optimize molecules for improved residence time in the brain.

Several model systems are available, employing monolayers of various cell types, for evaluation of active transport of pharmaceutically active substances. For example, monolayers of Caco-2 intestinal epithelial cells can be used to evaluate active transport of substances between the intestine and the bloodstream. When plated on a surface which allows the flow of material from apical to basolateral and vice versa, such cells form a biological membrane which can be used to simulate physiological absorption and bio-availability. In another example, mouse brain capillary endothelial cell (MBEC) lines have been established to evaluate active transport in and out of the central nervous system. Another example of such cells is HT29 human colon carcinoma cells. Further, monolayers expressing particular transporter proteins can be established using transfected cells. For example, Sasaki et al (2002) J. Biol. Chem. 8:6497 used a double-transfected Madin-Darby canine kidney cell monolayer to study transport of organic anions.

Alternatives to cell monolayers may of course be utilized to examine permeability. Alternatives typically comprise a biological structure capable of active transport and include, but are not limited to, organs of the digestive tract obtained from lab animals and reconstituted organs or membranes created in vitro from cells seeded in an artificial matrix.

In another aspect, the present invention provides a compound of the general formula I, wherein the compound is an inhibitor of Rho-kinase. Rho kinase (ROCK), a serine/threonine kinase, serves as a target protein for small GTP-binding protein Rho. It serves as an important mediator of numerous cellular functions, including focal adhesions, motility, smooth muscle contraction, and cytokinesis. In smooth muscle, ROCK plays an important role in $Ca^{2+}$ sensitization and the control of vascular tone. It modulates the level of phosphorylation of the myosin II light chain of myosin II, mainly through inhibition of myosin phosphatase, and contributes to agonist-induced $Ca^{2+}$ sensitization in smooth muscle contraction.

Rho kinase is found in two forms, ROCK 1 (ROCKβ; p160-ROCK) and ROCK 2 (ROCKα). Since for example a ROCK-mediated pathway plays an important role in vascular smooth muscle contraction, cell adhesion, and cell motility, it has gained importance in the pathogenesis of atherosclerosis. ROCK inhibitors are shown to suppress coronary artery spasms. A long-term inhibition of ROCK is reported to block the development of coronary arteriosclerotic lesions.

ROCK mediated pathways mediate numerous different cellular functions and ROCK inhibitors can be useful in treatments of patients in need thereof suffering from cardiovascular diseases such as hypertension, atherosclerosis, restenosis, cardiac hypertrophy, ocular hypertension, cerebral ischemia, cerebral vasospasm, penile erectile dysfunction, central nervous system disorders such as neuronal degeneration and spinal cord injury, and in neoplasias where inhibition of Rho-kinase has been shown to inhibit tumor cell growth and metastasis, angiogenesis, arterial thrombotic disorders such as platelet aggregation and leukocyte aggregation, asthma, regulation of intraoccular pressure, and bone resorption. Such treatment often relies on administering a therapeutic agent to a patient, wherein the therapeutic agent has a high specificity for a particular pathway or enzyme which is in need of regulation in the patient, by the therapeutic agent such as an enzyme inhibitor. In one aspect of the present invention there is provided, a compound which is an inhibitor of a Rho kinase (ROCK), preferably the compound of the present invention is an inhibitor of ROCK2.

Methods of determining kinase inhibition are well known in the art. For example, kinase activity of an enzyme and the inhibitory capacity of a test compound can be determined by measuring enzyme specific phosphorylation of a substrate. Commercial assays and kits can be employed. For example, kinase inhibition can be determined using an IMAP® assay (Molecular Devices). This assay method involves the use of a fluorescently-tagged peptide substrate. Phosphorylation of the tagged peptide by a kinase of interest promotes binding of the peptide to a trivalent metal-based nanoparticle via the specific, high affinity interaction between the phospho-group and the trivalent metal. Proximity to the nanoparticle results in increased fluorescence polarization. Inhibition of the kinase by a kinase inhibitor prevents phosphorylation of the substrate and thereby limits binding of the fluorescently-tagged substrate to the nanoparticle. Such an assay can be compatible with a microwell assay format, allowing simultaneous determination of $IC_{50}$ of multiple compounds.

In another aspect of the present invention there is provided a method of treating a patient suffering from a disease comprising administering to a patient in need of such treatment a therapeutically effective amount of a compound of the present invention, wherein the disease is cardiovascular diseases such as hypertension, atherosclerosis, restenosis, cardiac hypertrophy, ocular hypertension, cerebral ischemia, cerebral vasospasm, penile erectile dysfunction, central nervous system disorders such as neuronal degeneration and spinal cord injury, and in neoplasias where inhibition of Rho-kinase has been shown to inhibit tumor cell growth and metastasis, angiogenesis, arterial thrombotic disorders such as platelet aggregation and leukocyte aggregation, asthma, regulation of intraoccular pressure, and bone resorption.

In another aspect, the present invention provides pharmaceutically acceptable compositions which comprise a therapeutically-effective amount of one or more of the compounds of the present invention, including but not limited to the compounds described above and those shown in the Figures, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" 0 and B books, Corvallis, Ore., U.S.A., 1977).

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). The polymers used in the present invention have a significantly smaller molecular weight, approximately 100 daltons, compared to the large MW of 5000 daltons or greater that used in standard pegylation techniques. Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

EXAMPLES

The invention now being generally described, it will be more readily understood by reference to the following examples, which are included merely for purposes of illustration of certain aspects and embodiments of the present invention, and are not intended to limit the invention.

Abbreviations used in the following examples and preparations include:

Ac$_2$O Acetic anhydride
AcOH Acetic acid
Bn Benzyl
Celite® Diatomaceous earth
1,2 DCE 1,2-Dichloroethane
d Doublet
dd Double Doublet
DIEA Di-isopropylethyl amine
DMAP 4-Dimethylamino Pyridine
DME 1,2 Dimethoxyethane
DMF Dimethylformamide
DMSO Dimethyl sulfoxide
EDC 1-(3-Dimethylaminopropyl)-3-ethylcarbodiimide Hydrochloride
EtOAc Ethyl Acetate
EtOH Ethyl Alcohol or Ethanol
Et$_2$O Ethyl Ether
Et$_3$N Triethylamine
g grams
HOBt 1-Hydroxybenzotriazole
HPLC High Pressure Liquid Chromatography
h Hour(s)
hr Hour(s)
m Multiplet
mins. Minutes
MeOH Methyl Alcohol or Methanol
min Minute(s)
mmol millimoles
mmole millimoles
MS Mass Spectrometry
NMR Nuclear Magnetic Resonance
o/n overnight
$^i$PrOH Iso-propanol
PPAA 1-Propanephosphonic Acid Cyclic Anhydride
PyBOP® Benzotriazol-1-yl-oxytripyrrolidinophosphonium hexafluorophosphate
q Quartet
RT (or rt) room temperature (about 20-25° C.)
s Singlet
sat. Saturated
t Triplet
TBAF Tetra-Butyl Ammonium Fluoride
TFA Trifluoroacetic Acid
THF Tetrahydrofuran
v/v volume/volume
wt/v weight/volume Mass spectrometry was conducted by: SynPep Co., 6905 Sierra Ct. Dublin, Calif. 94568, or it was recorded on an LC-MS: Waters 2695 Separations Module with a Waters ZQ 2000 single quadrapole MS detector. Unless stated all mass spectrometry was run in ESI mode.

$^1$H NMR spectra were recorded on a Varian 400 MHz machine using Mercury software.

Analytical HPLC was run on an Agilent 1100 Series machine using an YMC ProC18 column (4.6×50 mm, 5 μm particle size). Unless stated the method used was 5-95-10 which refers to a gradient of 5% of buffer A increased to 95% over 10 minutes with Buffer B. Buffer A is 0.1% TFA/H$_2$0 and Buffer B is 0.0085% TFA/MeCN.

Preparative HPLC was performed on Waters Delta machine (600 and 515 Pumps) using an YMC—Pack ProC18 (150×20 mm I.D.) column using a combination of Buffer A (0.1% TFA/H$_2$0) and Buffer B (0.0085% TFA/MeCN) as the mobile phase.

In sofar the synthesis of the following examples of compounds of the present invention is not explicitly described in such example, the synthesis is as described herein in general

Example 1

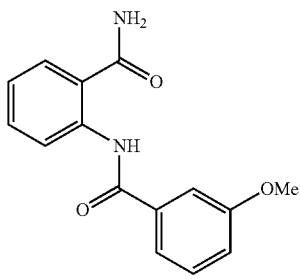 [SMILES: COc1cccc(C(=O)Nc2ccccc2C(N)=O)c1]

To a solution of anthranilamide (7.0 g, 51.41 mmole) in CHCl₃ (260 mL) was added pyridine (8.13 g, 102.8 mmole, 8.28 mL) followed by slow addition of m-anisoyl chloride (9.20 g, 53.94 mmole, 7.35 mL). The reaction mixture was stirred at ambient temperature for 6 h and then concentrated in vacuo and subsequently dried under high vacuum for 4 h to give the product. (13.89 g, mmol, 100%)

Example 2

2-(3-Methoxyphenyl)quinazolin-4(3H)-one

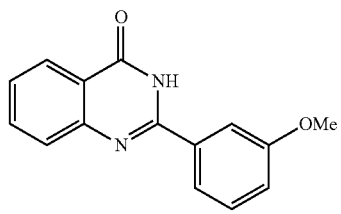 [SMILES: COc1cccc(-c2nc3ccccc3c(=O)[nH]2)c1]

A solution of 2 N NaOH (250 mL) was added to the amide from example 1 (13.89 g, 51.41 mmole) and the reaction mixture was refluxed for 4 h. The reaction was cooled to ambient temperature and then adjusted to pH=7 with 1 N HCl. The resulting solid was stirred at ambient temperature for 2 h and then filtered. The filtered solid was washed with water, ether and dried under high vacuum overnight. The crude product was also azeotroped from MeOH (1×) and toluene (2×) and dried under high vacuum for several hours to give 2-(3-methoxyphenyl)quinazolin-4(3H)-one. (15.5 g, mmol, %)

Example 3

2-(3-Hydroxyphenyl)quinazolin-4(3H)-one

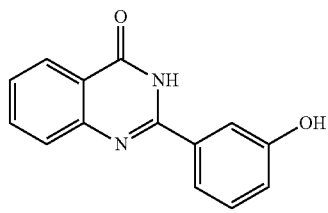 [SMILES: O=c1[nH]c(-c2cccc(O)c2)nc2ccccc12]

To 2-(3-methoxyphenyl)quinazolin-4(3H)-one (11.6 g, 45.98 mmole) was added of CH₂Cl₂ (120 mL) and the mixture was cooled to −78° C. Then, a 1 M solution of BBr₃ in CH₂Cl₂ (60 mL, 60.0 mmol) was added drop wise and the reaction was stirred at −78° C. for 1 h and then ambient temperature for 3 h. The reaction was re-cooled to −78° C. and cautiously quenched with MeOH (20 mL). The ice bath was removed and the system allowed to stir at ambient temperature for 0.5 h. The pH was adjusted to 7 with 10% w/w NaHCO₃ solution. The solid was filtered, washed with ether, dried and then azeotroped from toluene (3×) and dried under high vacuum overnight to give 2-(3-hydroxyphenyl)quinazolin-4(3H)-one. (11.0 g, mmol, 100%).

Example 4

3-(4-Oxo-3,4-dihydroquinazolin-2-yl)phenyl acetate

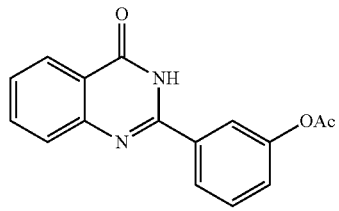 [SMILES: CC(=O)Oc1cccc(-c2nc3ccccc3c(=O)[nH]2)c1]

To 2-(3-hydroxyphenyl)quinazolin-4(3H)-one (11.0 g, 45.98 mmole) was added pyridine (16.06 mL, 15.71 g, 0.199 mmole) followed by addition of acetic anhydride (145 mL) and the reaction mixture was heated to 105° C. and stirred for 3.5 h. The reaction mixture was cooled to ambient temperature and then poured onto ice-water (800 mL) and stirred for 2 h. The solid was then filtered and washed with water, ethanol, ether and finally hexane and dried for several hours under high vacuum to give 3-(4-oxo-3,4-dihydroquinazolin-2-yl)phenyl acetate. (8.4 g, mmol, 65%).

Example 5

3-(4-Chloroquinazolin-2-yl)phenyl acetate

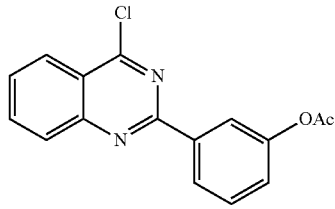 [SMILES: CC(=O)Oc1cccc(-c2nc(Cl)c3ccccc3n2)c1]

To 3-(4-oxo-3,4-dihydroquinazolin-2-yl)phenyl acetate was added thionyl chloride (100 mL) and DMF (2 mL) and the reaction was heated to reflux for 4 h. The flask was allowed to cool to RT and then concentrated in vacuo. The crude product was azeotroped with toluene (2×50 mL), taken up in $CH_2Cl_2$ (300 mL) and washed with saturated $NaHCO_3$ (3×50 mL), water (1×50 mL) and brine (1×50 mL), dried with $MgSO_4$ and concentrated in vacuo to give 3-(4-chloroquinazolin-2-yl)phenyl acetate. (9.77 g, mmol, 100%).

Example 6 tert-Butyl 5-(2-(3-acetoxyphenyl)quinazolin-4-ylamino)-1H-indazole-1-carboxylate

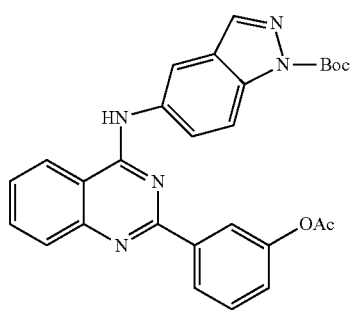 [SMILES: CC(=O)Oc1cccc(-c2nc(Nc3ccc4c(cnn4C(=O)OC(C)(C)C)c3)c3ccccc3n2)c1]

3-(4-Chloroquinazolin-2-yl)phenyl acetate (9.77 g, 29.97 mmole) was dissolved in isopropanol (290 mL) and tert-butyl 5-amino-1H-indazole-1-carboxylate (6.99 g, 29.97 mmole) was added. The solution was heated to 95° C. and stirred for 0.25 h. A gelatinous formation developed which was manually broken up and dissolution gradually occurred followed by formation of a yellow precipitate. The reaction was stirred for an additional 0.25 h, cooled to ambient temperature and filtered. The filtered solid was washed with ether and then dried under high vacuum overnight to give tert-butyl 5-(2-(3-acetoxyphenyl)quinazolin-4-ylamino)-1H-indazole-1-carboxylate. (14.58 g, mmol, 98%)

Example 7 tert-Butyl 5-(2-(3-hydroxyphenyl)quinazolin-4-ylamino)-1H-indazole-1-carboxylate

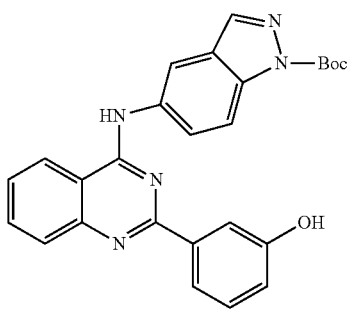 [SMILES: CC(C)(C)OC(=O)n1ncc2cc(Nc3nc(-c4cccc(O)c4)nc4ccccc34)ccc21]

To a solution of give tert-butyl 5-(2-(3-acetoxyphenyl)quinazolin-4-ylamino)-1H-indazole-1-carboxylate (5.85 g, 11.8 mmole) in anhydrous MeOH (400 mL) was added 28% (wt/v) $NH_4OH$ solution (6.50 mL). The reaction mixture was stirred at ambient temperature for 48 h. The crude product was filtered and washed with ether followed by hexane and dried under high vacuum overnight to give tert-butyl 5-(2-(3-hydroxyphenyl)-quinazolin-4-ylamino)-1H-indazole-1-carboxylate. (4.85 g, mmol, 91%).

Example 8

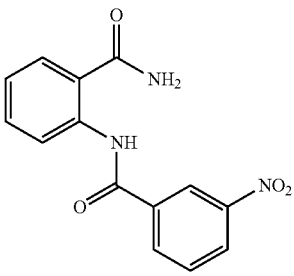 [SMILES: NC(=O)c1ccccc1NC(=O)c1cccc([N+](=O)[O-])c1]

To a suspension of anthranilamide (24.0 g, 176.28 mmole) and 3-nitro benzoyl chloride (34.5 g, 186.3 mmole) $CHCl_3$ (700 ml) was added pyridine (30 ml) drop wise at RT. The reaction mixture was stirred at ambient temperature for 8 h.

The solvent was removed in vacuo and residue dried under high vacuum to give the product. (73 g, mmol, %)

Example 9

2-(3-Nitrophenyl)quinazolin-4(3H)-one

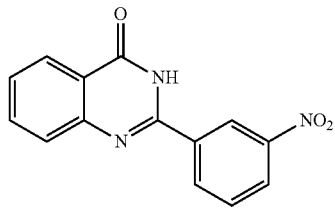 [SMILES: O=c1[nH]c(-c2cccc([N+](=O)[O-])c2)nc2ccccc12]

A suspension of amide from example 8 (estimated 176.3 mmole) was taken up in 2 N NaOH (800 mL) and was refluxed for 7 h. The reaction mixture was cooled to ambient temperature and then pH adjusted to 7 with 3 N HCl. The suspension was stirred at RT for 2 h, filtered, and the filtered solid washed with water and dried under high vacuum to give 2-(3-nitrophenyl)quinazolin-4(3H)-one. (45 g, mmol, 96% from anthranilamide).

Example 10

4-Chloro-2-(3-nitrophenyl)quinazoline

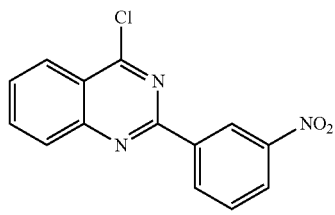 [SMILES: O=[N+]([O-])c1cccc(-c2nc(Cl)c3ccccc3n2)c1]

To a suspension of 2-(3-nitrophenyl)quinazolin-4(3H)-one (5.7 g, 21.32 mmole) in thionyl chloride (70 mL) was added of DMF (2 mL). The reaction mixture was refluxed for 4.5 h. The reaction was then concentrated in vacuo and residue suspended in a mixture of CH$_2$Cl$_2$ (400 mL) and CHCl$_3$ (500 mL). The organic layer was washed with water, saturated NaHCO$_3$, water, brine, dried with Na$_2$SO$_4$ and concentrated in vacuo. The residue was dried under high vacuum to afford 4-chloro-2-(3-nitrophenyl)quinazoline as an off-white solid. (6.0 g, mmol, 97%).

Example 11 tert-Butyl 5-(2-(3-nitrophenyl)quinazolin-4-ylamino)-1H-indazole-1-carboxylate

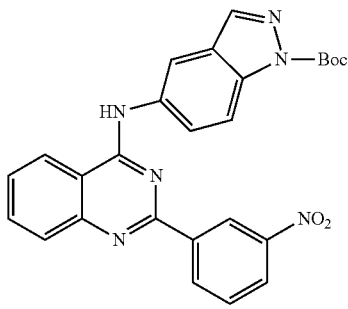 [SMILES: CC(C)(C)OC(=O)n1ncc2cc(Nc3nc(-c4cccc(N)c4)nc4ccccc34)ccc21]

A suspension of 4-chloro-2-(3-nitrophenyl)quinazoline (6.3 g, 21.9 mmole), tert-butyl 5-amino-1H-indazole-1-carboxylate (5.10 g, 21.9 mmole) in isopropanol (300 mL) was heated at 95° C. for 1.5 h. The suspension was filtered and the filtered solid was washed with isopropanol. The product was dried under high vacuum for several hours to give the desired product tert-butyl 5-(2-(3-nitrophenyl)quinazolin-4-ylamino)-1H-indazole-1-carboxylate. (8.3 g, mmol, 79%).

Example 12

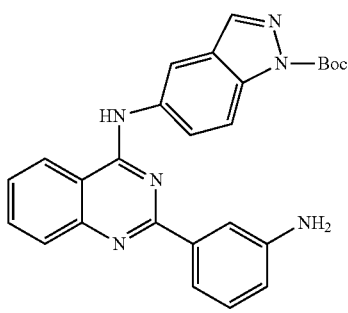

A suspension of product tert-butyl 5-(2-(3-nitrophenyl) quinazolin-4-ylamino)-1H-indazole-1-carboxylate (9.0 g, 18.65 mmole) in a mixture of DME/MeOH (300 mL/100 mL) was hydrogenated in the presence of 10% Pd/C (1.25 g) at RT using a balloon filled with hydrogen gas. The reaction was stirred for 16 h and the reaction mixture filtered through Celite™. The pad of Celite™ was washed with a 1:1 mixture of MeOH/CH$_2$Cl$_2$ (200 mL). The filtrate was then concentrated in vacuo and dried under high vacuum overnight to give tert-butyl 5-(2-(3-aminophenyl)quinazolin-4-ylamino)-1H-indazole-1-carboxylate. (8.8 g, mmol, %).

Example 13 tert-butyl 5-(2-(3-(2-(tert-butoxycarbonyl)acetamido)phenyl)quinazolin-4-ylamino)-1H-indazole-1-carboxylate

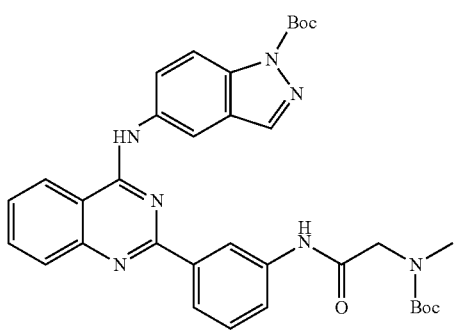 [SMILES: CN(CC(=O)Nc1cccc(-c2nc(Nc3ccc4c(cnn4C(=O)OC(C)(C)C)c3)c3ccccc3n2)c1)C(=O)OC(C)(C)C]

A suspension of 2-(tert-butoxycarbonyl)acetic acid (21 mg, 0.11 mmol), PyBOP® (57 mg, 0.11 mmol), DIEA (38 µL, 0.22 mmol) in anhydrous CH₂Cl₂ (0.5 mL) was stirred at RT for 10 minutes. This solution of activated acid was added to a suspension of tert-butyl 5-(2-(3-aminophenyl)quinazolin-4-ylamino)-1H-indazole-1-carboxylate (100 mg, 0.22 mmol) and anhydrous CH₂Cl₂ (1 mL). The reaction mixture was stirred at RT for 1 h. Activated and added another 0.5 equivalent of the acid as described above and stirred for 1 h. Activated and added another 0.3 equivalents of the acid as described above. Stirred for and additional hour and diluted with CH₂Cl₂. Extracted with H₂O (3×) and the organic layer was dried under Na₂SO₄ and concentrated in vacuo. The residue was purified by flash chromatography on silica (1:1 EtOAc:Hexanes) to give the desired product tert-butyl 5-(2-(3-(2-(tert-butoxycarbonyl)acetamido)phenyl)quinazolin-4-ylamino)-1H-indazole-1-carboxylate. (123 mg, 0.20 mmol, 90%).

Example 14

N-(3-(4-(1H-indazol-5-ylamino)quinazolin-2-yl)phenyl)-2-(methylamino)acetamide

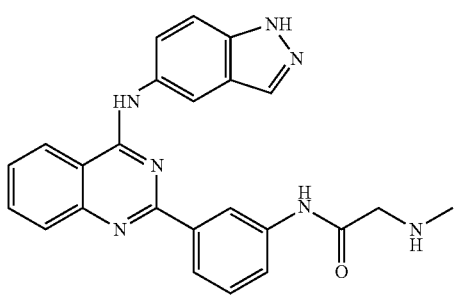 [SMILES: CNCC(=O)Nc1cccc(-c2nc(Nc3ccc4[nH]ncc4c3)c3ccccc3n2)c1]

To tert-butyl 5-(2-(3-(2-(tert-butoxycarbonyl)acetamido)phenyl)quinazolin-4-ylamino)-1H-indazole-1-carboxylate (123 mg, 0.20 mmol) was added a solution of 1:1 TFA:CH₂Cl₂ (4 mL) and stirred at RT for 2 h. The reaction mixture was concentrated in vacuo and the residue was triturated with ethyl ether to afford 2-methoxyacetyl chloride N-(3-(4-(1H-indazol-5-ylamino)quinazolin-2-yl)phenyl)-2-(dimethylamino)acetamide. (95 mg, 0.22 mmol, 100%)

Example 15 tert-butyl 5-(2-(3-(3-(2-(dimethylamino)ethyl)ureido)phenyl)quinazolin-4-ylamino)-1H-indazole-1-carboxylate

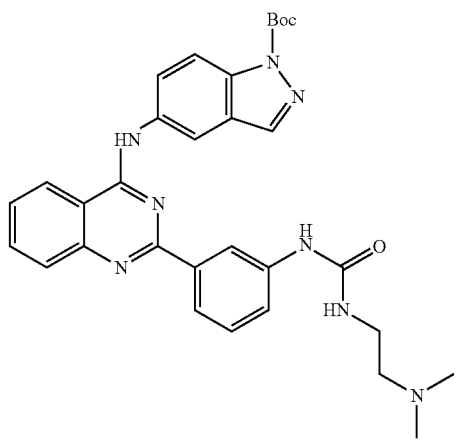 [SMILES: CN(C)CCNC(=O)Nc1cccc(-c2nc(Nc3ccc4c(cnn4C(=O)OC(C)(C)C)c3)c3ccccc3n2)c1]

To a solution of tert-butyl 5-(2-(3-aminophenyl)quinazolin-4-ylamino)-1H-indazole-1-carboxylate (100 mg, 0.22 mmol) in anhydrous CH₂Cl₂ (2 mL) added Et₃N (45 mg, 0.44 mmol) and 4-nitrophenyl carbonochloridate (47 mg 0.23 mmol). The solution was stirred at RT for 2 h. To the reaction mixture added N,N-dimethylethane-1,2-diamine (36 µL, 0.33 mmol) and stirred for 16 h. Concentrated in vacuo to afford the crude tert-butyl 5-(2-(3-(3-(2-(dimethylamino)ethyl)ureido)phenyl)quinazolin-4-ylamino)-1H-indazole-1-carboxylate.

Example 16

1-(3-(4-(1H-indazol-5-ylamino)quinazolin-2-yl)phenyl)-3-(2-(dimethylamino)ethyl)urea

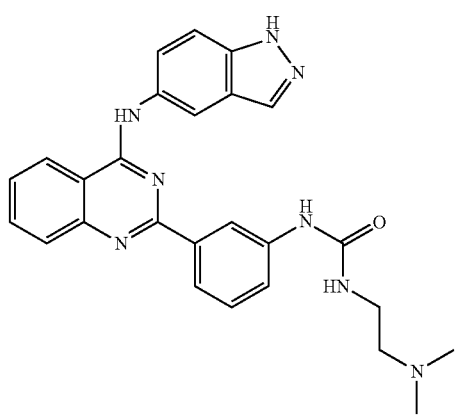 [SMILES: CN(C)CCNC(=O)Nc1cccc(-c2nc(Nc3ccc4[nH]ncc4c3)c3ccccc3n2)c1]

To tert-butyl 5-(2-(3-(2-methoxyacetamido)phenyl)quinazolin-4-ylamino)-1H-indazole-1-carboxylate was added a solution of 1:1 TFA:CH$_2$Cl$_2$ (2 mL) and stirred at RT for 2 h. The reaction mixture was concentrated in vacuo and the residue was triturated with ethyl ether to get a yellow solid. Product was purified using prep HPLC (method 15-50_90 mins) to afford 1-(3-(4-(1H-indazol-5-ylamino) quinazolin-2-yl)phenyl)-3-(2-(dimethylamino)ethyl)urea. (20 mg, 0.042 mmol)

Example 17 tert-butyl 5-(2-(3-(2-(dimethylamino)acetamido) phenyl)quinazolin-4-ylamino)-1H-indazole-1-carboxylate

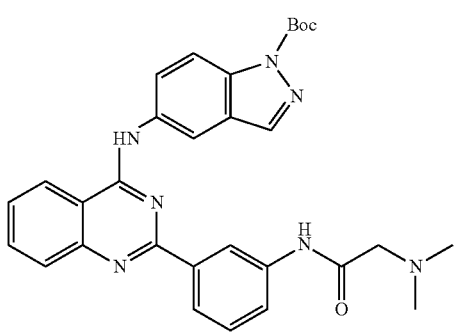 [SMILES: CN(C)CC(=O)Nc1cccc(-c2nc(Nc3ccc4c(cnn4C(=O)OC(C)(C)C)c3)c3ccccc3n2)c1]

A suspension of 2-(dimethylamino)acetic acid (57 mg, 0.55 mmol), PyBOP® (286 mg, 0.55 mmol), DIEA (240 µL, 1.38 mmol) in CH$_2$Cl$_2$ (2 mL) was stirred at RT for 10-15 minutes. This solution of activated acid was added to a suspension of tert-butyl 5-(2-(3-aminophenyl)quinazolin-4-ylamino)-1H-indazole-1-carboxylate (500 mg, 1.10 mmol) and CH$_2$Cl$_2$ (4 mL). The reaction mixture was stirred at RT for 1.5 h. Activated another 1.5 equivalent of the acid as described above and stirred for 16 h. Diluted with more CH$_2$Cl$_2$ and extracted with H$_2$O (3×). Organic layer was dried under Na$_2$SO$_4$ and concentrated in vacuo. The residue was purified by flash chromatography on silica (9:1 CH$_2$Cl$_2$: MeOH) to give the desired product tert-butyl 5-(2-(3-(2-(dimethylamino)acetamido)phenyl)quinazolin-4-ylamino)-1H-indazole-1-carboxylate. (570 mg, 1.06 mmol, 96%).

Example 18

N-(3-(4-(1H-indazol-5-ylamino)quinazolin-2-yl) phenyl)-2-(dimethylamino)acetamide

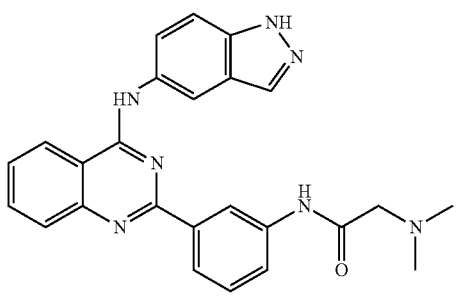 [SMILES: CN(C)CC(=O)Nc1cccc(-c2nc(Nc3ccc4[nH]ncc4c3)c3ccccc3n2)c1]

To tert-butyl 5-(2-(3-(2-(dimethylamino)acetamido)phenyl)quinazolin-4-ylamino)-1H-indazole-1-carboxylate (560 mg, 1.04 mmol) was added a solution of 1:1 TFA:CH$_2$Cl$_2$ (6 mL) and stirred at RT for 2 h. The reaction mixture was concentrated in vacuo and the residue was triturated with ethyl ether and drops of CH$_2$Cl$_2$ to afford 2-methoxyacetyl chloride N-(3-(4-(1H-indazol-5-ylamino)quinazolin-2-yl) phenyl)-2-(dimethylamino)acetamide. (325 mg, 0.74 mmol, 71%)

Example 19 tert-butyl 5-(2-(3-(2-methoxyacetamido)phenyl) quinazolin-4-ylamino)-1H-indazole-1-carboxylate

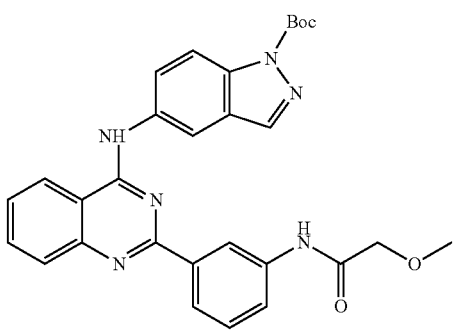 [SMILES: COCC(=O)Nc1cccc(-c2nc(Nc3ccc4c(cnn4C(=O)OC(C)(C)C)c3)c3ccccc3n2)c1]

A suspension of tert-butyl 5-(2-(3-aminophenyl)quinazolin-4-ylamino)-1H-indazole-1-carboxylate (100 mg, 22.0 mmol), 4-methoxyacetyl chloride (40 µL, 0.44 mmol), Et$_3$N (61 µL, 0.44 mmol), in CH$_2$Cl$_2$ (1 mL) was stirred at RT temperature for 30 minutes. The reaction was then concentrated in vacuo and residue was triturated with MeOH and drops of CH$_2$Cl$_2$. The solid was filtered under high vacuum to afford tert-butyl 5-(2-(3-(2-methoxyacetamido)phenyl) quinazolin-4-ylamino)-1H-indazole-1-carboxylate. (98 mg, 85%)

Example 20

N-(3-(4-(1H-indazol-5-ylamino)quinazolin-2-yl) phenyl)-2-methoxyacetamide

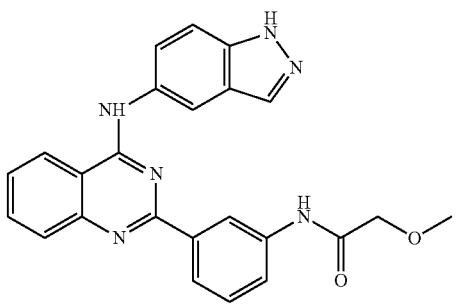 [SMILES: COCC(=O)Nc1cccc(-c2nc(Nc3ccc4[nH]ncc4c3)c3ccccc3n2)c1]

To tert-butyl 5-(2-(3-(2-methoxyacetamido)phenyl) quinazolin-4-ylamino)-1H-indazole-1-carboxylate (95 mg, 0.18 mmol) was added a solution of 1:1 TFA:CH$_2$Cl$_2$ (2 mL) and stirred at RT for 2 h. The reaction mixture was concentrated in vacuo and the residue was triturated with ethyl ether to get a yellow solid. Product was purified using prep HPLC (method 25-50_70 mins) to afford 2-methoxyacetyl chloride N-(3-(4-(1H-indazol-5-ylamino)quinazolin-2-yl)phenyl)-2-methoxyacetamide. (45 mg, 59%)

Example 21 tert-butyl 5-(2-(3-((R)-1-(2,2,2-trifluoroacetyl)pyrrolidine-2-carboxamido)phenyl)quinazolin-4-ylamino)-1H-indazole-1-carboxylate

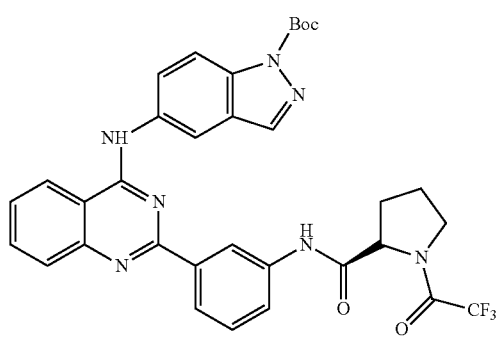

To a suspension of tert-butyl 5-(2-(3-aminophenyl)quinazolin-4-ylamino)-1H-indazole-1-carboxylate (20 mg, 0.044 mmol) and 1-(2,2,2-trifluoroacetyl)pyrrolidine-2-carbonyl chloride (880 μL, 0.088 mmol, 0.1M solution in CH₂Cl₂) was added Et₃N (12 μL, 0.088 mmol), catalytic amount of DMAP, and CH₂Cl₂ (1 mL). The reaction mixture was stirred at RT for 2 h after which 2 equivalents each of 1-(2,2,2-trifluoroacetyl)pyrrolidine-2-carbonyl chloride and Et₃N were added. Continued to stir at ambient temperature for 16 hours. The reaction was concentrated in vacuo and the residue was purified by flash chromatography on silica (10:1 CH₂Cl₂:MeOH). The product tert-butyl 5-(2-(3-((R)-1-(2,2,2-trifluoroacetyl)pyrrolidine-2-carboxamido)phenyl)quinazolin-4-ylamino)-1H-indazole-1-carboxylate was isolated. (130 mg, 46%)

Example 22 tert-butyl 5-(2-(3-((R)-pyrrolidine-2-carboxamido)phenyl)quinazolin-4-ylamino)-1H-indazole-1-carboxylate

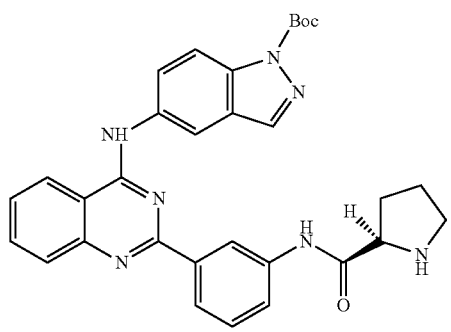

To a suspension of tert-butyl 5-(2-(3-((R)-1-(2,2,2-trifluoroacetyl)pyrrolidine-2-carboxamido)phenyl)quinazolin-4-ylamino)-1H-indazole-1-carboxylate (100 mg, 0.15 mmol) in MeOH (5.7 mL) and H₂O (345 mL) was added K₂CO₃ (108 mg, 0.78 mmol). Reaction mixture was refluxed for 2 h. Cooled to RT temperature and concentrated in vacuo. The residue was dissolved in EtOAc and extracted with H₂O (3×). Dried the organic layer under Na₂SO₄ and concentrated in vacuo. The aqueous layer was basicified with 1 N NaOH, extracted with CHCl₃ (3×), dried under Na₂SO₄ and concentrated in vacuo. The two organic layers were combined to afford tert-butyl 5-(2-(3-((R)-pyrrolidine-2-carboxamido)phenyl)quinazolin-4-ylamino)-1H-indazole-1-carboxylate. (65 mg, 79%).

Example 23

(2R)—N-(3-(4-(1H-indazol-5-ylamino)quinazolin-2-yl)-phenyl)pyrrolidine-2-carboxamide

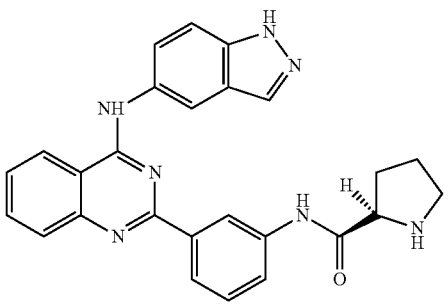

To tert-butyl 5-(2-(3-((R)-pyrrolidine-2-carboxamido)phenyl)quinazolin-4-ylamino)-1H-indazole-1-carboxylate (65 mg, 0.12 mmol) was added a solution of 1:1 TFA:CH₂Cl₂ (2 mL) and stirred at RT for 2 h. The reaction mixture was concentrated in vacuo and the residue was triturated with ethyl ether to get a yellow solid. Product was purified using prep HPLC (method 25-50_70 mins) to afford (2R)—N-(3-(4-(1H-indazol-5-ylamino)quinazolin-2-yl)phenyl)pyrrolidine-2-carboxamide. (64 mg, 100%).

Example 24 tert-butyl 5-(2-(3-(2-methoxy-2-oxoacetamido)phenyl)quinazolin-4-ylamino)-1H-indazole-1-carboxylate

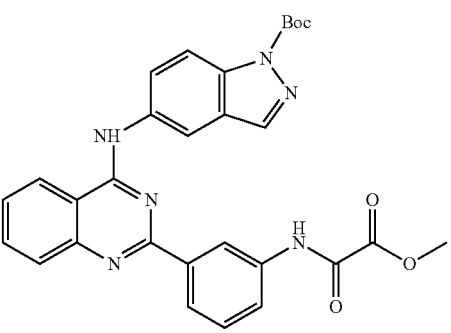 [SMILES: COC(=O)C(=O)Nc1cccc(-c2nc(Nc3ccc4c(cnn4C(=O)OC(C)(C)C)c3)c3ccccc3n2)c1]

To a suspension of tert-butyl 5-(2-(3-aminophenyl)quinazolin-4-ylamino)-1H-indazole-1-carboxylate (85 mg, 0.19 mmol) and methyl 2-chloro-2-oxoacetate (35 μL, 0.38 mmol) in CH₂Cl₂ (1 mL) was added Et₃N (53 μL, 0.38 mmol), and catalytic amount of DMAP. The reaction mixture was stirred at RT for 3 h. The reaction was concentrated in vacuo and the residue was purified by flash chromatography on silica (10:1 CH$_2$Cl$_2$:MeOH). The product tert-butyl 5-(2-(3-(2-methoxy-2-oxoacetamido)phenyl)quinazolin-4-ylamino)-1H-indazole-1-carboxylate was isolate. (18 mg, 18%)

Example 25 methyl 2-(3-(4-(1H-indazol-5-ylamino)quinazolin-2-yl)phenylamino)-2-oxoacetate

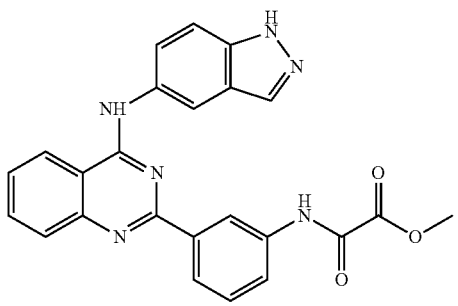 [SMILES: COC(=O)C(=O)Nc1cccc(-c2nc(Nc3ccc4[nH]ncc4c3)c3ccccc3n2)c1]

To tert-butyl 5-(2-(3-(2-methoxy-2-oxoacetamido)phenyl)quinazolin-4-ylamino)-1H-indazole-1-carboxylate (18 mg, 0.033 mmol) was added a solution of 1:1 TFA:CH$_2$Cl$_2$ (2 mL) and stirred at RT for 2 h. The reaction mixture was concentrated in vacuo and the residue was triturated with ethyl ether to get a yellow solid to afford methyl 2-(3-(4-(1H-indazol-5-ylamino)quinazolin-2-yl)phenylamino)-2-oxoacetate. (15 mg, 100%).

Example 26 tert-butyl 5-(2-(3-((S)-2-(tert-butoxycarbonyl)propanamido)phenyl)quinazolin-4-ylamino)-1H-indazole-1-carboxylate

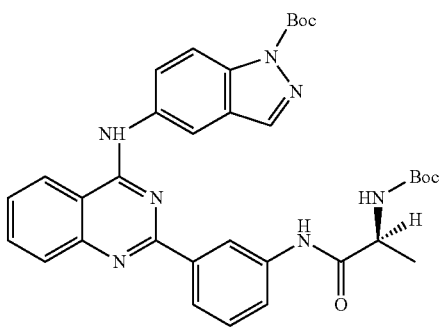 [SMILES: C[C@H](NC(=O)OC(C)(C)C)C(=O)Nc1cccc(-c2nc(Nc3ccc4c(cnn4C(=O)OC(C)(C)C)c3)c3ccccc3n2)c1]

A suspension of (S)-2-(tert-butoxycarbonyl)propanoic acid (21 mg, 0.11 mmol), PyBOP® (57 mg, 0.11 mmol), DIEA (49 µL, 0.28 mmol) in CH$_2$Cl$_2$ (0.5 mL) was stirred at RT for 10-15 minutes. This solution of activated acid was added to a suspension of tert-butyl 5-(2-(3-aminophenyl)quinazolin-4-ylamino)-1H-indazole-1-carboxylate (100 mg, 0.22 mmol) and CH$_2$Cl$_2$ (1 mL). The reaction mixture was stirred at RT for 1.5 h. Activated another 0.5 equivalent of the acid as described above and it was once again added to the reaction mixture. Stirred for 16 h, diluted with more CH$_2$Cl$_2$ and extracted with H$_2$O (3×). Organic layer was dried under Na$_2$SO$_4$ and concentrated in vacuo to give the desired product tert-butyl 5-(2-(3-((S)-2-(tert-butoxycarbonyl)propanamido)phenyl)quinazolin-4-ylamino)-1H-indazole-1-carboxylate. (95 mg, 69%).

Example 27

(2S)—N-(3-(4-(1H-indazol-5-ylamino)quinazolin-2-yl)phenyl)-2-aminopropanamide

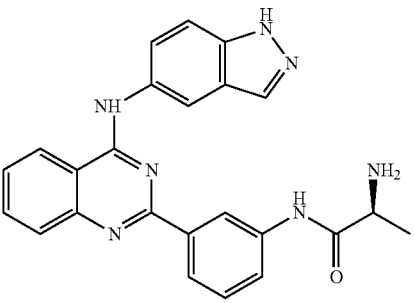 [SMILES: C[C@H](N)C(=O)Nc1cccc(-c2nc(Nc3ccc4[nH]ncc4c3)c3ccccc3n2)c1]

To tert-butyl 5-(2-(3-((S)-2-(tert-butoxycarbonyl)propanamido)phenyl)-quinazolin-4-ylamino)-1H-indazole-1-carboxylate (95 mg, 0.15 mmol) was added a solution of 1:1 TFA:CH$_2$Cl$_2$ (2 mL) and stirred at RT for 2 h. The reaction mixture was concentrated in vacuo and the crude product was purified by prep HPLC (method 10-35_90 mins) to afford (2S)—N-(3-(4-(1H-indazol-5-ylamino)quinazolin-2-yl)phenyl)-2-aminopropanamide. (29 mg, 43%)

Example 28 tert-butyl 5-(2-(3-((S)-1-methylpyrrolidine-2-carboxamido)phenyl)quinazolin-4-ylamino)-1H-indazole-1-carboxylate

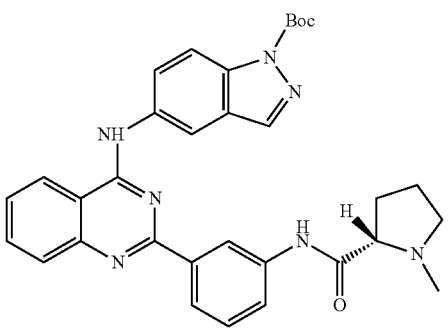 [SMILES: CN1CCC[C@H]1C(=O)Nc1cccc(-c2nc(Nc3ccc4c(cnn4C(=O)OC(C)(C)C)c3)c3ccccc3n2)c1]

A suspension of (S)-1-methylpyrrolidine-2-carboxylic acid monohydrate (14 mg, 0.11 mmol), PyBOP® (57 mg, 0.11 mmol), DIEA (49 µL, 0.28 mmol) in CH$_2$Cl$_2$ (0.5 mL) was stirred at RT for 10-15 minutes. This solution of activated acid was added to a suspension of tert-butyl 5-(2-(3-aminophenyl)quinazolin-4-ylamino)-1H-indazole-1-carboxylate (100 mg, 0.22 mmol) and CH$_2$Cl$_2$ (1 mL). The reaction mixture was stirred at RT for 1.5 h. Activated another 0.5 equivalent of the acid as described above and it was once again added to the reaction mixture. Stirred for 16 h, diluted with more CH$_2$Cl$_2$ and extracted with H$_2$O (3×). Organic layer was dried under Na$_2$SO$_4$ and concentrated in vacuo to give the desired oil product tert-butyl 5-(2-(3-((S)-1-methylpyrrolidine-2-carboxamido)phenyl)-quinazolin-4-ylamino)-1H-indazole-1-carboxylate.

Example 29

(2S)—N-(3-(4-(1H-indazol-5-ylamino)quinazolin-2-yl)phenyl)-1-methylpyrrolidine-2-carboxamide

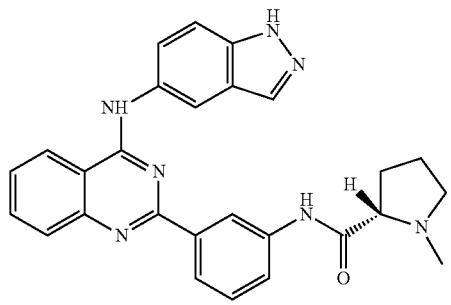 [SMILES: CN1CCC[C@H]1C(=O)Nc1cccc(-c2nc(Nc3ccc4[nH]ncc4c3)c3ccccc3n2)c1]

To tert-butyl 5-(2-(3-((S)-1-methylpyrrolidine-2-carboxamido)phenyl)-quinazolin-4-ylamino)-1H-indazole-1-carboxylate (22 mmol) was added a solution of 1:1 TFA:CH$_2$Cl$_2$ (2 mL) and stirred at RT for 2 h. The reaction mixture was concentrated in vacuo and the crude product was purified by prep HPLC (method 10-35_90 mins) to afford (2S)—N-(3-(4-(1H-indazol-5-ylamino)quinazolin-2-yl)phenyl)-1-methylpyrrolidine-2-carboxamide. (25 mg, 25%)

Example 30 tert-butyl 5-(2-(3-((R)-2-(tert-butoxycarbonyl)propanamido)phenyl)quinazolin-4-ylamino)-1H-indazole-1-carboxylate

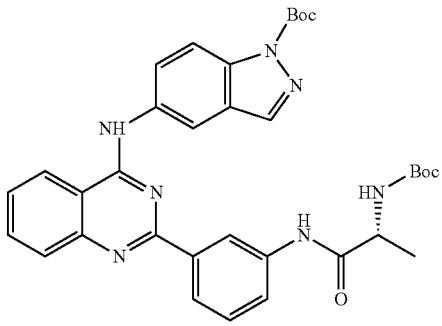 [SMILES: C[C@@H](NC(=O)OC(C)(C)C)C(=O)Nc1cccc(-c2nc(Nc3ccc4c(cnn4C(=O)OC(C)(C)C)c3)c3ccccc3n2)c1]

A suspension of (R)-2-(tert-butoxycarbonyl)propanoic acid (21 mg, 0.11 mmol), PyBOP® (57 mg, 0.11 mmol), DIEA (49 µL, 0.28 mmol) in CH$_2$Cl$_2$ (0.5 mL) was stirred at RT for 10-15 minutes. This solution of activated acid was added to a suspension of tert-butyl 5-(2-(3-aminophenyl)quinazolin-4-ylamino)-1H-indazole-1-carboxylate (100 mg, 0.22 mmol) and CH$_2$Cl$_2$ (1 mL). The reaction mixture was stirred at RT for 1.5 h. Activated another 0.5 equivalent of the acid as described above and it was once again added to the reaction mixture. Stirred for 16 h, diluted with more CH$_2$Cl$_2$ and extracted with H2O (3x). Organic layer was dried under Na$_2$SO$_4$ and concentrated in vacuo to give the desired product tert-butyl 5-(2-(3-((R)-2-(tert-butoxycarbonyl)propanamido)phenyl)quinazolin-4-ylamino)-1H-indazole-1-carboxylate. (95 mg, 69%).

Example 31

(2R)—N-(3-(4-(1H-indazol-5-ylamino)quinazolin-2-yl)phenyl)-2-aminopropanamide

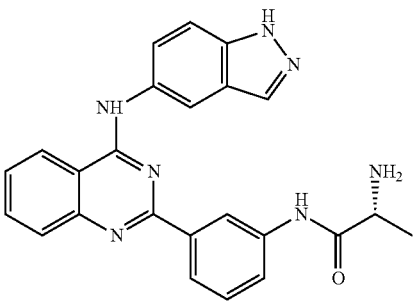 [SMILES: C[C@@H](N)C(=O)Nc1cccc(-c2nc(Nc3ccc4[nH]ncc4c3)c3ccccc3n2)c1]

To tert-butyl 5-(2-(3-((R)-2-(tert-butoxycarbonyl)propanamido)phenyl)-quinazolin-4-ylamino)-1H-indazole-1-carboxylate (100 mg, 0.16 mmol) was added a solution of 1:1 TFA:CH$_2$Cl$_2$ (2 mL) and stirred at RT for 2 h. The reaction mixture was concentrated in vacuo and the crude product was purified by prep HPLC (method 10-35_90 mins) to afford (2R)—N-(3-(4-(1H-indazol-5-ylamino)quinazolin-2-yl)phenyl)-2-aminopropanamide. (24 mg, 38%)

Example 32 tert-butyl 5-(2-(3-(2-morpholinoacetamido)phenyl)quinazolin-4-ylamino)-1-1H-indazole-1-carboxylate

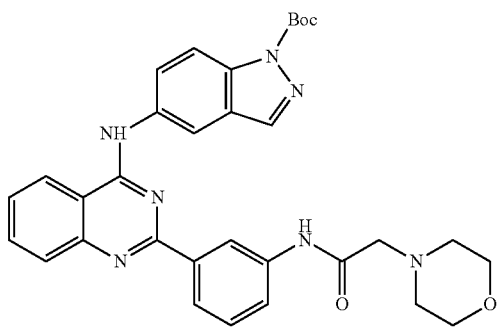 [SMILES: CC(C)(C)OC(=O)n1ncc2cc(Nc3nc(-c4cccc(NC(=O)CN5CCOCC5)c4)nc4ccccc34)ccc21]

A suspension of 2-morpholinoacetic acid (16 mg, 0.11 mmol), PyBOP® (57 mg, 0.11 mmol), DIEA (96 µL, 0.55 mmol) in CH$_2$Cl$_2$ (0.5 mL) was stirred at RT for 10-15 minutes. This solution of activated acid was added to a suspension of tert-butyl 5-(2-(3-aminophenyl)quinazolin-4-ylamino)-1H-indazole-1-carboxylate ( ) (100 mg, 0.22 mmol) and CH$_2$Cl$_2$ (1 mL). The reaction mixture was stirred at RT for 1.5 h. Activated another 0.5 equivalent of the acid as described above and it was once again added to the reaction mixture and stirred for 1.5 h. Added two more 0.5 equivalents of activated acid while stirring 1.5 hr between each addition. Diluted with more CH$_2$Cl$_2$ and extracted with H$_2$O (3x). Organic layer was dried under Na$_2$SO$_4$ and concentrated in vacuo to give the desired oil product tert-butyl 5-(2-(3-(2-morpholinoacetamido)phenyl)quinazolin-4-ylamino)-1H-indazole-1-carboxylate.

Example 33

N-(3-(4-(1H-indazol-5-ylamino)quinazolin-2-yl)phenyl)-2-morpholinoacetamide

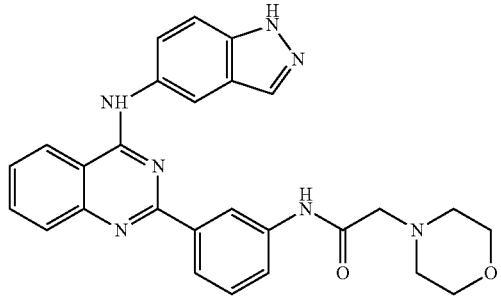 [SMILES: O=C(CN1CCOCC1)Nc1cccc(-c2nc(Nc3ccc4[nH]ncc4c3)c3ccccc3n2)c1]

To tert-butyl 5-(2-(3-((R)-2-(tert-butoxycarbonyl)propanamido)phenyl)-quinazolin-4-ylamino)-1H-indazole-1-carboxylate (100 mg, 0.16 mmol) was added a solution of 1:1 TFA:CH$_2$Cl$_2$ (2 mL) and stirred at RT for 2 h. The reaction mixture was concentrated in vacuo and the crude product was purified by prep HPLC (method 10-35_90 mins) to afford N-(3-(4-(1H-indazol-5-ylamino)quinazolin-2-yl)phenyl)-2-morpholinoacetamide. (24 mg, 38%)

Example 34 tert-butyl 5-(2-(3-(2-chloroacetamido)phenyl)quinazolin-4-ylamino)-1-1H-indazole-1-carboxylate

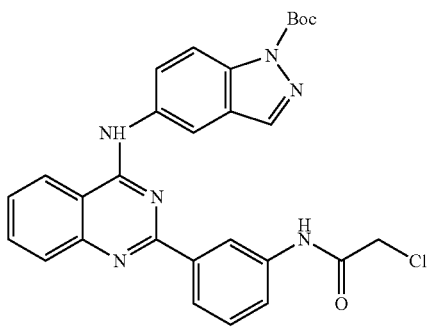 [SMILES: CC(C)(C)OC(=O)n1ncc2cc(Nc3nc(-c4cccc(NC(=O)CCl)c4)nc4ccccc34)ccc21]

To a suspension of tert-butyl 5-(2-(3-aminophenyl)quinazolin-4-ylamino)-1H-indazole-1-carboxylate (1.0 g, 2.21 mmol) in EtOAc:THF:sat'd NaHCO$_3$ (110 mL: 30 mL: 50 mL) was added 2-chloroacetyl chloride (1 mL, 12.6 mmol) and stirred at RT for 2.5 hr. The reaction mixture was stirred at RT for 1.5 h. Another addition of 2-chloroacetyl chloride (0.5 mL) was added and continued to stir for 2 h. Concentrated in vacuo to remove volatiles and residue was washed with 5% citric acid (2×50 mL), water (2×100 mL), and sat'd NaCl (1×50 mL). The organic layer was dried under Na$_2$SO$_4$ and concentrated in vacuo to give the desired product tert-butyl 5-(2-(3-(2-chloroacetamido)phenyl)quinazolin-4-ylamino)-1H-indazole-1-carboxylate. (1.02 g, 87%)

Example 35 tert-butyl 5-(2-(3-(3-(4-isopropylpiperazin-1-yl)propanamido)phenyl)quinazolin-4-ylamino)-1H-indazole-1-carboxylate

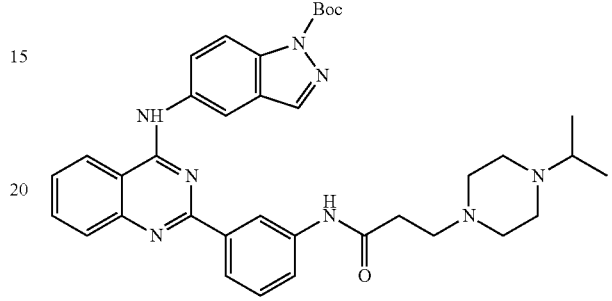

A suspension of tert-butyl 5-(2-(3-(2-chloroacetamido)phenyl)quinazolin-4-ylamino)-1H-indazole-1-carboxylate (112 mg, 0.223 mmol), 1-isopropylpiperazine (52 mg, 0.406 mmol), DIEA (51 mg, 0.402 mmol) in DMF (2 mL) was stirred at 75° C. for 4 h. The reaction mixture was cooled to RT and the residue was poured into ice-water. The resulting white solid was filtered and dried for several hours under high vacuum. The crude product was purified by prep TLC using CH$_2$Cl$_2$:MeOH, (9:1) as the mobile phase to afford tert-butyl 5-(2-(3-(3-(4-isopropylpiperazin-1-yl)propanamido)phenyl)quinazolin-4-ylamino)-1H-indazole-1-carboxylate. (60 mg, 0.094 mmol, 42%)

Example 36

N-(3-(4-(1H-indazol-5-ylamino)quinazolin-2-yl)phenyl)-3-(4-isopropylpiperazin-1-yl)propanamide

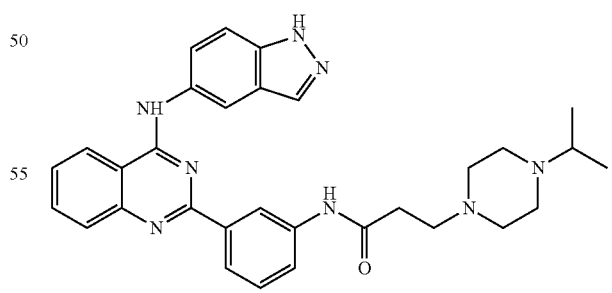

To tert-butyl 5-(2-(3-(3-(4-isopropylpiperazin-1-yl)propanamido)phenyl)-quinazolin-4-ylamino)-1H-indazole-1-carboxylate (60 mg, 0.094 mmol) was added a solution of 1:1 TFA:CH$_2$Cl$_2$ (4 mL) and stirred at RT for 2 h. The reaction mixture was concentrated in vacuo and the crude product was purified by prep HPLC (method 10-35_90 mins) to afford N-(3-(4-(1H-indazol-5-ylamino)quinazolin-2-yl)phenyl)-3-(4-isopropylpiperazin-1-yl)propanamide. (61 mg, 0.11 mmol, 100%).

Example 37 tert-butyl 5-(2-(3-(2-morpholinoacetamido)phenyl)quinazolin-4-ylamino)-1-1H-indazole-1-carboxylate

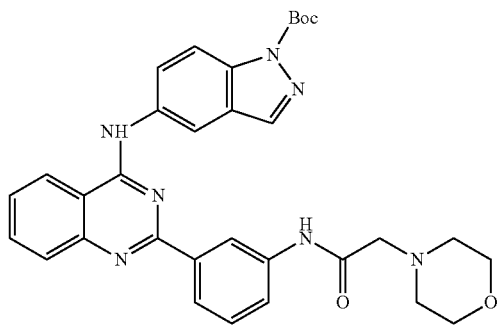 [SMILES: CC(C)(C)OC(=O)n1ncc2cc(Nc3nc(-c4cccc(NC(=O)CN5CCOCC5)c4)nc4ccccc34)ccc21]

To a suspension of tert-butyl 5-(2-(3-(2-chloroacetamido)phenyl)-quinazolin-4-ylamino)-1H-indazole-1-carboxylate (1.0 g, 1.89 mmol) in DMF:THF (3 mL:4 mL) was added morpholine (1.8 mL, 20.6 mmol). The reaction mixture was stirred at RT for 2.5 h. The reaction mixture was concentrated in vacuo to remove volatiles. The residue was poured into ice-water and the resulting white solid was filtered and dried for several hours under high vacuum. The crude product re-crystallized using absolute EtOH to afford tert-butyl 5-(2-(3-(2-morpholinoacetamido)-phenyl)quinazolin-4-ylamino)-1H-indazole-1-carboxylate. (830 mg, 75%)

Example 38

N-(3-(4-(1H-indazol-5-ylamino)quinazolin-2-yl)phenyl)-2-morpholinoacetamide

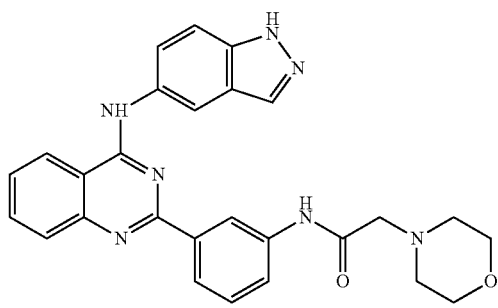 [SMILES: O=C(CN1CCOCC1)Nc1cccc(-c2nc(Nc3ccc4[nH]ncc4c3)c3ccccc3n2)c1]

To tert-butyl 5-(2-(3-((R)-2-(tert-butoxycarbonyl)propanamido)phenyl)-quinazolin-4-ylamino)-1H-indazole-1-carboxylate (805 mg, 1.39 mmol) was added a solution of 1:1 TFA:CH₂Cl₂ (10 mL) and stirred at RT for 3 h. Added an additional portion of TFA (1.5 mL) and stirred for another 2 h. The reaction mixture was diluted with ethyl ether (200 mL) and solid was filtered and dried for several hours under high vacuum to afford N-(3-(4-(1H-indazol-5-ylamino)quinazolin-2-yl)phenyl)-2-morpholinoacetamide. (917 mg, 100%)

Example 39 tert-butyl 5-(2-(3-(2-(4-methylpiperazin-1-yl)acetamido)phenyl)quinazolin-4-ylamino)-1H-indazole-1-carboxylate

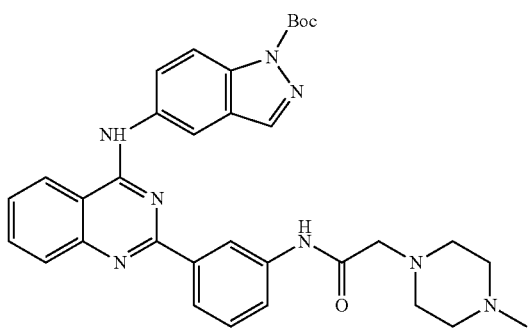 [SMILES: CN1CCN(CC(=O)Nc2cccc(-c3nc(Nc4ccc5c(cnn5C(=O)OC(C)(C)C)c4)c4ccccc4n3)c2)CC1]

A suspension of 2-(4-methylpiperazin-1-yl)acetic acid (34 mg, 0.22 mmol), PyBOP® (11 mg, 0.22 mmol), DIEA (300 µL, 1.72 mmol) in CH₂Cl₂ (0.5 mL) was stirred at RT for 10-15 minutes. This solution of activated acid was added to a suspension of tert-butyl 5-(2-(3-aminophenyl)quinazolin-4-ylamino)-1H-indazole-1-carboxylate (100 mg, 0.22 mmol) and CH₂Cl₂ (1 mL). The reaction mixture was stirred at RT for 1.5 h. Activated another 1 equivalent of the acid as described above and it was once again added to the reaction mixture. Stirred for 16 h, diluted with more CH₂Cl₂ and extracted with H₂O (3×). Organic layer was dried under Na₂SO₄ and concentrated in vacuo to give the desired product tert-butyl 5-(2-(3-(2-(4-methylpiperazin-1-yl)acetamido)phenyl)quinazolin-4-ylamino)-1H-indazole-1-carboxylate.

Example 40

N-(3-(4-(1H-indazol-5-ylamino)quinazolin-2-yl)phenyl)-2-(4-methylpiperazin-1-yl)acetamide

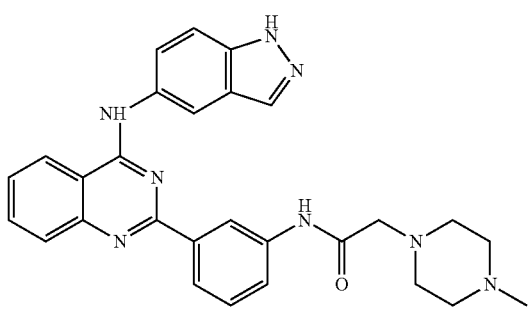 [SMILES: CN1CCN(CC(=O)Nc2cccc(-c3nc(Nc4ccc5[nH]ncc5c4)c4ccccc4n3)c2)CC1]

To tert-butyl 5-(2-(3-(2-(4-methylpiperazin-1-yl)acetamido)phenyl)-quinazolin-4-ylamino)-1H-indazole-1-carboxylate (22 mmol) was added a solution of 1:1 TFA:CH₂Cl₂ (2 mL) and stirred at RT for 2 h. The reaction mixture was concentrated in vacuo and the crude product was purified by prep HPLC (method 10-35_90 mins) to afford N-(3-(4-(1H- indazol-5-ylamino)quinazolin-2-yl)phenyl)-2-(4-methylpiperazin-1-yl)acetamide. (33 mg, 33%)

Example 41 tert-butyl 5-(2-(3-(morpholine-4-carboxamido)phenyl)quinazolin-4-ylamino)-1-1H-indazole-1-carboxylate

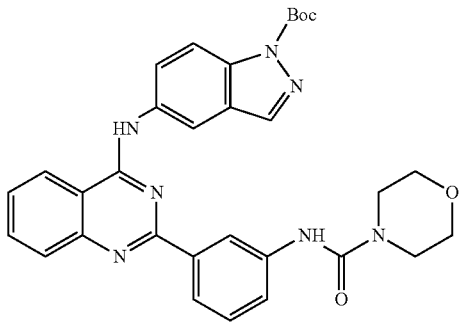 [SMILES: CC(C)(C)OC(=O)n1ncc2cc(Nc3nc(-c4cccc(NC(=O)N5CCOCC5)c4)nc4ccccc34)ccc21]

To a suspension of tert-butyl 5-(2-(3-aminophenyl)quinazolin-4-ylamino)-1H-indazole-1-carboxylate (100 mg, 0.22 mmol) and morpholine-4-carbonyl chloride (51 μL, 0.44 mmol) in $CH_2Cl_2$ (2 mL) was added $Et_3N$ (61 μL, 0.44 mmol) and catalytic amount of DMAP. The reaction mixture was stirred at RT for 2 h after which 2 equivalents each of morpholine-4-carbonyl chloride and $Et_3N$ were added. After 2 h of stirring another 2 equivalents of both the chloride and $Et_3N$ were added and continued to stir at ambient temperature for 16 hours. The reaction was concentrated in vacuo and the residue was purified by flash chromatography on silica (12:1 $CH_2Cl_2$:MeOH). The product tert-butyl 5-(2-(3-(morpholine-4-carboxamido)phenyl)quinazolin-4-ylamino)-1H-indazole-1-carboxylate was isolated. (80 mg, 65%)

Example 42

N-(3-(4-(1H-indazol-5-ylamino)quinazolin-2-yl)phenyl)morpholine-4-carboxamide

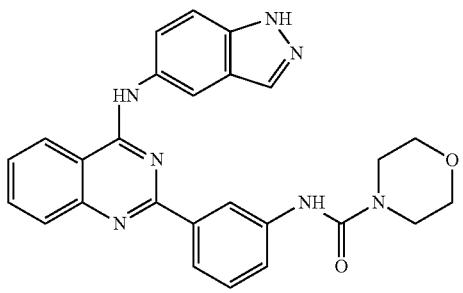 [SMILES: O=C(Nc1cccc(-c2nc(Nc3ccc4[nH]ncc4c3)c3ccccc3n2)c1)N1CCOCC1]

To tert-butyl 5-(2-(3-(morpholine-4-carboxamido)phenyl)quinazolin-4-ylamino)-1H-indazole-1-carboxylate (25 mg, 0.044 mmol) was added a solution of 1:1 TFA:$CH_2Cl_2$ (2 mL) and stirred at RT for 2 h. The reaction mixture was concentrated in vacuo and the product triturated with ethyl ether to afford N-(3-(4-(1H-indazol-5-ylamino)quinazolin-2-yl)phenyl)morpholine-4-carboxamide. (24 mg, 100%)

Example 43 tert-butyl 5-(2-(3-(1-methylpiperazine-4-carboxamido)phenyl)quinazolin-4-ylamino)-1H-indazole-1-carboxylate

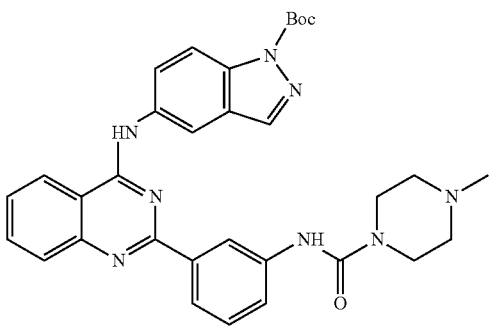 [SMILES: CN1CCN(C(=O)Nc2cccc(-c3nc(Nc4ccc5c(cnn5C(=O)OC(C)(C)C)c4)c4ccccc4n3)c2)CC1]

To a suspension of tert-butyl 5-(2-(3-aminophenyl)quinazolin-4-ylamino)-1H-indazole-1-carboxylate (100 mg, 0.22 mmol) and 4-methylpiperazine-1-carbonyl chloride hydrochloride (88 mg, 0.44 mmol) in $CH_2Cl_2$ (2 mL) was added $Et_3N$ (92 μL, 0.66 mmol) and catalytic amount of DMAP. The reaction mixture was stirred at RT for 2 h after which 2 equivalents each of 4-methylpiperazine-1-carbonyl chloride hydrochloride and 3 equivalents of $Et_3N$ were added. Continued to stir at ambient temperature for 16 hours. The reaction was concentrated in vacuo and the residue was purified by flash chromatography on silica (8:1 $CH_2Cl_2$:MeOH). The product tert-butyl 5-(2-(3-(1-methylpiperazine-4-carboxamido)phenyl)-quinazolin-4-ylamino)-1H-indazole-1-carboxylate was isolated. (160 mg, 100%)

Example 44

N-(3-(4-(1H-indazol-5-ylamino)quinazolin-2-yl)phenyl)-4-methylpiperazine-1-carboxamide

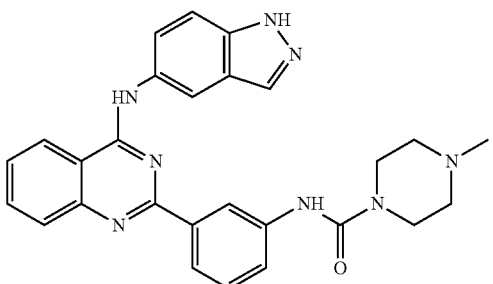

To tert-butyl 5-(2-(3-(1-methylpiperazine-4-carboxamido)phenyl)quinazolin-4-ylamino)-1H-indazole-1-carboxylate (165 mg, 0.22 mmol) was added a solution of 1:1 TFA:$CH_2Cl_2$ (6 mL) and stirred at RT for 2 h. The reaction mixture was concentrated in vacuo and left under high vacuum for several hours. The crude product was purified by prep HPLC (method 25-50_70 mins) to afford N-(3-(4-(1H- indazol-5-ylamino)quinazolin-2-yl)phenyl)-4-methylpiperazine-1-carboxamide. (88 mg, 69%)

Example 45 tert-butyl 5-(2-(3-(3,3-dimethylureido)phenyl)quinazolin-4-ylamino)-1-1H-indazole-1-carboxylate

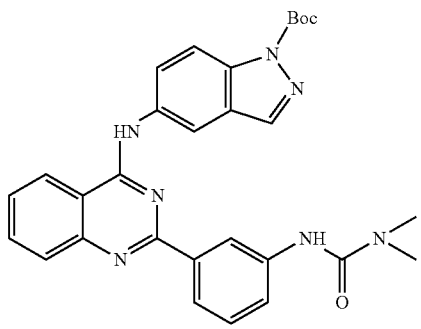 [SMILES: CN(C)C(=O)Nc1cccc(-c2nc(Nc3ccc4c(cnn4C(=O)OC(C)(C)C)c3)c3ccccc3n2)c1]

To a suspension of tert-butyl 5-(2-(3-aminophenyl)quinazolin-4-ylamino)-1H-indazole-1-carboxylate (75 mg, 0.17 mmol) and dimethylcarbamic chloride (30 µL, 0.33 mmol) in CH$_2$Cl$_2$ (2 mL) was added Et$_3$N (46 µL, 0.33 mmol) and catalytic amount of DMAP. The reaction mixture was stirred at RT for 2 h after which 2 equivalents each of dimethylcarbamic chloride and Et$_3$N were added. After 2 h of stirring another 2 equivalents of both the chloride and Et$_3$N were added. Upon the addition of the third addition of the chloride and the Et3N the temperature was raised to 45° C. The reaction mixture was stirred for 48 h. Concentrated in vacuo and the residue was purified by flash chromatography on silica (10:1 CH$_2$Cl$_2$:MeOH). The product tert-butyl 5-(2-(3-(3,3-dimethylureido)phenyl)-quinazolin-4-ylamino)-1H-indazole-1-carboxylate was isolated. (62 mg, 70%)

Example 46

3-(3-(4-(1H-indazol-5-ylamino)quinazolin-2-yl)phenyl)-1,1-dimethylurea

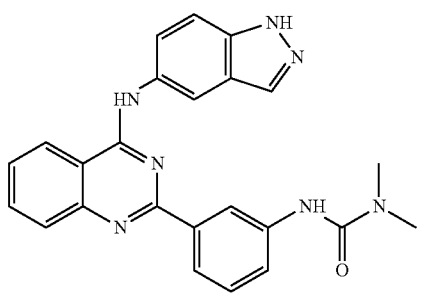 [SMILES: CN(C)C(=O)Nc1cccc(-c2nc(Nc3ccc4[nH]ncc4c3)c3ccccc3n2)c1]

To tert-butyl 5-(2-(3-(3,3-dimethylureido)phenyl)quinazolin-4-ylamino)-1H-indazole-1-carboxylate (50 mg, 0.10 mmol) was added a solution of 1:1 TFA:CH$_2$Cl$_2$ (3 mL) and stirred at RT for 2 h. The reaction mixture was concentrated in vacuo and left under high vacuum for several hours. The crude product was triturated with ethyl ether and the yellow solid was purified by prep HPLC (method 25-50_70 mins) to afford 3-(3-(4-(1H-indazol-5-ylamino)quinazolin-2-yl)phenyl)-1,1-dimethylurea. (36 mg, 86%)

Example 47 tert-butyl 5-(2-(3-(3-benzylureido)phenyl)quinazolin-4-ylamino)-1-1H-indazole-1-carboxylate

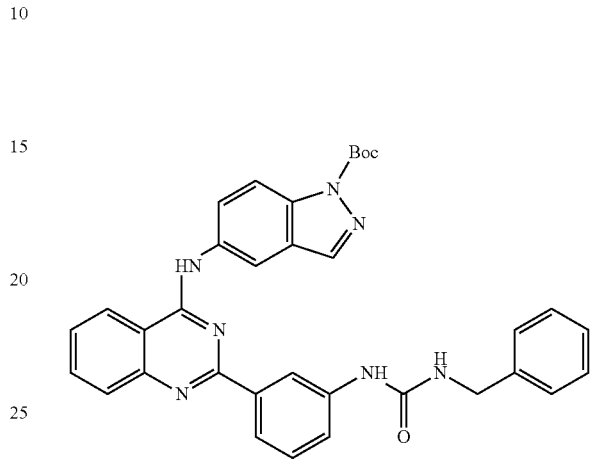

To a suspension of tert-butyl 5-(2-(3-aminophenyl)quinazolin-4-ylamino)-1H-indazole-1-carboxylate (150 mg, 0.33 mmol) and 1-(isocyanatomethyl)benzene (162 µL, 1.32 mmol) in CH$_2$Cl$_2$ (2 mL) was added Et$_3$N (1.38 mL, 9.9 mmol). The reaction mixture was stirred at RT for 4 h and concentrated in vacuo. The residue was triturated using MeOH and drops of CH$_2$Cl$_2$ to afford tert-butyl 5-(2-(3-(3-benzylureido)phenyl)quinazolin-4-ylamino)-1H-indazole-1-carboxylate. (100 mg, 52%)

Example 48

1-(3-(4-(1H-indazol-5-ylamino)quinazolin-2-yl)phenyl)-3-benzylurea

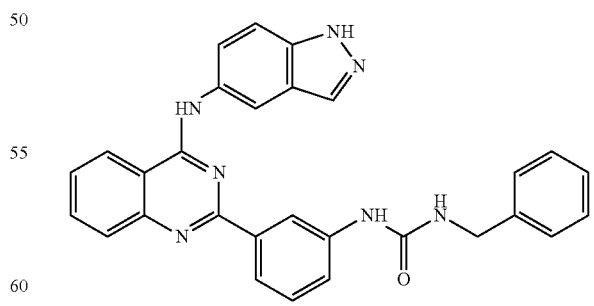

To tert-butyl 5-(2-(3-(3-benzylureido)phenyl)quinazolin-4-ylamino)-1H-indazole-1-carboxylate (30 mg, 0.051 mmol) was added a solution of 1:1 TFA:CH$_2$Cl$_2$ (2 mL) and stirred at RT for 2 h. The reaction mixture was concentrated in vacuo and left under high vacuum for several hours. The crude product was triturated with ethyl ether to afford 1-(3-(4-(1H-indazol-5-ylamino)quinazolin-2-yl)phenyl)-3-benzylurea. (25 mg, 100%)

Example 49 tert-butyl 5-(2-(3-(piperidine-4-carboxamido)phenyl)quinazolin-4-ylamino)-1-1H-indazole-1-carboxylate

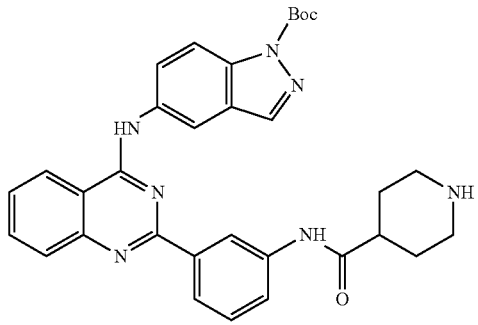 [SMILES: CC(C)(C)OC(=O)n1ncc2cc(Nc3nc(-c4cccc(NC(=O)C5CCNCC5)c4)nc4ccccc34)ccc21]

A suspension of tert-butyl 5-(2-(3-aminophenyl)quinazolin-4-ylamino)-1H-indazole-1-carboxylate (126 mg, 0.278 mmol), 1-(tert-butoxycarbonyl)piperidine-4-carboxylic acid (79 mg, 0.347 mmol), PyBOP® (212 mg, 0.455 mmol) and DIEA (250 µL, 1.43 mmol) in $CH_2Cl_2$ (10 mL) was stirred at RT for 72 h. Reaction mixture was diluted with more $CH_2Cl_2$ (50 mL) and extracted with $H_2O$ (3×). Organic layer was dried under $Na_2SO_4$ and concentrated in vacu. Crude product was purified by prep TLC to give the desired product tert-butyl 5-(2-(3-(piperidine-4-carboxamido)phenyl)quinazolin-4-ylamino)-1H-indazole-1-carboxylate.

Example 50

N-(3-(4-(1H-indazol-5-ylamino)quinazolin-2-yl)phenyl)piperidine-4-carboxamide

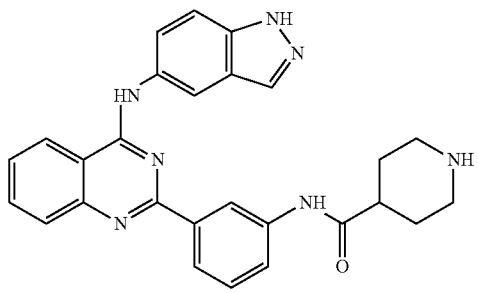 [SMILES: O=C(Nc1cccc(-c2nc(Nc3ccc4[nH]ncc4c3)c3ccccc3n2)c1)C1CCNCC1]

To tert-butyl 5-(2-(3-(piperidine-4-carboxamido)phenyl)quinazolin-4-ylamino)-1H-indazole-1-carboxylate (mg, mmol) was added a solution of 1:1 $TFA:CH_2Cl_2$ (4 mL) and stirred at RT for 2 h. The reaction mixture was concentrated in vacuo and left under high vacuum for several hours. The crude product was triturated with ethyl ether to afford N-(3-(4-(1H-indazol-5-ylamino)quinazolin-2-yl)phenyl)piperidine-4-carboxamide. (97 mg, 0.21 mmol, 75% over two steps)

Example 51 tert-Butyl 5-(2-(3-(2-tert-butoxy-2-oxoethoxy)phenyl)quinazolin-4-ylamino)-1-1H-indazole-1-carboxylate

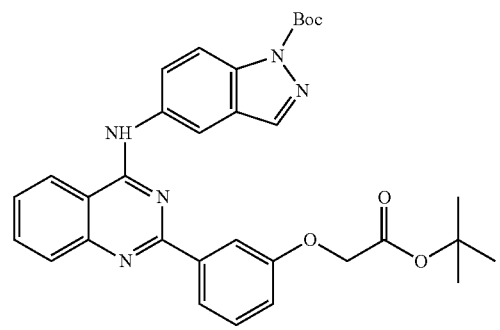 [SMILES: CC(C)(C)OC(=O)COc1cccc(-c2nc(Nc3ccc4c(cnn4C(=O)OC(C)(C)C)c3)c3ccccc3n2)c1]

A mixture of tert-butyl 5-(2-(3-hydroxyphenyl)quinazolin-4-ylamino)-1H-indazole-1-carboxylate (0.800 g, 1.76 mmol), tert-butyl 2-bromoacetate (130 µL, 0.88 mmol) and $K_2CO_3$ (0.972 g, 7.04 mmol) in DMF (35 mL) was heated at 80° C. for 2 h. Upon which additional tert-butyl 2-bromoacetate (130 µL, 0.88 mmol) was added, heating at 80° C. was continued for a further 1.5 h. The mixture was allowed to cool to RT and concentrated in vacuo. Diluted with $CH_2Cl_2$ and extracted with water (3×). Dried under $Na_2SO_4$ and concentrated in vacuo to give tert-Butyl 5-(2-(3-(2-tert-butoxy-2-oxoethoxy)phenyl)quinazolin-4-ylamino)-1H-indazole-1-carboxylate. (0.950 g, 1.68 mmol, 95%).

Example 52

2-(3-(4-(1H-indazol-5-ylamino)quinazolin-2-yl)phenoxy)acetic acid

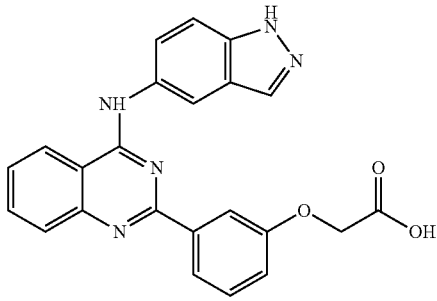 [SMILES: O=C(O)COc1cccc(-c2nc(Nc3ccc4[nH]ncc4c3)c3ccccc3n2)c1]

A solution of tert-butyl 5-(2-(3-(2-tert-butoxy-2-oxoethoxy)phenyl)-quinazolin-4-ylamino)-1H-indazole-1-carboxylate was stirred in $CH_2Cl_2$ (2 mL) and TFA (2 mL) for 1 h. The volatiles were removed in vacuo and the residue was triturated with ethyl ether. The crude product was purified using prep HPLC (method 10-35_90 mins) to afford to give 2-(3-(4-(1H-indazol-5-ylamino)quinazolin-2-yl)phenoxy) acetic acid. (0.43 mg, 0.10 mmol)

Example 53

2-(3-(4-(1H-indazol-5-ylamino)quinazolin-2-yl)phenoxy)-1-N-isopropyl-N-methylacetamide

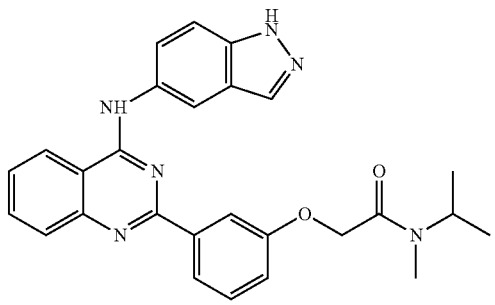 [SMILES: CC(C)N(C)C(=O)COc1cccc(-c2nc(Nc3ccc4[nH]ncc4c3)c3ccccc3n2)c1]

A suspension of 2-(3-(4-(1H-indazol-5-ylamino)quinazolin-2-yl)phenoxy)acetic acid (120 mg, 0.29 mmol), PyBOP® (150 mg, 0.29 mmol), DIEA (152 μL, 0.87 mmol) in CH$_2$Cl$_2$ (5 mL) was stirred at RT for 10-15 minutes. To this solution of activated acid was added N-methylpropan-2-amine (30 μL, 0.29 mmol). The reaction mixture was stirred at RT for 3 h and concentrated in vacuo. The crude product was purified using prep HPLC (method 5-25-50_80 mins) and was further washed with ethyl ether and drops of CH$_2$Cl$_2$ to afford 2-(3-(4-(1H-indazol-5-ylamino)quinazolin-2-yl)phenoxy)-N-isopropyl-N-methylacetamide. (12 mg, 0.025 mmol, 9%)

Example 54

2-(3-(4-(1H-indazol-5-ylamino)quinazolin-2-yl)phenoxy)-N-(2-methoxyethyl)acetamide

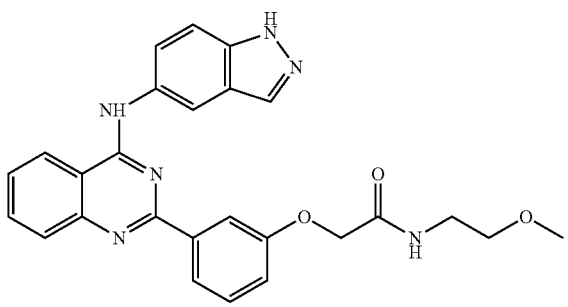 [SMILES: COCCNC(=O)COc1cccc(-c2nc(Nc3ccc4[nH]ncc4c3)c3ccccc3n2)c1]

A suspension of 2-(3-(4-(1H-indazol-5-ylamino)quinazolin-2-yl)phenoxy)acetic acid (100 mg, 0.24 mmol), PyBOP® (125 mg, 0.24 mmol), DIEA (125 μL, 0.72 mmol) in CH$_2$Cl$_2$: DMF (4 mL:0.5 mL) stirred at RT for 10-15 minutes. To this solution of activated acid was added 2-methoxyethanamine (21 μL, 0.24 mmol) and the reaction mixture was stirred at RT for 3 h. Concentrated in vacuo and the crude product was purified using prep HPLC (method 10-35_90 mins) and was further washed with ethyl ether and drops of CH$_2$Cl$_2$ to afford 2-(3-(4-(1H-indazol-5-ylamino)quinazolin-2-yl)phenoxy)-N-(2-methoxyethyl)acetamide. (25 mg, 0.053 mmol, 22%)

Example 55

2-(3-(4-(1H-indazol-5-ylamino)quinazolin-2-yl)phenoxy)-N-(pyridin-3-yl)acetamide

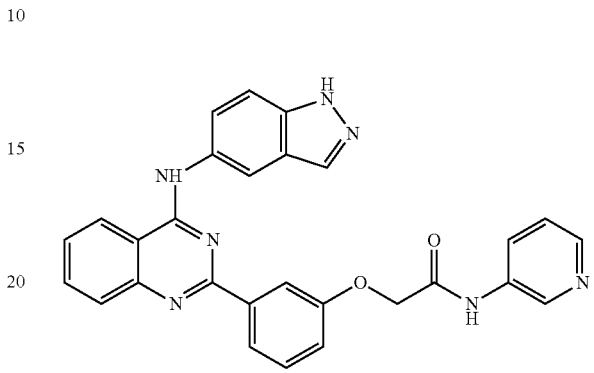

A suspension of 2-(3-(4-(1H-indazol-5-ylamino)quinazolin-2-yl)phenoxy)acetic acid (100 mg, 0.24 mmol), PyBOP® (125 mg, 0.24 mmol), DIEA (250 μL, 0.44 mmol) in CH$_2$Cl$_2$: DMF (4 mL:1 mL) stirred at RT for 10-15 minutes. To this solution of activated acid was added 3-amino pyridine (23 mg, 0.24 mmol) and the reaction mixture was stirred at 50° C. for 1.5 h. Concentrated in vacuo and the crude product was purified using prep HPLC (method 10-35_90 mins) to afford 2-(3-(4-(1H-indazol-5-ylamino)quinazolin-2-yl)phenoxy)-N-(pyridin-3-yl)acetamide. (11 mg, 0.023 mmol, 9%)

Example 56

2-(3-(4-(1H-indazol-5-ylamino)quinazolin-2-yl)phenoxy)-1-(4-methylpiperazin-1-yl)ethanone

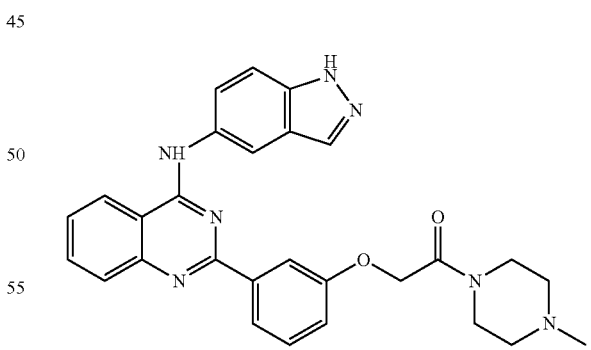

A suspension of 2-(3-(4-(1H-indazol-5-ylamino)quinazolin-2-yl)phenoxy)acetic acid (100 mg, 0.24 mmol), PyBOP® (125 mg, 0.24 mmol), DIEA (125 μL, 0.24 mmol) in CH$_2$Cl$_2$ (5 mL) stirred at RT for 10-15 minutes. To this solution of activated acid was added 1-methylpiperazine (27 μL, 0.24 mmol) and the reaction mixture was stirred at RT for 1.5 h. Concentrated in vacuo and the crude product was purified using prep HPLC (method 10-35_90 mins) to afford 2-(3-

(4-(1H-indazol-5-ylamino)quinazolin-2-yl)phenoxy)-1-(4-methylpiperazin-1-yl)ethanone. (32 mg, 0.065 mmol, 27%)

Example 57

2-chloro-N-(2-(dimethylamino)ethyl)acetamide

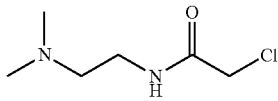

A suspension of 2-chloroacetic acid (214 mg, 2.27 mmol), PyBOP® (1.18, 2.27 mmol), DIEA (1.18 mL, 6.81 mmol) in CH$_2$Cl$_2$ (1 mL) was stirred at RT for 10-15 minutes. This solution of activated acid was added to a suspension of N1,N1-dimethylethane-1,2-diamine (249 µL, 2.27 mmol) and CH$_2$Cl$_2$ (4 mL). The reaction mixture was stirred at RT for 1.5 h. Diluted with more CH$_2$Cl$_2$ and extracted with H$_2$O (3×). Organic layer was dried under Na$_2$SO$_4$ and concentrated in vacuo to give the desired product 2-chloro-N-(2-(dimethylamino)ethyl)acetamide.

Example 58 tert-butyl 5-(2-(3-(2-(2-(dimethylamino)ethylamino)-2-oxoethoxy)phenyl)quinazolin-4-ylamino)-1H-indazole-1-carboxylate

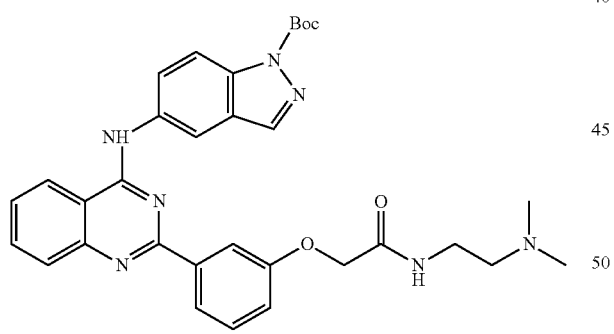

A suspension of tert-butyl 5-(2-(3-hydroxyphenyl)quinazolin-4-ylamino)-1H-indazole-1-carboxylate (80 mg, 0.18 mmol), 2-chloro-N-(2-(dimethylamino)-ethyl)acetamide (40 mg, 0.25 mmol), K$_2$CO$_3$ (162 mg, 1.17 mmol), in DMF (5 mL). Stirred at RT for 4 h upon which 2 equivalents each of 2-chloro-N-(2-(dimethylamino)-ethyl)acetamide and K$_2$CO$_3$ were added. Continued to stir for 16 h. Concentrated in vacuo to afford the crude tert-butyl 5-(2-(3-(2-(2-(dimethylamino)-ethylamino)-2-oxoethoxy)phenyl)quinazolin-4-ylamino)-1H-indazole-1-carboxylate. (0.18 mmol).

Example 59

2-(3-(4-(1H-indazol-5-ylamino)quinazolin-2-yl)phenoxy)-N-(2-(dimethylamino)ethyl)acetamide

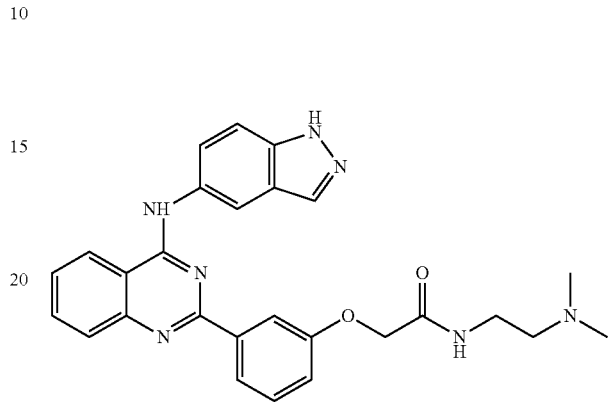

To tert-butyl 5-(2-(3-(2-(2-(dimethylamino)ethylamino)-2-oxoethoxy)phenyl)quinazolin-4-ylamino)-1H-indazole-1-carboxylate (0.18 mmol) was added a solution of 1:1 TFA:CH$_2$Cl$_2$ (2 mL) and stirred at RT for 2 h. The reaction mixture was concentrated in vacuo and the crude product was purified by prep HPLC (method 10-35_90 mins) to afford 2-(3-(4-(1H-indazol-5-ylamino)quinazolin-2-yl)phenoxy)-N-(2-(dimethylamino)ethyl)acetamide. (19 mg, 0.039 mmol, 22%).

Example 60 tert-butyl 5-(2-(3-(2-isopropoxy-2-oxoethoxy)phenyl)quinazolin-4-ylamino)-1H-indazole-1-carboxylate

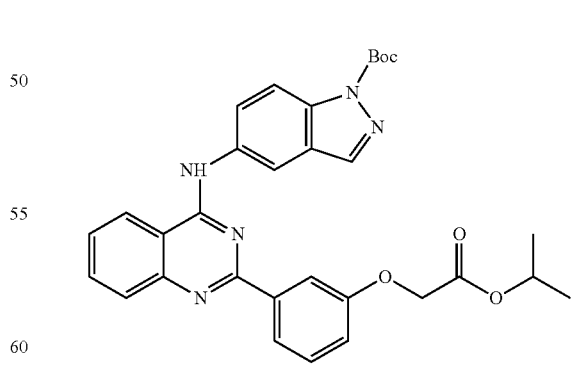

A suspension of tert-butyl 5-(2-(3-hydroxyphenyl)quinazolin-4-ylamino)-1H-indazole-1-carboxylate (120 mg, 0.26 mmol), isopropyl 2-chloroacetate (45 mL, 0.36 mmol), K$_2$CO$_3$ (125 µL, 0.24 mmol), in DMF (5 mL) stirred at RT for 2 h. Concentrated in vacuo to afford the crude tert-butyl 5-(2-(3-(2-isopropoxy-2-oxoethoxy)phenyl)quinazolin-4-ylamino)-1H-indazole-1-carboxylate ( ). (0.26 mmol)

Example 61 isopropyl 2-(3-(4-(1H-indazol-5-ylamino)quinazolin-2-yl)phenoxy)acetate

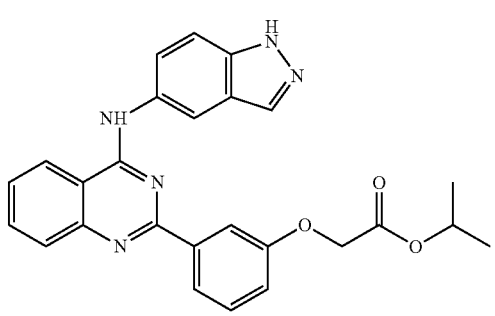 [SMILES: CC(C)OC(=O)COc1cccc(-c2nc(Nc3ccc4[nH]ncc4c3)c3ccccc3n2)c1]

To a suspension of tert-butyl 5-(2-(3-(2-isopropoxy-2-oxoethoxy)phenyl)quinazolin-4-ylamino)-1H-indazole-1-carboxylate (0.26 mmol) in 1,4-dioxane (0.5 mL) was added a 4M solution of hydrogen chloride in 1,4-dioxane (3 mL) and stirred at RT for 16 h. The reaction mixture was concentrated in vacuo residue was purified using prep HPLC (method 10-35_90 mins) to afford isopropyl 2-(3-(4-(1H-indazol-5-ylamino)quinazolin-2-yl)phenoxy)acetate. (28 mg, 0.062 mmol, 24%)

Example 62 tert-butyl 5-(2-(3-(oxazol-2-ylmethoxy)phenyl)quinazolin-4-ylamino)-1H-indazole-1-carboxylate

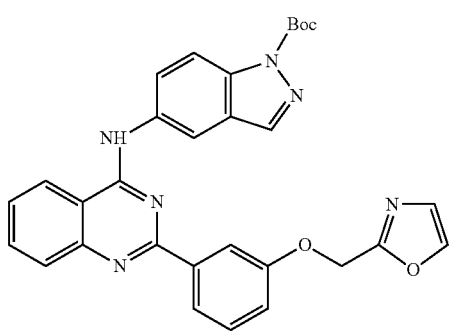 [SMILES: CC(C)(C)OC(=O)n1ncc2cc(Nc3nc(-c4cccc(OCc5ncco5)c4)nc4ccccc34)ccc21]

A suspension of tert-butyl 5-(2-(3-hydroxyphenyl)quinazolin-4-ylamino)-1H-indazole-1-carboxylate (100 mg, 0.22 mmol), 2-(chloromethyl)oxazole (31 mg, 0.26 mmol), KI (44 mg, 0.27 mmol), and K$_2$CO$_3$ (122 mg, 0.88 mmol) in dry DMF (1.5 mL) was stirred at 70° C. for 1 h. The mixture was poured into water, filtered, dried under high vacuum for several hours to afford tert-butyl 5-(2-(3-(oxazol-2-ylmethoxy)phenyl)-quinazolin-4-ylamino)-1H-indazole-1-carboxylate.

Example 63

N-(1H-indazol-5-yl)-2-(3-(oxazol-2-ylmethoxy)phenyl)quinazolin-4-amine

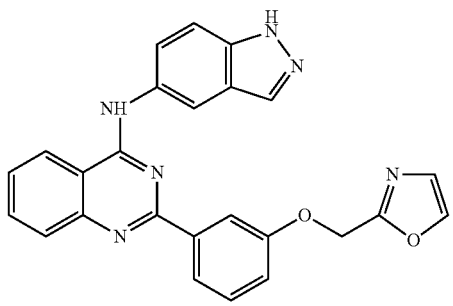 [SMILES: c1cc(OCc2ncco2)cc(-c2nc(Nc3ccc4[nH]ncc4c3)c3ccccc3n2)c1]

To tert-butyl 5-(2-(3-(2-(2-(dimethylamino)ethylamino)-2-oxoethoxy)-phenyl)quinazolin-4-ylamino)-1H-indazole-1-carboxylate was added a solution of 1:1 TFA:CH$_2$Cl$_2$ (3 mL) and stirred at RT for 2 h. The reaction mixture was concentrated in vacuo and the crude product was purified by prep HPLC (method 20-45_90 mins) to afford N-(1H-indazol-5-yl)-2-(3-(oxazol-2-ylmethoxy)phenyl)quinazolin-4-amine. (12 mg, 0.028 mmol).

Example 64

2-(3-(4-(1H-indazol-5-ylamino)quinazolin-2-yl)phenoxy)-1-morpholinoethanone

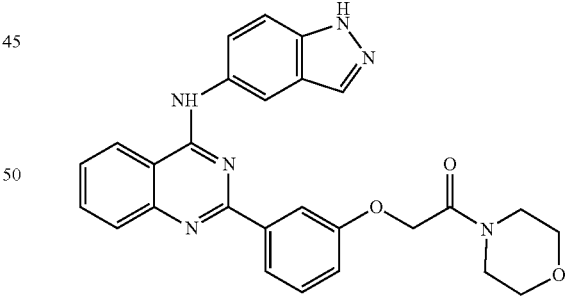

A suspension of 2-(3-(4-(1H-indazol-5-ylamino)quinazolin-2-yl)phenoxy)acetic acid (80 mg, 0.16 mmol), PyBOP® (46 mg, 0.088 mmol), DIEA (28 μL, 0.16 mmol) in dry CH$_2$Cl$_2$:DMF (2:0.1 mL) was stirred at RT for 15 minutes. To this solution of activated acid was added morpholine (8.7 mg, 0.10 mmol). After 30 minutes, 1.0 equivalent of DIEA and 0.55 equivalent of PyBOP® were added. After stirring the solution for 15 minutes, 0.65 equivalents of morpholine were added and the mixture was stirred for an additional 30 minutes. The solvent was removed in vacuo and the crude product was purified using prep HPLC (20-45_90 mins) to afford 2-(3-(4-(1H-indazol-5-ylamino)quinazolin-2-yl)phenoxy)-1-morpholinoethanone. (13 mg, 0.027 mmol, 17%)

Example 65

2-(3-(4-(1H-indazol-5-ylamino)quinazolin-2-yl)phenoxy)-N-methylacetamide

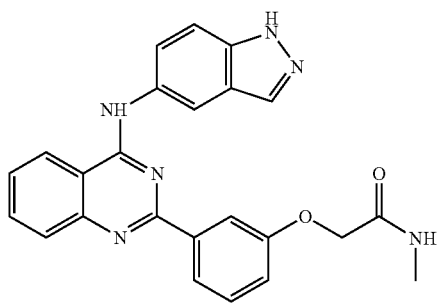 [SMILES: CNC(=O)COc1cccc(-c2nc(Nc3ccc4[nH]ncc4c3)c3ccccc3n2)c1]

To a solution of 2-(3-(4-(1H-indazol-5-ylamino)quinazolin-2-yl)phenoxy)acetic acid (80 mg, 0.16 mmol) in dry CH$_2$Cl$_2$:DMF (2.0:0.1 mL), added DIEA (29 µL, 0.16 mmol) and PyBOP® (46 mg, 0.088 mmol). After stirring the mixture at RT for 15 minutes, methanamine was bubbled through the solution for 15 minutes. Added another 1.0 equivalent of DIEA and 0.55 equivalents of PyBOP® after stirring the solution for 15 minutes, followed by methanamine bubbling for an additional 15 minutes. The solvent was removed in vacuo and the crude material was purified by prep HPLC (method 20-45_90 mins) to afford 2-(3-(4-(1H-indazol-5-ylamino)quinazolin-2-yl)phenoxy)-N-methylacetamide. (46 mg, 0.11 mmol, 68%).

Example 66

2-(3-(4-(1H-indazol-5-ylamino)quinazolin-2-yl)phenoxy)-N,N-dimethylacetamide

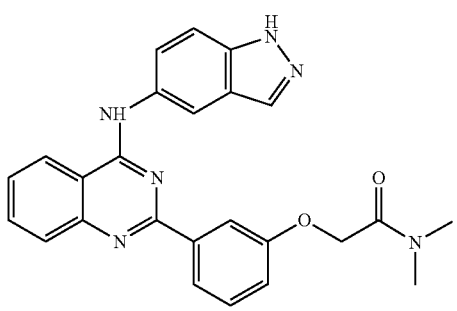 [SMILES: CN(C)C(=O)COc1cccc(-c2nc(Nc3ccc4[nH]ncc4c3)c3ccccc3n2)c1]

To a solution of 2-(3-(4-(1H-indazol-5-ylamino)quinazolin-2-yl)phenoxy)acetic acid (80 mg, 0.16 mmol) in dry CH$_2$Cl$_2$:DMF (2.0:0.1 mL), added DIEA (29 µL, 0.16 mmol) and PyBOP® (46 mg, 0.088 mmol). After stirring the mixture at RT for 15 minutes, dimethylamine was bubbled through the solution for 15 minutes. Added another 1.0 equivalent of DIEA and 0.55 equivalents of PyBOP® after stirring the solution for 15 minutes, followed by dimethylamine bubbling for an additional 15 minutes. The solvent was removed in vacuo and the crude material was purified by prep HPLC (method 20-45_90 mins) to afford 2-(3-(4-(1H-indazol-5-ylamino)quinazolin-2-yl)phenoxy)-N,N-dimethylacetamide (26 mg, 0.059 mmol, 37%).

Example 67 tert-butyl 5-(2-(3-((1-methyl-1H-imidazol-2-yl)methoxy)phenyl)quinazolin-4-ylamino)-1H-indazole-1-carboxylate

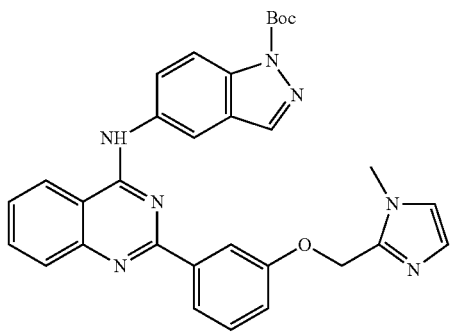 [SMILES: Cn1ccnc1COc1cccc(-c2nc(Nc3ccc4c(cnn4C(=O)OC(C)(C)C)c3)c3ccccc3n2)c1]

A solution of tert-butyl 5-(2-(3-hydroxyphenyl)quinazolin-4-ylamino)-1H-indazole-1-carboxylate (50 mg, 0.11 mmol), 2-(chloromethyl)-1-methyl-1H-imidazole (22 mg, 0.13 mmol), KI (22 mg, 0.13 mmol), K$_2$CO$_3$ (76 mg, 0.55 mmol) in anhydrous DMF (1.2 mL) was heated at 50° C. for 100 minutes. Added 1.2 equivalents each of 2-(chloromethyl)-1-methyl-1H-imidazole and KI and heated for another 35 minutes. Added 2.4 equivalents each of 2-(chloromethyl)-1-methyl-1H-imidazole and KI along with 2.0 equivalents of K$_2$CO$_3$ and heated for 1 h. The solution was diluted with CH$_2$Cl$_2$ and washed with aqueous saturated NaCl (2×). The organic phase was dried under Na$_2$SO$_4$ and concentrated in vacuo to afford tert-butyl 5-(2-(3-((1-methyl-1H-imidazol-2-yl)methoxy)-phenyl)quinazolin-4-ylamino)-1H-indazole-1-carboxylate.

Example 68

N-(1H-indazol-5-yl)-2-(3-((1-methyl-1H-imidazol-2-yl)methoxy)phenyl)-1-quinazolin-4-amine

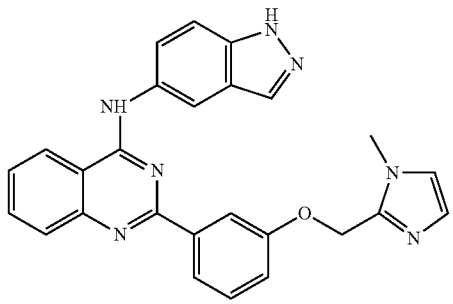 [SMILES: Cn1ccnc1COc1cccc(-c2nc(Nc3ccc4[nH]ncc4c3)c3ccccc3n2)c1]

To tert-butyl 5-(2-(3-((1-methyl-1H-imidazol-2-yl)methoxy)phenyl)-quinazolin-4-ylamino)-1H-indazole-1-carboxylate was added a solution of 1:1 TFA:CH$_2$Cl$_2$ (2 mL) and stirred at RT for 2 h. The reaction mixture was concentrated in vacuo and the crude product was purified by prep HPLC (method 10-35_90 mins) to afford N-(1H-indazol-5-yl)-2-(3-((1-methyl-1H-imidazol-2-yl)methoxy)phenyl)-quinazolin-4-amine. (5.4 mg, 0.012 mmol).

Example 69

2-(3-(4-(1H-indazol-5-ylamino)quinazolin-2-yl)phenoxy)-N-(cyclopropylmethyl)acetamide

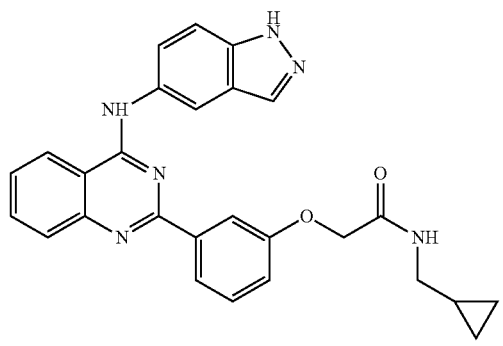 [SMILES: O=C(COc1cccc(-c2nc(Nc3ccc4[nH]ncc4c3)c3ccccc3n2)c1)NCC1CC1]

A suspension of 2-(3-(4-(1H-indazol-5-ylamino)quinazolin-2-yl)phenoxy)acetic acid (80 mg, 0.16 mmol), PyBOP® (46 mg, 0.088 mmol), DIEA (28 µL, 0.16 mmol) in dry $CH_2Cl_2$:DMF (2:0.1 mL) was stirred at RT for 15 minutes. To this solution of activated acid was added cyclopropylmethanamine (7.1 mg, 0.10 mmol). After 30 minutes, 1.0 equivalent of DIEA and 0.55 equivalents of PyBOP® were added. After stirring the solution for 15 minutes, 0.65 equivalents of cyclopropylmethanamine were added and the mixture was stirred for an additional 30 minutes. The solvent was removed in vacuo and the crude product was purified using prep HPLC (20-45_90 mins) to afford 2-(3-(4-(1H-indazol-5-ylamino)quinazolin-2-yl)phenoxy)-N-(cyclopropylmethyl)acetamide. (60 mg, 0.13 mmol, 81%)

Example 70

(3R)-tert-butyl 3-(2-(3-(4-(1H-indazol-5-ylamino)quinazolin-2-yl)phenoxy)acetamido)pyrrolidine-1-carboxylate

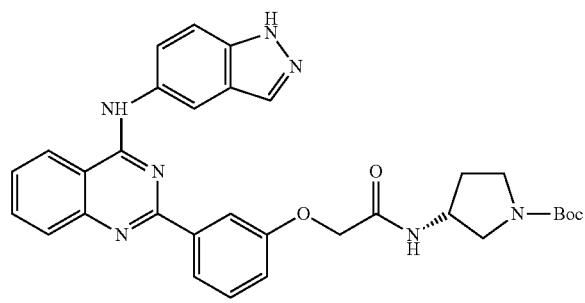

A suspension of 2-(3-(4-(1H-indazol-5-ylamino)quinazolin-2-yl)phenoxy)acetic acid (67 mg, 0.13 mmol), PyBOP® (37 mg, 0.072 mmol), DIEA (23 µL, 0.13 mmol) in dry $CH_2Cl_2$:DMF (2:0.1 mL) was stirred at RT for 15 minutes. To this solution of activated acid was added (R)-tert-butyl 3-aminopyrrolidine-1-carboxylate (16 mg, 0.084 mmol). After 30 minutes, 1.0 equivalent of DIEA and 0.55 equivalent of PyBOP® were added. After stirring the solution for 15 minutes, 0.65 equivalent of (R)-tert-butyl 3-aminopyrrolidine-1-carboxylate were added and the mixture was stirred for an additional 30 minutes. The solvent was removed in vacuo to afford the crude (3R)-tert-butyl 3-(2-(3-(4-(1H-indazol-5-ylamino)quinazolin-2-yl)phenoxy)acetamido)pyrrolidine-1-carboxylate.

Example 71

2-(3-(4-(1H-indazol-5-ylamino)quinazolin-2-yl)phenoxy)-1-N—((R)-pyrrolidin-3-yl)acetamide

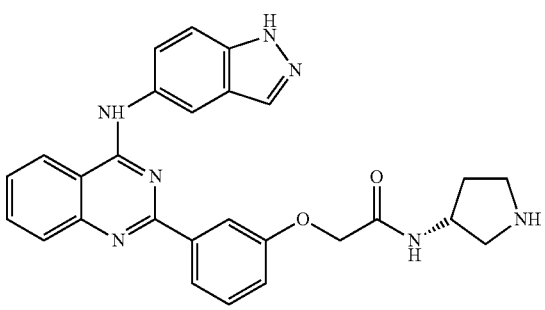

To (3R)-tert-butyl 3-(2-(3-(4-(1H-indazol-5-ylamino)quinazolin-2-yl)phenoxy)acetamido)pyrrolidine-1-carboxylate was added a solution of 1:1 TFA:$CH_2Cl_2$ (3 mL) and stirred at RT for 2 h. The reaction mixture was concentrated in vacuo and the crude product was purified by prep HPLC (method 10-35_90 mins) to afford 2-(3-(4-(1H-indazol-5-ylamino)quinazolin-2-yl)phenoxy)-N—((R)-pyrrolidin-3-yl)acetamide. (45 mg, 0.094 mmol)

Example 72

(3S)-tert-butyl 3-(2-(3-(4-(1H-indazol-5-ylamino)quinazolin-2-yl)phenoxy)acetamido)pyrrolidine-1-carboxylate

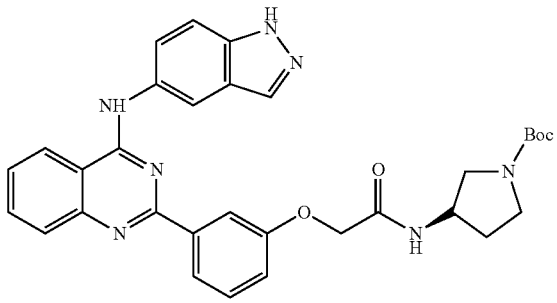

A suspension of 2-(3-(4-(1H-indazol-5-ylamino)quinazolin-2-yl)phenoxy)acetic acid (50 mg, 0.098 mmol), PyBOP® (28 mg, 0.054 mmol), DIEA (17 µL, 0.098 mmol) in dry $CH_2Cl_2$:DMF (2:0.1 mL) was stirred at RT for 15 minutes. To this solution of activated acid was added (S)-tert-butyl 3-aminopyrrolidine-1-carboxylate (16 mg, 0.084 mmol). After 30 minutes, 1.0 equivalent of DIEA and 0.55 equivalent of PyBOP® were added. After stirring the solution for 15 minutes, 0.65 equivalent of (S)-tert-butyl 3-aminopyrrolidine-1- carboxylate were added and the mixture was stirred for an additional 30 minutes. The solvent was removed in vacuo to afford the crude (3S)-tert-butyl 3-(2-(3-(4-(1H-indazol-5-ylamino)quinazolin-2-yl)phenoxy)acetamido)pyrrolidine-1-carboxylate.

Example 73

2-(3-(4-(1H-indazol-5-ylamino)quinazolin-2-yl)phenoxy)-N—((S)-pyrrolidin-3-yl)acetamide

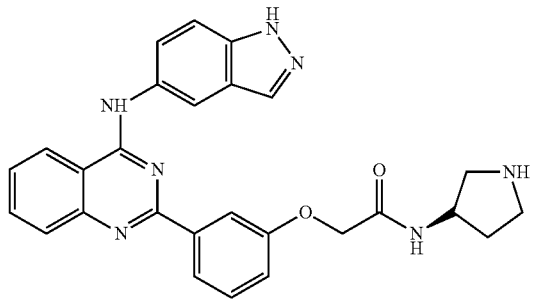

To (3S)-tert-butyl 3-(2-(3-(4-(1H-indazol-5-ylamino)quinazolin-2-yl)phenoxy)acetamido)pyrrolidine-1-carboxylate was added a solution of 1:1 TFA:CH$_2$Cl$_2$ (3 mL) and stirred at RT for 2 h. The reaction mixture was concentrated in vacuo and the crude product was purified by prep HPLC (method 10-35_90 mins) to afford 2-(3-(4-(1H-indazol-5-ylamino)quinazolin-2-yl)phenoxy)-N—((S)-pyrrolidin-3-yl)acetamide. (33 mg, 0.069 mmol)

Example 74

2-(3-(4-(1H-indazol-5-ylamino)quinazolin-2-yl)phenoxy)-N-(1-methylpiperidin-4-yl)acetamide

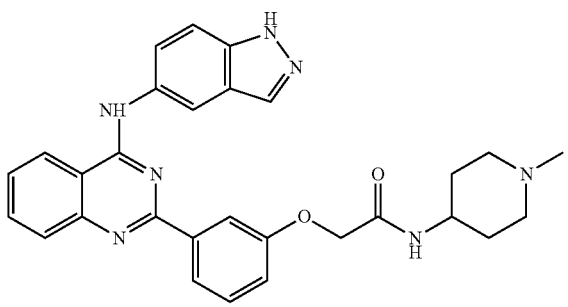 [SMILES: CN1CCC(NC(=O)COc2cccc(-c3nc(Nc4ccc5[nH]ncc5c4)c4ccccc4n3)c2)CC1]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 μL, 0.14 mmol) in dry CH$_2$Cl$_2$:DMF (2:0.1 mL) was stirred at RT for 15 minutes. To this solution of activated acid was added 1-methylpiperidin-4-amine (10 mg, 0.091 mmol). After 30 minutes, 1.0 equivalent of DIEA and 0.55 equivalents of PyBOP® were added. After stirring the solution for 15 minutes, 0.65 equivalents of 1-methylpiperidin-4-amine were added and the mixture was stirred for an additional 30 minutes. The solvent was removed in vacuo and the crude product was purified using prep HPLC (10-35_90 mins) to afford 2-(3-(4-(1H-indazol-5-ylamino)quinazolin-2-yl)phenoxy)-N-(1-methylpiperidin-4-yl)acetamide. (49 mg, 0.097 mmol, 69%)

Example 75

2-(3-(4-(1H-indazol-5-ylamino)quinazolin-2-yl)phenoxy)-N-(tetrahydro-2H-pyran-4-yl)acetamide

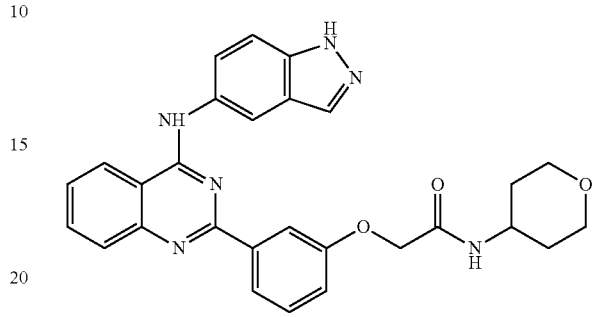

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 μL, 0.14 mmol) in dry CH$_2$Cl$_2$:DMF (2:0.1 mL) was stirred at RT for 15 minutes. To this solution of activated acid was added tetrahydro-2H-pyran-4-amine hydrochloride (13 mg, 0.091 mmol). After 30 minutes, 1.0 equivalent of DIEA and 0.55 equivalents of PyBOP® were added. After stirring the solution for 15 minutes, 0.65 equivalents of tetrahydro-2H-pyran-4-amine hydrochloride were added and the mixture was stirred for an additional 30 minutes. The solvent was removed in vacuo and the crude product was purified using prep HPLC (15-40_90 mins) to afford 2-(3-(4-(1H-indazol-5-ylamino)quinazolin-2-yl)phenoxy)-N-(tetrahydro-2H-pyran-4-yl)acetamide. (32 mg, 0.065 mmol, 46%)

Example 76

2-(3-(4-(1H-indazol-5-ylamino)quinazolin-2-yl)phenoxy)-N—((R)-tetrahydrofuran-3-yl)acetamide

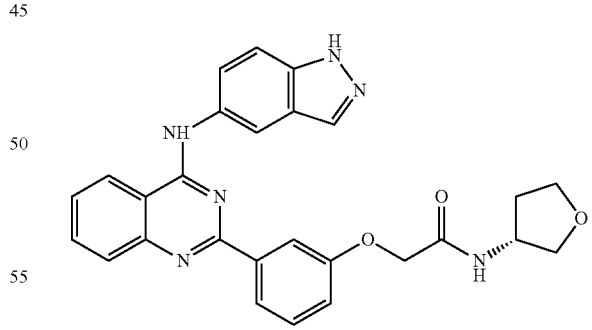

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 μL, 0.14 mmol) in dry CH$_2$Cl$_2$:DMF (2:0.1 mL) was stirred at RT for 15 minutes. To this solution of activated acid was added (R)-tetrahydrofuran-3-aminium 4-methylbenzenesulfonate (24 mg, 0.091 mmol). After 30 minutes, 1.0 equivalent of DIEA and 0.55 equivalents of PyBOP® were added. After stirring the solution for 15 minutes, 0.65 equivalents of (R)-tetrahydrofuran-3- aminium 4-methylbenzenesulfonate were added and the mixture was stirred for an additional 30 minutes. The solvent was removed in vacuo and the crude product was purified using prep HPLC (15-40__90 mins) to afford 2-(3-(4-(1H-indazol-5-ylamino)quinazolin-2-yl)phenoxy)-N—((R)-tetrahydrofuran-3-yl)acetamide. (41 mg, 0.085 mmol, 61%).

Example 77

2-(3-(4-(1H-indazol-5-ylamino)quinazolin-2-yl)phenoxy)-1-(piperidin-1-yl)ethanone

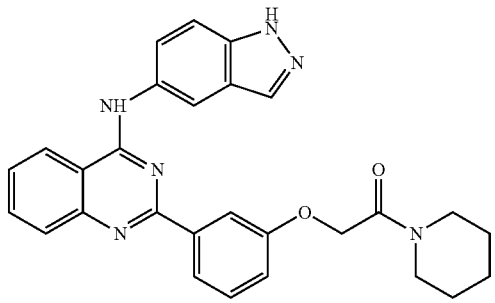 [SMILES: O=C(COc1cccc(-c2nc(Nc3ccc4[nH]ncc4c3)c3ccccc3n2)c1)N1CCCCC1]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 µL, 0.14 mmol) in dry $CH_2Cl_2$:DMF (2:0.1 mL) was stirred at RT for 15 minutes. To this solution of activated acid was added piperidine (7.7 mg, 0.091 mmol). After 30 minutes, 1.0 equivalent of DIEA and 0.55 equivalents of PyBOP® were added. After stirring the solution for 15 minutes, 0.65 equivalents of piperidine were added and the mixture was stirred for an additional 30 minutes. The solvent was removed in vacuo and the crude product was purified using prep HPLC (25-55__90 mins) to afford 2-(3-(4-(1H-indazol-5-ylamino)quinazolin-2-yl)phenoxy)-1-(piperidin-1-yl)ethanone. (29 mg, 0.061 mmol, 43%).

Example 78

2-(3-(4-(1H-indazol-5-ylamino)quinazolin-2-yl)phenoxy)-N-tert-butylacetamide

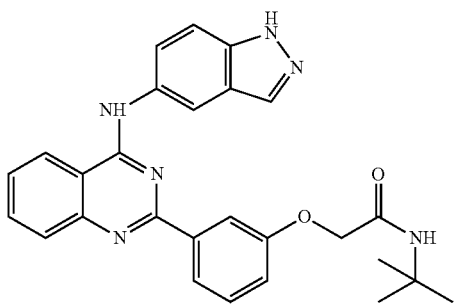 [SMILES: CC(C)(C)NC(=O)COc1cccc(-c2nc(Nc3ccc4[nH]ncc4c3)c3ccccc3n2)c1]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 µL, 0.14 mmol) in dry $CH_2Cl_2$:DMF (2:0.1 mL) was stirred at RT for 15 minutes. To this solution of activated acid was added 2-methylpropan-2-amine (6.7 mg, 0.091 mmol). After 30 minutes, 1.0 equivalent of DIEA and 0.55 equivalents of PyBOP® were added. After stirring the solution for 15 minutes, 0.65 equivalents of 2-methylpropan-2-amine were added and the mixture was stirred for an additional 30 minutes. The solvent was removed in vacuo and the crude product was purified using prep HPLC (25-55__90 mins) to afford 2-(3-(4-(1H-indazol-5-ylamino)quinazolin-2-yl)phenoxy)-N-tert-butylacetamide. (36 mg, 0.061 mmol, 55%).

Example 79

2-(3-(4-(1H-indazol-5-ylamino)quinazolin-2-yl)phenoxy)-N-ethylacetamide

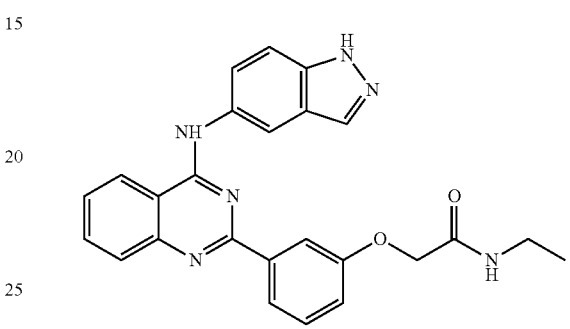

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 µL, 0.14 mmol) in dry $CH_2Cl_2$:DMF (2:0.1 mL) was stirred at RT for 15 minutes. To this solution of activated acid was added ethanamine hydrochloride (7.4 mg, 0.091 mmol). After 30 minutes, 1.0 equivalent of DIEA and 0.55 equivalents of PyBOP® were added. After stirring the solution for 15 minutes, 0.65 equivalents of ethanamine hydrochloride were added and the mixture was stirred for an additional 30 minutes. The solvent was removed in vacuo and the crude product was purified using prep HPLC (15-40__90 mins) to afford 2-(3-(4-(1H-indazol-5-ylamino)quinazolin-2-yl)phenoxy)-N-ethylacetamide. (19 mg, 0.043 mmol, 31%)

Example 80

2-(3-(4-(1H-indazol-5-ylamino)quinazolin-2-yl)phenoxy)-N-cyclobutylacetamide

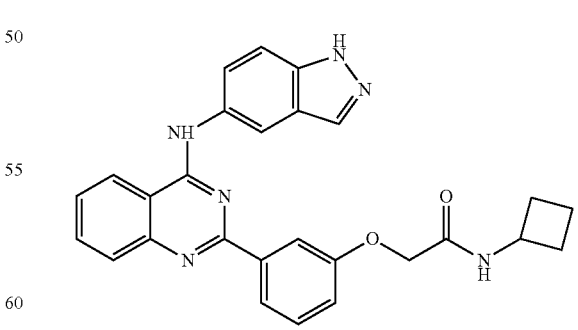

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 µL, 0.14 mmol) in dry $CH_2Cl_2$:DMF (2:0.1 mL) was stirred at RT for 15 minutes. To this solution of activated acid was added cyclobutanamine (6.5 mg, 0.091 mmol). After 30 minutes, 1.0 equivalent of DIEA and 0.55 equivalents of PyBOP® were added. After stirring the solution for 15 minutes, 0.65 equivalents of cyclobutanamine were added and the mixture was stirred for an additional 30 minutes. The solvent was removed in vacuo and the crude product was purified using prep HPLC (25-50_90 mins) to afford 2-(3-(4-(1H-indazol-5-ylamino)quinazolin-2-yl)phenoxy)-N-cyclobutylacetamide. (36 mg, 0.077 mmol, 55%).

Example 81

2-(3-(4-(1H-indazol-5-ylamino)quinazolin-2-yl)phenoxy)-N-(cyanomethyl)acetamide

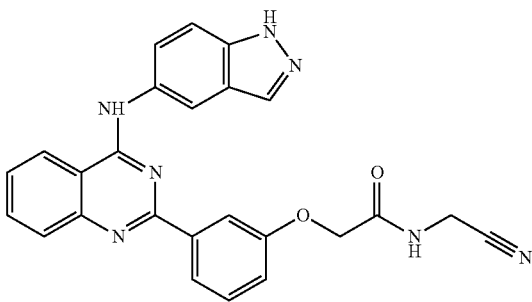 [SMILES: N#CCNC(=O)COc1cccc(-c2nc(Nc3ccc4[nH]ncc4c3)c3ccccc3n2)c1]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 µL, 0.14 mmol) in dry CH$_2$Cl$_2$:DMF (2:0.1 mL) was stirred at RT for 15 minutes. To this solution of activated acid was added aminoacetonitrile monosulfate (14 mg, 0.091 mmol). After 30 minutes, 1.0 equivalent of DIEA and 0.55 equivalents of PyBOP® were added. After stirring the solution for 15 minutes, 0.65 equivalents of aminoacetonitrile monosulfate were added and the mixture was stirred for an additional 30 minutes. The solvent was removed in vacuo and the crude product was purified using prep HPLC (15-40_90 mins) to afford 2-(3-(4-(1H-indazol-5-ylamino)quinazolin-2-yl)phenoxy)-N-(cyanomethyl)acetamide. (12 mg, 0.027 mmol, 19%).

Example 82

2-(3-(4-(1H-indazol-5-ylamino)quinazolin-2-yl)phenoxy)-N-isopropylacetamide

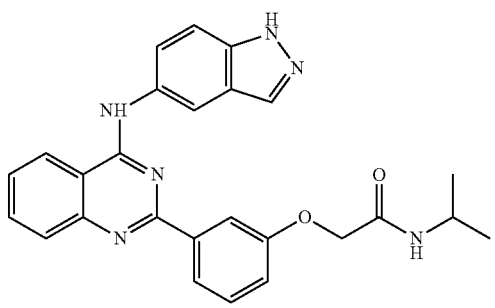 [SMILES: CC(C)NC(=O)COc1cccc(-c2nc(Nc3ccc4[nH]ncc4c3)c3ccccc3n2)c1]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 µL, 0.14 mmol) in dry CH$_2$Cl$_2$:DMF (2:0.1 mL) was stirred at RT for 15 minutes. To this solution of activated acid was added propan-2-amine (5.4 mg, 0.091 mmol). After 30 minutes, 1.0 equivalent of DIEA and 0.55 equivalents of PyBOP® were added. After stirring the solution for 15 minutes, 0.65 equivalents of propan-2-amine were added and the mixture was stirred for an additional 30 minutes. The solvent was removed in vacuo and the crude product was purified using prep HPLC (25-50_90 mins) to afford 2-(3-(4-(1H-indazol-5-ylamino)quinazolin-2-yl)phenoxy)-N-isopropylacetamide. (40 mg, 0.086 mmol, 61%).

Example 83

2-(3-(4-(1H-indazol-5-ylamino)quinazolin-2-yl)phenoxy)-N—(R)-sec-butylacetamide

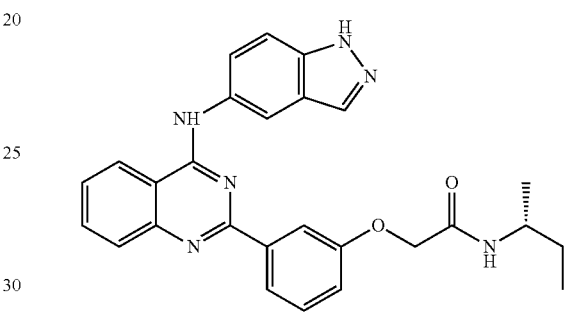

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 µL, 0.14 mmol) in dry CH$_2$Cl$_2$:DMF (2:0.1 mL) was stirred at RT for 15 minutes. To this solution of activated acid was added (R)-butan-2-amine (6.6 mg, 0.091 mmol). After 30 minutes, 1.0 equivalent of DIEA and 0.55 equivalents of PyBOP® were added. After stirring the solution for 15 minutes, 0.65 equivalents of (R)-butan-2-amine were added and the mixture was stirred for an additional 30 minutes. The solvent was removed in vacuo and the crude product was purified using prep HPLC (15-40_90 mins) to afford 2-(3-(4-(1H-indazol-5-ylamino)quinazolin-2-yl)phenoxy)-N—(R)-sec-butylacetamide. (34 mg, 0.073 mmol, 52%).

Example 84

2-(3-(4-(1H-indazol-5-ylamino)quinazolin-2-yl)phenoxy)acetamide

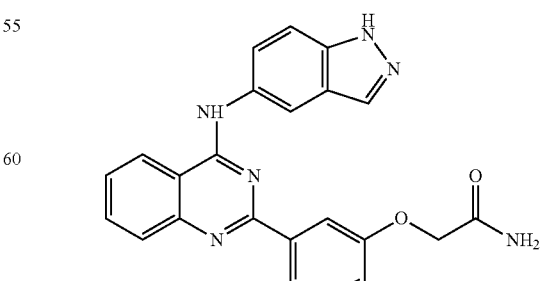

To a solution of 2-(3-(4-(1H-indazol-5-ylamino)quinazolin-2-yl)phenoxy)acetic acid (70 mg, 0.14 mmol) in dry $CH_2Cl_2$:DMF (2.0:0.1 mL), added DIEA (24 μL, 0.14 mmol) and PyBOP® (40 mg, 0.077 mmol). After stirring the mixture at RT for 15 minutes, ammonia was bubbled through the solution for 15 minutes. Added another 1.0 equivalent of DIEA and 0.55 equivalents of PyBOP® after stirring the solution for 15 minutes, followed by ammonia bubbling for an additional 15 minutes. The solvent was removed in vacuo and the crude material was purified by prep HPLC (method 10-35_90 mins) to afford 2-(3-(4-(1H-indazol-5-ylamino)quinazolin-2-yl)phenoxy)acetamide. (27 mg, 0.066 mol, 47%).

Example 85

2-(3-(4-(1H-indazol-5-ylamino)quinazolin-2-yl)phenoxy)-N-(2,2,2-trifluoroethyl)acetamide

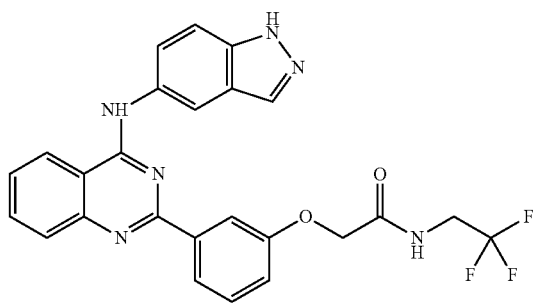 [SMILES: O=C(COc1cccc(-c2nc(Nc3ccc4[nH]ncc4c3)c3ccccc3n2)c1)NCC(F)(F)F]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 μL, 0.14 mmol) in dry $CH_2Cl_2$:DMF (2:0.1 mL) was stirred at RT for 15 minutes. To this solution of activated acid was added 2,2,2-trifluoroethanamine (9.0 mg, 0.091 mmol). After 30 minutes, 1.0 equivalent of DIEA and 0.55 equivalents of PyBOP® were added. After stirring the solution for 15 minutes, 0.65 equivalents of 2,2,2-trifluoroethanamine were added and the mixture was stirred for an additional 30 minutes. The solvent was removed in vacuo and the crude product was purified using prep HPLC (25-50_90 mins) to afford 2-(3-(4-(1H-indazol-5-ylamino) quinazolin-2-yl)phenoxy)-N-(2,2,2-trifluoroethyl)acetamide. (16 mg, 0.032 mmol, 23%).

Example 86

2-(3-(4-(1H-indazol-5-ylamino)quinazolin-2-yl)phenoxy)-N-cyclohexylacetamide

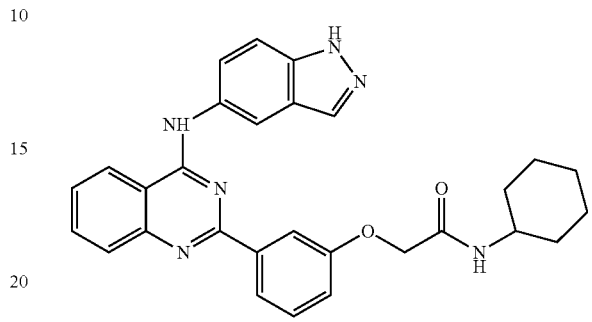

A suspension of 2-(3-(4-(1H-indazol-5-ylamino)quinazolin-2-yl)phenoxy)acetic acid 0 (70 mg, 0.14 mmol), PyBOP® (40 mg, 0.077 mmol), DIEA (24 μL, 0.14 mmol) in dry $CH_2Cl_2$:DMF (2:0.1 mL) was stirred at RT for 15 minutes. To this solution of activated acid was added cyclohexanamine (9.0 mg, 0.091 mmol). After 30 minutes, 1.0 equivalent of DIEA and 0.55 equivalents of PyBOP® were added. After stirring the solution for 15 minutes, 0.65 equivalents of cyclohexanamine were added and the mixture was stirred for an additional 30 minutes. The solvent was removed in vacuo and the crude product was purified using prep HPLC (20-50_90 mins) to afford 2-(3-(4-(1H-indazol-5-ylamino)quinazolin-2-yl)phenoxy)-N-cyclohexylacetamide. (27 mg, 0.055 mmol, 39%).

Example 87

2-(3-(4-(1H-indazol-5-ylamino)quinazolin-2-yl)phenoxy)-N-(2-methylbut-3-yn-2-yl)acetamide

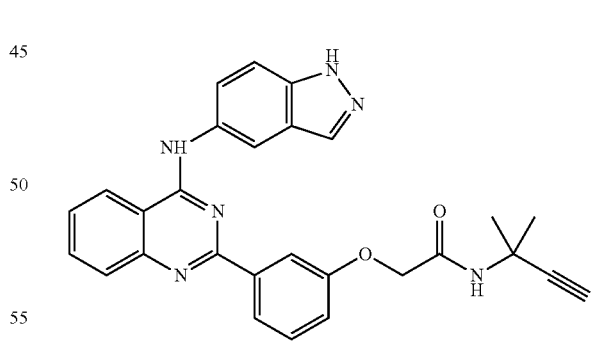

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 μL, 0.14 mmol) in dry $CH_2Cl_2$:DMF (2:0.1 mL) was stirred at RT for 15 minutes. To this solution of activated acid was added 2-methylbut-3-yn-2-amine (7.6 mg, 0.091 mmol). After 30 minutes, 1.0 equivalent of DIEA and 0.55 equivalents of PyBOP® were added. After stirring the solution for 15 minutes, 0.65 equivalents of 2-methylbut-3-yn-2-amine were added and the mixture was stirred for an additional 30 minutes. The solvent was removed in vacuo and the crude product was purified using prep HPLC (20-45_90 mins) to afford 2-(3-(4-(1H-indazol-5-ylamino)quinazolin-2-yl)phenoxy)-N-(2-methylbut-3-yn-2-yl)acetamide. (22 mg, 0.046 mmol, 33%).

Example 88

2-(3-(4-(1H-indazol-5-ylamino)quinazolin-2-yl)phenoxy)-N-neopentylacetamide

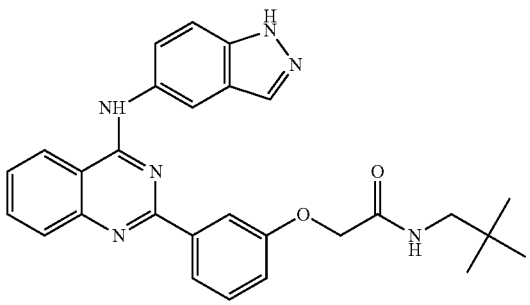 [SMILES: CC(C)(C)CNC(=O)COc1cccc(-c2nc(Nc3ccc4[nH]ncc4c3)c3ccccc3n2)c1]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 μL, 0.14 mmol) in dry CH$_2$Cl$_2$:DMF (2:0.1 mL) was stirred at RT for 15 minutes. To this solution of activated acid was added 2,2-dimethylpropan-1-amine (7.9 mg, 0.091 mmol). After 30 minutes, 1.0 equivalent of DIEA and 0.55 equivalents of PyBOP® were added. After stirring the solution for 15 minutes, 0.65 equivalents of 2,2-dimethylpropan-1-amine were added and the mixture was stirred for an additional 30 minutes. The solvent was removed in vacuo and the crude product was purified using prep HPLC (25-50_90 mins) to afford 2-(3-(4-(1H-indazol-5-ylamino)quinazolin-2-yl)phenoxy)-N-neopentylacetamide. (40 mg, 0.083 mmol, 59%).

Example 89

2-(3-(4-(1H-indazol-5-ylamino)quinazolin-2-yl)phenoxy)-N-(prop-2-ynyl)acetamide

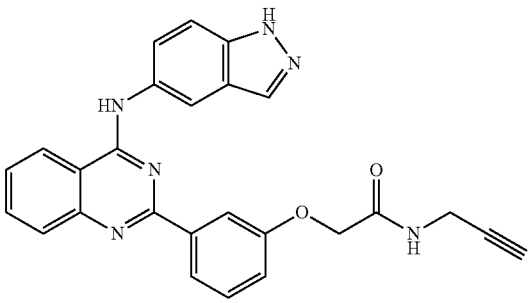 [SMILES: C#CCNC(=O)COc1cccc(-c2nc(Nc3ccc4[nH]ncc4c3)c3ccccc3n2)c1]

A suspension of 2-(3-(4-(1H-indazol-5-ylamino)quinazolin-2-yl)phenoxy)acetic acid (70 mg, 0.14 mmol), PyBOP® (40 mg, 0.077 mmol), DIEA (24 μL, 0.14 mmol) in dry CH$_2$Cl$_2$:DMF (2:0.1 mL) was stirred at RT for 15 minutes. To this solution of activated acid was added prop-2-yn-1-amine (5.0 mg, 0.091 mmol). After 30 minutes, 1.0 equivalent of DIEA and 0.55 equivalents of PyBOP® were added. After stirring the solution for 15 minutes, 0.65 equivalents of prop-2-yn-1-amine were added and the mixture was stirred for an additional 30 minutes. The solvent was removed in vacuo and the crude product was purified using prep HPLC (15-28_90 mins and 0-15_90 mins) to afford 2-(3-(4-(1H-indazol-5-ylamino)quinazolin-2-yl)phenoxy)-N-(prop-2-ynyl)acetamide. (14 mg, 0.031 mmol, 22%).

Example 90

2-Bromo-N-isopropylacetamide

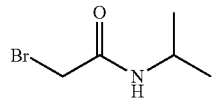

A solution of iso-propyl amine (5.0 g, 7.20 mL, 84.6 mmole) in 63 mL of ethylene dichloride was cooled to −10° C. To this was added a solution of α-bromoacetylbromide (8.53 g, 3.68 mL, 42.3 mmole) in 10.5 mL of ethylene dichloride. The reaction mixture was stirred for 10 mins. The isopropylammonium hydrobromide was filtered from the mixture and the filtrate then concentrated in vacuo to give 2-bromo-N-isopropylacetamide as a white solid. (5.30 g, 29.4 mmol 70%).

Example 91 tert-Butyl 5-(2-(3-(2-(isopropylamino)-2-oxoethoxy)phenyl)quinazolin-4-ylamino)-1H-indazole-1-carboxylate

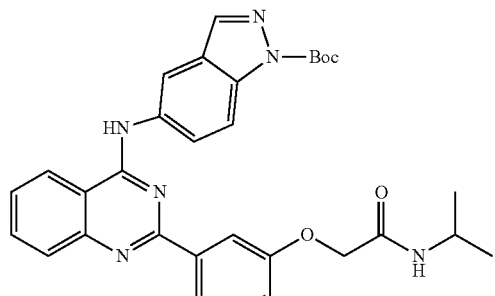

A solution of tert-butyl 5-(2-(3-hydroxyphenyl)quinazolin-4-ylamino)-1H-indazole-1-carboxylate (0.3 g, 0.66 mmol), N-isopropylbromoacetamide (0.132 g, 0.726 mmole), and K$_2$CO$_3$ (0.183 g, 1.32 mmole) in DMF (3.6 mL) was heated overnight at 30° C. The crude product was poured onto ice-water (ca. 50 mL) and the suspension was stirred for approximately 0.5 h, filtered and dried (Na$_2$SO$_4$). The crude product was recrystallized from absolute EtOH (10 mL) to afford tert-butyl 5-(2-(3-(2-(isopropylamino)-2-oxoethoxy)-phenyl)quinazolin-4-ylamino)-1H-indazole-1-carboxylate (0.160 g, mmol, 45%).

Example 92

2-(3-(4-(1H-indazol-5-ylamino)quinazolin-2-yl)phenoxy)-N-isopropylacetamide

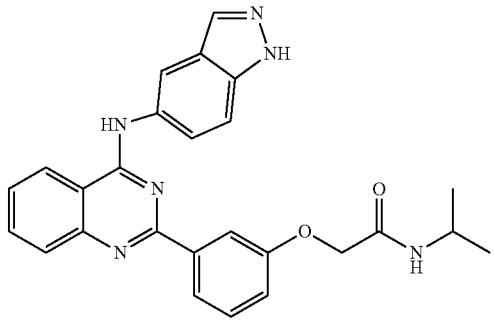 [SMILES: CC(C)NC(=O)COc1cccc(-c2nc(Nc3ccc4[nH]ncc4c3)c3ccccc3n2)c1]

A solution of tert-butyl 5-(2-(3-(2-(isopropylamino)-2-oxoethoxy)phenyl)-quinazolin-4-ylamino)-1H-indazole-1-carboxylate (4.30 g, 7.79 mmole) in TFA (20 mL) and $CH_2Cl_2$ (20 mL) was stirred at room temperature for 1 h. The reaction mixture was concentrated in vacuo, and to the crude residue was added ca. 50 mL $Et_2O$. The resulting bright yellow suspension was stirred for 15 minutes and filtered and dried giving 2-(3-(4-(1H-indazol-5-ylamino)quinazolin-2-yl)phenoxy)-N-isopropylacetamide trifluoroacetate salt. (4.1 g, mmol, %).

Example 93

4,5-Dimethoxy-2-nitrobenzamide

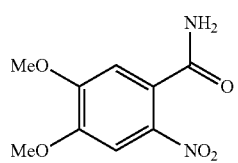 [SMILES: COc1cc(C(N)=O)c([N+](=O)[O-])cc1OC]

To a suspension of 4,5-dimethoxy-2-nitrobenzoic acid (4.95 g, 21.8 mmol) in anhydrous benzene (30 mL) was added $SOCl_2$ (1.75 mL). The resulting mixture was heated at 75° C. for 3.5 h. The solvent was evaporated under reduced pressure and the residue was dried under high vacuum. The residue was dissolved in anhydrous THF (30 mL) and cooled to 0° C. To the cooled solution was added a saturated solution of ammonia in THF (ca. 50 mL). A precipitate began to form and stirring was continued for 12 hours at RT. The solvent was removed under reduced pressure and the residue was dried under high vacuum to give 4,5-dimethoxy-2-nitrobenzamide which was used without further purification (6.0 g). HPLC retention time 4.438 mins.

Example 94

2-Amino-4,5-dimethoxybenzamide

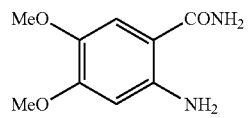

A suspension of 4,5-dimethoxy-2-nitrobenzamide (5.8 g, 25.6 mmol) in a 1:1 mixture of DME/MeOH (total volume 200 ml) and 10% Pd/C (0.7 g) was hydrogenated at RT using a balloon filled with hydrogen gas. The reaction was stirred for 16 h and the reaction mixture filtered through Celite®. The pad of Celite® was washed with a 1:1 mixture of MeOH/$CH_2Cl_2$ (200 mL). The filtrate was then concentrated in vacuo and dried under high vacuum overnight to give 2-amino-4,5-dimethoxybenzamide. (5.0 g, 25.5 mmol, 99%). HPLC retention time 2.303 mins.

Example 95

4,5-Di-methoxy-2-(3-fluoro-4-(phenyl)phenyl)benzamide

To a solution of 2-amino-4,5-dimethoxybenzamide (3.1 g, 15.8 mmol) in $CHCl_3$ (100 mL) was added acid chloride (3.41 g, 15.8 mmol) as a solution in $CHCl_3$ (40 mL) and pyridine (12 mL). The resulting mixture was stirred at RT for 16 h. The mixture was then heated at 55° C. for 2 h. The volatiles were removed in vacuo and the residue was triturated with water/ 1N HCl resulting in a solid which was washed with 1N HCl and water. The solid was dried under vacuum and washed with $CH_2Cl_2$ and dried under vacuum to give the desired product which was used directly in the next step (3.0 g). HPLC retention time 8.33 mins.

Example 96

2-(3-fluoro-4-(phenyl)phenyl)-6,7-dimethoxyquinazolin-4(3H)-one

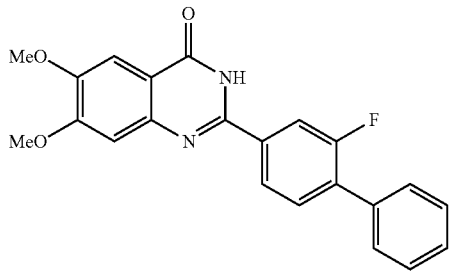

A suspension of the 4,5-Di-methoxy-2-(3-fluoro-4-(phenyl)phenyl)-benzamide (4.25 g) in 2N NaOH (120 mL) was heated at 105° C. for 5 h. The mixture was allowed to cool to RT. The mixture was neutralized with 6N HCl with cooling. A solid separated out which was collected via filtration and washed with $Et_2O$ and hexane to give the desired product 2-(3-fluoro-4-(phenyl)phenyl)-6,7-dimethoxyquinazolin-4 (3H)-one (4.00 g, 10.6 mmol, 67% over two steps). HPLC retention time 7.9 mins.

Example 97

2-(3-fluoro-4-(phenyl)phenyl)-6-hydroxy-7-methoxyquinazolin-4(3H)-one

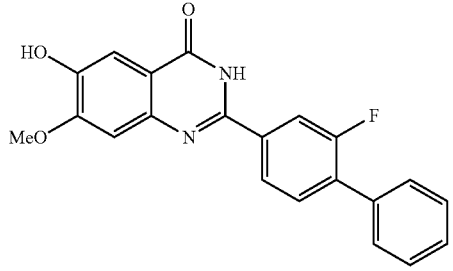 [SMILES: COc1cc2nc(-c3ccc(-c4ccccc4)c(F)c3)[nH]c(=O)c2cc1O]

A mixture of 2-(3-fluoro-4-(phenyl)phenyl)-6,7-dimethoxyquinazolin-4(3H)-one (3.83 g, 10.2 mmol) and methionine (2.1 g, 14.1 mmol) in methanesulfonic acid was heated 110° C. for 4 h. Additional methionine (0.75 g) was added and heating was continued for another 1.5 h. The mixture was allowed to cool to RT and was poured into ice-water (300 mL). A solid separated out, which was collected via filtration. The solid was suspended in sat. $NaHCO_3$ and the after the effervescence subsided the solid was again collected via filtration. The solid was washed with water and EtOH to give the desired product 2-(3-fluoro-4-(phenyl)phenyl)-6-hydroxy-7-methoxyquinazolin-4(3H)-one (3.2 g, 8.83 mmol, 87%). HPLC retention time 7.06 mins.

Example 98

2-(3-fluoro-4-(phenyl)phenyl)-7-methoxy-4-oxo-3,4-dihydroquinazolin-6-yl acetate

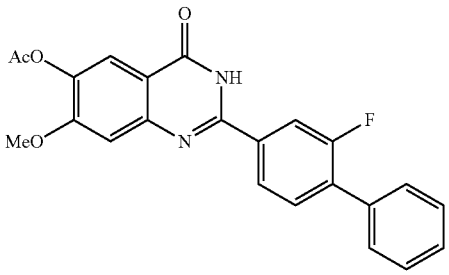 [SMILES: COc1cc2nc(-c3ccc(-c4ccccc4)c(F)c3)[nH]c(=O)c2cc1OC(C)=O]

A mixture of 2-(3-fluoro-4-(phenyl)phenyl)-6-hydroxy-7-methoxyquinazolin-4(3H)-one (3.2 g, 8.83 mmol), $Ac_2O$ (40 mL) and pyridine (5 mL) was heated at 105° C. for 4 h. The mixture was poured onto ice-water (300 mL). The mixture was stirred for 1 h, upon which the solid which had formed was collected via filtration. The solid was washed with water and EtOH and dried under vacuum to give the desired product 2-(3-fluoro-4-(phenyl)phenyl)-7-methoxy-4-oxo-3,4-dihydroquinazolin-6-yl acetate. MS 405.2 (M+1) HPLC retention time 8.23 mins.

Example 99

4-chloro-2-(3-fluoro-4-(phenyl)phenyl)-7-methoxyquinazolin-6-yl acetate

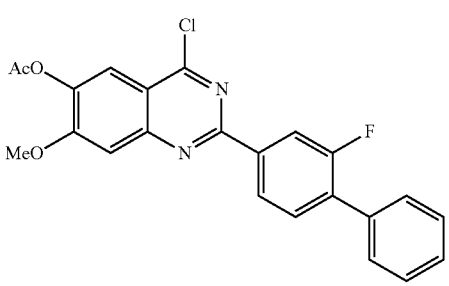 [SMILES: COc1cc2nc(-c3ccc(-c4ccccc4)c(F)c3)nc(Cl)c2cc1OC(C)=O]

A suspension of 2-(3-fluoro-4-(phenyl)phenyl)-7-methoxy-4-oxo-3,4-dihydroquinazolin-6-yl acetate (3.0 g, 7.42 mmol) in $SOCl_2$ (60 mL) with DMF (1.4 mL) was heated at reflux for 5 h. the mixture was allowed to cool to RT and the volatiles were removed in vacuo. The residue was taken up in $CHCl_3$ (300 mL) and washed with water (100 mL), sat. $NaHCO_3$ (100 mL), water (100 mL) and brine (100 mL). The organic layer was dried ($Na_2SO_4$), filtered and concentrated in vacuo to give the desired product 4-chloro-2-(3-fluoro-4-

(phenyl)phenyl)-7-methoxyquinazolin-6-yl acetate (3.14 g, 7.42 mmol, 100%). HPLC retention time 11.30 minutes (5-95-13 method).

Example 100 tert-butyl 5-(6-acetoxy-2-(3-fluoro-4-(phenyl)phenyl)-7-methoxyquinazolin-4-ylamino)-1H-indazole-1-carboxylate

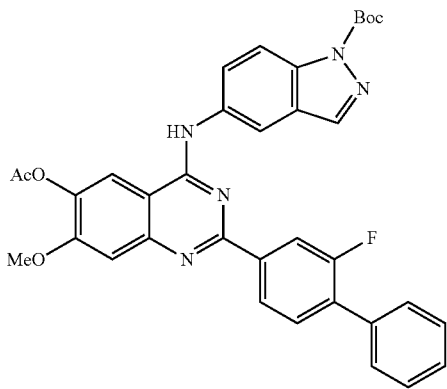 [SMILES: COc1cc2nc(-c3ccc(-c4ccccc4)c(F)c3)nc(Nc3ccc4c(cnn4C(=O)OC(C)(C)C)c3)c2cc1OC(C)=O]

A mixture of 4-chloro-2-(3-fluoro-4-(phenyl)phenyl)-7-methoxyquinazolin-6-yl acetate (3.14 g, 7.42 mmol) and tert-butyl 5-amino-1H-indazole-1-carboxylate (1.85 g, 7.93 mmol) in IPA (180 mL) was heated at 95° C. for 5 h. The mixture was allowed to cool to RT and the solid was collected via filtration. The solid was subjected to flash chromatography (SiO$_2$, CH$_2$Cl$_2$/MeOH) to give the desired compound tert-butyl 5-(6-acetoxy-2-(3-fluoro-4-(phenyl)phenyl)-7-methoxyquinazolin-4-ylamino)-1H-indazole-1-carboxylate (2.70 g, 4.36 mmol, 59%). MS 620.4 (M+1). HPLC retention time 8.10 mins (5-95-13 method).

Example 101 tert-butyl 5-(2-(3-fluoro-4-(phenyl)phenyl)-6-hydroxy-7-methoxyquinazolin-4-ylamino)-1H-indazole-1-carboxylate

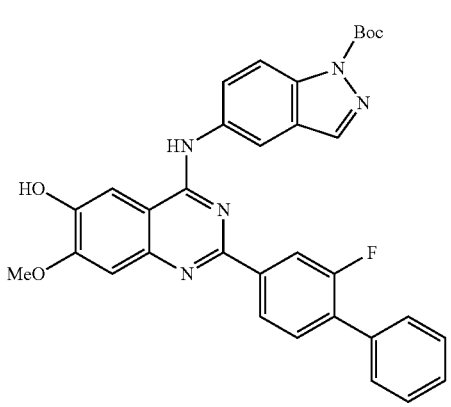 [SMILES: COc1cc2nc(-c3ccc(-c4ccccc4)c(F)c3)nc(Nc3ccc4c(cnn4C(=O)OC(C)(C)C)c3)c2cc1O]

A mixture of tert-butyl 5-(6-acetoxy-2-(3-fluoro-4-(phenyl)phenyl)-7-methoxyquinazolin-4-ylamino)-1H-indazole-1-carboxylate (2.6 g) and 28% NH$_4$OH (2.8 mL) in MeOH (160 mL) was stirred at RT for 24 h. A solid separated out which was collected via filtration. The solid was triturated with hexane and dried under vacuum to give the desired compound tert-butyl 5-(2-(3-fluoro-4-(phenyl)phenyl)-6-hydroxy-7-methoxyquinazolin-4-ylamino)-1H-indazole-1-carboxylate (0.6 g). MS 578.4 (M+1). HPLC retention time 7.66 mins.

Example 102 tert-butyl 5-(6-(2-chloroethoxy)-2-(3-fluoro-4-(phenyl)phenyl)-7-methoxyquinazolin-4-ylamino)-1H-indazole-1-carboxylate

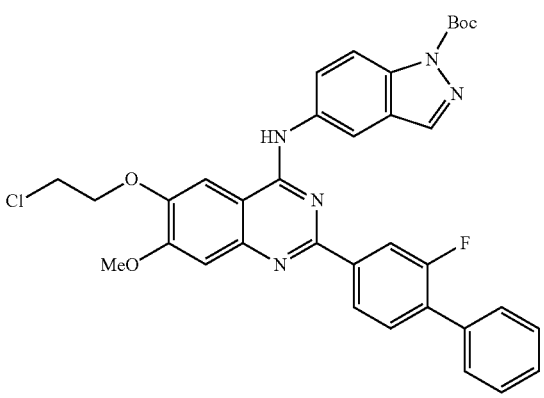 [SMILES: COc1cc2nc(-c3ccc(-c4ccccc4)c(F)c3)nc(Nc3ccc4c(cnn4C(=O)OC(C)(C)C)c3)c2cc1OCCCl]

A mixture of tert-butyl 5-(2-(3-fluoro-4-(phenyl)phenyl)-6-hydroxy-7-methoxyquinazolin-4-ylamino)-1H-indazole-1-carboxylate (0.61 g, 1.06 mmol), 1-bromo-2-chloro ethane (0.475 g, 3.31 mmol) and K$_2$CO$_3$ (0.533 g, 3.86 mmol) in DMF (5 mL) was heated at 85° C. for 2.5 h. the mixture was allowed to cool to RT upon which, it was poured into water. A solid separated out which was collected via filtration and dried under vacuum. The residue was purified via preparative TLC (SiO$_2$, CH$_2$Cl$_2$:MeOH 9:1) to give the desired compound tert-butyl 5-(6-(2-chloroethoxy)-2-(3-fluoro-4-(phenyl)phenyl)-7-methoxyquinazolin-4-ylamino)-1H-indazole-1-carboxylate (0.37 g, 0.578 mmol, 55%). MS 640.3 (M+1 Cl isotope pattern).

Example 103

2-(3-fluoro-4-(phenyl)phenyl)-N-(1H-indazol-5-yl)-7-methoxy-6-(2-(4-methylpiperazin-1-yl)ethoxy)quinazolin-4-amine

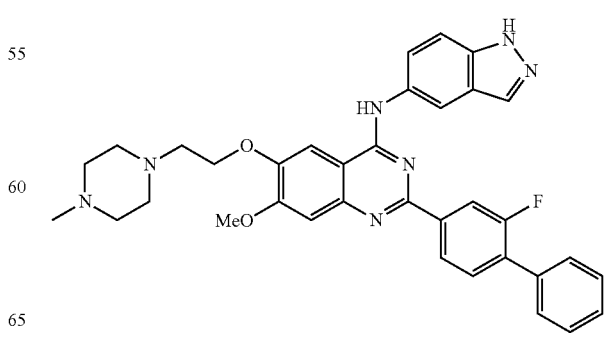

A mixture of 5-(6-(2-chloroethoxy)-2-(3-fluoro-4-(phenyl)phenyl)-7-methoxyquinazolin-4-ylamino)-1H-indazole-1-carboxylate (0.35 g, 0.55 mmol) and 4-methyl piperazine in DMSO (1.5 mL) was heated at 85° C. for 3 h. The mixture was allowed to cool to RT, upon which it was poured into water (100 mL). The solid that formed was collected via filtration and purified by preparative TLC (SiO₂, CH₂Cl₂:MeOH 9:1) to give the desired compound. The lower running spot was isolated and then taken up in CH₂Cl₂ (6 mL) and TFA (5 mL). The mixture was stirred for 2.5 h at RT. The volatiles were removed in vacuo to give a solid which was triturated with Et₂O, filtered and dried under vacuum to give the desired product 2-(3-fluoro-4-(phenyl)phenyl)-N-(1H-indazol-5-yl)-7-methoxy-6-(2-(4-methylpiperazin-1-yl)ethoxy)quinazolin-4-amine (0.111 g, 0.184 mmol, 33%). MS 604.5 (M+1). HPLC retention time 5.10 mins.

Example 104

6-(2-(dimethylamino)ethoxy)-2-(3-fluoro-4-(phenyl)phenyl)-N-(1H-indazol-5-yl)-7-methoxyquinazolin-4-amine

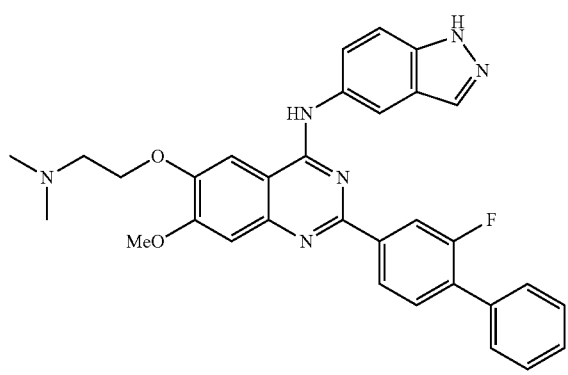 [SMILES: COc1cc2nc(-c3ccc(-c4ccccc4)c(F)c3)nc(Nc3ccc4[nH]ncc4c3)c2cc1OCCN(C)C]

To an ice-cold solution of 5-(6-(2-chloroethoxy)-2-(3-fluoro-4-(phenyl)phenyl)-7-methoxyquinazolin-4-ylamino)-1H-indazole-1-carboxylate (0.26 g, 0.55 mmol) in DMSO (3 mL) was bubbled dimethylamine for 3-4 minutes. The mixture was heated at 85° C. for 2 h. The mixture was allowed to cool to RT, upon which it was poured into water (100 mL). The solid that formed was collected via filtration and purified by preparative TLC (SiO₂, CH₂Cl₂:MeOH 9:1) to give the desired compound.
The purified compound was taken up in CH₂Cl₂ (5 mL) and TFA (5 mL). The mixture was stirred for 3 h at RT. The volatiles were removed in vacuo to give a solid which was dried under vacuum to give the desired product 6-(2-(dimethylamino)ethoxy)-2-(3-fluoro-4-(phenyl)phenyl)-N-(1H-indazol-5-yl)-7-methoxyquinazolin-4-amine (0.173 g, 0.315 mmol, 57%). MS 548.5 (M+). HPLC retention time 5.38 mins.

Example 105

2-(3-fluoro-4-(phenyl)phenyl)-N-(1H-indazol-5-yl)-7-methoxy-6-(2-(pyrrolidin-1-yl)ethoxy)quinazolin-4-amine

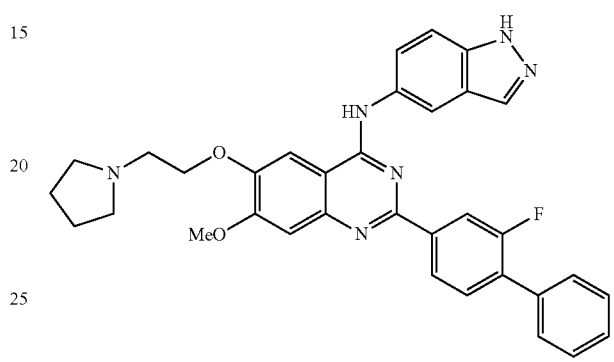

A mixture of 5-(6-(2-chloroethoxy)-2-(3-fluoro-4-(phenyl)phenyl)-7-methoxyquinazolin-4-ylamino)-1H-indazole-1-carboxylate (0.200 g, 0.31 mmol) and pyrrolidine (0.385 g, 5.41 mmol) in DMSO (1.5 mL) was heated at 75° C. for 1.5 h. The mixture was allowed to cool to RT, upon which it was poured into water (100 mL). The solid that formed was collected via filtration and purified by preparative TLC (SiO₂, CH₂Cl₂:MeOH 9:1) to give the desired compound 2-(3-fluoro-4-(phenyl)phenyl)-N-(1H-indazol-5-yl)-7-methoxy-6-(2-(pyrrolidin-1-yl)ethoxy)quinazolin-4-amine (0.15 g, 0.261 mmol, 84%). MS 575.4 (M+1) HPLC retention time 5.40 mins.

Example 106

4,5-Di-methoxy-2-(3-phenyl)phenyl)benzamide

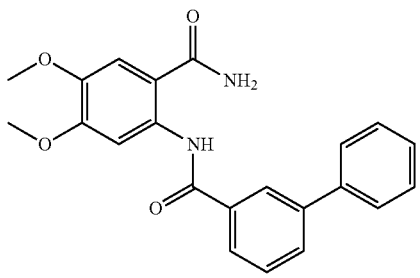 [SMILES: COc1cc(NC(=O)c2cccc(-c3ccccc3)c2)c(C(N)=O)cc1OC]

To a mixture of 2-amino-4,5-dimethoxybenzamide (8.42 g, 38.86 mmole) and pyridine (11.64 g, 147.4 mmole) in CHCl₃ (180 mL) was added 3-phenylbenzoyl chloride (7.23 g, 36.86 mmole) and the reaction was stirred at RT for 5 h. The volatiles were removed in vacuo and the product 2-(benzoylamino)-4,5-dimethoxybenzamide was used immediately without future purification. HPLC retention time 7.92 mins.

Example 107

2-[(3-phenyl)phenyl]-6,7-dimethoxyquinazolin-4(3H)-one

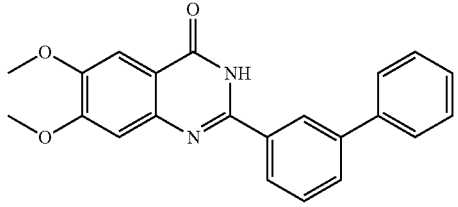 [SMILES: COc1cc2nc(-c3cccc(-c4ccccc4)c3)[nH]c(=O)c2cc1OC]

A mixture of 2 N NaOH (185 mL, 370 mmole) and 4,5-dimethoxy-2-(3-phenyl)phenyl)benzamide (38.9 mmole) was stirred under reflux for 16 h. The mixture was cooled and then pH adjusted to 7 with 1 N HCl. The crude product was filtered from solution, and the cake was washed with ether, hexane and dried under vacuum to give 2-[(3-phenyl)phenyl]-6,7-dimethoxyquinazolin-4(3H)-one (9.97 g, 27.82 mmole, 76% over two steps). HPLC retention time 7.23 mins.

Example 108

2-[(3-phenyl)phenyl]-6-hydroxy-7-methoxyquiazolin-4(3H)-one

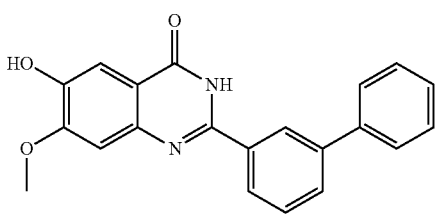 [SMILES: COc1cc2nc(-c3cccc(-c4ccccc4)c3)[nH]c(=O)c2cc1O]

To a solution of 2-[(3-phenyl)phenyl]-6,7-dimethoxyquinazolin-4(3H)-one (9.97 g, 27.8 mmole) in methanesulfonic acid (100 mL) was added L-methionine (5.00 g, 33.49 mmoles) and the reaction was stirred at 100° C. for 24 h. The solution was cooled to RT and poured onto ice-water (800 mL) and the resulting precipitate was filtered and washed with water. To the crude product was added ethanol (400 mL) and the suspension was stirred at 60° C. for 1 h. The product was then filtered and the cake was washed with ether, hexane and dried under vacuum to afford 2-[(3-phenyl)phenyl]-6-hydroxy-7-methoxyquiazolin-4(3H)-one (3.84 g, 11.15 mmole, 40%). HPLC retention time 6.37 mins.

Example 109

2-[(3-phenyl)phenyl]-7-methoxy-4-oxo-3,4-dihydroquinazolin-6-yl acetate

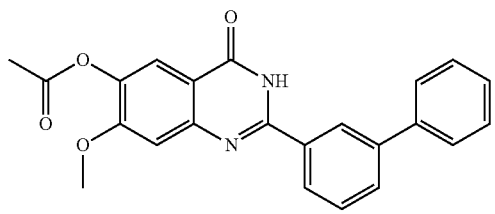 [SMILES: COc1cc2nc(-c3cccc(-c4ccccc4)c3)[nH]c(=O)c2cc1OC(C)=O]

To a mixture of 2-[(3-phenyl)phenyl]-6-hydroxy-7-methoxyquiazolin-4(3H)-one (3.40 g, 9.87 mmole) in acetic anhydride (40 mL, 43.2 g, 423.16 mmole) was added pyridine (4 mL, 3.91 g, 49.46 mmole) and the reaction was stirred at 105° C. for 3 h. The suspension was cooled to RT and poured onto ice-water (800 mL) and stirred for 20 min. The crude product was filtered, washed with water and dried under vacuum to give 2-[(3-phenyl)phenyl]-7-methoxy-4-oxo-3,4-dihydroquinazolin-6-yl acetate (186-036, 3.6 g, 9.32 mmole, 94%). HPLC retention time 7.81 mins.

Example 110

4-chloro-2-[(3-phenyl)phenyl]-7-methoxyquinazolin-6-yl acetate

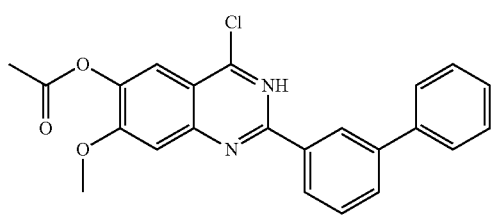 [SMILES: COc1cc2nc(-c3cccc(-c4ccccc4)c3)nc(Cl)c2cc1OC(C)=O]

To a mixture of 2-[(3-phenyl)phenyl]-7-methoxy-4-oxo-3,4-dihydroquinazolin-6-yl acetate (3.6 g, 9.32 mmole) in SOCl$_2$ (40 mL) was added DMF (1 mL) and the reaction was stirred at reflux for 16 h. The mixture was cooled to RT and then the volatiles were removed in vacuo. The crude product was dissolved in CHCl$_3$ (300 mL) and washed with saturated NaHCO$_3$ solution (3×150 mL), water (2×150 mL) and brine (1×150 mL) and dried with Na$_2$SO$_4$. The solution was concentrated in vacuo to yield 4-chloro-2-[(3-phenyl)phenyl]-7-

Example 111 tert-butyl 5-(6-acetoxy-2-[(3-phenyl)phenyl]-7-methoxyquinazolin-4-ylamino)-1H-indazole-1-carboxylate

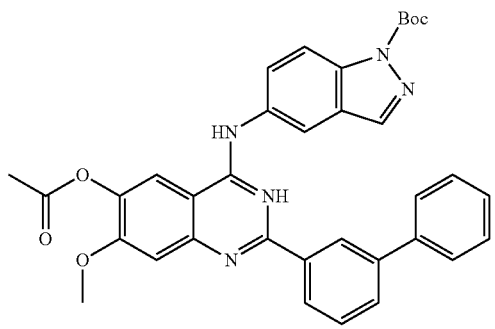 [SMILES: COc1cc2nc(-c3cccc(-c4ccccc4)c3)nc(Nc3ccc4c(cnn4C(=O)OC(C)(C)C)c3)c2cc1OC(C)=O]

A mixture of 4-chloro-2-[(3-phenyl)phenyl]-7-methoxyquinazolin-6-yl acetate (4.00 g, 9.88 mmole), tert-butyl 5-amino-1H-indazole-1-carboxylate (2.42 g, 10.37 mmole) in iso-propanol (130 mL) was stirred at 95° C. for 2 h. The reaction was cooled to RT and the crude product was filtered and then washed with ether, iso-propanol, and hexane and dried under vacuum to give tert-butyl 5-(6-acetoxy-2-[(3-phenyl)phenyl]-7-methoxyquinazolin-4-ylamino)-1H-indazole-1-carboxylate (4.33 g, 7.20 mmole, 77% over two steps). MS 602 (M+1). HPLC retention time 6.47 mins.

Example 112

5-(2-[(3-phenyl)phenyl]-6-hydroxy-7-methoxyquinazolin-4-ylamino)-1H-indazole-1-carboxylate

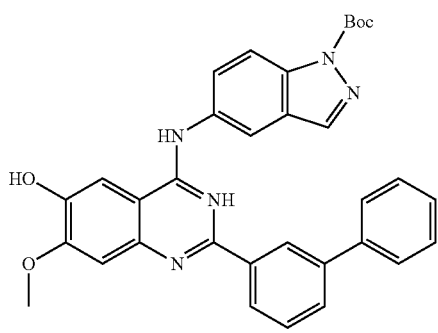 [SMILES: COc1cc2nc(-c3cccc(-c4ccccc4)c3)nc(Nc3ccc4c(cnn4C(=O)OC(C)(C)C)c3)c2cc1O]

To a mixture of tert-butyl 5-(6-acetoxy-2-[(3-phenyl)phenyl]-7-methoxyquinazolin-4-ylamino)-1H-indazole-1-carboxylate (4.30 g, 7.15 mmole) in $CH_3OH$ (300 mL) was added 28% $NH_4OH$, and the reaction was stirred at RT for 16 h. The solution was concentrated in vacuo and the resulting solid was triturated with toluene and then hexane, followed by filtration to give tert-butyl 5-(2-[(3-phenyl)phenyl]-6-hydroxy-7-methoxyquinazolin-4-ylamino)-1H-indazole-1-carboxylate (4.40 g, 7.87 mmole). MS 560 (M+1). HPLC retention time 7.62 mins.

Example 113 tert-butyl 5-[6-(2-tert-butoxy-2-oxoethoxy)-2-(3-phenyl)phenyl]-7-methoxyquinazolin-4-ylamino)-1H-indazole-1-carboxylate

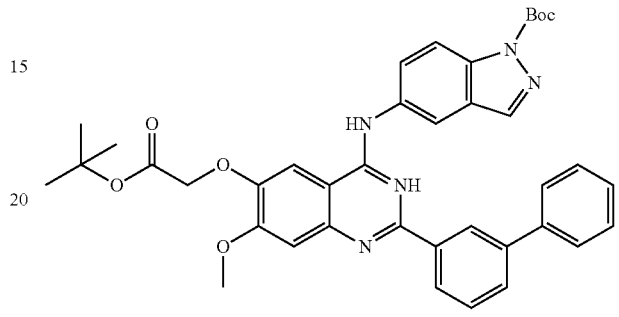

A mixture of tert-butyl 5-(2-[(3-phenyl)phenyl]-6-hydroxy-7-methoxyquinazolin-4-ylamino)-1H-indazole-1-carboxylate (1.0 g, 1.79 mmole), tert-butylbromoacetate (0.174 g, 0.132 mL, 0.895 mmole), potassium carbonate (0.99 g, 7.16 mmole) in DMF (20 mL) was stirred at 80° C. for 2 h. Then, a second portion of tert-butylbromoacetate (0.174 g, 0.132 mL, 0.895 mmole) was added and the reaction for stirred for an additional 2 h at 80° C. The mixture was cooled to RT and the volatiles were removed in vacuo. The crude product was partitioned between dichloromethane and water and the organic layer was dried with sodium sulfate and concentrated in vacuo. The crude product tert-butyl 5-[6-(2-tert-butoxy-2-oxoethoxy)-2-(3-phenyl)phenyl]-7-methoxyquinazolin-4-ylamino)-1H-indazole-1-carboxylate was used immediately without further purification. MS 618 (M–$^t$Bu+1). HPLC retention time 8.48 mins.

Example 114

2-(4-(1H-indazol-5-ylamino)-2-[(3-phenyl)phenyl]-7-methoxyquinazolin-6-yloxy)acetic acid

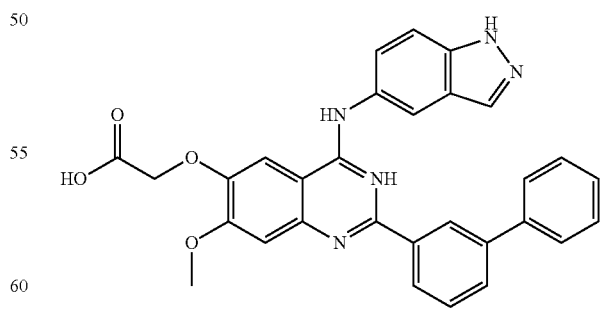

To tert-butyl 5-[6-(2-tert-butoxy-2-oxoethoxy)-2-(3-phenyl)phenyl]-7-methoxyquinazolin-4-ylamino)-1H-indazole-1-carboxylate (1.79 mmole) was added TFA (15 mL) at RT, and the solution was stirred for 2 h. The volatiles were removed in vacuo and the crude product was then triturated

Example 115

2-(4-(1H-indazol-5-ylamino)-2-[(3-phenyl)phenyl)-7-methoxyquinazolin-6-yloxy)-1-(4-methylpiperazin-1-yl)ethanone

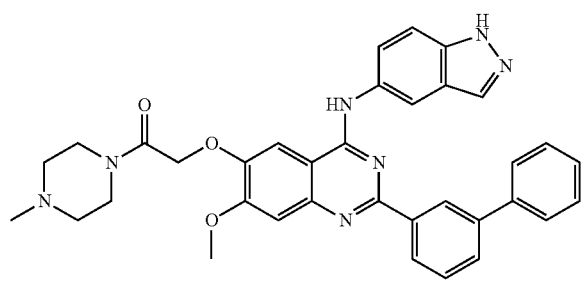 [SMILES: COc1cc2nc(-c3cccc(-c4ccccc4)c3)nc(Nc3ccc4[nH]ncc4c3)c2cc1OCC(=O)N1CCN(C)CC1]

To a mixture of 2-(4-(1H-indazol-5-ylamino)-2-[(3-phenyl)phenyl)-7-methoxyquinazolin-6-yloxy)acetic acid (0.25 g, 0.48 mmole) in DMF (1 mL)/CH$_2$Cl$_2$ (7 mL) was added PyBOP® (0.25 g, 0.48 mmole), and DIEA (0.186 g, 0.251 mL, 1.44 mmole). The mixture was then stirred for 15 minutes and 1-methylpiperazine (0.048 g, 0.053 mL, 0.48 mmole) was added and the reaction was stirred at RT for 3 h. The volatiles were then removed in vacuo. Upon adding CH$_2$Cl$_2$, the crude product precipitated and was subsequently filtered. The cake was washed with ether, hexane, CH$_3$OH, CH$_2$Cl$_2$ and finally hexane. The crude product was purified by reverse phase HPLC (25 to 55% CH$_3$CN/H$_2$O, 90 minute run time) to yield 2-(4-(1H-indazol-5-ylamino)-2-[(3-phenyl)phenyl)-7-methoxyquinazolin-6-yloxy)-1-(4-methylpiperazin-1-yl)ethanone (0.015 g, 5%). MS 600 (M+1). HPLC retention time 5.22 mins.

Example 116 tert-butyl 5-(2-[(3-(phenyl)phenyl)-7-methoxy-6-(2-methoxyethoxy)quinazolin-4-ylamino)-1H-indazole-1-carboxylate

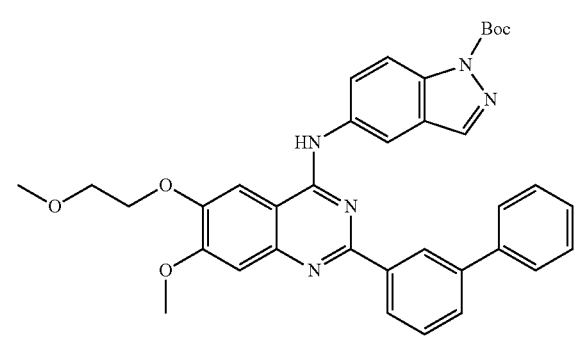 [SMILES: COCCOc1cc2c(Nc3ccc4c(cnn4C(=O)OC(C)(C)C)c3)nc(-c3cccc(-c4ccccc4)c3)nc2cc1OC]

A mixture of tert-butyl 5-(24(3-phenyl)phenyl]-6-hydroxy-7-methoxyquinazolin-4-ylamino)-1H-indazole-1-carboxylate (0.055 g, 0.098 mmole), 2-bromoethyl methyl ether (0.031 g, 0.021 mL, 0.226 mmole), K$_2$CO$_3$ (0.036 g, 0.26 mmole), and DMF (2.5 mL) was stirred at 85° C. for 3.5 h. The mixture was poured onto ice-water (200 mL) and the crude product was filtered. The product was then dissolved in ether and was washed with water and the organic layer was concentrated in vacuo. The crude product was purified by preparative TLC (SiO$_2$, 7:2.6:0.4 (CH$_2$Cl$_2$:EtOAc:CH$_3$OH) to give tert-butyl 5-(2-[(3-(phenyl)phenyl)-7-methoxy-6-(2-methoxyethoxy)quinazolin-4-ylamino)-1H-indazole-1-carboxylate (0.110 g). HPLC retention time 7.89 mins.

Example 117

2-[(3-(phenyl)phenyl)-N-(1H-indazol-5-yl)-7-methoxy-6-(2-methoxyethoxy)quinazolin-4-amine

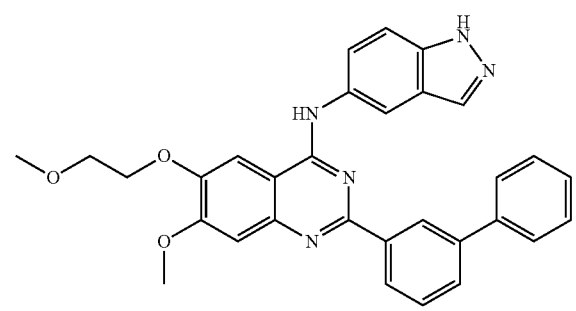 [SMILES: COCCOc1cc2c(Nc3ccc4[nH]ncc4c3)nc(-c3cccc(-c4ccccc4)c3)nc2cc1OC]

TFA (4 mL) was added to tert-butyl 5-(2-[(3-(phenyl)phenyl)-7-methoxy-6-(2-methoxyethoxy)quinazolin-4-ylamino)-1H-indazole-1-carboxylate (0.110 g, mmole) and the reaction was stirred at RT for 2 h. The solution was concentrated in vacuo and then azeotroped from hexane (1×) The crude product was triturated with ether and filtered, dried under vacuum to give 2-[(3-(phenyl)phenyl)-N-(1H-indazol-5-yl)-7-methoxy-6-(2-methoxyethoxy)quinazolin-4-amine (0.024 g, 0.046 mmole, 47% over 2 steps). MS 518.4 (M+1). HPLC retention time 6.47 mins.

Example 118 tert-butyl 5-(6-(2-chloroethoxy)-2-[(3-phenyl)phenyl)-7-methoxyquinazolin-4-ylamino)-1H-indazole-1-carboxylate

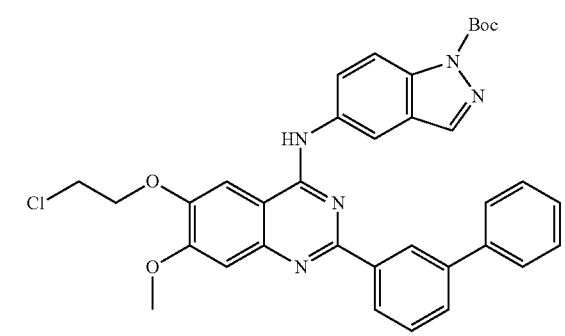 [SMILES: COc1cc2nc(-c3cccc(-c4ccccc4)c3)nc(Nc3ccc4c(cnn4C(=O)OC(C)(C)C)c3)c2cc1OCCCl]

A mixture of tert-butyl 5-(24(3-phenyl)phenyl]-6-hydroxy-7-methoxyquinazolin-4-ylamino)-1H-indazole-1-carboxylate (1.5 g, 2.68 mmole), 1-bromo-2-chloroethane (1.32 g, 0.76 mL, 9.17 mmole), K$_2$CO$_3$ (1.55 g, 11.21 mmole), and DMF (15 mL) was stirred at 85° C. for 2.5 h. The mixture was poured onto ice-water and the crude product was filtered. The product was then dissolved in a mixture of $CH_2Cl_2$ and $CH_3OH$ and the solution was concentrated in vacuo to give tert-butyl 5-(6-(2-chloroethoxy)-2-[(3-phenyl)phenyl)-7-methoxyquinazolin-4-ylamino)-1H-indazole-1-carboxylate (1.55 g, 2.49 mmol, 93%). HPLC retention time 8.22 mins.

Example 119

6-(2-(dimethylamino)ethoxy)-N-(1H-indazol-5-yl)-7-methoxy-2-(3-(phenyl)phenyl)quinazolin-4-amine

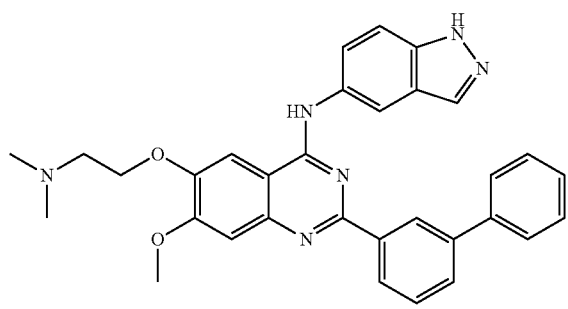 [SMILES: COc1cc2nc(-c3cccc(-c4ccccc4)c3)nc(Nc3ccc4[nH]ncc4c3)c2cc1OCCN(C)C]

A solution of tert-butyl 5-(6-(2-chloroethoxy)-2-[(3-phenyl)phenyl)-7-methoxyquinazolin-4-ylamino)-1H-indazole-1-carboxylate (0.25 g, 0.40 mmole) in DMSO (3 mL) was cooled to 0° C. To this was added dimethylamine gas (bubbled into solution for 15 minutes) and the reaction was slowly heated to 85° C. and stirred for 2 h. The mixture was poured onto ice-water and the crude product was filtered. The product was then dissolved in a mixture of $CH_2Cl_2$ and $CH_3OH$ and the solution was concentrated in vacuo. The residue was purified via preparative TLC ($SiO_2$, 10% $CH_2Cl_2/CH_3OH$). To the crude product was added TFA (5 mL) and the reaction was stirred at RT for 1 h. The solution was concentrated in vacuo and the residue was triturated with ether, filtered and dried under vacuum to give 6-(2-(dimethylamino)ethoxy)-N-(1H-indazol-5-yl)-7-methoxy-2-(3-(phenyl)phenyl)quinazolin-4-amine (0.096 g, 0.18 mmole, 45% over 2 steps). MS 531 (M+1). HPLC retention time 5.18 mins.

Example 120

2-[(3-phenyl)phenyl]-N-(1H-indazol-5-yl)-7-methoxy-6-(2-(pyrrolidin-1-yl)ethoxy)quinazolin-4-amine

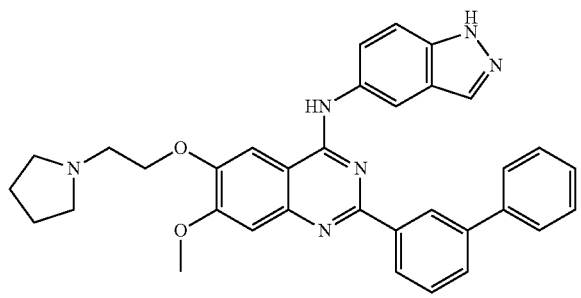 [SMILES: COc1cc2nc(-c3cccc(-c4ccccc4)c3)nc(Nc3ccc4[nH]ncc4c3)c2cc1OCCN1CCCC1]

To a mixture of tert-butyl 5-(6-(2-chloroethoxy)-2-[(3-phenyl)phenyl)-7-methoxyquinazolin-4-ylamino)-1H-indazole-1-carboxylate (0.25 g, 0.040 mmole) in DMSO (2 mL) was added pyrrolidine (0.143 g, 0.16 mL, 2.00 mmole) and the reaction was stirred at 85° C. for 4 h. The mixture was poured onto ice-water and the crude product was filtered. The product was then dissolved in a mixture of $CH_2Cl_2$ and $CH_3OH$ and the solution was concentrated in vacuo. The residue was purified via preparative TLC ($SiO_2$, 10% $CH_2Cl_2/CH_3OH$) to give 2-[(3-phenyl)phenyl]-N-(1H-indazol-5-yl)-7-methoxy-6-(2-(pyrrolidin-1-yl)ethoxy)quinazolin-4-amine (0.042 g, 0.075 mmole, 19%). MS 557 (M+1). HPLC retention time 5.34 mins.

Example 121

2-((2-(4-(1H-indazol-5-ylamino)-2-[(3-phenyl)phenyl)-7-methoxyquinazolin-6-yloxy)ethyl)(methyl)amino)-N,N-dimethylacetamide

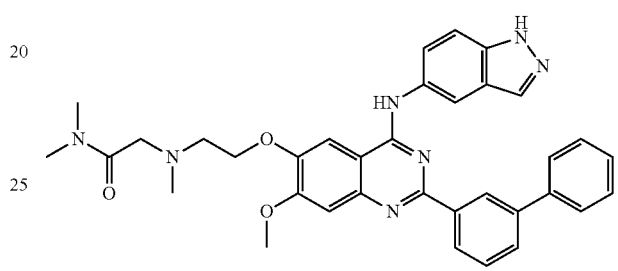

To a mixture of tert-butyl 5-(6-(2-chloroethoxy)-2-[(3-phenyl)phenyl)-7-methoxyquinazolin-4-ylamino)-1H-indazole-1-carboxylate (0.25 g, 0.40 mmole) in DMSO (2 mL) was added N,N-dimethyl-2-(methylamino)acetamide (0.232 g, 2.00 mmole) and the reaction was stirred at 85° C. for 4 h. The mixture was poured onto ice-water and the crude product was filtered. The product was then dissolved in a mixture of $CH_2Cl_2$ and $CH_3OH$ and the solution was concentrated in vacuo. The residue was purified via preparative TLC ($SiO_2$, 10% $CH_2Cl_2/CH_3OH$). To the product was added TFA (4 mL) and the reaction was stirred at RT for 2 h. The solution was concentrated in vacuo and the residue was triturated with ether, filtered and dried under vacuum to give 2-((2-(4-(1H-indazol-5-ylamino)-2-[(3-phenyl)phenyl)-7-methoxyquinazolin-6-yloxy)ethyl)(methyl)amino)-N,N-dimethylacetamide (0.178 g, 0.30 mmole, 74%). MS 602.6 (M+1). HPLC retention time 5.24 mins.

Example 122 tert-butyl 5-(2-[(3-phenyl)phenyl)-7-methoxy-6-(2-(4-methylpiperazin-1-yl)ethoxy)quinazolin-4-ylamino)-1H-indazole-1-carboxylate

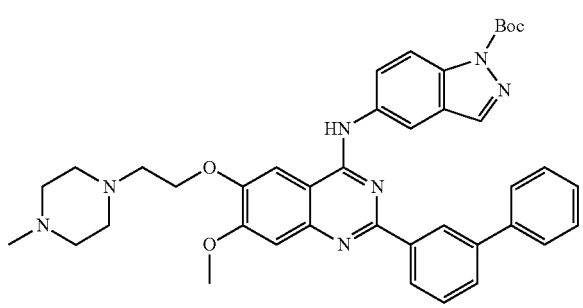 [SMILES: COc1cc2nc(-c3cccc(-c4ccccc4)c3)nc(Nc3ccc4c(cnn4C(=O)OC(C)(C)C)c3)c2cc1OCCN1CCN(C)CC1]

To a mixture of tert-butyl 5-(6-(2-chloroethoxy)-2-[(3-phenyl)phenyl)-7-methoxyquinazolin-4-ylamino)-1H-indazole-1-carboxylate (0.30 g, 0.44 mmole) in DMSO (2 mL) was added 1-methylpiperazine (0.903 g, 1.00 mL, 9.02 mmole) and the reaction was stirred at 85° C. for 3 h. The mixture was poured onto ice-water (100 mL) and the crude product was filtered. The product was then dissolved in a mixture of CH$_2$Cl$_2$ and CH$_3$OH and the solution was concentrated in vacuo. The residue was purified via preparative TLC (SiO$_2$, 10% CH$_2$Cl$_2$/CH$_3$OH— with 0.1% NH$_4$OH) to give tert-butyl 5-(2-[(3-phenyl)phenyl)-7-methoxy-6-(2-(4-methylpiperazin-1-yl)ethoxy)quinazolin-4-ylamino)-1H-indazole-1-carboxylate which was taken on to the next step. HPLC retention time 6.00 mins.

Example 123

2-[(3-phenyl)phenyl]-N-(1H-indazol-5-yl)-7-methoxy-6-(2-(4-methylpiperazin-1-yl)ethoxy)quinazolin-4-amine

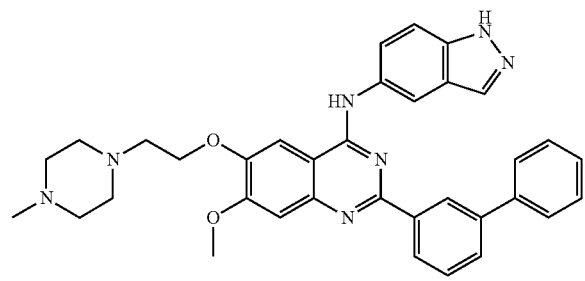 [SMILES: COc1cc2nc(-c3cccc(-c4ccccc4)c3)nc(Nc3ccc4[nH]ncc4c3)c2cc1OCCN1CCN(C)CC1]

TFA (4 mL) was added to 5-(2-[(3-phenyl)phenyl)-7-methoxy-6-(2-(4-methylpiperazin-1-yl)ethoxy)quinazolin-4-ylamino)-1H-indazole-1-carboxylate and the reaction was stirred at RT for 1.5 h. The solution was concentrated in vacuo and the crude product was triturated with ether and filtered, dried under vacuum to give 2-[(3-phenyl)phenyl]-N-(1H-indazol-5-yl)-7-methoxy-6-(2-(4-methylpiperazin-1-yl)ethoxy)quinazolin-4-amine (0.166 g, 0.283 mmole, 64% over two steps). MS 586.4 (M+1). HPLC retention time 5.06 mins.

Example 124

2-[(3-phenyl)phenyl]-N-(1H-indazol-5-yl)-7-methoxy-6-(2-morpholinoethoxy)quinazolin-4-amine

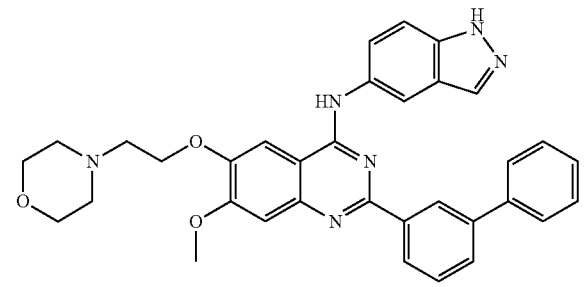 [SMILES: COc1cc2nc(-c3cccc(-c4ccccc4)c3)nc(Nc3ccc4[nH]ncc4c3)c2cc1OCCN1CCOCC1]

To a mixture of tert-butyl 5-(6-(2-chloroethoxy)-2-[(3-phenyl)phenyl)-7-methoxyquinazolin-4-ylamino)-1H-indazole-1-carboxylate (0.25 g, 0.40 mmole) in DMSO (2 mL) was added morpholine (1.32 g, 1.33 mL, 15.2 mmole) and the reaction was stirred at 85° C. for 48 h. The mixture was poured onto ice-water and the crude product was filtered. The product was then dissolved in a mixture of CH$_2$Cl$_2$ and CH$_3$OH and the solution was concentrated in vacuo. The residue was purified via preparative TLC (SiO$_2$, 10% CH$_2$Cl$_2$/CH$_3$OH) to give 2-[(3-phenyl)phenyl]-N-(1H-indazol-5-yl)-7-methoxy-6-(2-morpholinoethoxy)quinazolin-4-amine (0.131 g, 0.20 mmole, 50%). MS 572.2 (M+). HPLC retention time 5.27 mins.

Example 125 tert-butyl 5-(2-[(3-phenyl)phenyl)-7-methoxy-6-(2-(4-methyl-1,4-diazepan-1-yl)ethoxy)quinazolin-4-ylamino)-1H-indazole-1-carboxylate

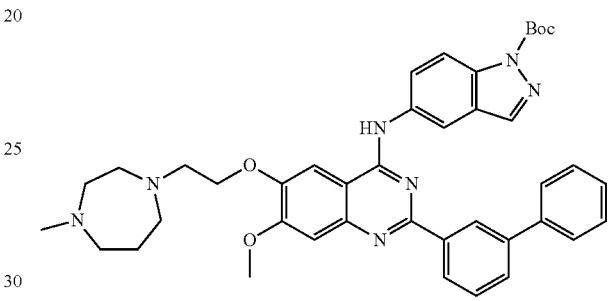

A mixture of tert-butyl 5-(6-(2-chloroethoxy)-2-[(3-phenyl)phenyl)-7-methoxyquinazolin-4-ylamino)-1H-indazole-1-carboxylate (0.25 g, 0.402 mmole), 1-methyl-1,4-diazepane (0.23 g, 0.25 mL, 2.00 mmoles) in DMSO was stirred at 85° C. for 2.5 h. The suspension was poured onto ice-water, filtered and re-dissolved in a mixture of CH$_2$Cl$_2$ and CH$_3$OH and the solution was concentrated in vacuo. The residue was purified via preparative TLC (SiO$_2$, 10% CH$_2$Cl$_2$/CH$_3$OH— with 0.1% NH$_4$OH) to give tert-butyl 5-(2-[(3-phenyl)phenyl)-7-methoxy-6-(2-(4-methyl-1,4-diazepan-1-yl)ethoxy)quinazolin-4-ylamino)-1H-indazole-1-carboxylate which taken on directly to the next step. HPLC retention time 5.96 mins.

Example 126

2-[(3-phenyl)phenyl]-N-(1H-indazol-5-yl)-7-methoxy-6-(2-(4-methyl-1,4-diazepan-1-yl)ethoxy)quinazolin-4-amine

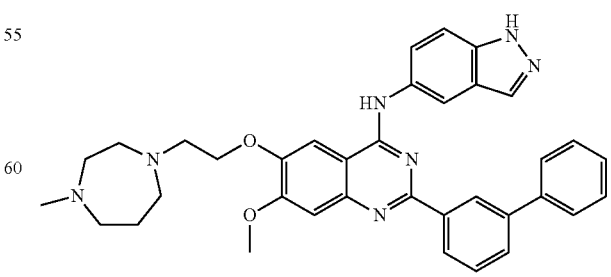

To a solution of 5-(2-[(3-phenyl)phenyl)-7-methoxy-6-(2-(4-methyl-1,4-diazepan-1-yl)ethoxy)quinazolin-4- ylamino)-1H-indazole-1-carboxylate in CH$_2$Cl$_2$ (2 mL) was added HCl as a 4.0 M solution in 1,4 dioxane (8 mL) and the reaction was stirred at RT for 5 h. The volatiles were removed in vacuo and the crude product was washed with hexane and dried under vacuum to yield 2-[(3-phenyl)phenyl)-N-(1H-indazol-5-yl)-7-methoxy-6-(2-(4-methyl-1,4-diazepan-1-yl)ethoxy)quinazolin-4-amine (0.063 g, 0.105 mmole, 26% over 2 steps). MS 600.4 (M+1). HPLC retention time 5.01 mins.

Example 127

5-Methoxy-2-nitrobenzamide

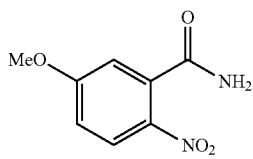 [SMILES: COc1ccc([N+](=O)[O-])c(C(N)=O)c1]

To a suspension of 5-methoxy-2-nitrobenzoic acid (7.5 g, 38.0 mmol) in anhydrous benzene (50 mL), was added thionyl chloride (3.8 mL, 52.05 mmol) followed by the addition of anhydrous DMF (0.4 mL). The resulting reaction mixture was refluxed for 5 h, upon which the volatiles were removed in vacuo. The residue was dissolved in anhydrous THF (60 mL) and added to an ice-cold saturated solution of ammonia in THF (60 mL). The resulting heterogeneous reaction mixture was allowed to warm room temperature and stirring was continued at RT for 48 h. The s volatiles were removed in vacuo and the residue was used without further purification for next step. HPLC retention time 3.29 mins.

Example 128

5-Methoxy-2-aminobenzamide

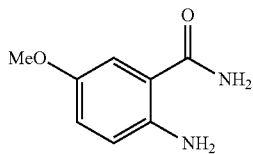

To a suspension of 5-methoxy-2-nitrobenzamide (38.0 mmol) in methanol (150 mL), was added 10% Pd—C (1.2 g) under an atmosphere of argon followed by addition of ammonium formate (18.0 g, 285.4 mmole). T resulting reaction mixture was refluxed for 2.5 h, upon which, the mixture was allowed to cool to RT and was filtered through a pad of Celite®. The filtrate was concentrated under reduced pressure and the residue was washed with water to give a solid (4.74 g). The filtrate, was extracted with ethyl acetate (2×300 mL), dried (Na$_2$SO$_4$), filtered, concentrated in vacuo and combined with the previous solid. The resulting solid was dried under vacuum to give 5-methoxy-2-aminobenzamide (4.74 g, 35.7 mmol, 94%). HPLC retention time 3.16 mins.

Example 129

5-Methoxy-2-(3-nitrophenyl)aminobenzamide

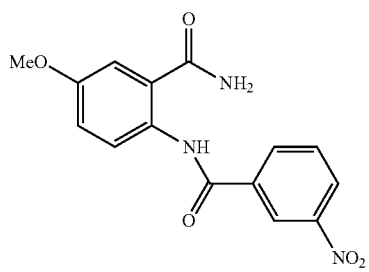 [SMILES: COc1ccc(NC(=O)c2cccc([N+](=O)[O-])c2)c(C(N)=O)c1]

To a suspension of 2-amino-5-methoxybenzamide (2.42 g, 14.6 mmol) and pyridine (6 mL) in CHCl$_3$ (120 mL) was added 3-nitrobenzoyl chloride (3.0 g, 16.1 mmol). The resulting mixture was stirred at RT for 6 h. The volatiles were removed in vacuo and the resultant solid was washed with Et$_2$O to give the 5-Methoxy-2-(3-nitrobenzoyl)aminobenzamide (6.15 g) which was taken directly on to the next step. HPLC retention time 6.58 mins.

Example 130

6-methoxy-2-(3-nitrophenyl)quinazolin-4(3H)-one

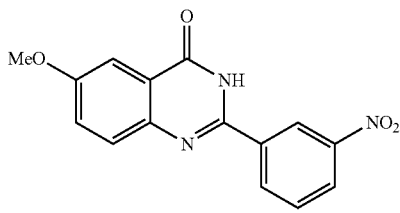

A suspension of the amide from the previous step (6.0 g) in 3N NaOH (160 mL) was heated at 100° C. for 9 h. The mixture was allowed to cool to RT and stirring was continued overnight at RT. The mixture was neutralized with 6N HCl to pH 7. A solid precipitated out and was collected via filtration and dried under vacuum to give the desired product 6-methoxy-2-(3-nitrophenyl)quinazolin-4(3H)-one (4.0 g, 13.5 mmol, 95%). HPLC retention time 6.721 min.

Example 131

6-hydroxy-2-(3-nitrophenyl)quinazolin-4(3H)-one

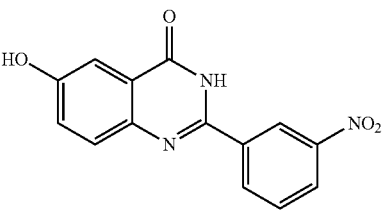 [SMILES: O=c1[nH]c(-c2cccc([N+](=O)[O-])c2)nc2ccc(O)cc12]

To a suspension of 6-methoxy-2-(3-nitrophenyl)quinazolin-4(3H)-one (3.90 g, 13.1 mmol), in CH$_2$Cl$_2$ (30 mL) cooled to −78° C. under an atmosphere of N$_2$ was added BBr$_3$ as a 1.0M solution in CH$_2$Cl$_2$ (20 mL, 20.0 mmol). The resulting mixture was stirred at −78° C. for 1 h, then allowed to warm to RT upon which it was stirred for a further 3 h. The mixture was re-cooled to −78° C. and stirred overnight. The reaction was quenched by the addition of EtOH (60 mL) and allowed to warm to RT. Stirring was continued for 1 h at RT, upon which a precipitate formed. Sat. NaHCO$_3$ solution was added and the yellow solid was collected via filtration and washed with Et$_2$O and EtOH and dried under vacuum to give 6-hydroxy-2-(3-nitrophenyl)quinazolin-4(3H)-one (2.96 g, 10.5 mmol, 80%). HPLC retention time 5.588 min.

Example 132

2-(3-nitrophenyl)-4-oxo-3,4-dihydroquinazolin-6-yl acetate

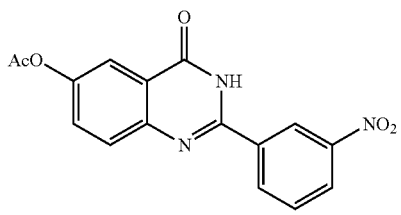 [SMILES: CC(=O)Oc1ccc2nc(-c3cccc([N+](=O)[O-])c3)[nH]c(=O)c2c1]

A mixture of 6-hydroxy-2-(3-nitrophenyl)quinazolin-4(3H)-one (2.92 g, 10.3 mmol) Ac$_2$O (30 mL) and pyridine (4 mL) was heated at 105° C. for 4 h. The mixture was allowed to cool to RT and was poured into ice-water (300 mL). The resulting slurry was stirred for 2-3 h at RT, then the solid was collected via filtration, washed with water, EtOH and Et$_2$O and dried under vacuum to give the product 2-(3-nitrophenyl)-4-oxo-3,4-dihydroquinazolin-6-yl acetate (3.35 g, 10.3 mmol, 100%). HPLC retention time 6.559 min.

Example 133

4-chloro-2-(3-nitrophenyl)quinazolin-6-yl acetate

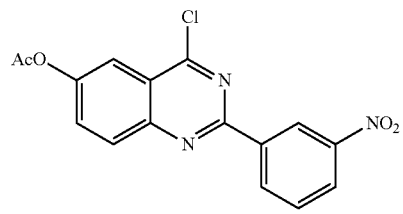 [SMILES: CC(=O)Oc1ccc2nc(-c3cccc([N+](=O)[O-])c3)nc(Cl)c2c1]

A suspension of 2-(3-nitrophenyl)-4-oxo-3,4-dihydroquinazolin-6-yl acetate (3.30 g, 10.1 mmol) in SOCl$_2$ (65 mL) was added DMF (2 mL). The mixture was refluxed for 2.5 h, upon which the volatiles were removed in vacuo. The residue was taken up in CHCl$_3$ (450 mL) and washed with sat NaHCO$_3$ (200 ml) and water (200 mL). The organic layer was dried (Na$_2$SO$_4$), filtered and concentrated in vacuo to give the product 4-chloro-2-(3-nitrophenyl)quinazolin-6-yl acetate (3.53 g, 10.3 mmol). HPLC retention time 9.748 min.

Example 134 tert-butyl 5-(6-acetoxy-2-(3-nitrophenyl)quinazolin-4-ylamino)-1H-indazole-1-carboxylate

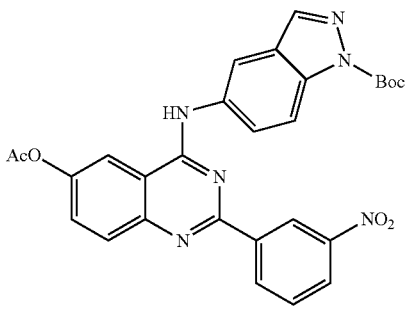 [SMILES: CC(=O)Oc1ccc2nc(-c3cccc([N+](=O)[O-])c3)nc(Nc3ccc4c(cnn4C(=O)OC(C)(C)C)c3)c2c1]

A mixture of 4-chloro-2-(3-nitrophenyl)quinazolin-6-yl acetate (1.63 g, 4.74 mmol) and tert-butyl 5-amino-1H-indazole-1-carboxylate (1.16 g, 4.28 mmol) in IPA (80 mL) were heated at 95° C. for 5 h. The mixture was allowed to cool to RT, the yellow solid was collected via filtration and washed with Et$_2$O to give the product tert-butyl 5-(6-acetoxy-2-(3- nitrophenyl)quinazolin-4-ylamino)-1H-indazole-1-carboxylate (2.14 g, 3.96 mmol, 84%). HPLC retention time 9.649 min.

Example 135 tert-butyl 5-(6-acetoxy-2-(3-aminophenyl)quinazolin-4-ylamino)-1H-indazole-1-carboxylate

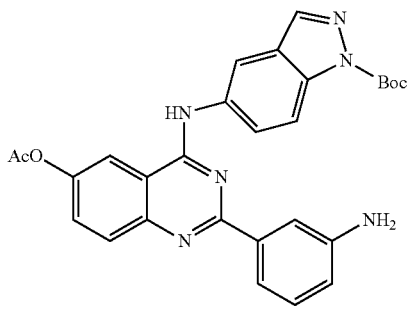

A mixture of tert-butyl 5-(6-acetoxy-2-(3-nitrophenyl)quinazolin-4-ylamino)-1H-indazole-1-carboxylate (0.84 g, 1.55 mmol) in MeOH (200 mL) was added 10% Pd/C under an atmosphere of $N_2$. The mixture was stirred under an atmosphere of $H_2$ (balloon pressure) for 48 h at RT. The mixture was filtered through a pad of Celite® washing with MeOH. The volatiles were removed in vacuo to give tert-butyl 5-(6-acetoxy-2-(3-aminophenyl)quinazolin-4-ylamino)-1H-indazole-1-carboxylate (0.811 g, 1.59 mmol). HPLC retention time 5.51 min.

Example 136 tert-butyl 5-(6-acetoxy-2-(3-(nicotinamido)phenyl)quinazolin-4-ylamino)-1H-indazole-1-carboxylate

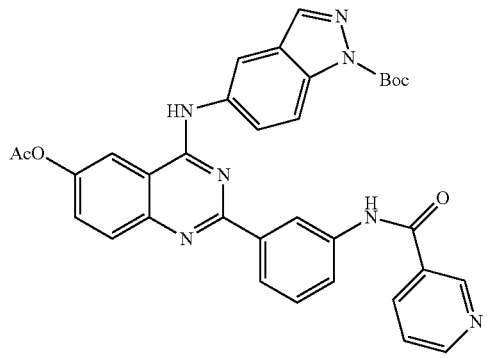 [SMILES: CC(=O)Oc1ccc2nc(-c3cccc(NC(=O)c4cccnc4)c3)nc(Nc3ccc4c(cnn4C(=O)OC(C)(C)C)c3)c2c1]

A suspension of tert-butyl 5-(6-acetoxy-2-(3-aminophenyl)quinazolin-4-ylamino)-1H-indazole-1-carboxylate (0.50 g, 0.98 mmol), nicotinoyl chloride hydrochloride (0.224 g, 1.26 mmol) and DIEA (0.45 g, 3.48 mmol) in $CH_2Cl_2$ (15 mL) was stirred at RT for 7 h. The volatiles were removed in vacuo and the residue was purified by preparative TLC (SiO_2, $CH_2Cl_2$:MeOH 9:1) to give the product tert-butyl 5-(6-acetoxy-2-(3-(nicotinamido)phenyl)quinazolin-4-ylamino)-1H-indazole-1-carboxylate (0.374 g, 0.608 mmol, 62%).

Example 137 tert-butyl 5-(6-hydroxy-2-(3-(nicotinamido)phenyl)quinazolin-4-ylamino)-1H-indazole-1-carboxylate

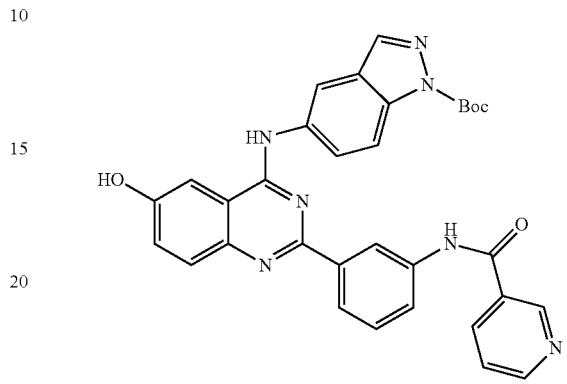

A mixture of 5-(6-acetoxy-2-(3-(nicotinamido)phenyl)quinazolin-4-ylamino)-1H-indazole-1-carboxylate (0.374 g, 0.607 mmol) and 28% $NH_4OH$ (0.45 mL) in MeOH (50 mL) was stirred at RT for 24 h. The volatiles were removed in vacuo and the residue was washed with $Et_2O$ to give the product tert-butyl 5-(6-hydroxy-2-(3-(nicotinamido)phenyl)quinazolin-4-ylamino)-1H-indazole-1-carboxylate (0.318 g, 0.554 mmol, 91%).

Example 138

N-(3-(4-(1H-indazol-5-ylamino)-6-(2-(dimethylamino)ethoxy)quinazolin-2-yl)phenyl)nicotinamide

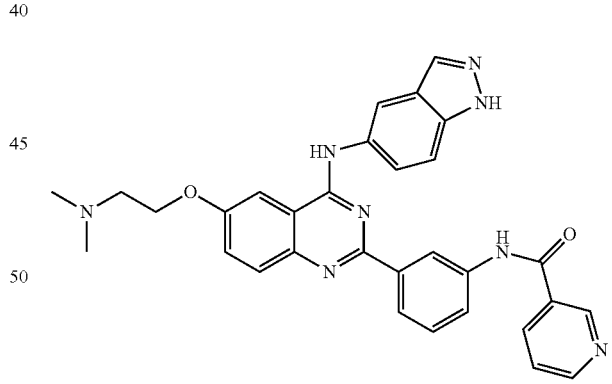

A mixture of 5-(6-hydroxy-2-(3-(nicotinamido)phenyl)quinazolin-4-ylamino)-1H-indazole-1-carboxylate (0.127 g, 0.221 mmol), 2-chloro-N,N-dimethylethanamine (0.065 g, 0.45 mmol) and $K_2CO_3$ (0.131 g, 0.948 mmol) in DMF (2 mL) was heated at 70° C. for 2 h. The mixture was diluted with $CH_2Cl_2$ (75 mL), washed with water (10 mL), dried ($Na_2SO_4$), filtered and concentrated in vacuo.

The material was taken up in $CH_2Cl_2$ (2 mL) and TFA (3 mL) was added. The mixture was stirred at RT for 3 h. The volatiles were removed in vacuo and the residue was triturated with $Et_2O$ and dried under vacuum to give the desired product N-(3-(4-(1H-indazol-5-ylamino)-6-(2-(dimethylamino)ethoxy)quinazolin-2-yl)phenyl)nicotinamide (0.077 g, 0.141 mmol, 64%). MS 545.3 (M+1). HPLC retention time 3.67 mins.

Example 139

N-(3-(4-(1H-indazol-5-ylamino)-6-(2-methoxyethoxy)quinazolin-2-yl)phenyl)nicotinamide

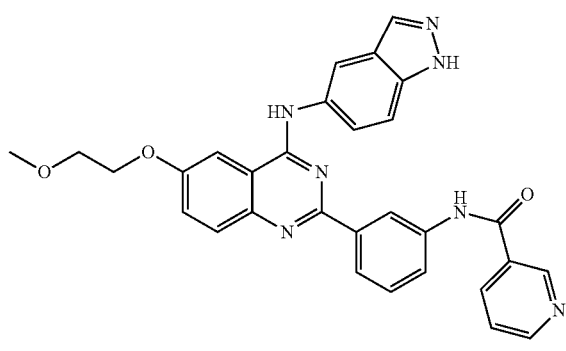 [SMILES: COCCOc1ccc2nc(-c3cccc(NC(=O)c4cccnc4)c3)nc(Nc3ccc4[nH]ncc4c3)c2c1]

A mixture of tert-butyl 5-(6-hydroxy-2-(3-(nicotinamido)phenyl)quinazolin-4-ylamino)-1H-indazole-1-carboxylate (0.107 g, 0.186 mmol), 1-bromo-2-methoxyethane (0.056 g, 0.403 mmol) and $K_2CO_3$ (0.068 g, 0.492 mmol) in DMF (1 mL) was heated at 70° C. for 2.5 h. the mixture was allowed to cool to RT upon which, the mixture was diluted with $CH_2Cl_2$ (75 mL), washed with water (10 mL), dried ($Na_2SO_4$), filtered and concentrated in vacuo.

The material was taken up in $CH_2Cl_2$ (2 mL) and TFA (3 mL) was added. The mixture was stirred at RT for 3 h. The volatiles were removed in vacuo and the residue was triturated with $Et_2O$ and dried under vacuum to give the desired product N-(3-(4-(1H-indazol-5-ylamino)-6-(2-methoxyethoxy)quinazolin-2-yl)phenyl)nicotinamide (0.078 g, 0.147 mmol, 79%). MS 532.4 (M+1). HPLC retention time 4.5 mins.

Example 140 tert-butyl 5-(2-(3-butyramidophenyl)-6-hydroxyquinazolin-4-ylamino)-1H-indazole-1-carboxylate

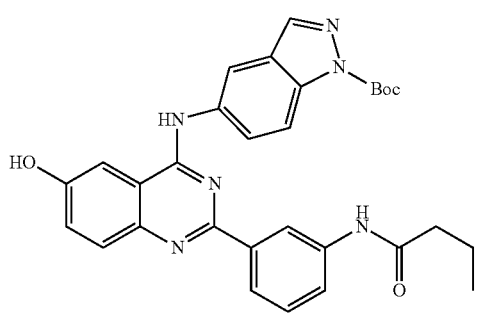 [SMILES: CCCC(=O)Nc1cccc(-c2nc(Nc3ccc4c(cnn4C(=O)OC(C)(C)C)c3)c3cc(O)ccc3n2)c1]

A mixture of tert-butyl 5-(6-acetoxy-2-(3-aminophenyl)quinazolin-4-ylamino)-1H-indazole-1-carboxylate (0.570 g, 1.12 mmol), butryl chloride (0.18 g, 1.69 mmol), and DIEA (0.65 g, 5.03 mmol) in $CH_2Cl_2$ (20 mL) was stirred at RT for 7 h. the volatiles were removed in vacuo and the residue was triturated with water. The resultant solid was collected by filtration, washed with water and dried under vacuum.

The residue was taken up in MeOH (50 mL) and 28% $NH_4OH$ (0.9 mL) was added. The mixture was stirred at RT for 24 h. The volatiles were removed in vacuo and the residue was triturated with MeOH/$Et_2O$ to give the product tert-butyl 5-(2-(3-butyramidophenyl)-6-hydroxyquinazolin-4-ylamino)-1H-indazole-1-carboxylate (0.354 g, 0.657 mmol, 59%). HPLC retention time 6.342 min.

Example 141

N-(3-(4-(1H-indazol-5-ylamino)-6-(2-(dimethylamino)ethoxy)quinazolin-2-yl)phenyl)butyramide

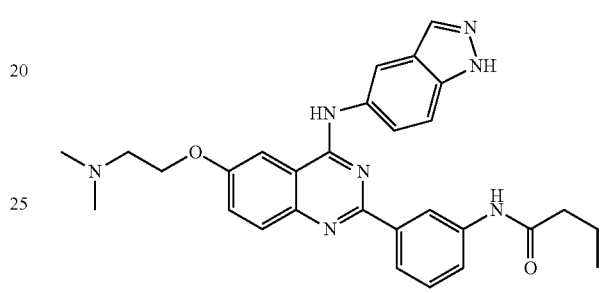

To a mixture of tert-butyl 5-(2-(3-butyramidophenyl)-6-hydroxyquinazolin-4-ylamino)-1H-indazole-1-carboxylate (0.107 g, 0.199 mmol), 2-chloro-N,N-dimethylethanamine hydrochloride (0.065 g, 0.451 mmol), $K_2CO_3$ (0.065 g, 0.451 mmol) in DMF (1.2 mL) was heated at 70° C. for 2.5 h. The mixture was allowed to cool to RT upon which, the mixture was diluted with $CH_2Cl_2$ (75 mL), washed with water (10 mL), dried ($Na_2SO_4$), filtered and concentrated in vacuo.

The material was taken up in $CH_2Cl_2$ (2 mL) and TFA (3 mL) was added. The mixture was stirred at RT for 3 h. The volatiles were removed in vacuo and the residue was triturated with $Et_2O$ and dried under vacuum to give the desired product N-(3-(4-(1H-indazol-5-ylamino)-6-(2-(dimethylamino)ethoxy)quinazolin-2-yl)phenyl)butyramide (0.037 g, 72.6 mmol, 36%). MS 510.4 (M+1). HPLC retention time 5.16 min.

Example 142

N-(3-(4-(1H-indazol-5-ylamino)-6-(3-(dimethylamino)propoxy)quinazolin-2-yl)phenyl)butyramide

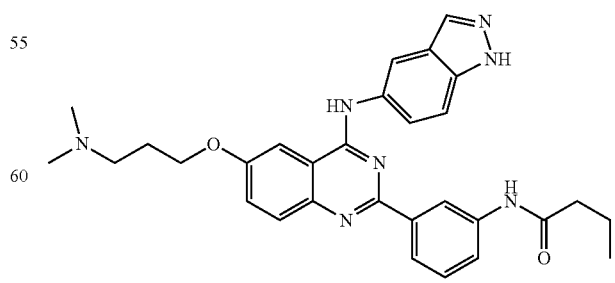

To a mixture of tert-butyl 5-(2-(3-butyramidophenyl)-6-hydroxyquinazolin-4-ylamino)-1H-indazole-1-carboxylate (0.106 g, 0.197 mmol), 3-chloro-N,N-dimethylpropan-1-amine (0.081 g, 0.451 mmol), K₂CO₃ (0.065 g, 0.512 mmol) in DMF (1.2 mL) was heated at 70° C. for 2.5 h. The mixture was allowed to cool to RT upon which, the mixture was diluted with CH₂Cl₂ (75 mL), washed with water (10 mL), dried (Na₂SO₄), filtered and concentrated in vacuo. The material was purified by preparative TLC (SiO₂, CH₂Cl₂:MeOH 9:1).

The purified material was taken up in CH₂Cl₂ (2 mL) and TFA (3 mL) was added. The mixture was stirred at RT for 3 h. The volatiles were removed in vacuo and the residue was triturated with Et₂O and dried under vacuum to give the desired product N-(3-(4-(1H-indazol-5-ylamino)-6-(3-(dimethylamino)propoxy)quinazolin-2-yl)phenyl)butyramide (0.057 g, 0.109 mmol, 55%). MS 524.6 (M+1). HPLC retention time.

Example 143

4,5-Dimethoxy-2-(3-nitrophenyl)aminobenzamide

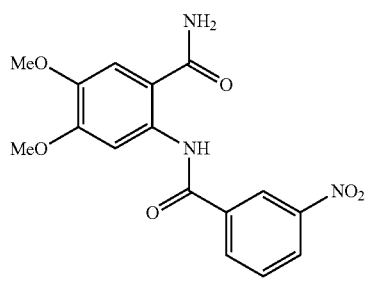 [SMILES: COc1cc(NC(=O)c2cccc([N+](=O)[O-])c2)c(C(N)=O)cc1OC]

To a suspension of 2-amino-4,5-dimethoxybenzamide (5.05 g, 25.7 mmole) and 3-nitro benzoyl chloride (5.2 g, 28.0 mmole) CHCl₃ (120 ml) was added pyridine (50 ml) drop wise at RT. The reaction mixture was stirred at RT for 24 h. The solvent was removed in vacuo and residue was triturated with Et₂O, filtered and dried under high vacuum to give 4,5-dimethoxy-2-(3-nitrophenyl)aminobenzamide, which was used directly in the next step.

Example 144

6,7-Dimethoxy-2-(3-nitrophenyl)quinazolin-4(3H)-one

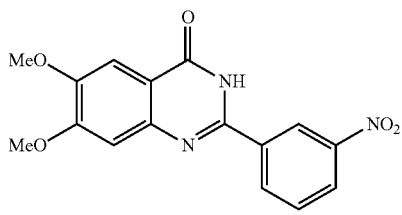 [SMILES: COc1cc2nc(-c3cccc([N+](=O)[O-])c3)[nH]c(=O)c2cc1OC]

A suspension of 4,5-dimethoxy-2-(3-nitrophenyl)aminobenzamide (9.5 g) was taken up in 2 N NaOH (200 mL) and was refluxed for 8 h. The reaction mixture was cooled to RT and left to stand overnight. The pH adjusted to 7 with 3 N HCl and the mixture was filtered. The filtered solid washed with water and dried under high vacuum to give 6,7-dimethoxy-2-(3-nitrophenyl)quinazolin-4(3H)-one. (6.2 g, 18.9 mmol, 74% over two steps) HPLC retention time 6.15 mins.

Example 145

6-Hydroxy-7-methoxy-2-(3-nitrophenyl)quinazolin-4(3H)-one

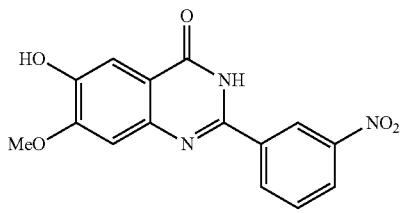 [SMILES: COc1cc2nc(-c3cccc([N+](=O)[O-])c3)[nH]c(=O)c2cc1O]

A mixture of 6,7-dimethoxy-2-(3-nitrophenyl)quinazolin-4(3H)-one (5.72 g, 17.5 mmol) and L-methionine (3.1 g, 20.7 mmol) in methanesulfonic acid (40 mL) was heated at 100° C. for 4.5 h. An additional aliquot of L-methionine (0.45 g, 1.36 mmol) and methanesulfonic acid (10 mL) were added and the mixture was heated for a further 2 h. The mixture was allowed to cool to RT, poured into ice water (ca. 500 mL) and was neutralized with sat. NaHCO₃ solution. A solid separated out which was collected by filtration and dried under vacuum to give the desired 6-hydroxy-7-methoxy-2-(3-nitrophenyl)quinazolin-4(3H)-one. (7.3 g). HPLC retention time 5.486 min.

Example 146

Benzyl 3-(benzyloxy)-4-methoxybenzoate

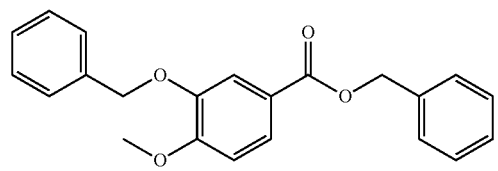 [SMILES: COc1ccc(C(=O)OCc2ccccc2)cc1OCc1ccccc1]

To an ice cold mixture of isovanillic acid 1 (4.3 g, 25.5 mmol) and K₂CO₃ (10.5 g, 0.152 mol) in anhydrous DMF (40 mL) was added benzyl bromide (8.7 g, 6.05 mL, 51.1 mmol). The resulting reaction mixture stirred at RT overnight. An additional aliquot of benzyl bromide was added (1.0 ml) and stirring was continued for 1.5 h. The reaction mixture was poured into brine (100 mL) and the solid was collected via filtration, washed with water and dried under high vacuum to give benzyl 3-(benzyloxy)-4-methoxybenzoate as a white solid (7.99 g, 23.0 mmol, 90%).

Example 147

Benzyl 5-(benzyloxy)-4-methoxy-2-nitrobenzoate

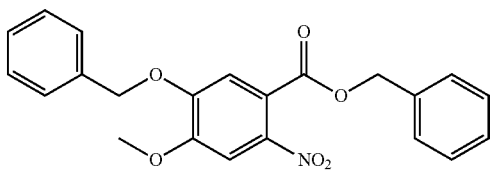 [SMILES: COc1cc([N+](=O)[O-])c(C(=O)OCc2ccccc2)cc1OCc1ccccc1]

To a solution of benzyl 3-(benzyloxy)-4-methoxybenzoate (6.32 g, 18.1 mmol) in Ac$_2$O (62 mL) cooled to −10° C. under an atmosphere of N$_2$ was added fuming HNO$_3$ (1.5 mL, 37.1 mmol) in one portion. Stirring was continued at −10° C. for 10 minutes, then at RT for 3 hours. The reaction mixture was carefully poured into ice-water and the pH adjusted to ca. pH=5 with 5N NaOH, sat. NaHCO$_3$ and 0.5 NaOH. The mixture was extracted with CH$_2$Cl$_2$ (3×200 mL). The combined organics were dried (Na$_2$SO$_4$), filtered and concentrated in vacuo. The residue was azeotroped with heptane to give benzyl 5-(benzyloxy)-4-methoxy-2-nitrobenzoate as red colored oil (6.55 g, 16.7 mmol, 93%).

Example 148

5-(Benzyloxy)-4-methoxy-2-nitrobenzoic acid

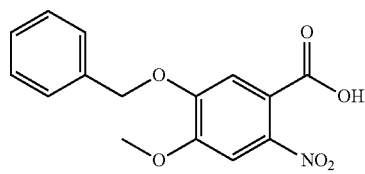 [SMILES: COc1cc([N+](=O)[O-])c(C(=O)O)cc1OCc1ccccc1]

To a solution of benzyl 5-(benzyloxy)-4-methoxy-2-nitrobenzoate (1.4 g, 3.56 mmol) in EtOH (10 mL) was added 1N NaOH (4.27 mL, 4.27 mmol). The mixture was stirred at RT for 1 h, upon which an additional aliquot of NaOH (4.27 mL, 4.27 mmol) was added. Stirring was continued at RT overnight. The mixture was diluted with water (20 mL) and washed with CH2Cl2 (2×25 mL). The aqueous layer was acidified to pH=2 with 0.5 N HCl and extracted with EtOAc (3×50 mL). The combined organics were dried (Na2SO4), filtered and concentrated in vacuo to give 5-(benzyloxy)-4-methoxy-2-nitrobenzoic acid (1.02 g, 3.37 mmol, 94%).

Example 149

4-Methoxy-5-benzyloxy-2-nitrobenzamide

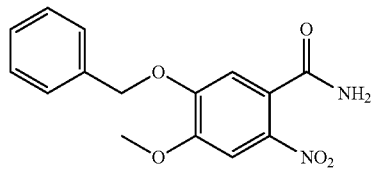

To a suspension of 4-methoxy-5-benzyloxy-2-nitrobenzoic acid (10.0 g, 33.3 mmol) in anhydrous THF (100 mL) was added oxalyl chloride (4.90 mL, 56.2 mmol) followed by one drop of anhydrous DMF. The mixture was stirred at RT for 16 h, upon which the mixture was poured into water (300 mL) and ammonium hydroxide (50 mL). A solid was separated out, which was collected by filtration and dried under vacuo. The solid was taken up in refluxing methanol (500 mL) and the insoluble solid was collected via filtration and dried under vacuum to give 4-methoxy-5-benzyloxy-2-nitrobenzamide (6.50 g, 21.5 mmol, 65%). HPLC retention time 6.154 min.

Example 150

4-Methoxy-5-benzyloxy-2-aminobenzamide

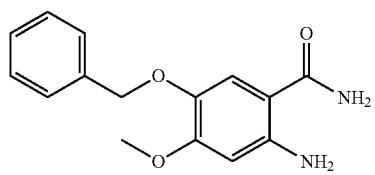 [SMILES: COc1cc([N+](=O)[O-])c(C(N)=O)cc1OCc1ccccc1]

A mixture of 4-methoxy-5-benzyloxy-2-nitrobenzamide (6.60 g, 21.9 mmol) and iron powder (8.14 g, 0.146 mol) in acetic acid/methanol (80 mL/80 mL) was heated at 85±5° C. for 1.5 h. The reaction mixture was allowed to cool to RT and the iron was removed by filtration, and volatiles were removed in vacuo. The residue was taken up in sat. sodium bicarbonate and the mixture was extracted with ethyl acetate (600 mL×3). The combined organic layers were washed with water (1×150 mL), brine (1×150 mL), dried (Na$_2$SO$_4$), filtered and concentrated in vacuo to give 4-methoxy-5-benzyloxy-2-aminobenzamide (5.2 g, 19.1 mmol, 87%). MS 273.2. (M+). HPLC retention time 4.585 min.

Example 151

4-Methoxy-5-benzyloxy-2-(3-nitrobenzoylamino)benzamide

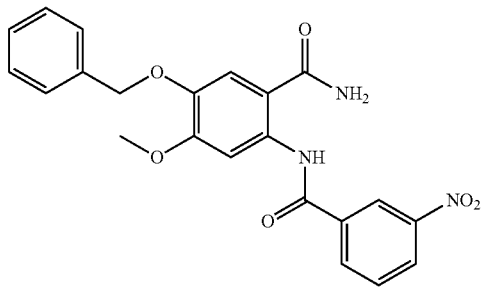 [SMILES: COc1cc(NC(=O)c2cccc([N+](=O)[O-])c2)c(C(N)=O)cc1OCc1ccccc1]

To a suspension of 6-methoxy-7-benzyloxy-2-aminobenzamide (4.86 g, 17.9 mmol) and pyridine (10 mL) in chloroform (600 mL), was added 3-nitrobenzoyl chloride (3.60 g, 19.4 mmol) slowly. The resulting reaction mixture was stirred at room temperature for 24 h, upon which the volatiles were removed under reduced pressure, and resulting residue was dried under vacuum. The residue upon trituration with $Et_2O$ gave a light yellow colored solid in quantitative yield (Note: Possesses some pyridine. HCl). HPLC retention time 8.384 min.

Example 152

6-(Benzyloxy)-7-methoxy-2-(3-nitrophenyl)quinazolin-4(3H)-one

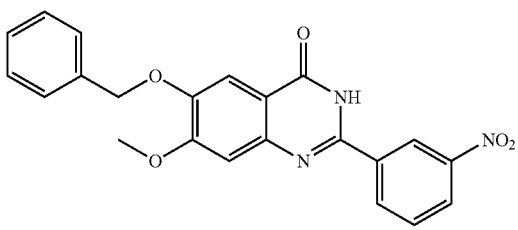 [SMILES: COc1cc2nc(-c3cccc([N+](=O)[O-])c3)[nH]c(=O)c2cc1OCc1ccccc1]

A suspension of 4-methoxy-5-benzyloxy-2-(3-nitrobenzoylamino)benzamide (8.00 g, possesses some pyridine.HCl) in 4N NaOH (200 mL) was heated at 100±5° C. for 10 h. The reaction mixture was allowed to cool to room temperature and pH was adjusted to 7-7.5 with 6 N HCl. A solid separated out, which was collected by filtration, washed with water (100 mL) and dried under vacuum to give 6-(benzyloxy)-7-methoxy-2-(3-nitrophenyl)quinazolin-4(3H)-one (3.22 g, 7.99 mmol, 47% over two steps). MS 404 (M+1) HPLC retention time 8.026 min.

Example 153

6-Hydroxy-7-methoxy-2-(3-nitrophenyl)quinazolin-4(3H)-one

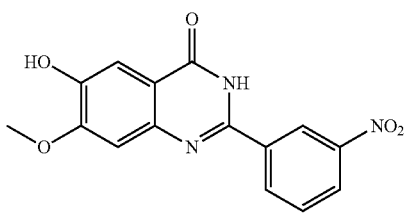 [SMILES: COc1cc2nc(-c3cccc([N+](=O)[O-])c3)[nH]c(=O)c2cc1O]

To a suspension of 6-(benzyloxy)-7-methoxy-2-(3-nitrophenyl)quinazolin-4(3H)-one (3.21 g, 7.95 mmol) in trifluoroacetic acid (45 mL) was heated at 75±5° C. for 2.5 h. The volatiles were removed in vacuo and residue was taken up with sat. $NaHCO_3$ solution. A light yellow colored solid separated out, which was collected via filtration. The solid was washed with water and dried under vacuum to give 6-hydroxy-7-methoxy-2-(3-nitrophenyl)quinazolin-4(3H)-one (2.38 g, 7.60 mmol, 96%). HPLC retention time 5.486 min.

Example 154

7-Methoxy-2-(3-nitrophenyl)-4-oxo-3,4-dihydroquinazolin-6-yl acetate

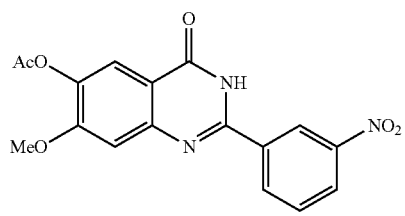

A mixture of 6-hydroxy-7-methoxy-2-(3-nitrophenyl)quinazolin-4(3H)-one (2.3 g, 7.34 mmol), $Ac_2O$ (40 mL) and pyridine (4 mL) were heated at 105° C. for 3.5 h. The reaction mixture was allowed to cool and poured into ice-water (ca. 300 mL) and the resulting slurry was stirred for 2 h. The solid was collected by filtration and washed with water, EtOH and $Et_2O$ and dried under high vacuum to give 7-methoxy-2-(3- nitrophenyl)-4-oxo-3,4-dihydroquinazolin-6-yl acetate. (2.6 g, 7.31 mmol, 99%). HPLC retention time 6.24 min.

Example 155

4-Chloro-7-methoxy-2-(3-nitrophenyl)quinazolin-6-yl acetate

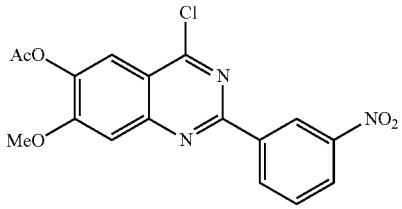 [SMILES: COc1cc2nc(-c3cccc([N+](=O)[O-])c3)nc(Cl)c2cc1OC(C)=O]

A mixture of the 7-methoxy-2-(3-nitrophenyl)-4-oxo-3,4-dihydroquinazolin-6-yl acetate (1.70 g, 4.79 mmol), thionyl chloride (30 mL) and anhydrous DMF (0.6 mL) were refluxed for 2.5 h. The volatiles were removed in vacuo and the residue dissolved in CH$_2$CL$_2$ (500 mL) and was washed with water, sat. NaHCO$_3$, water and brine, dried (Na$_2$SO$_4$), filtered and concentrated in vacuo to 4-chloro-7-methoxy-2-(3-nitrophenyl)quinazolin-6-yl acetate. (1.6 g, 4.23 mmol, 88%). HPLC retention time 9.75 min.

Example 156 tert-Butyl 5-(6-acetoxy-7-methoxy-2-(3-nitrophenyl)quinazolin-4-ylamino)-1H-indazole-1-carboxylate

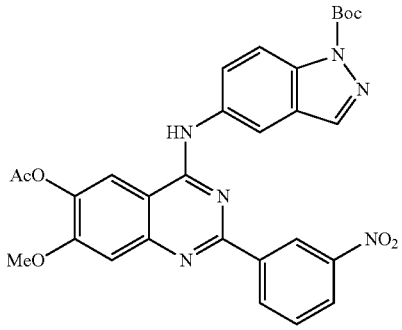 [SMILES: COc1cc2nc(-c3cccc([N+](=O)[O-])c3)nc(Nc3ccc4c(cnn4C(=O)OC(C)(C)C)c3)c2cc1OC(C)=O]

A mixture of 4-chloro-7-methoxy-2-(3-nitrophenyl)quinazolin-6-yl acetate (1.60 g, 4.23 mmol) and tert-butyl 5-amino-1H-indazole-1-carboxylate (1.0 g, 4.28 mmol) were refluxed in anhydrous iso-propanol (60 mL) for 5 h. The mixture was allowed to cool to RT, upon which the solid was collected via filtration and was washed with Et$_2$O to give tert-butyl 5-(6-acetoxy-7-methoxy-2-(3-nitrophenyl) quinazolin-4-ylamino)-1H-indazole-1-carboxylate. (2.2 g, 4.23 mmol, 100%). HPLC retention time=7.75 mins.

Example 157 tert-Butyl 5-(6-hydroxy-7-methoxy-2-(3-nitrophenyl)quinazolin-4-ylamino)-1H-indazole-1-carboxylate

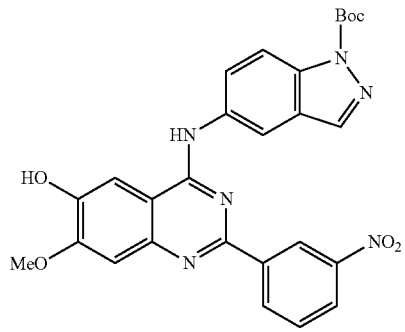 [SMILES: COc1cc2nc(-c3cccc([N+](=O)[O-])c3)nc(Nc3ccc4c(cnn4C(=O)OC(C)(C)C)c3)c2cc1O]

To a suspension of tert-butyl 5-(6-acetoxy-7-methoxy-2-(3-nitrophenyl)-quinazolin-4-ylamino)-1H-indazole-1-carboxylate (1.150 g, 2.01 mmol) in MeOH (100 mL) was added 28% aq. NH$_4$OH solution (0.7 mL). The mixture was stirred at RT for 20 h. The solid was collected via filtration and dried under vacuum to give tert-butyl 5-(6-hydroxy-7-methoxy-2-(3-nitrophenyl)quinazolin-4-ylamino)-1H-indazole-1-carboxylate. (0.800 g, 1.51 mmol, 75%). HPLC retention time 6.57 mins.

Example 158 tert-butyl 5-(7-methoxy-6-(3-morpholinopropoxy)-2-(3-nitrophenyl)quinazolin-4-ylamino)-1H-indazole-1-carboxylate

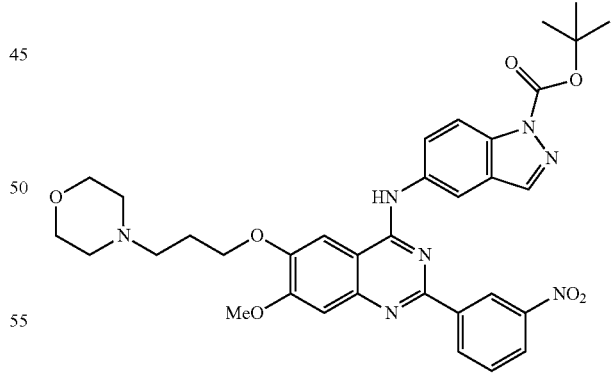

A mixture of tert-Butyl 5-(6-hydroxy-7-methoxy-2-(3-nitrophenyl)quinazolin-4-ylamino)-1H-indazole-1-carboxylate (0.70 g, 1.32 mmol), 4-(3-chloropropyl)morpholine (0.32 g, 1.96 mmol) and K$_2$CO$_3$ (1.33 g, 9.62 mmol) in DMF (10 mL) was heated at 80° C. for 2.5 h. The mixture was allowed to cool to RT and the volatiles were removed in vacuo. The crude product was purified by column chromatography (SiO$_2$, CH$_2$Cl$_2$ 97:3 to 94:6 to 90:10) to give the desired compound tert-butyl 5-(7-methoxy-6-(3-morpholinopropoxy)-2-(3-nitrophenyl)quinazolin-4-ylamino)-1H-indazole-1-carboxylate. HPLC retention time (5.76 min).

Example 159 tert-butyl 5-(2-(3-aminophenyl)-7-methoxy-6-(3-morpholinopropoxy)quinazolin-4-ylamino)-1H-indazole-1-carboxylate

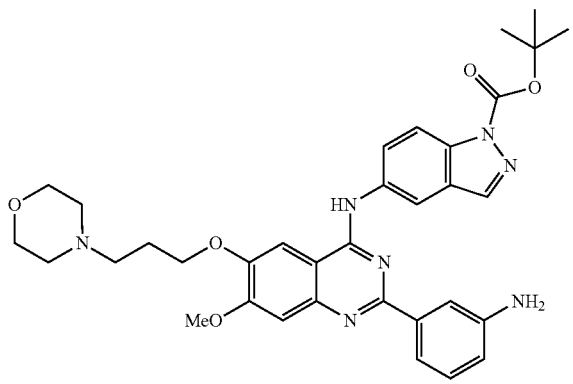 [SMILES: COc1cc2nc(-c3cccc([N+](=O)[O-])c3)nc(Nc3ccc4c(cnn4C(=O)OC(C)(C)C)c3)c2cc1OCCCN1CCOCC1]

To a mixture of 5-(7-methoxy-6-(3-morpholinopropoxy)-2-(3-nitrophenyl)quinazolin-4-ylamino)-1H-indazole-1-carboxylate (0.215 g) in MeOH (60 mL) was added Pd/C (0.21 g) and $NH_4CO_2$ (0.21 g). The mixture was heated at 60° C. for 40 mins, upon which an additional portion of $NH_4CO_2$ (0.095 g) was added, heating was continued for a further 20 minutes. The mixture was filtered to remove the Pd/C and the filtrate was concentrated under reduced pressure. The residue was taken up in $CH_2Cl_2$ (300 mL) wand was washed with water and brine. The mixture was dried ($Na_2SO_4$) and the volatiles removed in vacuo. The material was combined with an identical experiment using 0.2 g and the residue was subjected to preparative TLC ($SiO_2$, $CH_2Cl_2$:MeOH 9:1) to give the desired product tert-butyl 5-(2-(3-aminophenyl)-7-methoxy-6-(3-morpholinopropoxy)quinazolin-4-ylamino)-1H-indazole-1-carboxylate. HPLC retention time 4.67 mins.

Example 160

N-(3-(4-(1H-indazol-5-ylamino)-7-methoxy-6-(3-morpholinopropoxy)quinazolin-2-yl)phenyl)butyramide

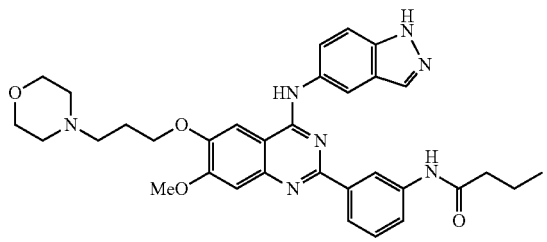 [SMILES: CCCC(=O)Nc1cccc(-c2nc(Nc3ccc4[nH]ncc4c3)c3cc(OCCCN4CCOCC4)c(OC)cc3n2)c1]

To a solution of tert-butyl 5-(2-(3-aminophenyl)-7-methoxy-6-(3-morpholinopropoxy)quinazolin-4-ylamino)-1H-indazole-1-carboxylate (0.076 g, 0.121 mmol) in $CH_2Cl_2$ (4 mL), DIEA (0.040 g, 0.30 mmol) and butryl chloride (0.026 g) were added were added. The resulting mixture was stirred at RT for 2.5 h. The volatiles were removed in vacuo and the residue was taken up in $CH_2Cl_2$ (15 mL), washed with NaHCO₃ solution, water and brine, dried ($Na_2SO_4$) and filtered.

The residue was taken up in $CH_2Cl_2$ (3 mL) and TFA (3 mL) was added. The mixture was stirred at RT for 2.5 h. The volatiles were removed in vacuo and the residue was washed with $Et_2O$ and hexane. The solid was dried under vacuum to give the desired product N-(3-(4-(1H-indazol-5-ylamino)-7-methoxy-6-(3-morpholinopropoxy)quinazolin-2-yl)phenyl)butyramide (0.066 g, 0.110 mmol, 91%). MS 596.3 (M+1). HPLC retention time 4.60 mins.

Example 161

N-(3-(4-(1H-indazol-5-ylamino)-7-methoxy-6-(3-morpholinopropoxy)quinazolin-2-yl)phenyl)isonicotinamide

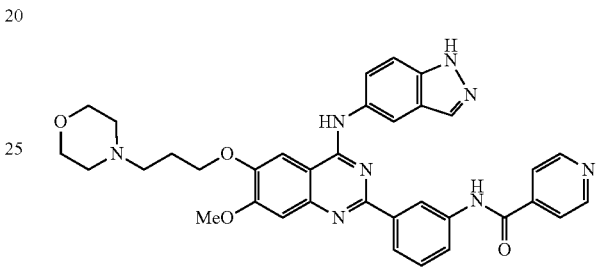

To a solution of tert-butyl 5-(2-(3-aminophenyl)-7-methoxy-6-(3-morpholinopropoxy)quinazolin-4-ylamino)-1H-indazole-1-carboxylate (0.064 g, 0.102 mmol) in $CH_2Cl_2$ (4 mL), DIEA (0.041 g, 0.32 mmol) and isonicotinoyl chloride (0.022 g, 0.123 mmol) were added were added. The resulting mixture was stirred at RT for 2.5 h. The volatiles were removed in vacuo and the residue was taken up in $CH_2Cl_2$ (15 mL), washed with NaHCO₃ solution, water and brine, dried ($Na_2SO_4$) and filtered.

The residue was taken up in $CH_2Cl_2$ (3 mL) and TFA (3 mL) was added. The mixture was stirred at RT for 2.5 h. The volatiles were removed in vacuo and the residue was washed with $Et_2O$ and hexane. The solid was dried under vacuum to give the desired product N-(3-(4-(1H-indazol-5-ylamino)-7-methoxy-6-(3-morpholinopropoxy)quinazolin-2-yl)phenyl)isonicotinamide (0.073 g, 0.098 mmol, 96%). MS 631.3 (M+1). HPLC retention time 3.94 mins Example 162

N-(3-(4-(1H-indazol-5-ylamino)-7-methoxy-6-(3-morpholinopropoxy)quinazolin-2-yl)phenyl)nicotinamide

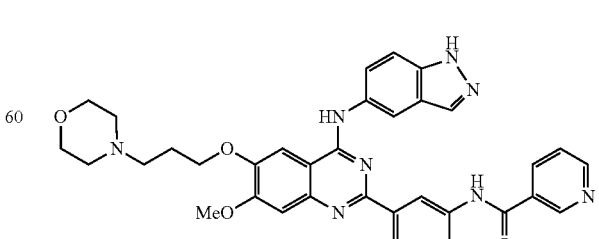

To a solution of tert-butyl 5-(2-(3-aminophenyl)-7-methoxy-6-(3-morpholinopropoxy)quinazolin-4-ylamino)-1H-indazole-1-carboxylate (0.035 g, 0.056 mmol) in CH₂Cl₂ (4 mL), DIEA (0.036 g, 0.28 mmol) and isonicotinoyl chloride hydrochloride (0.013 g, 0.073 mmol) were added were added. The resulting mixture was stirred at RT for 2.5 h. The volatiles were removed in vacuo and the residue was purified by preparative TLC (SiO₂ CHCl₃:MeOH 9:1).

The crude material was taken up in CH₂Cl₂ (2 mL) and TFA (2.5 mL) was added. The mixture was stirred at RT for 2.5 h. The volatiles were removed in vacuo and the residue was washed with Et₂O and dried under vacuum to give the desired product N-(3-(4-(1H-indazol-5-ylamino)-7-methoxy-6-(3-morpholinopropoxy)quinazolin-2-yl)phenyl)nicotinamide. MS 631.7 (M+1). HPLC retention time 3.779 mins.

Example 163 tert-butyl 5-(6-acetoxy-2-(3-aminophenyl)-7-methoxyquinazolin-4-ylamino)-1H-indazole-1-carboxylate

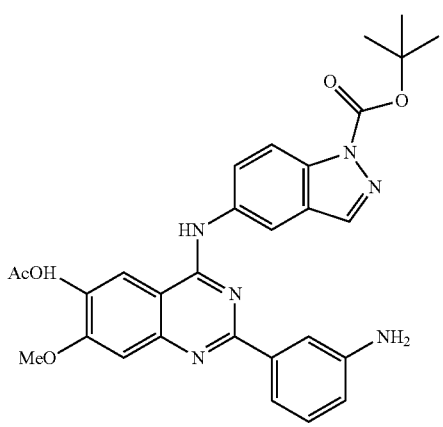

To a mixture of tert-butyl 5-(6-acetoxy-7-methoxy-2-(3-nitrophenyl)quinazolin-4-ylamino)-1H-indazole-1-carboxylate (0.40 g, 0.70 mmol) in MeOH (100 mL) was added Pd/C (0.15 g) under an atmosphere of N₂. The mixture was then stirred under an atmosphere of H₂ (balloon pressure) for 48 h at RT. The mixture was filtered through a pad of Celite® washing with MeOH. The filtrate was concentrated in vacuo to give the desired product tert-butyl 5-((6-acetoxy-2-(3-aminophenyl)-7-methoxyquinazolin-4-ylamino)-1H-indazole-1-carboxylate. (0.23 g, 0.43 mmol, 61%). HPLC retention time 5.748 mins.

Example 164 tert-Butyl 5-(6-hydroxy-7-methoxy-2-(3-(2-morpholinoacetamido)phenyl)quinazolin-4-ylamino)-1H-indazole-1-carboxylate

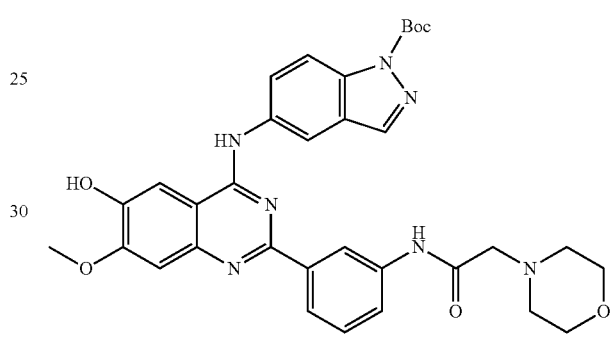

To a solution of tert-butyl 5-(6-acetoxy-2-(3-aminophenyl)-7-methoxyquinazolin-4-ylamino)-1H-indazole-1-carboxylate (0.538 g, 0.995 mmol) in EtOAc:THF (80 mL:20 mL) was added sat. NaHCO₃ (30 mL) followed by 2-chloroacetyl chloride (0.5 mL). The resulting mixture was stirred at RT for 3 h, upon which an additional aliquot of 2-chloroacetyl chloride (0.5 mL) was added. The mixture was stirred at RT for a further 2 h. The layers were separated and the organic layer was washed with 50% citric acid (2×50 mL), water (2×100 mL) and brine (1×50 mL), dried (Na₂SO₄), filtered and concentrated in vacuo.

The crude mixture was dissolved in DMF/THF (10 mL 1:1 v/v) and morpholine (1.5 mL) was added. The mixture was stirred at RT for 4 h, upon which it was diluted with water (200 mL) and extracted with EtOAc (2×300 mL). The combined organics were washed with water (1×100 mL), dried (Na₂SO₄), filtered and concentrated in vacuo.

The residue was taken up in MeOH (50 mL) and 28% NH₄OH (0.8 mL) was added. The subsequent mixture was stirred at RT for 24 h, upon which the volatiles were removed in vacuo to give tert-butyl 5-(6-hydroxy-7-methoxy-2-(3-(2-morpholinoacetamido)phenyl)quinazolin-4-ylamino)-1H-

149 indazole-1-carboxylate (0.330 g, 0.527 mmol, 53% over three steps). HPLC retention time 5.181 mins.

Example 165 tert-Butyl 5-(6-(2-chloroethoxy)-7-methoxy-2-(3-(2-morpholinoacetamido)phenyl)quinazolin-4-ylamino)-1H-indazole-1-carboxylate

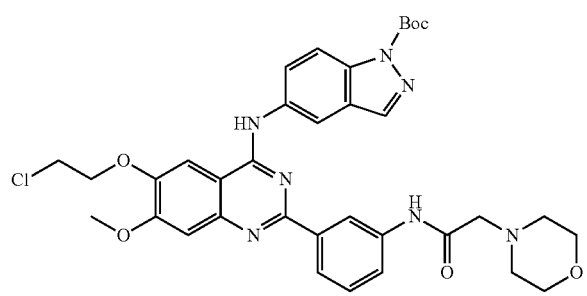 [SMILES: COc1cc2nc(-c3cccc(NC(=O)CN4CCOCC4)c3)nc(Nc3ccc4c(cnn4C(=O)OC(C)(C)C)c3)c2cc1OCCCl]

A mixture of tert-butyl 5-(6-hydroxy-7-methoxy-2-(3-(2-morpholinoacetamido)phenyl)quinazolin-4-ylamino)-1H-indazole-1-carboxylate (0.330 g, 0.527 mmol), 1-bromo-2-chloroethane (0.287 g, 2.00 mmol) and $K_2CO_3$ (0.330 g, 2.39 mmol) in DMF (3 mL) was heated at 85° C. for 3 h. The mixture was allowed to cool to RT, upon which it was diluted with water (200 mL) and the resulting precipitate was collected via filtration. The solid was taken up in EtOAc (250 mL) and washed with water (1×100 mL) and brine (1×100 mL), dried ($Na_2SO_4$), filtered and concentrated in vacuo to give tert-butyl 5-(6-(2-chloroethoxy)-7-methoxy-2-(3-(2-morpholinoacetamido)-phenyl)quinazolin-4-ylamino)-1H-indazole-1-carboxylate which was used without further purification (0.300 g, 0.436 mmol, 83%). HPLC retention time 5.842 mins.

Example 166 tert-Butyl 5-(7-methoxy-2-(3-(2-morpholinoacetamido)phenyl)-6-(2-(pyrrolidin-1-yl)ethoxy)quinazolin-4-ylamino)-1H-indazole-1-carboxylate

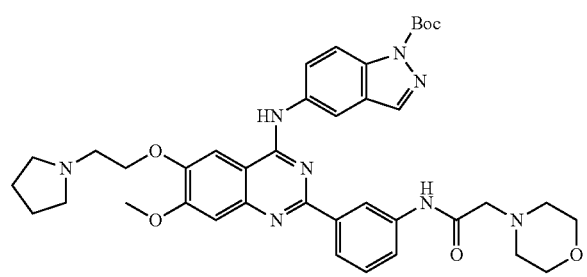 [SMILES: COc1cc2nc(-c3cccc(NC(=O)CN4CCOCC4)c3)nc(Nc3ccc4c(cnn4C(=O)OC(C)(C)C)c3)c2cc1OCCN1CCCC1]

To a mixture of tert-butyl 5-(6-(2-chloroethoxy)-7-methoxy-2-(3-(2-morpholinoacetamido)phenyl)quinazolin-4-ylamino)-1H-indazole-1-carboxylate (0.280 g, 0.407 mmol) in DMF (2 mL) and THF (3 mL) was added pyrrolidine (0.8 mL). The resultant mixture was heated at 85° C. for 2 h, upon which it was allowed to cool to RT, the volatiles were removed in vacuo and the residue was taken up in ice-water (200 mL). The resulting precipitate was collected via filtra-

150 tion and subjected to preparative TLC ($SiO_2$, $CH_2Cl_2$:MeOH 83:17) to give tert-butyl 5-(7-methoxy-2-(3-(2-morpholinoacetamido)-phenyl)-6-(2-(pyrrolidin-1-yl)ethoxy) quinazolin-4-ylamino)-1H-indazole-1-carboxylate (0.085 g, 0.118 mmol, 29%). HPLC retention time 3.81 minutes.

Example 167

N-(3-(4-(1H-Indazol-5-ylamino)-7-methoxy-6-(2-(pyrrolidin-1-yl)ethoxy)quinazolin-2-yl)phenyl)-2-morpholinoacetamide

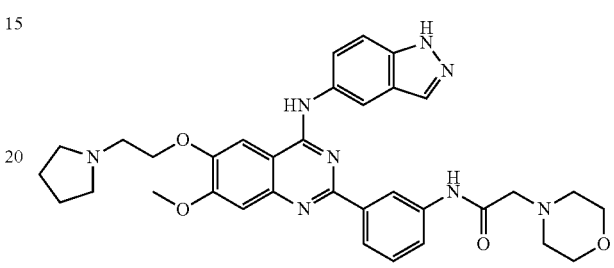

To a mixture of tert-butyl 5-(7-methoxy-2-(3-(2-morpholinoacetamido)-phenyl)-6-(2-(pyrrolidin-1-yl)ethoxy) quinazolin-4-ylamino)-1H-indazole-1-carboxylate (0.085 g, 0.118 mmol) in $CH_2Cl_2$ (4 mL) was added TFA (6 mL). The resultant mixture was stirred at RT for 1.25 h, upon which the volatiles were removed in vacuo and the residue was triturated with $Et_2O$ to give N-(3-(4-(1H-indazol-5-ylamino)-7-methoxy-6-(2-(pyrrolidin-1-yl)ethoxy)quinazolin-2-yl)phenyl)-2-morpholinoacetamide (0.090 g, 0.112 mmol, 95%). MS 623.2 (M+1). HPLC retention time 3.806 mins.

Example 168 tert-Butyl 5-(6-acetoxy-2-(3-butyramidophenyl)-7-methoxyquinazolin-4-ylamino)-1H-indazole-1-carboxylate

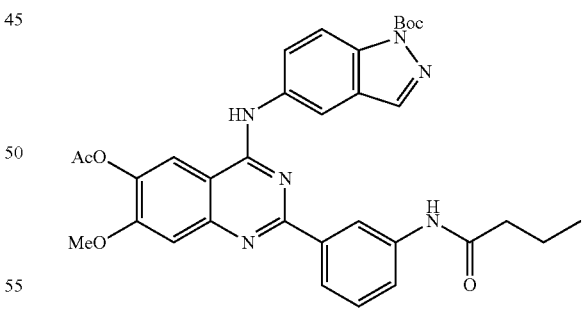

To a solution of tert-butyl 5-(6-acetoxy-2-(3-aminophenyl)-7-methoxyquinazolin-4-ylamino)-1H-indazole-1-carboxylate (2.51 g, 4.65 mmol) and DIEA (3.08 mL, 17.7 mmol) in dichloromethane (60 mL) was added butryl chloride (0.72 g, 6.76 mmol). The resulting reaction mixture was stirred at room temperature for 84 h upon which a solid separated out. The solid was collected by filtration and dried under vacuum (1.32 g). The filtrate was concentrated in vacuo and upon trituration with water gave an additional product (1.0 g). Combination of the two solids gave tert-butyl 5-(6- acetoxy-2-(3-butyramidophenyl)-7-methoxyquinazolin-4-ylamino)-1H-indazole-1-carboxylate (2.32 g, 3.80 mmol, 82%). HPLC retention time 7.079 min.

Example 169 tert-butyl 5-(2-(3-butyramidophenyl)-6-hydroxy-7-methoxyquinazolin-4-ylamino)-1H-indazole-1-carboxylate

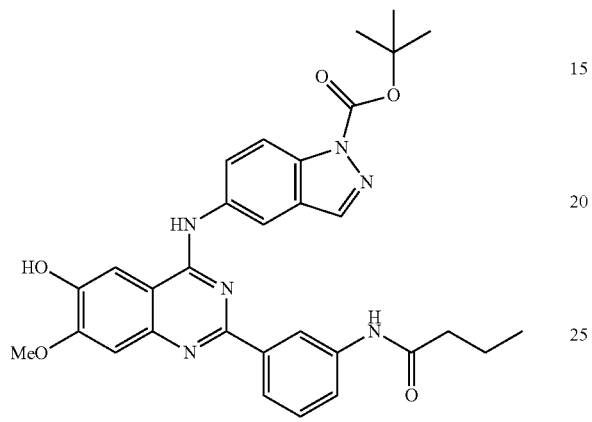

To a mixture of tert-butyl 5-(6-acetoxy-2-(3-aminophenyl)-7-methoxyquinazolin-4-ylamino)-1H-indazole-1-carboxylate (0.205 g, 0.38 mmol) in $CH_2Cl_2$ (10 mL) was added DIEA (0.180 g, 1.4 mmol) and butryl chloride (0.055 g, 0.52 mmol) respectively. The mixture was stirred at RT for 2 h. The mixture was concentrated in vacuo and taken up in $CH_2Cl_2$ (60 mL), the organic layer was washed with water and brine, dried ($Na_2SO_4$), filtered and concentrated in vacuo.

The residue was taken up in MeOH (40 mL) and 28% $NH_4OH$ (0.25 mL) was added to the mixture. The mixture was stirred at RT for 24 h. The volatiles were removed in vacuo and the residue was triturated with $Et_2O$ to give tert-butyl 5-(2-(3-butyramidophenyl)-6-hydroxy-7-methoxyquinazolin-4-ylamino)-1H-indazole-1-carboxylate (0.130 g, 0.24 mmol, 63%). HPLC retention time 6.49 min.

Example 170

N-(3-(4-(1H-indazol-5-ylamino)-6-(2-(dimethylamino)ethoxy)-7-methoxyquinazolin-2-yl)phenyl)butyramide

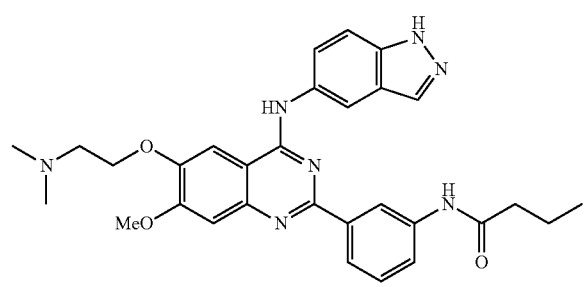 [SMILES: CCCC(=O)Nc1cccc(-c2nc(Nc3ccc4[nH]ncc4c3)c3cc(OCCN(C)C)c(OC)cc3n2)c1]

To a mixture of tert-butyl 5-(2-(3-butyramidophenyl)-6-hydroxy-7-methoxyquinazolin-4-ylamino)-1H-indazole-1-carboxylate (0.102 g, 0.168 mmol), 2-chloro-N,N-dimethylethanamine hydrochloride (0.053 g, 0.37 mmol) and $K_2CO_3$ (0.090 g, 0.65 mmol) in DMF (2.5 mL) was heated at 85° C. for 3 h. The mixture was allowed to cool to RT and was concentrated in vacuo. The residue was subjected to preparative TLC ($SiO_2$, $CH_2Cl_2$ 9:1).

After isolation, the product was immediately taken up $CH_2Cl_2$ (1 mL) and TFA (2 mL) was added. The mixture was stirred at RT for 3.5 h, the volatiles were removed in vacuo and the residue was triturated with $Et_2O$ and dried under vacuum to give the desired product N-(3-(4-(1H-indazol-5-ylamino)-6-(2-(dimethylamino)ethoxy)-7-methoxyquinazolin-2-yl)phenyl)butyramide. MS 540.5 (M+1). (HPLC retention time 4.55 mins.

Example 171

N-(3-(4-(1H-indazol-5-ylamino)-6-(2-(dimethylamino)-2-oxoethoxy)-7-methoxyquinazolin-2-yl)phenyl)nicotinamide

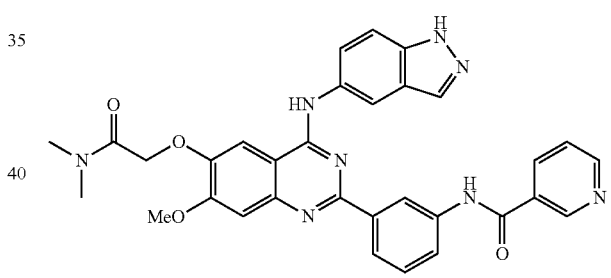

To a mixture of tert-butyl 5-(6-hydroxy-7-methoxy-2-(3-(nicotinamido)-phenyl)quinazolin-4-ylamino)-1H-indazole-1-carboxylate (0.106 g, 0.175 mmol), 2-chloro-N,N-dimethylacetamide (0.051 g, 0.418 mmol) and $K_2CO_3$ (0.053 g, 0.383 mmol) in DMF (2 mL) was heated at 85° C. for 3 h. The mixture was concentrated in vacuo and the residue subjected to preparative TLC ($SiO_2CH_2Cl_2$:MeOH 9:1).

The product from above was then taken up in $CH_2Cl_2$ (3 mL) and TFA (2.5 mL) was added. The mixture was stirred at RT for 3 h. The volatiles were removed in vacuo and the residue was triturated with $Et_2O$ wand dried under vacuum. The residue was purified by preparative HPLC (method 10-35-95) to give the desired product N-(3-(4-(1H-indazol-5-ylamino)-6-(2-(dimethylamino)-2-oxoethoxy)-7-methoxyquinazolin-2-yl)phenyl)nicotinamide (0.021 g, 35.7 μmol, 20%). MS 589.3 (M+1). HPLC retention time 4.31 mins.

Example 172 tert-Butyl 5-(6-(2-(dimethylamino)ethoxy)-7-methoxy-2-(3-nitrophenyl)quinazolin-4-ylamino)-1H-indazole-1-carboxylate

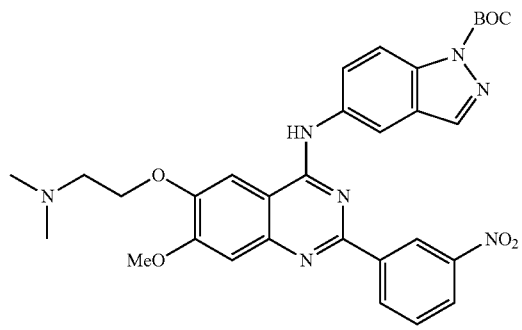 [SMILES: COc1cc2nc(-c3cccc([N+](=O)[O-])c3)nc(Nc3ccc4c(cnn4C(=O)OC(C)(C)C)c3)c2cc1OCCN(C)C]

A mixture of tert-butyl 5-(6-hydroxy-7-methoxy-2-(3-nitrophenyl)quinazolin-4-ylamino)-1H-indazole-1-carboxylate (0.475 g, 0.898 mmol), 2-chloro-N,N-dimethylethanamine (0.28 g, 1.94 mmol) and $K_2CO_3$ (1.18 g, 2.54 mmol) in DMF (8 mL) was heated at 85° C. for 3 h. The volatiles were removed in vacuo and the residue was taken up in $CHCl_3$/MeOH. The solid was removed via filtration and the filtrate was concentrated in vacuo. The residue was purified by column chromatography ($SiO_2$, $CHCl_3$/MeOH 93:7 then 90:10) to give tert-butyl 5-(6-(2-(dimethylamino)ethoxy)-7-methoxy-2-(3-nitrophenyl)quinazolin-4-ylamino)-1H-indazole-1-carboxylate. (0.087 g, 0.145 mmol, 16%). MS 600.4 (M+1).

Example 173 tert-Butyl 5-(2-(3-aminophenyl)-6-(2-(dimethylamino)ethoxy)-7-methoxyquinazolin-4-ylamino)-1H-indazole-1-carboxylate

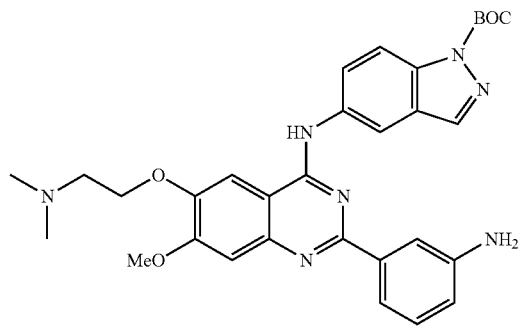

A mixture of tert-butyl 5-(6-(2-(dimethylamino)ethoxy)-7-methoxy-2-(3-nitrophenyl)quinazolin-4-ylamino)-1H-indazole-1-carboxylate (0.085 g, 0.142 mmol) and 10% Pd/C (0.100 g) in MeOH (20 ml) was hydrogenated at RT using a balloon filled with hydrogen gas. The reaction was heated at 55° C. for 1 h. The reaction mixture filtered through Celite® washing with MeOH. The filtrate was concentrated in vacuo to give tert-butyl 5-(2-(3-aminophenyl)-6-(2-(dimethylamino)ethoxy)-7-methoxyquinazolin-4-ylamino)-1H-indazole-1-carboxylate. (0.065 g, 0.128 mmol, 90%). HPLC retention time 3.42 mins.

Example 174

N-(3-(4-(1H-Indazol-5-ylamino)-6-(2-(dimethylamino)ethoxy)-7-methoxyquinazolin-2-yl)phenyl) nicotinamide

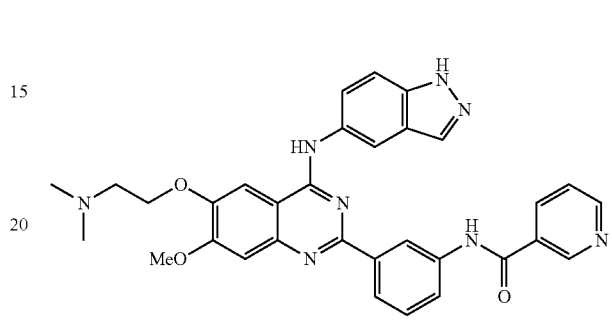

To a mixture of tert-butyl 5-(2-(3-aminophenyl)-6-(2-(dimethylamino)-ethoxy)-7-methoxyquinazolin-4-ylamino)-1H-indazole-1-carboxylate (0.067 g, 0.142 mmol) and di-iso-propylethylamine (0.075 g, 0.58 mmol) in $CH_2Cl_2$ (20 ml) was added nictinoyl chloride (0.032 g, 0.18 mmol). The reaction was stirred at RT for 8 h, upon which the volatiles were removed in vacuo. The residue was dissolved in $CH_2Cl_2$ (1 mL) and was treated with TFA (2.5 mL). The mixture was stirred at RT for 2 h, the volatiles were removed in vacuo and the residue was washed with $Et_2O$ and $CH_2Cl_2$. Purification was accomplished using preparative HPLC (10-35-90 method) to give N-(3-(4-(1H-indazol-5-ylamino)-6-(2-(dimethylamino)ethoxy)-7-methoxyquinazolin-2-yl)phenyl)nicotinamide. (0.017 g, 29.6 mmol, 21%). MS 575.3 (M+1). HPLC retention time 3.81 mins.

Example 175 tert-Butyl 5-(6-acetoxy-7-methoxy-2-(3-(nicotinamido)phenyl)quinazolin-4-ylamino)-1H-indazole-1-carboxylate

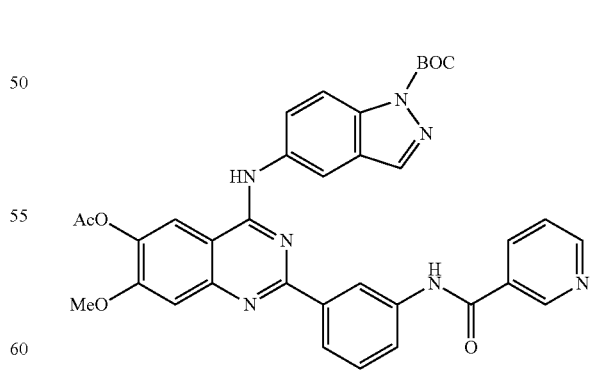

To a mixture of tert-butyl 5-(6-acetoxy-2-(3-aminophenyl)-7-methoxyquinazolin-4-ylamino)-1H-indazole-1-carboxylate (0.230 g, 0.43 mmol) and di-iso-propylethylamine (0.180 g, 0.14 mmol) in $CH_2Cl_2$ (20 ml) was added nictinoyl chloride (0.097 g, 0.54 mmol). The reaction was stirred at RT for 6 h, upon which the volatiles were removed in vacuo and the residue was purified via preparative TLC (SiO$_2$, CH$_2$Cl$_2$/MeOH 9:1) to give tert-butyl 5-(6-acetoxy-7-methoxy-2-(3-(nicotinamido)phenyl)quinazolin-4-ylamino)-1H-indazole-1-carboxylate. (0.168 g, 0.26 mmol, 60%). HPLC retention time 5.924 mins.

Example 176 tert-Butyl 5-(6-hydroxy-7-methoxy-2-(3-(nicotinamido)phenyl)quinazolin-4-ylamino)-1H-indazole-1-carboxylate

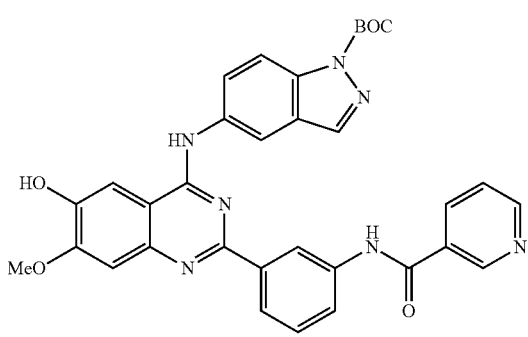 [SMILES: COc1cc2nc(-c3cccc(NC(=O)c4cccnc4)c3)nc(Nc3ccc4c(cnn4C(=O)OC(C)(C)C)c3)c2cc1O]

To a suspension of tert-butyl 5-(6-acetoxy-7-methoxy-2-(3-(nicotinamido)-phenyl)quinazolin-4-ylamino)-1H-indazole-1-carboxylate (0.163 g, 0.299 mmol) in MeOH (15 mL) was added aq. NH$_4$OH solution (0.12 mL). The mixture was stirred at RT for 24 h. The volatiles were removed in vacuo and the residue was triturated with Et$_2$O and dried under vacuum to give tert-butyl 5-(6-hydroxy-7-methoxy-2-(3-(nicotinamido)phenyl)-quinazolin-4-ylamino)-1H-indazole-1-carboxylate. (0.102 g, 0.188 mmol, 63%). HPLC retention time 5.04 mins.

Example 177 tert-Butyl 5-(7-methoxy-6-(2-methoxyethoxy)-2-(3-(nicotinamido)phenyl)quinazolin-4-ylamino)-1H-indazole-1-carboxylate

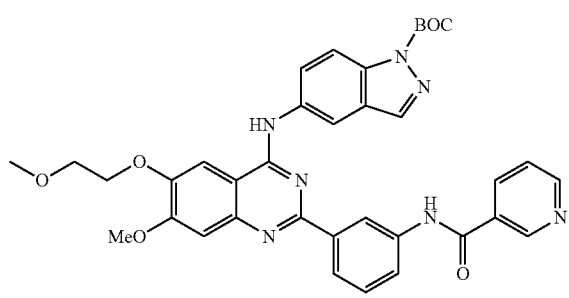 [SMILES: COCCOc1cc2c(Nc3ccc4c(cnn4C(=O)OC(C)(C)C)c3)nc(-c3cccc(NC(=O)c4cccnc4)c3)nc2cc1OC]

To a solution of tert-butyl 5-(6-hydroxy-7-methoxy-2-(3-(nicotinamido)-phenyl)quinazolin-4-ylamino)-1H-indazole-1-carboxylate (0.108 g, 0.179 mmol), 1-bromo-2-methoxyethane (0.054 g, 0.389 mmol) and K$_2$CO$_3$ (0.052 g, 0.449 mmol) in DMF (2 mL) were heated at 85° C. for 3 h. The mixture was allowed to cool to RT and the volatiles were removed in vacuo. The residue was purified by preparative tlc (SiO$_2$, CH$_2$Cl$_2$/MeOH 9:1) to give tert-butyl 5-(7-methoxy-6-(2-methoxyethoxy)-2-(3-(nicotinamido)phenyl)quinazolin-4-ylamino)-1H-indazole-1-carboxylate. The material was taken directly on to the next step. HPLC retention time 5.802 mins.

Example 178

N-(3-(4-(1H-Indazol-5-ylamino)-7-methoxy-6-(2-methoxyethoxy)quinazolin-2-yl)phenyl)nicotinamide

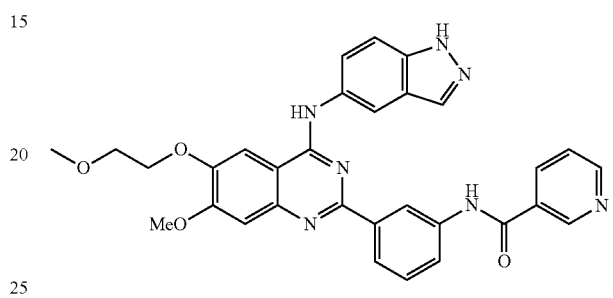

A solution of tert-butyl 5-(7-methoxy-6-(2-methoxyethoxy)-2-(3-(nicotinamido)phenyl)quinazolin-4-ylamino)-1H-indazole-1-carboxylate in CH$_2$Cl$_2$ (15 mL) and TFA (2.2 mL) was stirred at RT for 1 h. The volatiles were removed in vacuo and the residue was washed with Et$_2$O to give N-(3-(4-(1H-indazol-5-ylamino)-7-methoxy-6-(2-methoxyethoxy)quinazolin-2-yl)phenyl)nicotinamide trifluoroacetate salt (0.086 g, 0.127 mmol, 71% over two steps). MS 562.4 (M+1). HPLC retention time 4.92 mins.

Example 179

2-Methoxyethyl 4-methoxy-3-(2-methoxyethoxy)benzoate

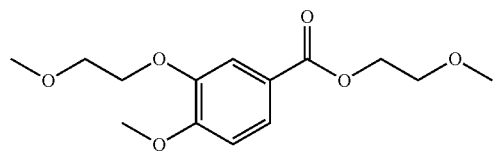

To a mixture of 3-hydroxy-4-methoxy benzoic acid (9.6 g, 57.1 mmol) in DMF (110 mL) cooled to 0° C. under an atmosphere of N$_2$ was added K$_2$CO$_3$ slowly. The mixture was stirred for 30 minutes upon which 2-bromoethyl methyl ether (10.7 mL, 114.2 mmol) was added slowly. The mixture was stirred at RT for 1 h and then at 80° C. for 12 hours, upon which another portion of 2-bromoethyl methyl ether (8.0 mL, 85.7 mmol) was added. Heating was continued for 2 h., upon which TLC indicated complete reaction. The reaction mixture was allowed to cool to RT and poured into ice-water. The mixture was extracted with EtOAc:hexane (4:1 v/v, 3×300 mL). The combined extracts were washed with brine (1×300 mL), dried (Na$_2$SO$_4$), filtered and concentrated in vacuo to give 2-methoxyethyl 4-methoxy-3-(2-methoxyethoxy)benzoate as a dark colored oil. (15.05 g, 52.9 mmol, 93%). MS 307.3 (M+Na). HPLC retention time 5.80 mins.

Example 180

2-Methoxyethyl 4-methoxy-5-(2-methoxyethoxy)-2-nitrobenzoate

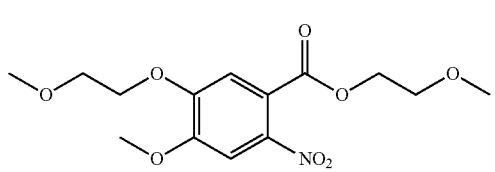

To a solution of 2-methoxyethyl 4-methoxy-3-(2-methoxyethoxy)benzoate (15.05 g, 52.9 mmol) in AcOH (54 mL) under an atmosphere of $N_2$ was added conc. $HNO_3$ (13.5 mL) in one portion. The reaction was stirred at RT for 72 h. The mixture was poured into ice-water (ca. 800 mL) and extracted with EtOAc (2×400 mL). The combined organics were washed with water (2×200 mL) and brine (1×200 mL), dried ($Na_2SO_4$) and conc. in vacuo. The residue was azeotroped with heptane (2×300 mL) to remove residual AcOH giving 2-methoxyethyl 4-methoxy-5-(2-methoxyethoxy)-2-nitrobenzoate as a dark colored oil. (15.5 g, 47.1 mmol, 89%). HPLC retention time 6.24 mins.

Example 181

4-Methoxy-5-(2-methoxyethoxy)-2-nitrobenzoic acid

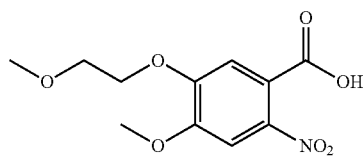 [SMILES: COCCOc1cc(C(=O)O)c([N+](=O)[O-])cc1OC]

To a solution of 2-methoxyethyl 4-methoxy-5-(2-methoxyethoxy)-2-nitrobenzoate (5.0 g, 15.2 mmol) in EtOH (40 mL) was added 2N NaOH (40 mL, 76.0 mmol, 5 eq.). The mixture was stirred at RT for 12 h. The mixture was diluted with water (100 mL) and washed with $CH_2Cl_2$ (1×100 mL). The aqueous layer was acidified to pH=1 using 1N HCl (A solid began to precipitate, this was dissolved by the addition of EtOAc). The aqueous mixture was extracted with EtOAc (2×200 mL). The combined organics were washed with brine (1×100 mL), dried ($Na_2SO_4$), filtered and concentrated in vacuo to give 4-methoxy-5-(2-methoxyethoxy)-2-nitrobenzoic acid as an off white solid (3.55 g, 12.4 mmol, 86%). HPLC retention time 4.94 mins.

Example 182

4-Methoxy-5-(2-methoxyethoxy)-2-nitrobenzamide

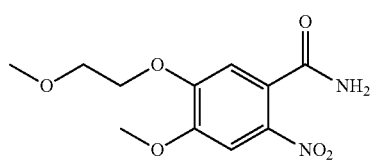

To a solution of 4-methoxy-5-(2-methoxyethoxy)-2-nitrobenzoic acid (3.35 g, 12.4 mmol) under an atmosphere of $N_2$ in anhydrous THF (50 mL) was added oxalyl chloride (2.25 mL, 1.7 eq. 25.5 mmol) and two drops of DMF. The mixture was stirred at RT for 30 minutes, upon which two more drops of DMF were added and stirring at RT was continued for 1 h. Tlc and HPLC analysis indicated complete formation of the acid chloride intermediate and the mixture was concentrated in vacuo to give the acid chloride intermediate as a yellow solid. The solid was dissolved in anhydrous THF (50 mL) and to this solution was added a saturated solution of $NH_3$ in THF (15 mL) via a cannula. A precipitate began to form and stirring was continued at RT for 12 h. The mixture was concentrated in vacuo to give 4-methoxy-5-(2-methoxyethoxy)-2-nitrobenzamide as an off-white solid. (4.5 g, contains some $NH_4Cl$, the mixture was taken on directly to the next step). HPLC retention time 8.55 mins.

Example 183

2-Amino-4-methoxy-5-(2-methoxyethoxy)benzamide

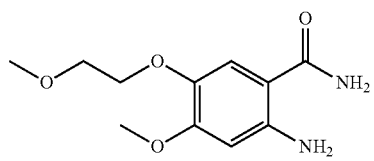 [SMILES: COCCOc1cc(C(N)=O)c([N+](=O)[O-])cc1OC]

A mixture of 4-methoxy-5-(2-methoxyethoxy)-2-nitrobenzamide (4.5 g, contains some $NH_4Cl$) and 10% Pd/C (ca. 0.5 g) in DME (200 mL) and MeOH (200 mL) was hydrogenated under a balloon of $H_2$ at RT for 12 h. The mixture was filtered through a pad of Celite® and concentrated in vacuo to give 2-amino-4-methoxy-5-(2-methoxyethoxy)benzamide as an off white solid (2.8 g, 11.6 mmol). HPLC retention time 2.80 mins.

Example 184

4-Methoxy-5-(2-methoxyethoxy)-(3-nitrophenyl) aminobenzamide

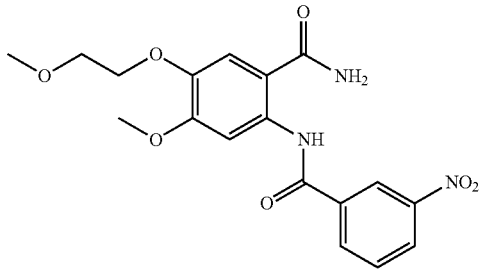 [SMILES: COCCOc1cc(C(N)=O)c(NC(=O)c2cccc([N+](=O)[O-])c2)cc1OC]

To a mixture of 2-amino-4-methoxy-5-(2-methoxyethoxy) benzamide (1.78 g, 7.40 mmol) and pyridine (2.40 mL, 29.6 mmol) in CHCl₃ (40 mL) was added 3-nitrobenzoyl chloride (1.44 g, 7.8 mmol). The mixture was stirred at RT for 2.5 h upon which the mixture was concentrated in vacuo to give the desired product, which was used directly in the next step without purification.

Example 185

7-Methoxy-6-(2-methoxyethoxy)-2-(3-nitrophenyl) quinazolin-4(3H)-one

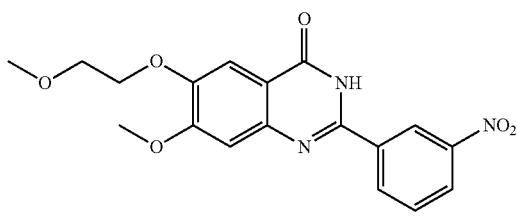 [SMILES: COCCOc1cc2c(=O)[nH]c(-c3cccc([N+](=O)[O-])c3)nc2cc1OC]

The crude product from the previous step (7.4 mmol theoretically) was taken up in 2N NaOH (40 mL) and refluxed for 4 h. the mixture was allowed to cool to RT and neutralized to pH=7 with 6 and 1 N HCl. Upon neutralization a precipitate appeared which was collected via filtration and washed with Et₂O. The solid was azeotroped with toluene (2×50 mL) to remove any residual water and dried under high vacuum to give 7-methoxy-6-(2-methoxyethoxy)-2-(3-nitrophenyl) quinazolin-4(3H)-one as an off white solid (2.60 g, 7.00 mmol, 95% over two steps). HPLC retention time 6.2 mins.

Example 186

4-Chloro-7-methoxy-6-(2-methoxyethoxy)-2-(3-nitrophenyl)quinazoline

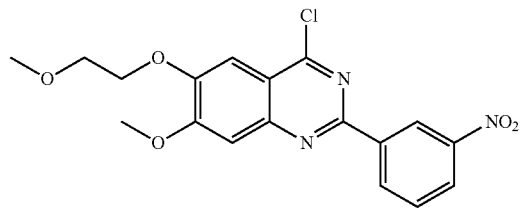 [SMILES: COCCOc1cc2c(Cl)nc(-c3cccc([N+](=O)[O-])c3)nc2cc1OC]

To a suspension of 7-methoxy-6-(2-methoxyethoxy)-2-(3-nitrophenyl)quinazolin-4(3H)-one (1.65 g, 4.46 mmol) in anhydrous THF (30 mL) was added oxalyl chloride (1.3 mL, 14.7 mmol) and 2 drops of DMF. The mixture was refluxed for 2 h, upon which the mixture was concentrated in vacuo, taken up in CHCl₃ (100 mL) and washed with sat. NaHCO₃ (3×50 mL), water (2×50 mL) and brine (1×50 mL). The organic layer was dried (Na₂SO₄), filtered and concentrated in vacuo to give 4-chloro-7-methoxy-6-(2-methoxyethoxy)-2-(3-nitrophenyl)quinazoline (1.18 g, 3.03 mmol, 68%). HPLC retention time 9.55 mins.

Example 187 tert-Butyl 5-(7-methoxy-6-(2-methoxyethoxy)-2-(3-nitrophenyl)quinazolin-4-ylamino)-1H-indazole-1-carboxylate

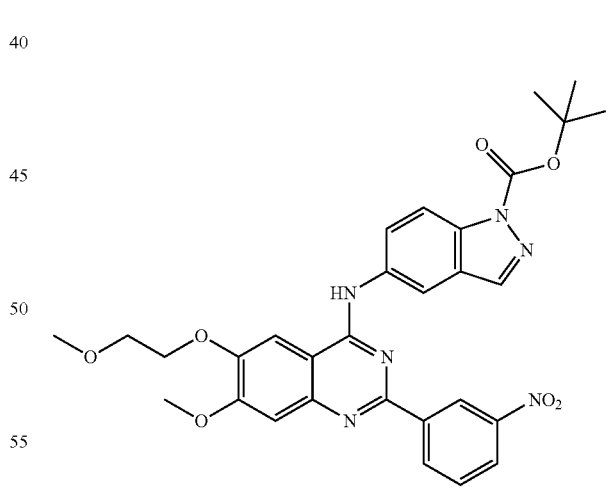

A mixture of 4-chloro-7-methoxy-6-(2-methoxyethoxy)-2-(3-nitrophenyl)quinazoline (0.500 g, 1.28 mmol) and 5-amino-1H-indazole-1-carboxylate (0.314 g, 1.34 mmol) in iso-propanol (30 mL) was heated at 95° C. for 30 minutes and at 95° C. for 8 h. The mixture was allowed to cool to RT and the solid was collected via filtration. The cake was washed with iso-propanol and Et₂O, triturated with CH₂Cl₂ and EtOAc and dried in vacuo to give tert-Butyl 5-(7-methoxy-6-(2-methoxyethoxy)-2-(3-nitrophenyl)quinazolin-4- ylamino)-1H-indazole-1-carboxylate (0.560 g, 0.955 mmol, 71%). MS 587 (M+1). HPLC retention time 7.21 mins.

Example 188 tert-Butyl 5-(2-(3-aminophenyl)-7-methoxy-6-(2-methoxyethoxy)quinazolin-4-ylamino)-1H-indazole-1-carboxylate

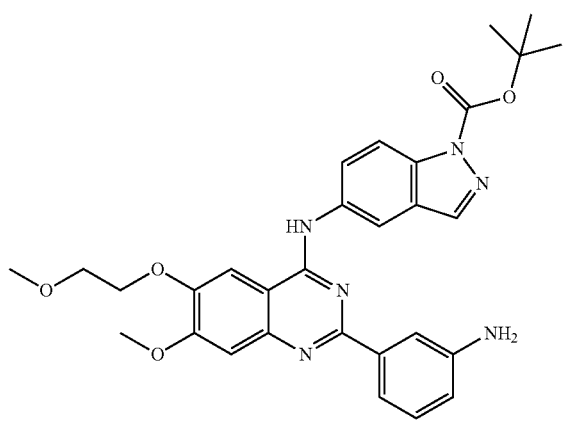 [SMILES: COCCOc1cc2c(Nc3ccc4c(cnn4C(=O)OC(C)(C)C)c3)nc(-c3cccc([N+](=O)[O-])c3)nc2cc1OC]

A mixture of tert-butyl 5-(7-methoxy-6-(2-methoxyethoxy)-2-(3-nitrophenyl)quinazolin-4-ylamino)-1H-indazole-1-carboxylate (0.560 g, 0.95 mmol) and 10% Pd/C (ca. 0.1 g) in DME (100 mL) and MeOH (100 mL) was hydrogenated under a balloon of $H_2$ at RT for 12 h. The mixture was filtered through a pad of Celite® and concentrated in vacuo to give tert-butyl 5-(2-(3-aminophenyl)-7-methoxy-6-(2-methoxyethoxy)quinazolin-4-ylamino)-1H-indazole-1-carboxylate as an off white solid (0.510 g, 0.92 mmol, 97%). HPLC retention time 5.62 mins.

Example 189 tert-butyl 5-(7-methoxy-6-(2-methoxyethoxy)-2-(3-(2-morpholinoacetamido)phenyl)quinazolin-4-ylamino)-1H-indazole-1-carboxylate

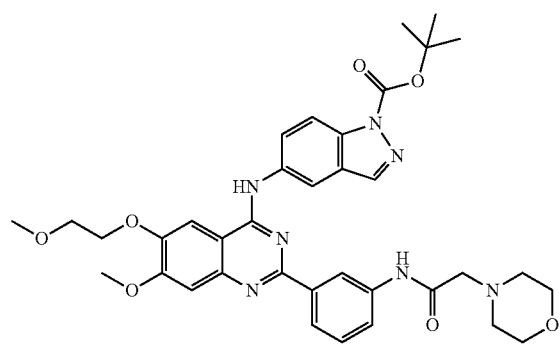 [SMILES: COCCOc1cc2c(Nc3ccc4c(cnn4C(=O)OC(C)(C)C)c3)nc(-c3cccc(NC(=O)CN4CCOCC4)c3)nc2cc1OC]

A mixture of 2-morpholinoacetic acid (0.034 g, 0.24 mmol), DIEA (0.165 mL, 0.94 mmol) and PyBOP® (0.125 g, 0.24 mmol) in $CH_2Cl_2$ (1 mL) was stirred at RT for 10 minutes, upon which it was added to a solution of tert-Butyl 5-(2-(3-aminophenyl)-7-methoxy-6-(2-methoxyethoxy)quinazolin-4-ylamino)-1H-indazole-1-carboxylate (0.260 g, 0.47 mmol) in $CH_2Cl_2$ (10 mL), the subsequent was stirred at RT for 1 hr upon which further aliquots of 2-morpholinoacetic acid (0.034 g, 0.24 mmol) and PyBOP® (0.125 g, 0.24 mmol) were added. The resulting mixture was stirred at RT overnight upon which the mixture was concentrated in vacuo and taken directly to the next step. HPLC retention time 5.35 mins.

Example 190

N-(3-(4-(1H-indazol-5-ylamino)-7-methoxy-6-(2-methoxyethoxy)quinazolin-2-yl)phenyl)-2-morpholinoacetamide

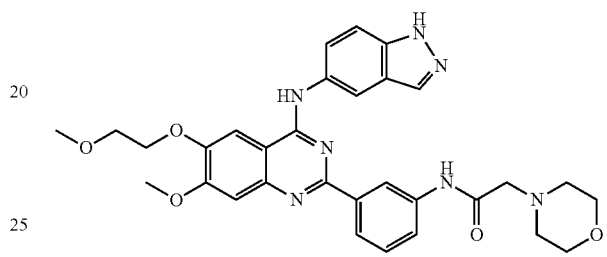

To a suspension of tert-butyl 5-(7-methoxy-6-(2-methoxyethoxy)-2-(3-(2-morpholinoacetamido)phenyl)quinazolin-4-ylamino)-1H-indazole-1-carboxylate. (0.321 g, 0.47 mmol) in $CH_2Cl_2$ (3 mL) was added TFA (3 mL). The resulting mixture was stirred at RT for 1.5 h, upon which it was concentrated in vacuo and the residue purified by preparative HPLC (10-35-90 method) to give N-(3-(4-(1H-indazol-5-ylamino)-7-methoxy-6-(2-methoxyethoxy)quinazolin-2-yl)phenyl)-2-morpholinoacetamide trifluoroacetate salt (0.141 g, 0.202 mmol, 43% over two steps). MS 584 (M+1). HPLC retention time 4.40 mins.

Example 191

2-(3-(benzyloxy)phenyl)-7-methoxy-6-(2-methoxyethoxy)quinazolin-4(3H)-one

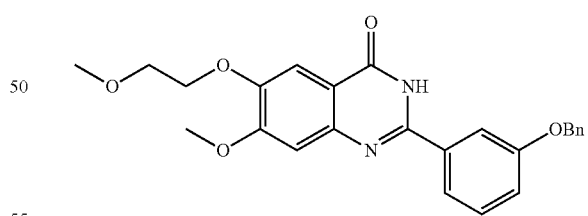

To mixture of 2-amino-4-methoxy-5-(2-methoxyethoxy)benzamide (2.20 g, 9.16 mmol) and 3-(benzyloxy)benzoyl chloride (2.50 g, 10.1 mmol) in $CHCl_3$ (50 mL) was added pyridine 2.9 mL). The mixture was stirred at RT for 3 h, upon which the volatiles were removed in vacuo.

The residue was taken up in 2N NaOH (60 mL) and heated at reflux overnight. The mixture was allowed to cool to RT, upon which it was neutralized with 1N HCl to pH=7. The mixture was allowed to stand for 2 h upon which the precipitate was collected via filtration. The solid was dried under high vacuum to give 2-(3-(benzyloxy)-phenyl)-7-methoxy- 6-(2-methoxyethoxy)quinazolin-4(3H)-one (3.28 g, 7.58 mmol, 83%). MS 433 (M+1). HPLC retention time 7.41 mins.

Example 192

2-(3-(benzyloxy)phenyl)-4-chloro-7-methoxy-6-(2-methoxyethoxy)quinazoline

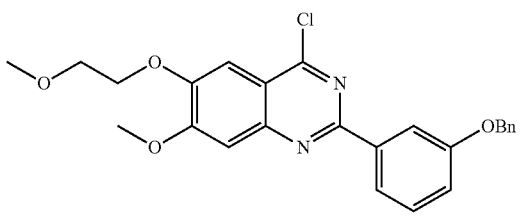

To a suspension of 2-(3-(benzyloxy)phenyl)-7-methoxy-6-(2-methoxyethoxy)quinazolin-4(3H)-one (3.28 g, 7.58 mmol) in CH$_2$Cl$_2$ (100 mL) was added oxalyl chloride (2.20 mL, 24.8 mmol) and 2 drops of DMF. The mixture was stirred at RT for 6 h. An additional aliquot of oxalyl chloride (1.20 mL, 13.5 mmol) was added. Stirring was continued at RT overnight, upon which the mixture was concentrated in vacuo, taken up in CHCl$_3$ (100 mL) and washed with sat. NaHCO$_3$ (3×50 mL), water (2×50 mL) and brine (1×50 mL). The organic layer was dried (Na$_2$SO$_4$), filtered and concentrated in vacuo to give 2-(3-(benzyloxy)phenyl)-4-chloro-7-methoxy-6-(2-methoxyethoxy)quinazoline (1.52 g, 3.37 mmol, 45%). MS 451 (M+1 Cl isotope pattern). HPLC retention time 10.84 mins. (10-95-13 method).

Example 193 tert-butyl 5-(2-(3-(benzyloxy)phenyl)-7-methoxy-6-(2-methoxyethoxy)quinazolin-4-ylamino)-1H-indazole-1-carboxylate

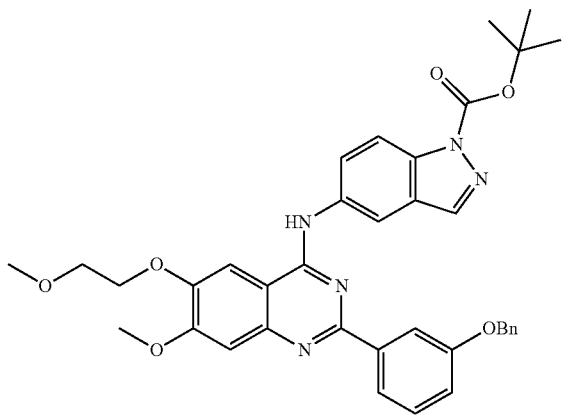 [SMILES: COCCOc1cc2c(Nc3ccc4c(cnn4C(=O)OC(C)(C)C)c3)nc(-c3cccc(O)c3)nc2cc1OC]

A mixture of 2-(3-(benzyloxy)phenyl)-4-chloro-7-methoxy-6-(2-methoxyethoxy)quinazoline (1.55 g, 3.44 mmol) and tert-butyl 5-amino-1H-indazole-1-carboxylate (0.842 g, 3.61 mmol) in iso-propanol (100 mL) was heated at 95° C. for 2 h, upon which the an additional aliquot of tert-butyl 5-amino-1H-indazole-1-carboxylate (0.100 g, 0.43 mmol) was added. Stirring was continued at 95° C. for a further 3 h upon which a third aliquot of tert-butyl 5-amino-1H-indazole-1-carboxylate (0.050 g, 0.22 mmol) was added. Stirring was continued at 95° C. for a further 1 h upon which the mixture was allowed to cool to RT and the precipitate was collected via filtration. The solid was washed with iso-propanol and dried under vacuum to give tert-butyl 5-(2-(3-(benzyloxy)phenyl)-7-methoxy-6-(2-methoxyethoxy)quinazolin-4-ylamino)-1H-indazole-1-carboxylate (2.35 g, 3.44 mmol, 100%). MS 648 (M+1). HPLC retention time 7.79 mins.

Example 194 tert-Butyl 5-(2-(3-hydroxyphenyl)-7-methoxy-6-(2-methoxyethoxy)quinazolin-4-ylamino)-1H-indazole-1-carboxylate

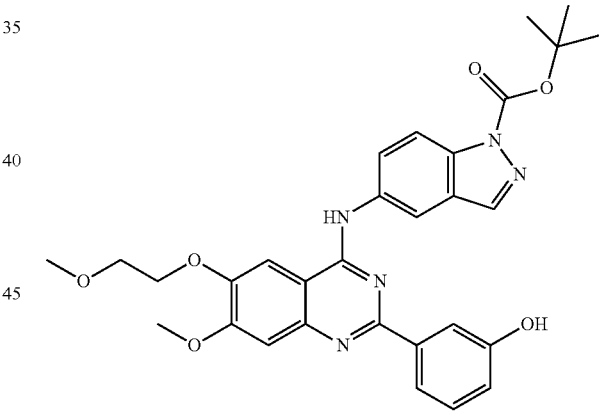

A suspension of tert-butyl 5-(2-(3-(benzyloxy)phenyl)-7-methoxy-6-(2-methoxyethoxy)quinazolin-4-ylamino)-1H-indazole-1-carboxylate (2.70 g, 4.17 mmol) in MeOH (400 mL) and DME (200 mL) was added Pd/C (10%, wet, 0.500 g) under an atmosphere of N$_2$. The N$_2$ was exchanged for H$_2$ and the mixture was stirred under an atmosphere of H2 (balloon pressure) overnight. The mixture was filtered through a pad of Celite® and the filtrate was concentrated in vacuo to give tert-Butyl 5-(2-(3-hydroxyphenyl)-7-methoxy-6-(2-methoxyethoxy)quinazolin-4-ylamino)-1H-indazole-1-carboxylate (2.25 g, 4.04 mmol, 97%). MS 558 (M+1). HPLC retention time 6.44 mins.

Example 195 tert-butyl 5-(2-(3-(2-(isopropylamino)-2-oxoethoxy)phenyl)-7-methoxy-6-(2-methoxyethoxy)quinazolin-4-ylamino)-1H-indazole-1-carboxylate

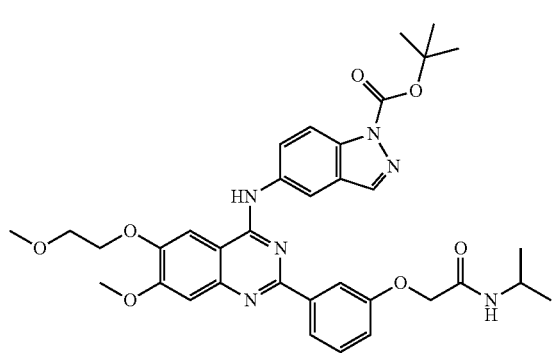 [SMILES: COCCOc1cc2c(Nc3ccc4c(cnn4C(=O)OC(C)(C)C)c3)nc(-c3cccc(OCC(=O)NC(C)C)c3)nc2cc1OC]

To a solution of tert-Butyl 5-(2-(3-hydroxyphenyl)-7-methoxy-6-(2-methoxyethoxy)quinazolin-4-ylamino)-1H-indazole-1-carboxylate (0.400 g, 0.72 mmol) and 2-chloro-N-isopropylacetamide (0.107 g, 0.79 mmol) in DMF (16 mL) was added $K_2CO_3$ (0.297 g, 1.44 mmol). The mixture was heated at 80° C. for 72 h. The mixture was concentrated in vacuo and taken on directly into the next step. HPLC retention time 6.76 mins.

Example 196

2-(3-(4-(1H-indazol-5-ylamino)-7-methoxy-6-(2-methoxyethoxy)quinazolin-2-yl)phenoxy)-N-isopropylacetamide

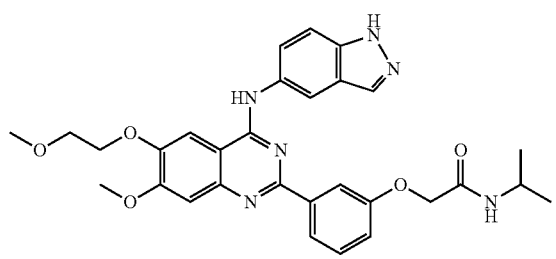 [SMILES: COCCOc1cc2c(Nc3ccc4[nH]ncc4c3)nc(-c3cccc(OCC(=O)NC(C)C)c3)nc2cc1OC]

The crude tert-butyl 5-(2-(3-(2-(isopropylamino)-2-oxoethoxy)phenyl)-7-methoxy-6-(2-methoxyethoxy)quinazolin-4-ylamino)-1H-indazole-1-carboxylate from the previous step was taken up in $CH_2Cl_2$ (2 mL) and TFA (5 mL). The mixture was stirred at RT for 2 h. The mixture was concentrated in vacuo and a portion of the residue was purified by preparative HPLC (10-35-90, 10-30-90, 0-15-90, 5-20-90 and 20-40-90 methods) to give 2-(3-(4-(1H-indazol-5-ylamino)-7-methoxy-6-(2-methoxyethoxy)-quinazolin-2-yl) phenoxy)-N-isopropylacetamide (0.039 g, 68.4 mmol). MS 557 (M+1). HPLC retention time 5.48 mins.

Example 197 tert-butyl 5-(2-(3-butyramidophenyl)-6-hydroxyquinazolin-4-ylamino)-1H-indazole-1-carboxylate

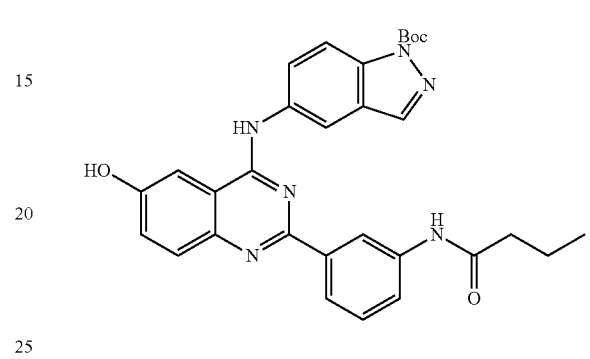

To a solution of tert-butyl 5-(6-acetoxy-2-(3-aminophenyl)quinazolin-4-ylamino)-1H-indazole-1-carboxylate (0.57 g, 1.12 mmol) and DIEA (0.65 g, 5.03 mmol) in dichloromethane (20 mL) was added butryl chloride (0.180 g, 1.69 mmol). The resulting reaction mixture was stirred at room temperature for 4 h. The volatiles were removed under reduced pressure and the residue was triturated with water causing formation of a precipitate. The solid was collected via filtration and dried under vacuum. The solid was suspended in anhydrous methanol (50 mL) and 28% ammonium hydroxide (0.9 mL) was added. The resulting reaction mixture was stirred at room temperature for 24 h. The volatiles were removed under reduced pressure and the residue upon trituration with ether gave tert-butyl 5-(2-(3-butyramidophenyl)-6-hydroxyquinazolin-4-ylamino)-1H-indazole-1-carboxylate (0.354 g, 0.66 mmol, 59% over two steps). HPLC retention time 6.342 min.

Example 198 tert-butyl 5-(2-(3-butyramidophenyl)-6-(2-chloroethoxy)quinazolin-4-ylamino)-1H-indazole-1-carboxylate

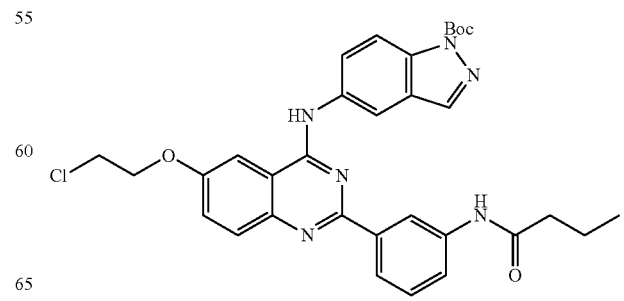

To a mixture of 5-(2-(3-butyramidophenyl)-6-hydroxyquinazolin-4-ylamino)-1H-indazole-1-carboxylate (1.50 g, 2.79 mmol) and potassium carbonate (1.64 g, 11.8 mmol) in anhydrous DMF (5 mL) was added 1-bromo-2-chloroethane (1.6 g, 11.2 mmol) The subsequent mixture was heated at 85° C. for 4 h, upon which it was allowed to cool to RT and it was poured onto ice-water. A solid was precipitated out, which collected via filtration and dried under vacuum. The solid was purified via silica gel column chromatography to give tert-butyl 5-(2-(3-butyramidophenyl)-6-(2-chloroethoxy)-quinazolin-4-ylamino)-1H-indazole-1-carboxylate (0.94 g, 1.56 mmol, 60%). HPLC retention time 7.479.

Example 199

N-(3-(4-(1H-Indazol-5-ylamino)-6-(2-(pyrrolidin-1-yl)ethoxy)-quinazolin-2-yl)phenyl)butyramide

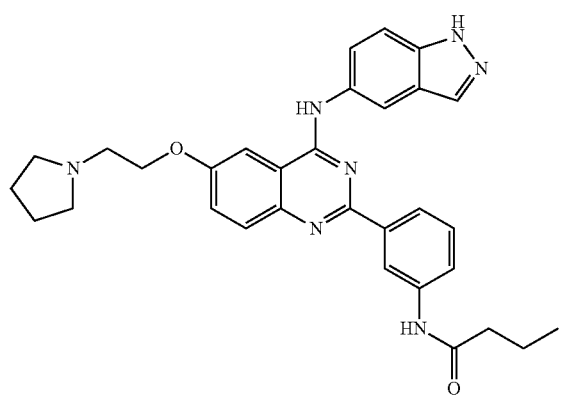 [SMILES: CCCC(=O)Nc1cccc(-c2nc(Nc3ccc4[nH]ncc4c3)c3cc(OCCN4CCCC4)ccc3n2)c1]

To a solution of tert-butyl 5-(2-(3-butyramidophenyl)-6-(2-chloroethoxy)quinazolin-4-ylamino)-1H-indazole-1-carboxylate (0.170 g, 0.282 mmol) in DMSO (2 mL) was added pyrrolidine (0.5 mL). The subsequent mixture was heated at 80° C. for 1.5 h upon which it was allowed to cool to RT and poured into ice-water (100 mL). A precipitate formed which was collected via filtration and it was dried under vacuum. The precipitate was purified via preparative TLC (SiO₂, CH₂Cl₂:MeOH 8:1).

The purified solid was taken up in HCl (4M in 1,4 dioxane, 2 mL) and stirred at RT for 2 h. The volatiles were removed in vacuo to give N-(3-(4-(1H-indazol-5-ylamino)-6-(2-(pyrrolidin-1-yl)ethoxy)quinazolin-2-yl)phenyl)butyramide di-hydrochloride salt (0.120 g, 0.198 mmol, 70% over two steps). MS 536 (M+1). HPLC retention time 4.61 mins.

Example 200

N-(3-(4-(1H-indazol-5-ylamino)-6-(2-(piperidin-1-yl)ethoxy)-quinazolin-2-yl)phenyl)butyramide

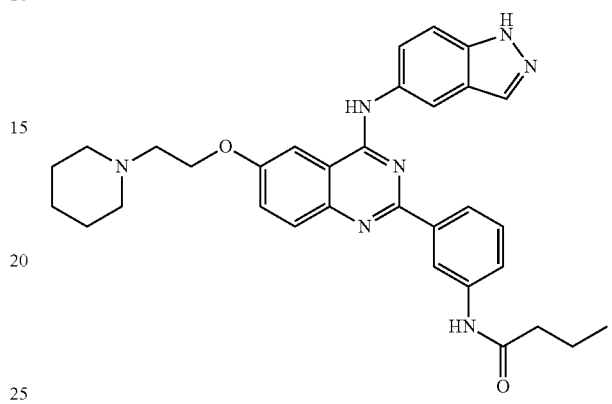

To a solution of tert-butyl 5-(2-(3-butyramidophenyl)-6-(2-chloroethoxy)quinazolin-4-ylamino)-1H-indazole-1-carboxylate (0.174 g, 0.290 mmol) in DMSO (1.5 mL) was added piperidine (0.5 mL). The subsequent mixture was heated at 80° C. for 1.5 h upon which it was allowed to cool to RT and poured into ice-water (100 mL). A precipitate formed which was collected via filtration and it was dried under vacuum. The precipitate was purified via preparative TLC (SiO₂, CH₂Cl₂:MeOH 8:1).

The purified solid was taken up in HCl (4M in 1,4 dioxane, 2 mL) and stirred at RT for 2 h. The volatiles were removed in vacuo to give N-(3-(4-(1H-indazol-5-ylamino)-6-(2-(piperidin-1-yl)ethoxy)quinazolin-2-yl)phenyl)butyramide di-hydrochloride salt (0.085 g, 0.137 mmol, 47% over two steps). MS 550 (M+1). HPLC retention time 4.67 mins.

Example 201

N-(3-(4-(1H-indazol-5-ylamino)-6-(2-methoxyethoxy)quinazolin-2-yl)phenyl)butyramide

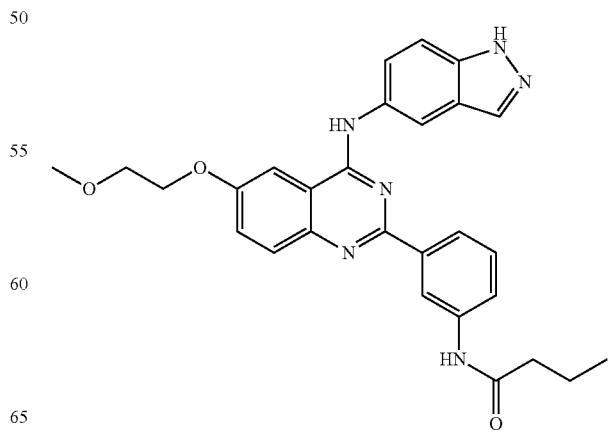

A mixture of tert-butyl 5-(2-(3-butyramidophenyl)-6-hydroxyquinazolin-4-ylamino)-1H-indazole-1-carboxylate (0.167 g, 0.31 mmol), 1-bromo-2-methoxyethane (0.118 g, 0.85 mmol) and $K_2CO_3$ (0.172 g, 1.25 mmol) in DMF (2 mL) was heated at 80° C. for 2.5 h. The mixture was allowed to cool to RT, upon which it was poured into water. A precipitate formed which was collected via filtration, dried under vacuum and purified via preparative TLC ($SiO_2$, $CH_2Cl_2$:MeOH 95:5).

The purified solid was taken up in HCl (4M in 1,4 dioxane, 30 mL) and stirred at RT for 4.5 h. The volatiles were removed in vacuo and the residue was triturated with $Et_2O$ to give N-(3-(4-(1H-indazol-5-ylamino)-6-(2-methoxyethoxy) quinazolin-2-yl)phenyl)butyramide hydrochloride (0.091 g, 0.171 mmol, 55% over two steps). MS 497 (M+1). HPLC retention time 5.547 mins.

Example 202

N-(3-(4-(1H-indazol-5-ylamino)-6-(2-((2-methoxyethyl)(methyl)amino)ethoxy)quinazolin-2-yl)phenyl) butyramide

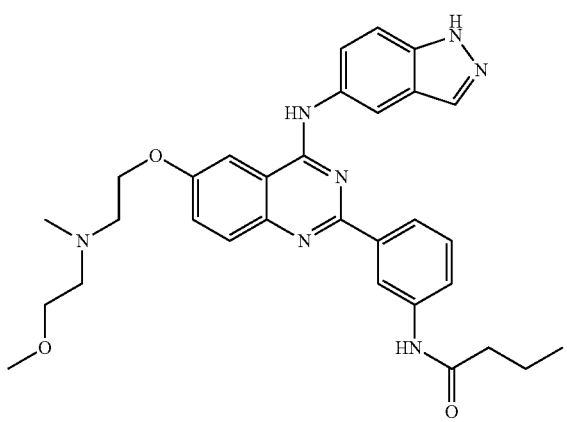 [SMILES: CCCC(=O)Nc1cccc(-c2nc(Nc3ccc4[nH]ncc4c3)c3cc(OCCN(C)CCOC)ccc3n2)c1]

To a solution of tert-butyl 5-(2-(3-butyramidophenyl)-6-(2-chloroethoxy)-quinazolin-4-ylamino)-1H-indazole-1-carboxylate (0.150 g, 0.250 mmol) in DMSO (2 mL) was added 2-methoxy-N-methylethanamine (0.5 mL). The subsequent mixture was heated at 75° C. for 1.5 h upon which it was allowed to cool to RT and poured into ice-water (100 mL). A precipitate formed which was collected via filtration and it was dried under vacuum. The precipitate was purified via preparative TLC ($SiO_2$, $CH_2Cl_2$:MeOH 8:1). Two compounds were isolated and combined.

The combined compounds were taken up in $CH_2Cl_2$ (2 mL) and HCl (4M in 1,4 dioxane, 25 mL) and stirred at RT for 7 h. The volatiles were removed in vacuo and the residue was washed with $CH_2Cl_2$ and $Et_2O$. The solid was dried under vacuum to give N-(3-(4-(1H-indazol-5-ylamino)-6-(2-((2-methoxyethyl)(methyl)amino)ethoxy)-quinazolin-2-yl)phenyl)butyramide di-hydrochloride salt (0.100 g, 0.160 mmol, 64% over two steps). MS 554 (M+1). HPLC retention time 4.52 mins.

Example 203

N-(3-(4-(1H-indazol-5-ylamino)-6-(2-(4-methylpiperazin-1-yl)ethoxy)-quinazolin-2-yl)phenyl)butyramide

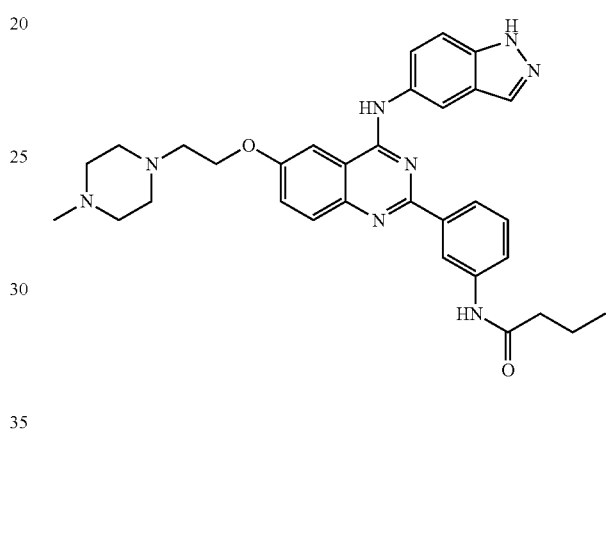

To a solution of tert-butyl 5-(2-(3-butyramidophenyl)-6-(2-chloroethoxy)quinazolin-4-ylamino)-1H-indazole-1-carboxylate (0.150 g, 0.250 mmol) in DMSO (2 mL) was added 1-methylpiperazine (0.5 mL). The subsequent mixture was heated at 85° C. for 2 h upon which an additional aliquot of 1-methylpiperazine (0.2 mL). Heating at 85° C. was continued for a further 1.5 h, upon which the mixture was allowed to cool to RT and poured into ice-water (100 mL). A precipitate formed which was collected via filtration and it was dried under vacuum. The precipitate was purified via preparative TLC ($SiO_2$, $CH_2Cl_2$:MeOH:$NH_4OH$ 9:1:0.1) to give two compounds.

The combined compounds were taken up in $CH_2Cl_2$ (2 mL) TFA (4 mL) was added. The resulting mixture was stirred at RT for 4 h, upon which the volatiles were removed in vacuo. The residue was neutralized with sat. $NaHCO_3$ and extracted with THF (3×25 mL). The combined organics were washed with brine (1×20 mL), dried ($Na_2SO_4$) and purified by preparative TLC ($SiO_2$, $CH_2Cl_2$:MeOH:$NH_4OH$ 9:1:0.1). The purified compound was taken up in $CH_2Cl_2$ (2 mL) and HCl (4M in 1,4 dioxane, 10 mL) and was stirred at RT for 4 h. The volatiles were removed in vacuo and the residue was triturated with $Et_2O$, filtered and dried under vacuum to give N-(3-(4-(1H-indazol-5-ylamino)-6-(2-(4-methylpiperazin-1-yl)ethoxy)quinazolin-2-yl)phenyl)butyramide di-hydrochloride salt (0.067 g, 0.105 mmol, 42% over two steps). MS 565 (M+1). HPLC retention time 4.30 mins.

Example 204

N-(3-(4-(1H-indazol-5-ylamino)-6-(2-(2-oxopyrrolidin-1-yl)ethoxy)-quinazolin-2-yl)phenyl)butyramide

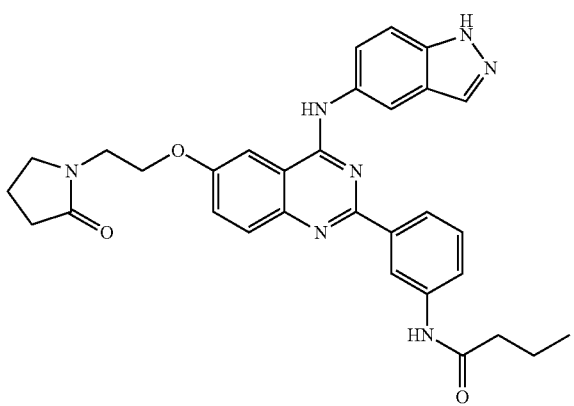 [SMILES: CCCC(=O)Nc1cccc(-c2nc(Nc3ccc4[nH]ncc4c3)c3cc(OCCN4CCCC4=O)ccc3n2)c1]

A mixture of tert-butyl 5-(2-(3-butyramidophenyl)-6-hydroxyquinazolin-4-ylamino)-1H-indazole-1-carboxylate (0.120 g, 0.186 mmol), 1-(2-bromoethyl)pyrrolidin-2-one (0.25 g, 1.31 mmol) and $K_2CO_3$ (0.415 g, 3.0 mmol) in DMF (1.5 mL) was heated at 75° C. for 5 h. The mixture was allowed to cool to RT, upon which it was poured into water. A precipitate formed which was collected via filtration, dried under vacuum and purified via preparative TLC ($SiO_2$, $CH_2Cl_2$:MeOH 95:5).

The purified solid was taken up in HCl (4M in 1,4 dioxane, 30 mL) and stirred at RT for 4 h. The volatiles were removed in vacuo and the residue was washed with $CH_2Cl_2$ to give N-(3-(4-(1H-indazol-5-ylamino)-6-(2-(2-oxopyrrolidin-1-yl)ethoxy)quinazolin-2-yl)phenyl)butyramide hydrochloride (0.025 g, 0.043 mmol, 23% over two steps). MS 550 (M+1). HPLC retention time 5.30 mins.

Example 205

N-(3-(4-(1H-indazol-5-ylamino)-6-(2-(3-hydroxypyrrolidin-1-yl)ethoxy)-quinazolin-2-yl)phenyl)butyramide

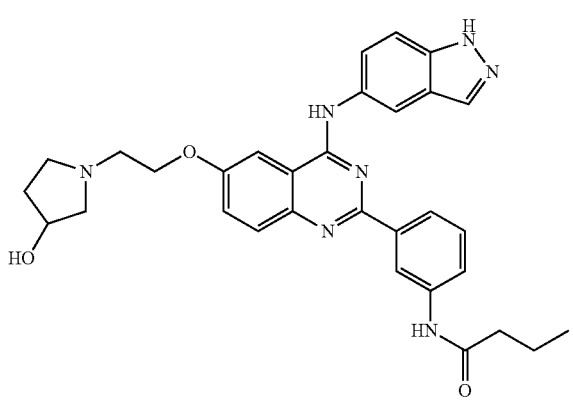 [SMILES: CCCC(=O)Nc1cccc(-c2nc(Nc3ccc4[nH]ncc4c3)c3cc(OCCN4CCC(O)C4)ccc3n2)c1]

To a solution of tert-butyl 5-(2-(3-butyramidophenyl)-6-(2-chloroethoxy)-quinazolin-4-ylamino)-1H-indazole-1-carboxylate (0.143 g, 0.240 mmol) in DMSO (1.5 mL) was added pyrrolidin-3-ol (0.5 mL). The subsequent mixture was heated at 75° C. for 1.5 h upon which it was allowed to cool to RT and poured into ice-water (100 mL). A precipitate formed which was collected via filtration and it was dried under vacuum. The precipitate was purified via preparative TLC ($SiO_2$, $CH_2Cl_2$:MeOH $NH_4OH$ 9:1:0.1).

The purified solid was taken up in MeOH/$CH_2Cl_2$ (3 mL 1:1) and HCl (4M in 1,4 dioxane, 2 mL) was added. The mixture was stirred at RT for 4 h. The volatiles were removed in vacuo and the residue was washed with $CH_2Cl_2$ to give N-(3-(4-(1H-indazol-5-ylamino)-6-(2-(3-hydroxypyrrolidin-1-yl)ethoxy)quinazolin-2-yl)phenyl)butyramide di-hydrochloride salt (0.095 g, 0.153 mmol, 64% over two steps). MS 552 (M+1). HPLC retention time 4.389 mins.

Example 206

N-(3-(4-(1H-indazol-5-ylamino)-7-methoxy-6-(2-(2-oxopyrrolidin-1-yl)ethoxy)quinazolin-2-yl)phenyl)butyramide

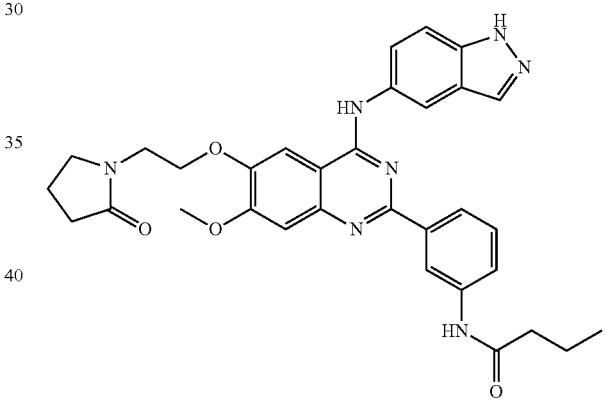

A mixture of tert-butyl 5-(2-(3-butyramidophenyl)-6-hydroxy-7-methoxyquinazolin-4-ylamino)-1H-indazole-1-carboxylate (0.200 g, 0.35 mmol), 2-(2-oxopyrrolidin-1-yl)ethyl methanesulfonate (0.300 g, 1.48 mmol) and $K_2CO_3$ (0.410 g, 2.97 mmol) in DMF (3 mL) was heated at 75° C. for 5 h. The mixture was allowed to cool to RT, upon which it was poured into water 50-80 mL). A precipitate formed which was collected via filtration, dried under vacuum and purified via preparative TLC ($SiO_2$, $CH_2Cl_2$:MeOH 95:5).

The purified solid was taken up in $CH_2Cl_2$/MeOH (3 mL 1:1) and HCl (4M in 1,4 dioxane, 30 mL) was added. The mixture was stirred at RT for 5 h. The volatiles were removed in vacuo to give N-(3-(4-(1H-indazol-5-ylamino)-7-methoxy-6-(2-(2-oxopyrrolidin-1-yl)ethoxy)quinazolin-2-yl)phenyl)butyramide hydrochloride (0.108, 0.176 mmol, 50% over two steps). MS 580 (M+1). HPLC retention time 5.523 mins.

Example 207

N-(3-(4-(1H-indazol-5-ylamino)-7-methoxy-6-(2-methoxyethoxy)-quinazolin-2-yl)phenyl)butyramide

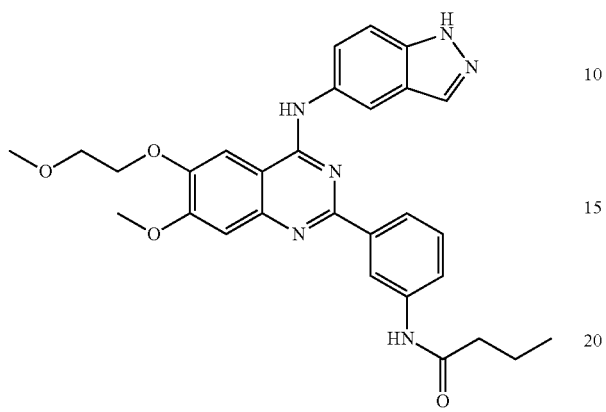

A mixture of tert-butyl 5-(2-(3-butyramidophenyl)-6-hydroxy-7-methoxyquinazolin-4-ylamino)-1H-indazole-1-carboxylate (0.176 g, 0.31 mmol), 1-bromo-2-methoxyethane (0.120 g, 0.86 mmol) and K$_2$CO$_3$ (0.120 g, 2.8 mmol) in DMSO (1.5 mL) was heated at 75° C. for 1.5 h. The mixture was allowed to cool to RT, upon which it was poured into water. A precipitate formed which was collected via filtration and dried under vacuum.

The solid was taken up CH$_2$Cl$_2$ (8 mL) and HCl (4M in 1,4 dioxane, 18 mL) was added. The subsequent mixture was stirred at RT for 4 h. The volatiles were removed in vacuo and the residue was triturated with Et$_2$O to give N-(3-(4-(1H-indazol-5-ylamino)-7-methoxy-6-(2-methoxyethoxy)quinazolin-2-yl)phenyl)butyramide hydrochloride (0.09 g, 0.160 mmol, 52% over two steps). MS 527 (M+1). HPLC retention time 5.71 mins.

Example 208 tert-Butyl 5-(2-(3-butyramidophenyl)-6-(2-chloroethoxy)-7-methoxyquinazolin-4-ylamino)-1H-indazole-1-carboxylate

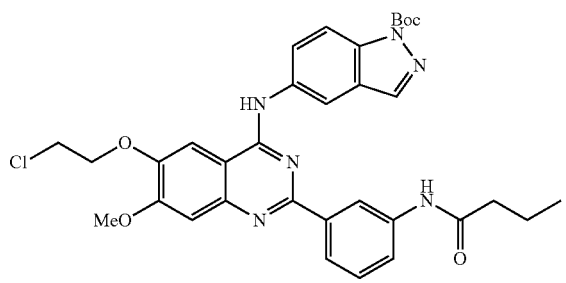 [SMILES: CCCC(=O)Nc1cccc(-c2nc(Nc3ccc4c(cnn4C(=O)OC(C)(C)C)c3)c3cc(OCCCl)c(OC)cc3n2)c1]

To a mixture of tert-butyl 5-(2-(3-butyramidophenyl)-6-hydroxy-7-methoxyquinazolin-4-ylamino)-1H-indazole-1-carboxylate (0.855 g, 1.50 mmol) and potassium carbonate (0.950 g, 6.87 mmol) in anhydrous DMF (8 mL) was added, 1-bromo-2-chloroethane (0.89 g, 6.20 mmol) and resulting reaction mixture was stirred at 85° C. for 3.5 h. The mixture was allowed to cool to room temperature upon which, it was poured into ice-water. A solid was precipitated out, which was collected via filtration and dried under vacuum to give tert-butyl 5-(2-(3-butyramidophenyl)-6-(2-chloroethoxy)-7-methoxyquinazolin-4-ylamino)-1H-indazole-1-carboxylate (0.864 g, 1.37 mmol, 91%). HPLC retention time 7.694 min.

Example 209

N-(3-(4-(1H-indazol-5-ylamino)-7-methoxy-6-(2-(4-methylpiperazin-1-yl)ethoxy)quinazolin-2-yl)phenyl)butyramide

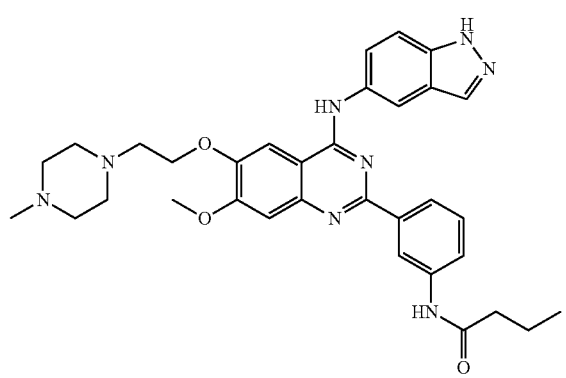 [SMILES: CCCC(=O)Nc1cccc(-c2nc(Nc3ccc4[nH]ncc4c3)c3cc(OCCN4CCN(C)CC4)c(OC)cc3n2)c1]

To a solution of tert-butyl 5-(2-(3-butyramidophenyl)-6-(2-chloroethoxy)-7-methoxyquinazolin-4-ylamino)-1H-indazole-1-carboxylate (0.170 g, 0.299 mmol) in DMSO (2 mL) was added 1-methylpiperazine (0.5 mL). The subsequent mixture was heated at 85° C. for 2.5 h upon which it was allowed to cool to RT and poured into ice-water (100 mL). A precipitate formed which was collected via filtration and it was dried under vacuum. The precipitate was purified via preparative TLC (SiO$_2$, CH$_2$Cl$_2$:MeOH:NH$_4$OH 9:1:0.1). The purified compound was taken up in CH$_2$Cl$_2$ (2 mL) and HCl (4M in 1,4 dioxane, 10 mL) and stirred at RT for 4 h. The volatiles were removed in vacuo and the residue was triturated with Et$_2$O, filtered and dried under vacuum to give N-(3-(4-(1H-indazol-5-ylamino)-7-methoxy-6-(2-(4-methylpiperazin-1-yl)ethoxy)-quinazolin-2-yl)phenyl)butyramide di-hydrochloride salt (0.085 g, 0.128 mmol, 43% over two steps). MS 595 (M+1). HPLC retention time 4.337 mins.

Example 210

N-(3-(4-(1H-indazol-5-ylamino)-6-(2-((S)-3-(dimethylamino)pyrrolidin-1-yl)ethoxy)-7-methoxyquinazolin-2-yl)phenyl)butyramide

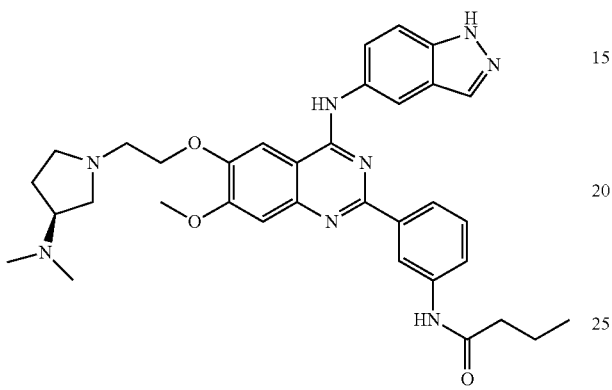

To a solution of tert-butyl 5-(2-(3-butyramidophenyl)-6-(2-chloroethoxy)-7-methoxyquinazolin-4-ylamino)-1H-indazole-1-carboxylate (0.180 g, 0.300 mmol) in DMSO (2 mL) was added (S)—N,N-dimethylpyrrolidin-3-amine (0.5 mL). The subsequent mixture was heated at 80° C. for 1.5 h upon which it was allowed to cool to RT and poured into ice-water (100 mL). A precipitate formed which was collected via filtration and it was dried under vacuum. The precipitate was purified via preparative TLC (SiO₂, CH₂Cl₂: MeOH:NH₄OH 9:1:0.1).

The purified solid was taken up in HCl (4M in 1,4 dioxane, 2 mL) and stirred at RT for 2 h. The volatiles were removed in vacuo to give N-(3-(4-(1H-indazol-5-ylamino)-6-(2-((S)-3-(dimethylamino)pyrrolidin-1-yl)ethoxy)-7-methoxyquinazolin-2-yl)phenyl)butyramide di-hydrochloride salt (0.090 g, 0.132 mmol, 44% over two steps). MS 609 (M+1). HPLC retention time 4.30 mins.

Example 211

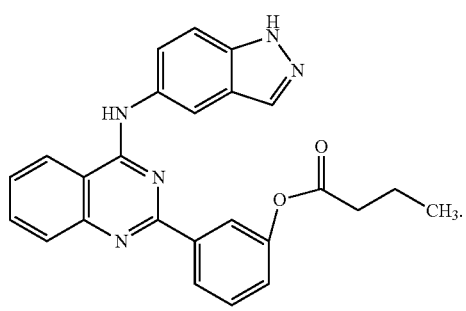 [SMILES: CCCC(=O)Oc1cccc(-c2nc(Nc3ccc4[nH]ncc4c3)c3ccccc3n2)c1]

Example 212

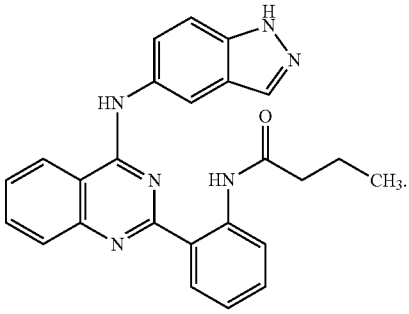 [SMILES: CCCC(=O)Nc1ccccc1-c1nc(Nc2ccc3[nH]ncc3c2)c2ccccc2n1]

Example 213

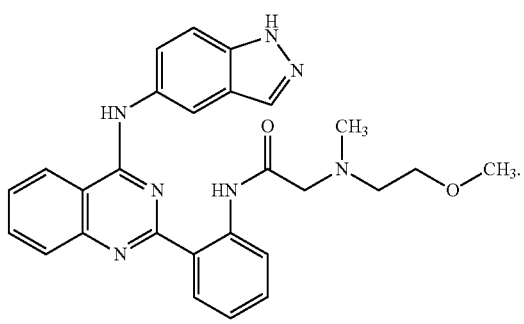 [SMILES: COCCN(C)CC(=O)Nc1ccccc1-c1nc(Nc2ccc3[nH]ncc3c2)c2ccccc2n1]

Example 214

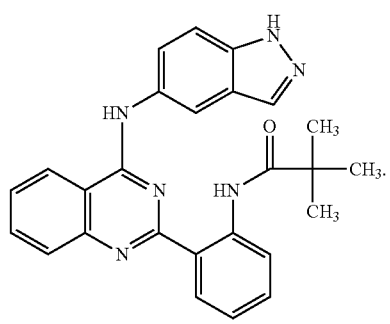 [SMILES: CC(C)(C)C(=O)Nc1ccccc1-c1nc(Nc2ccc3[nH]ncc3c2)c2ccccc2n1]

Example 215
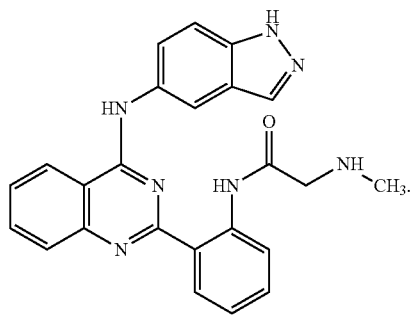 [SMILES: CNCC(=O)Nc1ccccc1-c1nc(Nc2ccc3[nH]ncc3c2)c2ccccc2n1]
Example 218
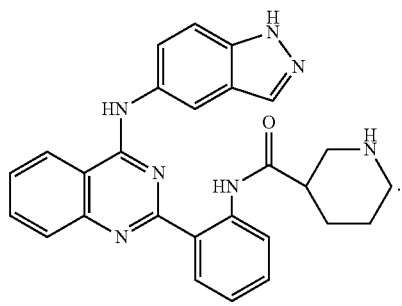
Example 216
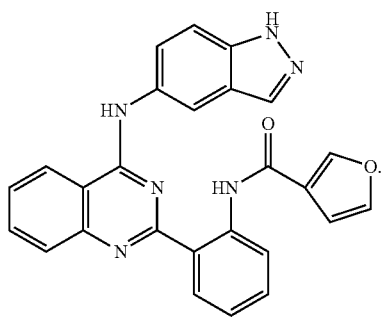 [SMILES: O=C(Nc1ccccc1-c1nc(Nc2ccc3[nH]ncc3c2)c2ccccc2n1)c1ccoc1]
Example 219
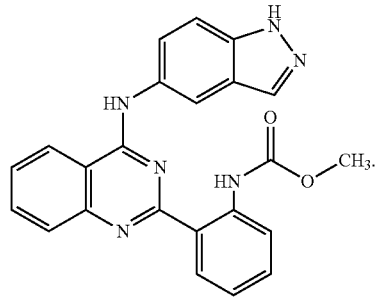
Example 217
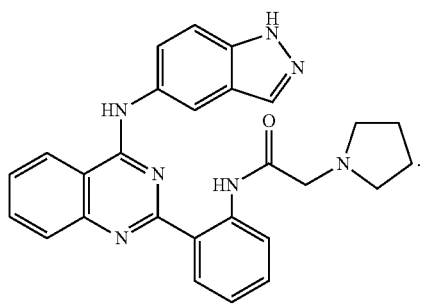 [SMILES: O=C(CN1CCCC1)Nc1ccccc1-c1nc(Nc2ccc3[nH]ncc3c2)c2ccccc2n1]
Example 220
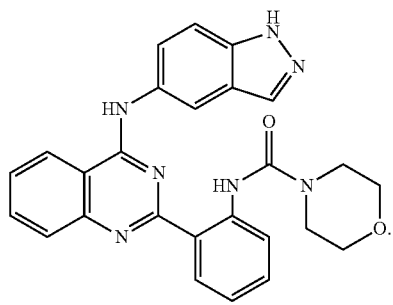 [SMILES: O=C(Nc1ccccc1-c1nc(Nc2ccc3[nH]ncc3c2)c2ccccc2n1)N1CCOCC1]

Example 221
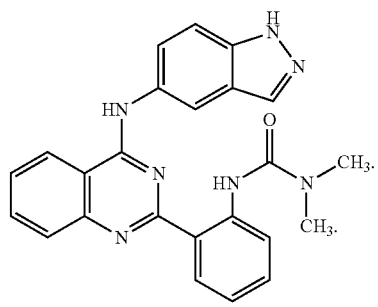 [SMILES: CN(C)C(=O)Nc1ccccc1-c1nc(Nc2ccc3[nH]ncc3c2)c2ccccc2n1]
Example 224
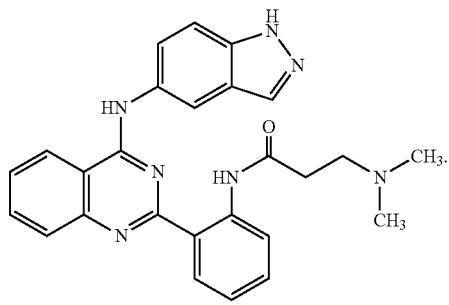
Example 222
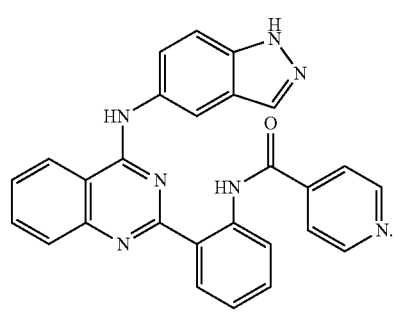 [SMILES: O=C(Nc1ccccc1-c1nc(Nc2ccc3[nH]ncc3c2)c2ccccc2n1)c1ccncc1]
Example 225
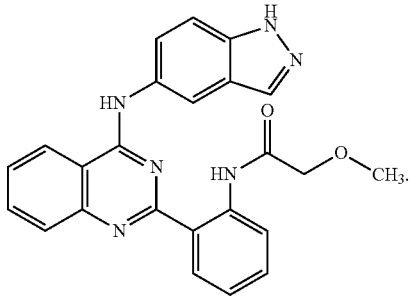
Example 223
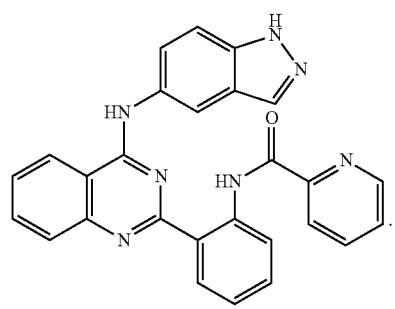 [SMILES: O=C(Nc1ccccc1-c1nc(Nc2ccc3[nH]ncc3c2)c2ccccc2n1)c1ccccn1]
Example 226
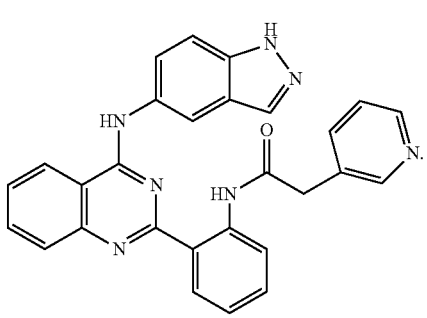 [SMILES: O=C(Cc1cccnc1)Nc1ccccc1-c1nc(Nc2ccc3[nH]ncc3c2)c2ccccc2n1]

181
Example 227
182
Example 230
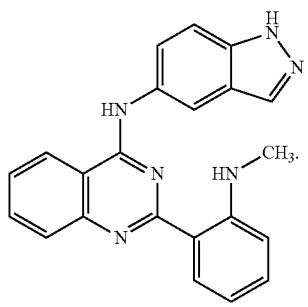 [SMILES: CNc1ccccc1-c1nc(Nc2ccc3[nH]ncc3c2)c2ccccc2n1]
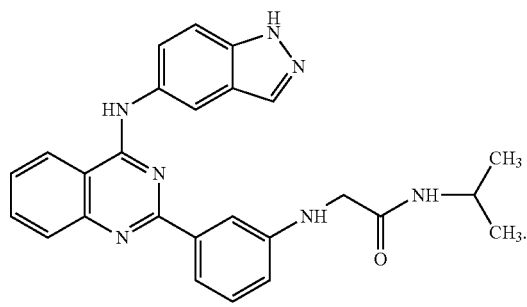
Example 228
Example 231
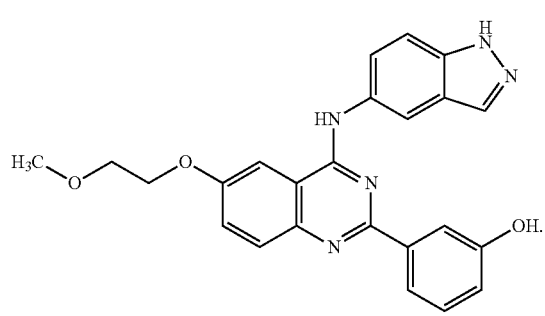 [SMILES: COCCOc1ccc2nc(-c3cccc(O)c3)nc(Nc3ccc4[nH]ncc4c3)c2c1]
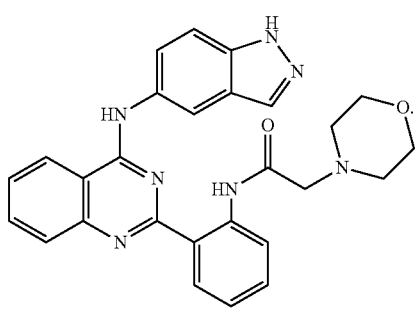
Example 229
Example 232
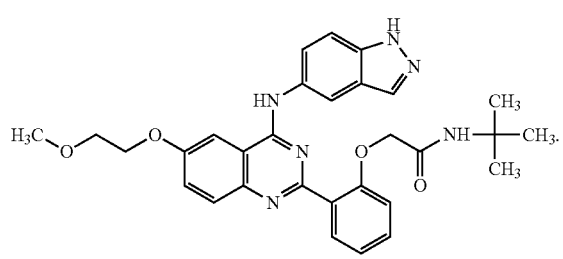 [SMILES: COCCOc1ccc2nc(-c3ccccc3OCC(=O)NC(C)(C)C)nc(Nc3ccc4[nH]ncc4c3)c2c1]
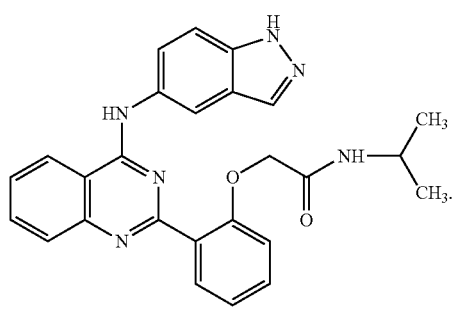 [SMILES: CC(C)NC(=O)COc1ccccc1-c1nc(Nc2ccc3[nH]ncc3c2)c2ccccc2n1]

183
Example 233
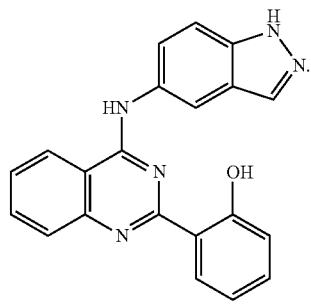 [SMILES: Oc1ccccc1-c1nc(Nc2ccc3[nH]ncc3c2)c2ccccc2n1]
184
Example 236
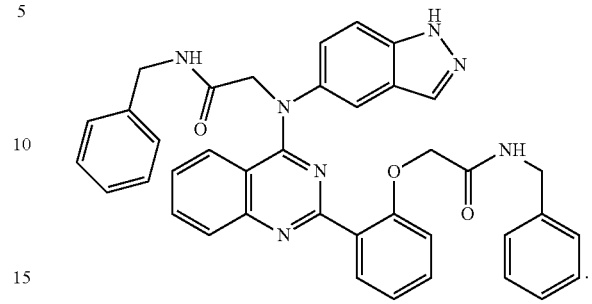
Example 234
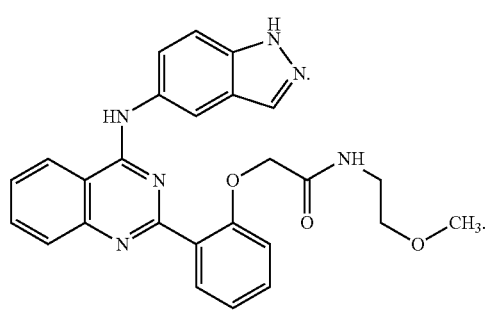 [SMILES: COCCNC(=O)COc1ccccc1-c1nc(Nc2ccc3[nH]ncc3c2)c2ccccc2n1]
Example 237
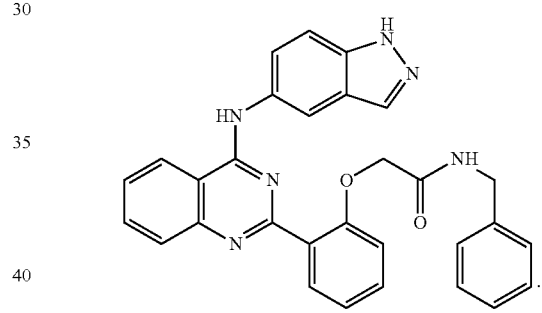
Example 235
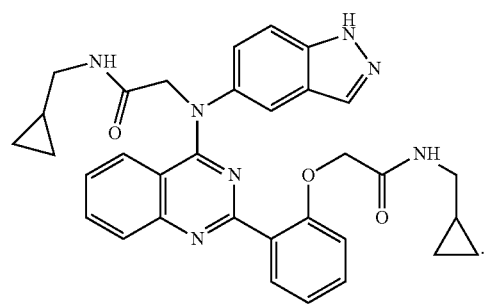 [SMILES: O=C(COc1ccccc1-c1nc(N(CC(=O)NCC2CC2)c2ccc3[nH]ncc3c2)c2ccccc2n1)NCC1CC1]
Example 238
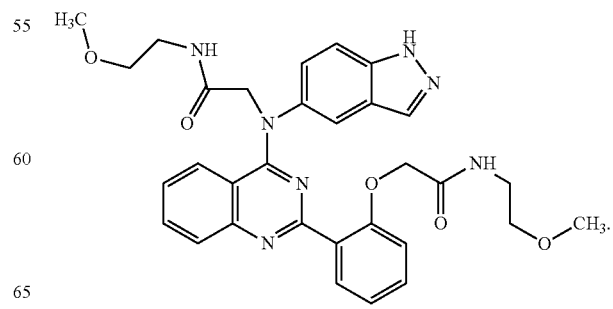

| 185 | 186 |
|---|---|
| Example 239 | Example 242 |
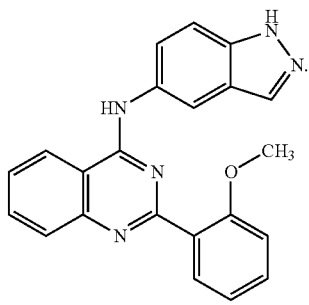 [SMILES: COc1ccccc1-c1nc(Nc2ccc3[nH]ncc3c2)c2ccccc2n1]
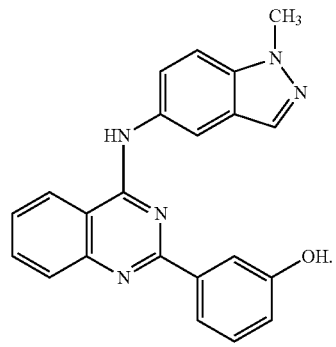
Example 240
Example 243
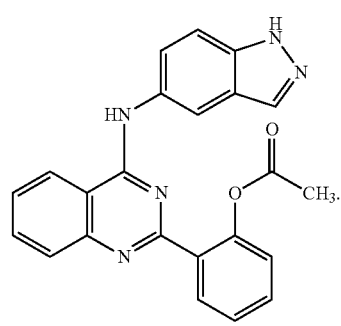 [SMILES: CC(=O)Oc1ccccc1-c1nc(Nc2ccc3[nH]ncc3c2)c2ccccc2n1]
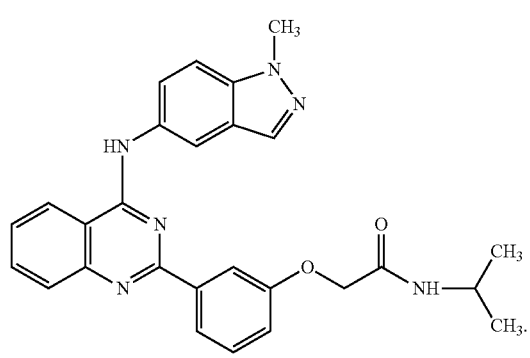 [SMILES: CC(C)NC(=O)COc1cccc(-c2nc(Nc3ccc4c(cnn4C)c3)c3ccccc3n2)c1]
Example 241
Example 244
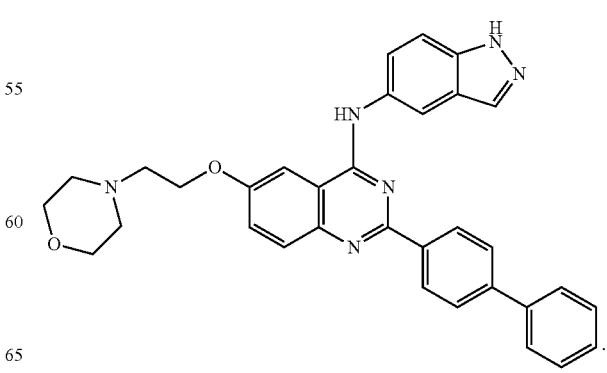

187
Example 245
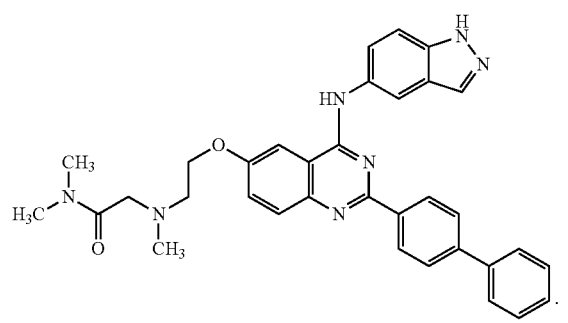 [SMILES: CN(CCOc1ccc2nc(-c3ccc(-c4ccccc4)cc3)nc(Nc3ccc4[nH]ncc4c3)c2c1)CC(=O)N(C)C]
Example 246
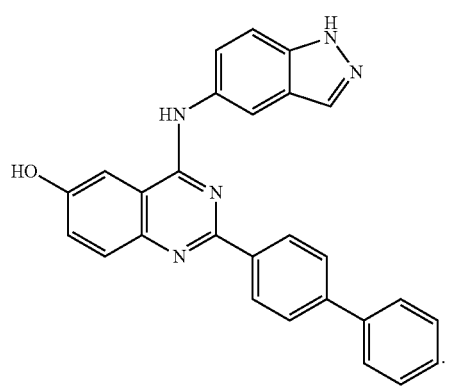 [SMILES: Oc1ccc2nc(-c3ccc(-c4ccccc4)cc3)nc(Nc3ccc4[nH]ncc4c3)c2c1]
Example 247
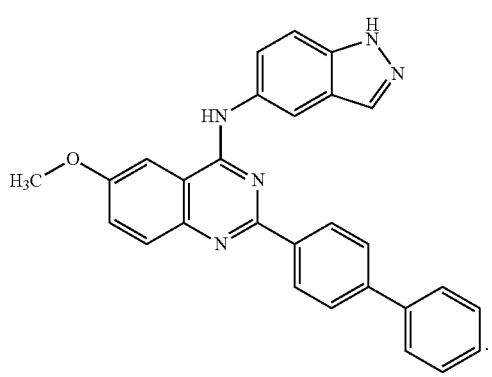 [SMILES: COc1ccc2nc(-c3ccc(-c4ccccc4)cc3)nc(Nc3ccc4[nH]ncc4c3)c2c1]
188
Example 248
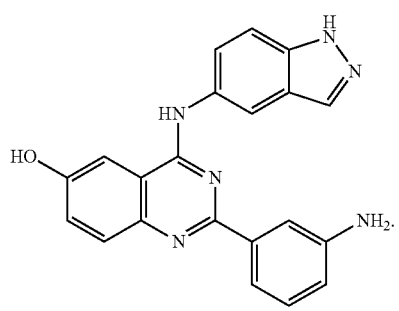 [SMILES: Nc1cccc(-c2nc(Nc3ccc4[nH]ncc4c3)c3cc(O)ccc3n2)c1]
Example 249
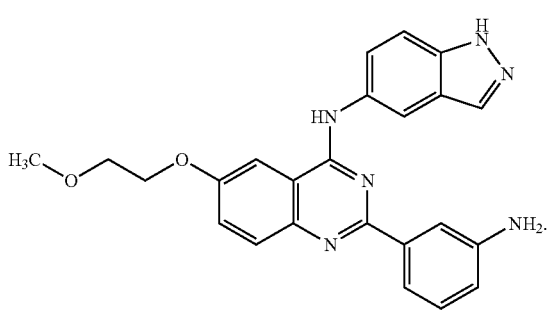 [SMILES: COCCOc1ccc2nc(-c3cccc(N)c3)nc(Nc3ccc4[nH]ncc4c3)c2c1]
Example 250
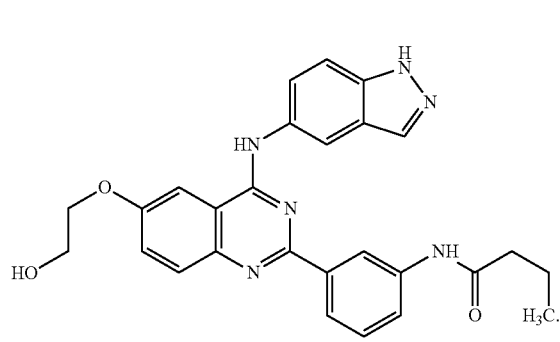 [SMILES: CCCC(=O)Nc1cccc(-c2nc(Nc3ccc4[nH]ncc4c3)c3cc(OCCO)ccc3n2)c1]

| 189 | 190 |
|---|---|
| Example 251 | Example 255 |
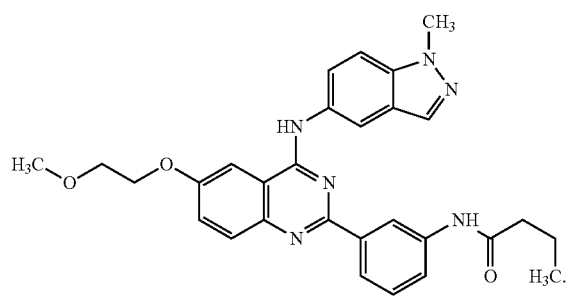 [SMILES: CCCC(=O)Nc1cccc(-c2nc(Nc3ccc4c(cnn4C)c3)c3cc(OCCOC)ccc3n2)c1] 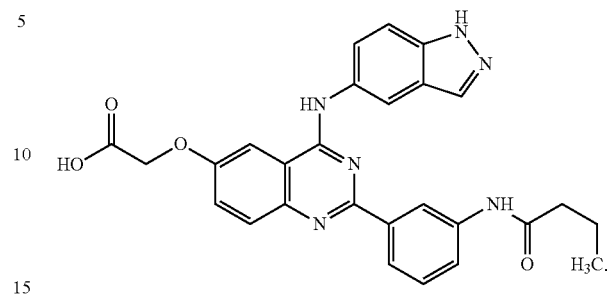
| Example 252 | Example 256 |
|---|---|
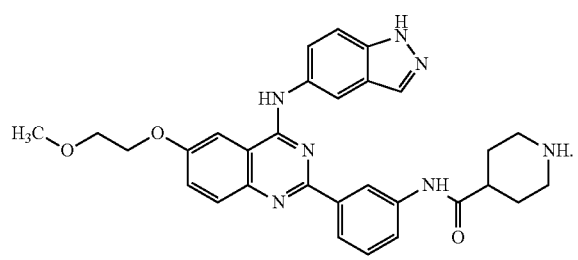 [SMILES: COCCOc1ccc2nc(-c3cccc(NC(=O)C4CCNCC4)c3)nc(Nc3ccc4[nH]ncc4c3)c2c1] 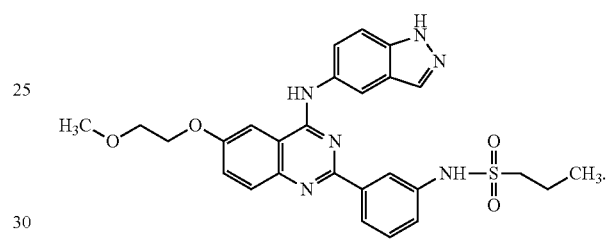
| Example 253 | Example 257 |
|---|---|
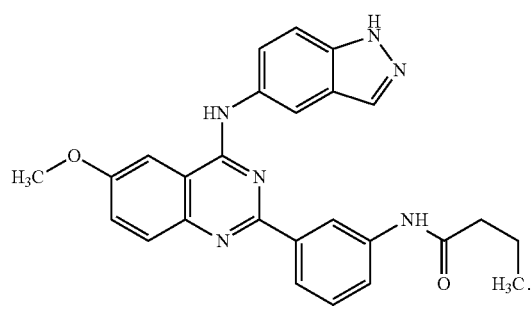 [SMILES: CCCC(=O)Nc1cccc(-c2nc(Nc3ccc4[nH]ncc4c3)c3cc(OC)ccc3n2)c1] 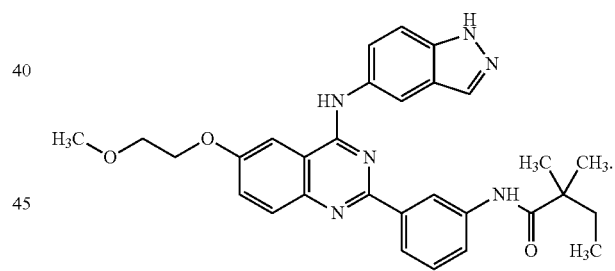
Example 254
Example 258
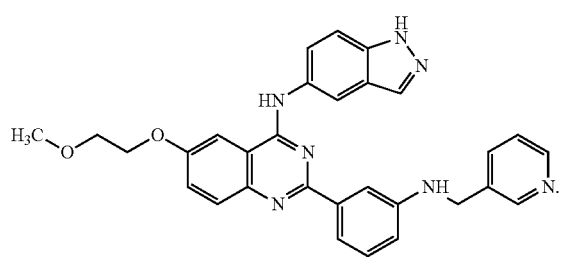 [SMILES: COCCOc1ccc2nc(-c3cccc(NCc4cccnc4)c3)nc(Nc3ccc4[nH]ncc4c3)c2c1] 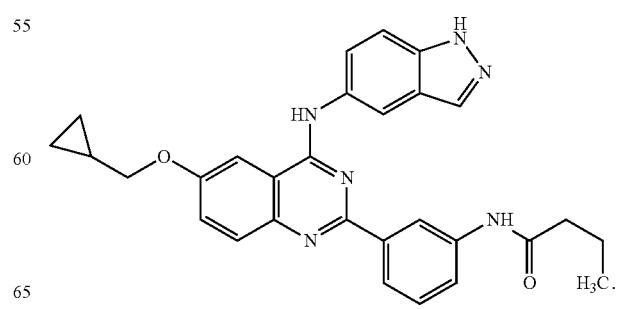

191 192
Example 259 Example 262
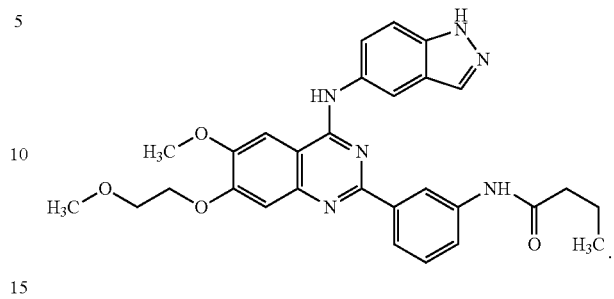
Example 263
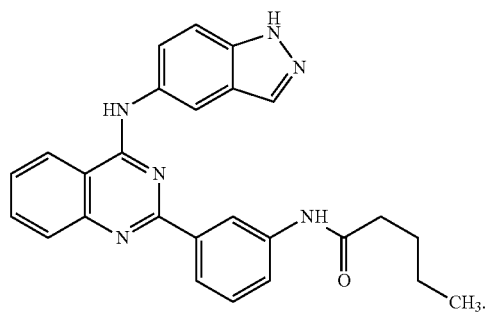 [SMILES: CCCCC(=O)Nc1cccc(-c2nc(Nc3ccc4[nH]ncc4c3)c3ccccc3n2)c1]
Example 260
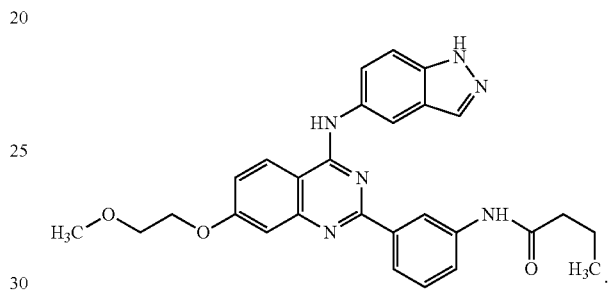
Example 264
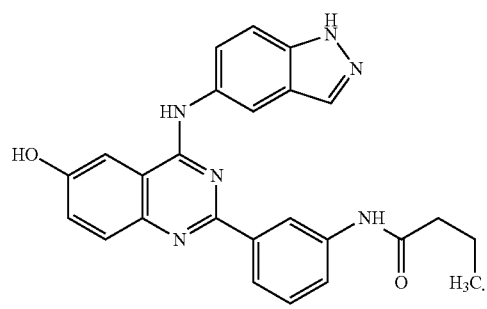 [SMILES: CCCC(=O)Nc1cccc(-c2nc(Nc3ccc4[nH]ncc4c3)c3cc(O)ccc3n2)c1]
Example 261
Example 265
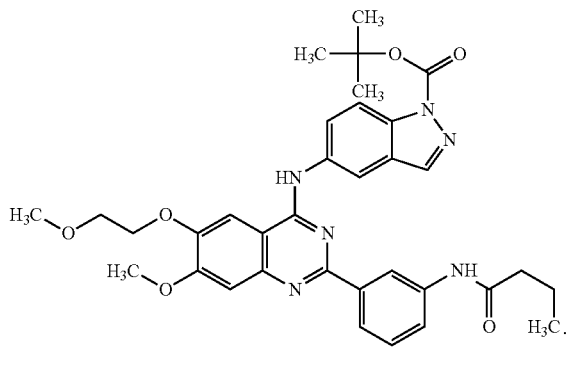 [SMILES: CCCC(=O)Nc1cccc(-c2nc(Nc3ccc4c(cnn4C(=O)OC(C)(C)C)c3)c3cc(OCCOC)c(OC)cc3n2)c1]
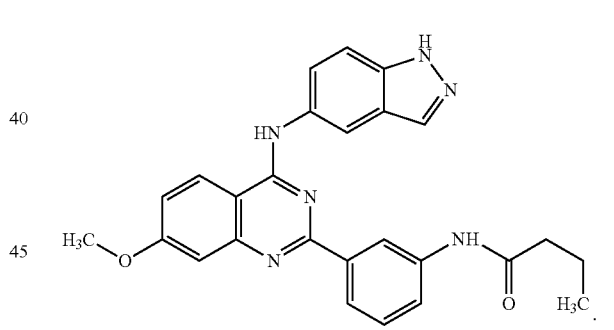

193
Example 266
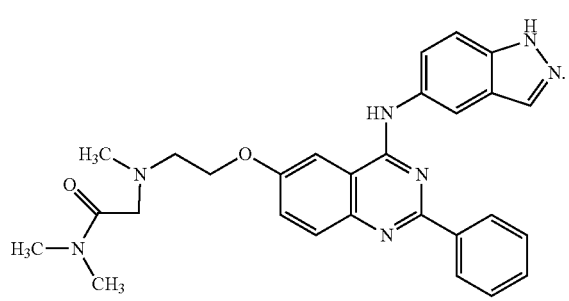 [SMILES: CN(CCOc1ccc2nc(-c3ccccc3)nc(Nc3ccc4[nH]ncc4c3)c2c1)CC(=O)N(C)C]
Example 267
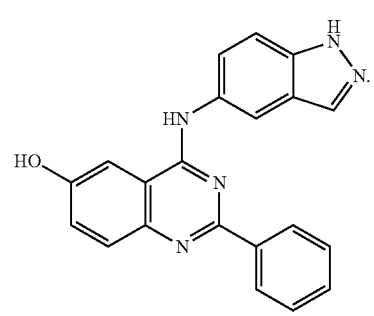 [SMILES: Oc1ccc2nc(-c3ccccc3)nc(Nc3ccc4[nH]ncc4c3)c2c1]
Example 268
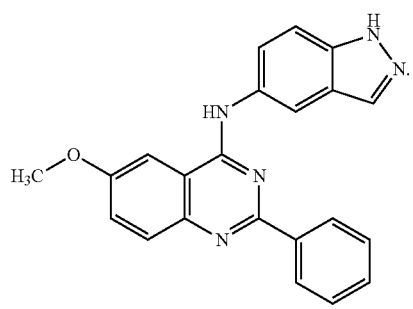 [SMILES: COc1ccc2nc(-c3ccccc3)nc(Nc3ccc4[nH]ncc4c3)c2c1]
194
Example 269
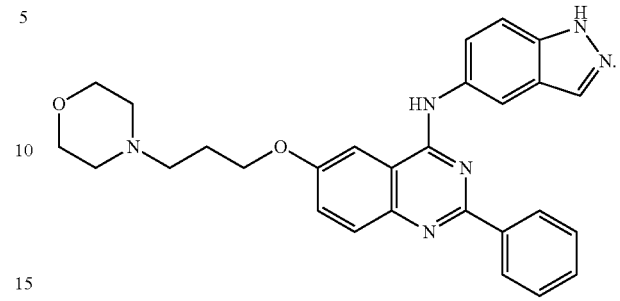
Example 270
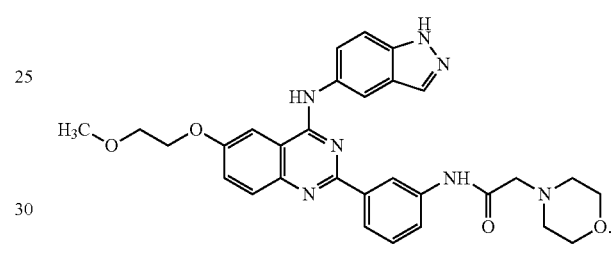
Example 271
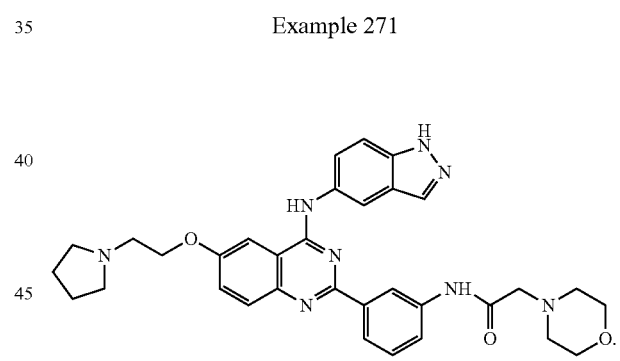
Example 272
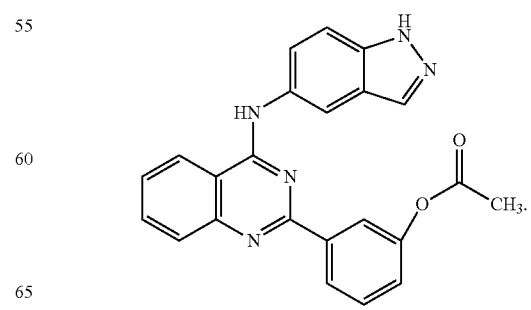

Example 273

1. ROCK Binding Assay

ROCK-II inhibitory activity can be measured using the ROCK-II Assay Kit (Molecular Devices, inc.; Sunnyvale, Calif.).

2. A Functional Measure of ROCK Activity in Cells

MLC Phosphorylation

Myosin regulatory light chain phosphorylation can be measures in vascular smooth muscle (VSM) cells. VSM cells are isolated from the pulmonary artery of newborn calves and used in the 2nd to 4th passage. Cells are maintained in low glucose DME (JRH Biosciences) supplemented with 2 mM glutamine, 100 U/ml penicillin 100 U/ml streptomycin, 10 mM Hepes (Life Technologies), and 10% fetal bovine serum (Hyclone) in 10% $CO_2$. Confluent monolayers are serum-starved for 72 hours in DME containing 0.4% fetal bovine serum prior to experiments. Quiescent cell monolayers are dissociated into single cells and plated at low. For experimental manipulation, cells are plated in DME containing 1% bovine serum albumin, transferrin (5 μg/ml; Collaborative Research), human high density lipoprotein (10 μg/ml; Intracel), 20 mM Hepes, sodium pyruvate (110 mg/L), penicillin G (100 units/ml), streptomycin (100 μg/ml) and L-glutamine (0.292 mg/ml). Cells are harvested in ice-cold 10% trichloroacetic acid supplemented with 10 mM dithiothreitol (Sigma) and centrifuged at 13,000 rpm for 15 minutes at 4° C. The pellets are washed once with ice cold distilled water, and once with cold acetone. Samples are then placed in sample buffer (10 M urea [#161-0730, Bio-Rad], 1× Tris-glycine running buffer, 150 mM dithiothreitol, 0.01% bromophenol blue), soniccated, loaded onto and run on electrophoretic gels at 6 mA. Proteins are transferred to nitrocellulose in 1× Tris/glycine buffer with 20% methanol, blocked in three percent bovine serum albumin in Tris Buffered Saline, and probed with antibodies to detect phosphorylated isoforms of myosin regulatory light chain (Cell Signaling Technologies) for two hours at room temperature. Signals are detected using a horseradish peroxidase-conjugated secondary antibody (NA-131, Amersham; 1:4000) and Renaissance Enhanced Luminol Reagent (NEN Life Sciences Products) as a chemiluminescent substrate. Signal intensity is normalized and analyzed using NIH Image.

Motility

Cellular motility can be assessed using a migration assay. Fluorescently-labeled HT1080 human fibrosarcoma cells are seeded into a Fluoroblok Transwell 8 μM pore 96-well plate (Becton Dickenson) at a density of 40,000 cells per well in serum-free, phenol-free MEM. Compounds are added to the cells in the transwell inserts at a final concentration of 0.5% dimethylsulfoxide. Compounds are also added to the bottom wells in phenol-free MEM containing 10% fetal bovine serum as the chemoattractant. Cells are incubated at 37° C. for 4 h, and fluorescence is measured from the bottom of the plate on a fluorescent plate reader (Analyst, LJL Biosystems).

3. Xenograft Studies

Procedures:
 Set up HRLN female nu/nu mice with 1 $mm^3$ tumor fragments sc in flank
 Do a pair match when tumors reach an average size of 80-120 mg, and begin treatment
 Prepare dosing solutions:
  Positive controls (cell line dependant)—daily, store at room temp
  QO1—daily
 Body Weight: qd×5 then 2×/wk to end
 Caliper Measurement: 2×/wk to end
 Endpoint: TGD. Animals are to be monitored individually. The endpoint of the experiment is a tumor volume of 1000 $mm^3$ or 60 days, whichever comes first; responders can be followed longer. When the endpoint is reached, the animals are to be euthanized
 Report any adverse reactions or death to TL, PM, RD or CEO immediately
 Return remaining compound & dosing solution to client
 Necropsy one animal/group at endpoint to examine for overt toxicity or metastasis.
 Report to consist of data, stats, graphs only.
Dosing Instructions:
 Dosing volume=10 mL/kg (0.2 mL/20 g mouse). Adjust volume accordingly for body weight.
 Stop dosing and monitor animals if group mean weight loss >20% or >1 animal dies.

Example 274

Inhibition of ROCK2 by various compounds was determined. $IC_{50}$ values are reported in Table 1. Differential inhibition of ROCK1 and ROCK2 has also been observed for several of the compounds as shown in Table 2.

TABLE 1

Inhibition of ROCK2

| Compound (Example #) | Molecular Weight | $IC_{50}$ (μM) (ROCK2) |
|---|---|---|
| 230 | 451.523 | >3.00E−06 |
| 211 | 423.467 | 1.29E−07 |
| 231 | 479.533 | >3.00E−06 |
| 212 | 422.482 | >1.00E−04 |
| 212 |  | >1.00E−05 |
| 213 | 481.549 | >1.00E−04 |
| 213 |  | >1.00E−05 |
| 232 | 452.508 | >1.00E−04 |
| 232 |  | >3.00E−06 |
| 233 | 353.377 | 2.00E−06 |
| 233 |  | 2.50E−06 |
| 214 | 436.508 | >1.00E−04 |
| 214 |  | >1.00E−05 |
| 215 | 423.470 | 1.70E−05 |
| 215 |  | >1.00E−05 |
| 234 | 468.507 | >1.00E−04 |
| 234 |  | >3.00E−06 |
| 235 | 575.660 | >1.00E−04 |
| 216 | 446.460 | >1.00E−04 |
| 236 | 647.724 | >1.00E−04 |
| 217 | 463.534 | 3.60E−05 |
| 237 | 500.551 | >1.00E−04 |
| 237 |  | >1.00E−04 |
| 238 | 583.638 | >1.00E−04 |
| 238 |  | >1.00E−04 |
| 218 | 463.534 | >1.00E−04 |
| 218 |  | >1.00E−04 |
| 219 | 410.428 | 2.90E−06 |
| 220 | 465.507 | >1.00E−04 |
| 221 | 423.470 | 4.90E−05 |
| 239 | 367.403 | >1.00E−04 |
| 222 | 457.486 | >1.00E−04 |
| 222 |  | >1.00E−04 |
| 223 | 457.487 | >1.00E−04 |
| 223 |  | 8.30E−06 |
| 224 | 451.523 | 5.30E−06 |
| 225 | 424.455 | 1.70E−06 |

TABLE 1-continued

Inhibition of ROCK2

| Compound (Example #) | Molecular Weight | IC$_{50}$ (μM) (ROCK2) |
|---|---|---|
| 240 | 395.413 | 2.30E−05 |
| 199 | 535.639 | 9.60E−09 |
| 199 | | 2.60E−08 |
| 199 | | 1.20E−08 |
| 199 | | 1.00E−08 |
| 200 | 549.666 | 1.40E−08 |
| 200 | | 3.20E−08 |
| 200 | | 1.70E−08 |
| 200 | | 1.20E−08 |
| 201 | 496.560 | 3.50E−08 |
| 201 | | 6.80E−08 |
| 201 | | 3.20E−08 |
| 201 | | 1.10E−08 |
| 201 | | 9.50E−08 |
| 201 | | 1.20E−07 |
| 201 | | 5.10E−08 |
| 201 | | 6.40E−08 |
| 258 | 492.572 | 2.55E−07 |
| 258 | | 1.82E−07 |
| 203 | 564.680 | 1.20E−08 |
| 203 | | 1.20E−08 |
| 203 | | 1.20E−08 |
| 203 | | 9.50E−09 |
| 204 | 549.623 | 1.51E−07 |
| 204 | | 1.06E−07 |
| 204 | | 6.70E−08 |
| 205 | 551.639 | 1.10E−08 |
| 205 | | 1.20E−08 |
| 205 | | 8.00E−09 |
| 205 | | 1.30E−08 |
| 206 | 579.649 | 4.80E−08 |
| 206 | | 6.40E−08 |
| 207 | 526.586 | 6.10E−08 |
| 207 | | 4.40E−08 |
| 207 | | 2.90E−08 |
| 209 | 594.707 | 1.60E−08 |
| 209 | | 1.40E−08 |
| 210 | 608.733 | 1.80E−08 |
| 210 | | 1.00E−08 |
| 259 | 436.508 | 2.90E−08 |
| 261 | 625.717 | >3.00E−07 |
| 243 | 523.629 | >3.00E−07 |
| 243 | | 4.00E−06 |
| 262 | 526.586 | 2.40E−08 |
| 265 | 466.534 | 6.50E−06 |
| 265 | | 7.30E−06 |
| 267 | 353.377 | 3.90E−06 |

Inhibitory activity for Rho kinase was determined for examples of compounds of the present invention. Inhibition of Rho kinase can be assayed as described. For each of these compounds their inhibitory activity for both ROCK 1 and ROCK 2 was determined. The following tables 2.1, 2.2, 2.3, and 2.4 show inhibition of Rho kinase, ROCK 1 and ROCK 2, by compounds of the invention which are based on Example 82 and compounds which are modified at position 6, position 7, or both positions 6 and 7 of compounds based on Example 82. The IC50 values (in μM) for each of these compounds show a selectivity for inhibiting ROCK2.

TABLE 2.1

Inhibition of ROCK 1 and ROCK 2 with compounds of the invention based on example 82.

| Example | IC50 for ROCK 1 (μM) | IC50 for ROCK 2 (μM) |
|---|---|---|
| 272 | >10 | 0.57 |
| 54 | >10 | 0.15 |
| 55 | >10 | 0.09 |
| 84 | 2.6 | 0.52 |

TABLE 2.2

Inhibition of ROCK 1 and ROCK 2 with compounds of the invention based on example 82 with modifications at the 6,7-position.

| Example | IC50 for ROCK 1 (μM) | IC50 for ROCK 2 (μM) |
|---|---|---|
| 167 | >3 | 0.06 |
| 160 | >3 | 0.05 |

TABLE 2.3

Inhibition of ROCK 1 and ROCK 2 with compounds of the invention based on example 82 with modifications at the 6 position.

| Example | IC50 for ROCK 1 (μM) | IC50 for ROCK 2 (μM) |
|---|---|---|
| 141 | >1 | 0.04 |

TABLE 2.4

Inhibition of ROCK 1 and ROCK 2 with compounds of the invention based on example 82 with modifications at the 7 position.

| Example | IC50 for ROCK 1 (μM) | IC50 for ROCK 2 (μM) |
|---|---|---|
| 263 | >3 | 0.09 |

INCORPORATION BY REFERENCE

All of the patents and publications cited herein are hereby incorporated by reference in their entireties.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound of formula I:

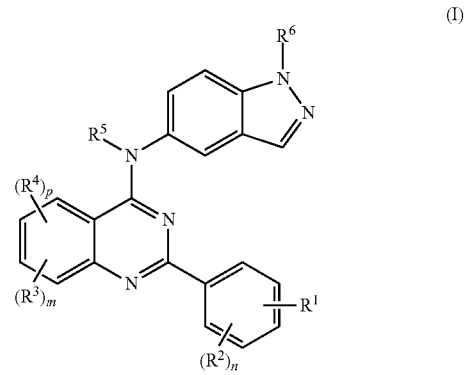

(I)

or a pharmaceutically acceptable salt thereof, wherein:

$R^1$ is selected from the group consisting of —O—$(CH_2)_y$— $CO_2R^{12}$, —O—$(CH_2)_y$—C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;

y is selected from 0 to 6;

z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^4$ is selected from H, —$(CH_2)_a$—$NR^{43}R^{44}$, —Y—$R^{42}$, —O—$(CH_2)_a$—$CO_2R^{42}$, —O—$(CH_2)_a$—C(=O)$NR^{43}R^{44}$, —O—$(CH_2)_a$-heteroaryl, —O—$(CH_2)_a$-cycloalkyl, —O—C(=O)—$(CH_2)_a$—$NR^{43}R^{44}$, —O—$(CH_2)_c$—$NR^{43}R^{44}$, —NH—C(=O)—$(CH_2)_a$—$NR^{43}R^{44}$, —NH—C(=O)—Y—$R^{45}$, —NH—C(=O)—$(CH_2)_a$—$NR^{43}R^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-$NR^{46}R^{47}$, —$CO_2R^{48}$, —O—$(CH_2)_b$—$CO_2R^{48}$, and —C(=O)$NR^{46}R^{47}$, $R^{46}$ and $R^{47}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

a is selected from 0 to 6;

b is selected from 0 to 6;

c is selected from 2 to 6;

$R^5$ is selected from the group consisting of H, $C_1$-$C_6$ alkyl, —(CH$_2$)$_d$—C(=O)—NR$^{53}$R$^{54}$, —C(=O)—(CH$_2$)$_d$—NR$^{53}$R$^{54}$, —C(=O)—X—R$^{55}$, and —C(=O)—(CH$_2$)$_d$—NR$^{53}$R$^{54}$;

$R^{53}$ and $R^{54}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{56}$R$^{57}$, —($C_1$-$C_6$ alkyl)-C(=O)NR$^{56}$R$^{57}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{53}$ and $R^{54}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{55}$ is selected from the group consisting of H, aryl, —($C_1$-$C_6$ alkyl)-O—($C_1$-$C_6$ alkyl), —($C_1$-$C_6$ alkyl)-NR$^{56}$R$^{57}$, —CO$_2$R$^{58}$, —O—(CH$_2$)$_e$—CO$_2$R$^{58}$, and —C(=O)NR$^{56}$R$^{57}$, $R^{56}$ and $R^{57}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{56}$ and $R^{57}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{58}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{56}$R$^{57}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

d is selected from 0 to 6;

e is selected from 0 to 6;

$R^6$ is selected from the group consisting of H, $C_1$-$C_6$ alkyl, —(CH$_2$)$_r$—C(=O)—NR$^{63}$R$^{64}$, —C(=O)—(CH$_2$)$_r$—NR$^{63}$R$^{64}$, —C(=O)—X—R$^{65}$, and —C(=O)—(CH$_2$)$_r$—NR$^{63}$R$^{64}$;

$R^{63}$ and $R^{64}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{66}$R$^{67}$, —($C_1$-$C_6$ alkyl)-C(=O)NR$^{66}$R$^{67}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{63}$ and $R^{64}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{65}$ is selected from the group consisting of H, aryl, —($C_1$-$C_6$ alkyl)-O—($C_1$-$C_6$ alkyl), —($C_1$-$C_6$ alkyl)-NR$^{66}$R$^{67}$, —CO$_2$R$^{68}$, —O—(CH$_2$)$_s$—CO$_2$R$^{68}$, and —C(=O)NR$^{66}$R$^{67}$, $R^{66}$ and $R^{67}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{66}$ and $R^{67}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{68}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{66}$R$^{67}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

r is selected from 0 to 6;

s is selected from 0 to 6;

n is selected from 0 to 4;

m is selected from 0 to 3; and p is selected from 0 and 1.

2. The method of claim 1, wherein $R^4$ and $R^5$ are independently selected from H and $C_1$-$C_6$ alkyl.

3. The method of claim 1, wherein $R^4$ and $R^5$ are H.

4. The method of claim 1, wherein the compound of formula I has the formula II:

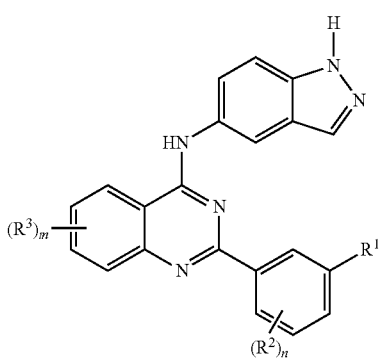

(II)

or a pharmaceutically acceptable salt thereof, wherein $R^1$, $R^2$, $R^3$, n and m are as for the compound of the formula I.

5. The method of claim 1, wherein the compound of formula I has the formula

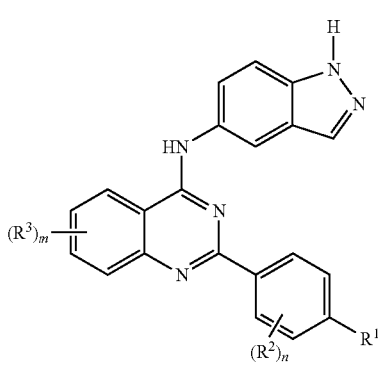

(III)

or a pharmaceutically acceptable salt thereof, wherein $R^1$, $R^2$, $R^3$, n and m are as for the compound of the formula I.

6. The method of claim 1, wherein the compound of formula I has the formula IV:

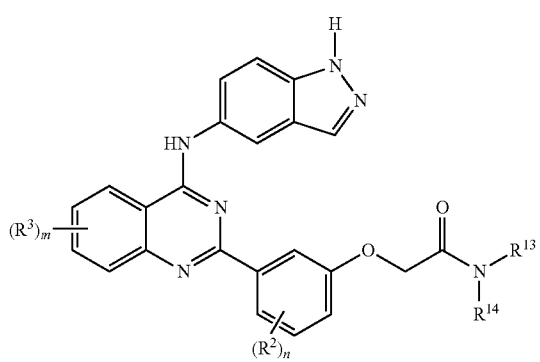

(IV)

or a pharmaceutically acceptable salt thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)
$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and
m is selected from 0 to 3.

7. The method of claim 1, wherein the compound of formula I has the formula $IV_a$:

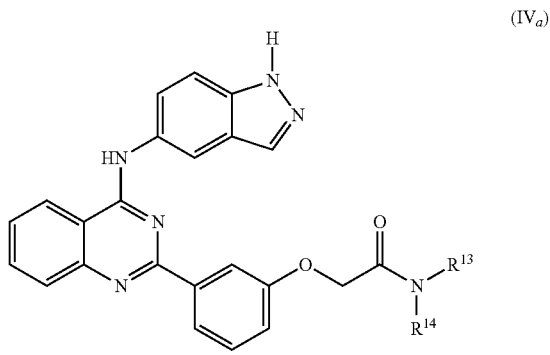

($IV_a$)

or a pharmaceutically acceptable salt thereof, wherein:
$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)
$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl.

8. The method of claim 1, wherein the compound of formula I has the formula V:

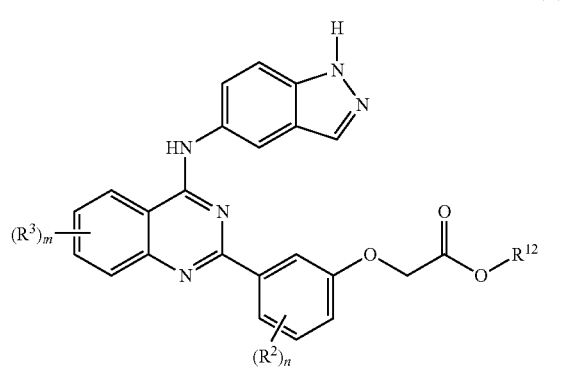

(V)

or a pharmaceutically acceptable salt thereof, wherein:

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and
m is selected from 0 to 3.

9. The method of claim 1, wherein the compound of formula I has the formula $V_a$:

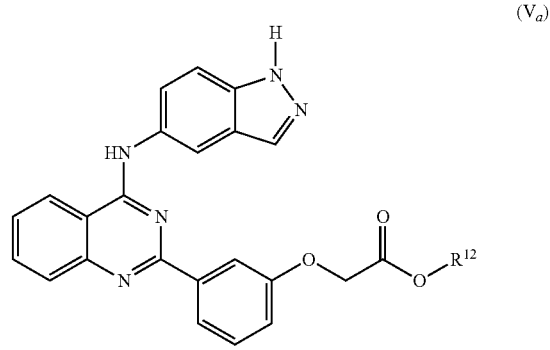

($V_a$)

or a pharmaceutically acceptable salt thereof, wherein:

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl.

10. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound of formula VI:

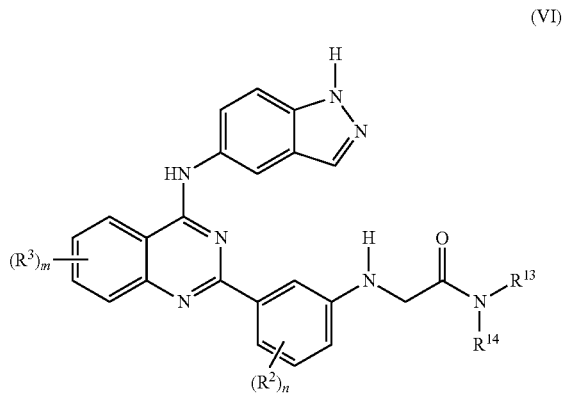

(VI)

or a pharmaceutically acceptable salt thereof, wherein:

$R^{13}$ and $R^{14}$ are independently selected from the group consisting of H, $C_1$-$C_8$ alkyl, $C_2$-$C_6$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and m is selected from 0 to 3.

11. The method of claim 10, wherein the compound of formula VI has the formula VI$_a$:

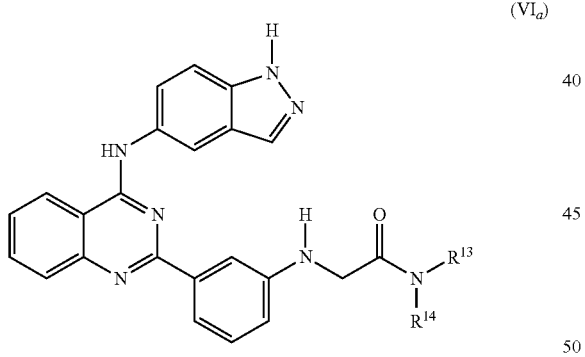

(VI$_a$)

or a pharmaceutically acceptable salt thereof, wherein:

$R^{13}$ and $R^{14}$ are independently selected from the group consisting of H, $C_1$-$C_8$ alkyl, $C_2$-$C_6$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl.

12. The method of claim 1, wherein the compound of formula I has the formula VII:

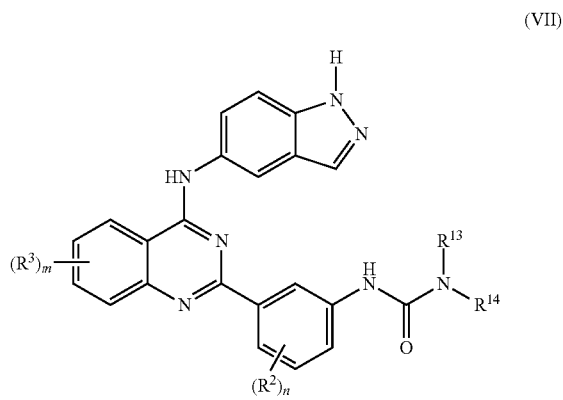

(VII)

or a pharmaceutically acceptable salt thereof, wherein:

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and m is selected from 0 to 3.

13. The method of claim 1, wherein the compound of formula I has the formula VII$_a$:

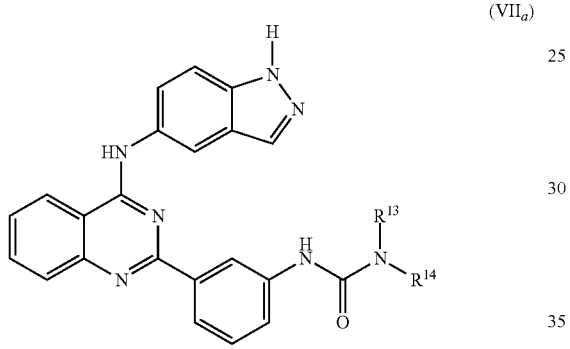

(VII$_a$)

or a pharmaceutically acceptable salt thereof, wherein:

$R^{13}$ and $R^{14}$ are independently selected from the group consisting of H, $C_1$-$C_8$ alkyl, $C_2$-$C_6$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl.

14. The method of claim 1, wherein the compound of formula I has the formula VIII:

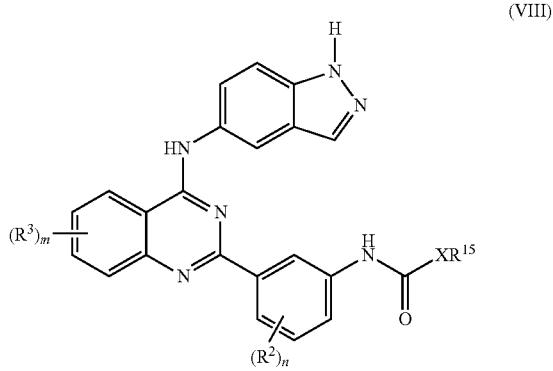

(VIII)

or a pharmaceutically acceptable salt thereof, wherein:

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-NR$^{16}$R$^{17}$, —CO$_2$R$^{18}$, —O—(CH$_2$)$_x$—CO$_2$R$^{18}$, and —C(=O)NR$^{16}$R$^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6, each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and m is selected from 0 to 3.

15. The method of claim 1, wherein the compound of formula I has the formula $VIII_a$:

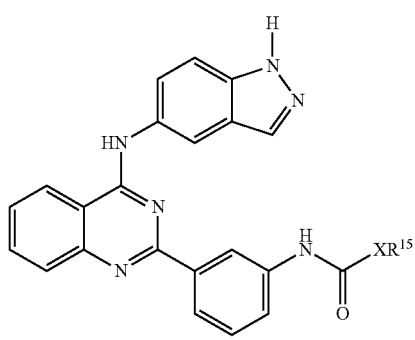

(VIII$_a$)

or a pharmaceutically acceptable salt thereof, wherein:
X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-NR$^{16}$R$^{17}$, —CO$_2$R$^{18}$, —O—(CH$_2$)$_x$—CO$_2$R$^{18}$, and —C(=O)NR$^{16}$R$^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl; and x is selected from 0 to 6.

16. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound of formula IX:

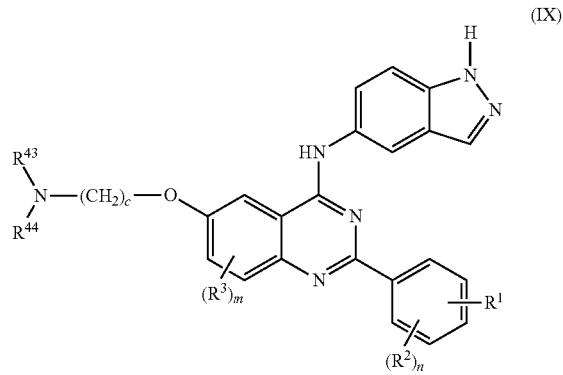

(IX)

or a pharmaceutically acceptable salt thereof, wherein:
$R^1$ is selected from the group consisting of aryl, —(CH$_2$)$_y$—NR$^{13}$R$^{14}$, —X—R$^{12}$, —O—(CH$_2$)$_y$—CO$_2$R$^{12}$, —O—(CH$_2$)$_y$—C(=O)NR$^{13}$R$^{14}$, —O—(CH$_2$)$_y$-heteroaryl, —O—(CH$_2$)$_y$-cycloalkyl, —O—C(=O)—(CH$_2$)$_y$—NR$^{13}$R$^{14}$, —O—(CH$_2$)$_z$—NR$^{13}$R$^{14}$, —NH—C(=O)—(CH$_2$)$_y$—NR$^{13}$R$^{14}$, —NH—C(=O)—X—R$^{15}$, —NH—(CH$_2$)$_y$—NR$^{13}$R$^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-C(=O)NR$^{16}$R$^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-NR$^{16}$R$^{17}$, —CO$_2$R$^{18}$, —O—(CH$_2$)$_x$—CO$_2$R$^{18}$, and —C(=O)NR$^{16}$R$^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;

y is selected from 0 to 6;

z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^{43}$ and $R^{44}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{46}$ and $R^{47}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

c is selected from 2 to 6;

n is selected from 0 to 4; and m is selected from 0 to 3.

17. The method of claim 1, wherein the compound of formula I has the formula X:

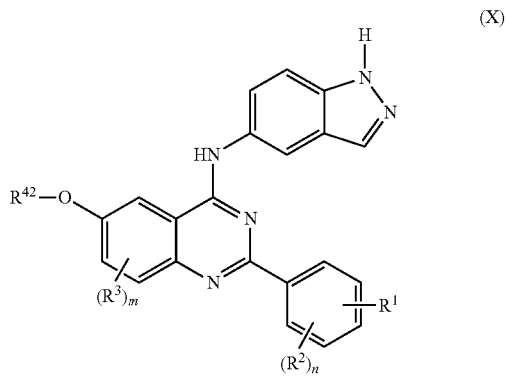

or a pharmaceutically acceptable salt thereof, wherein:

$R^1$ is selected from the group consisting of —O—$(CH_2)_y$, —$CO_2R^{12}$, —O—$(CH_2)_y$—C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{46}$ and $R^{47}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

n is selected from 0 to 4; and
m is selected from 0 to 3.

18. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound of formula XI:

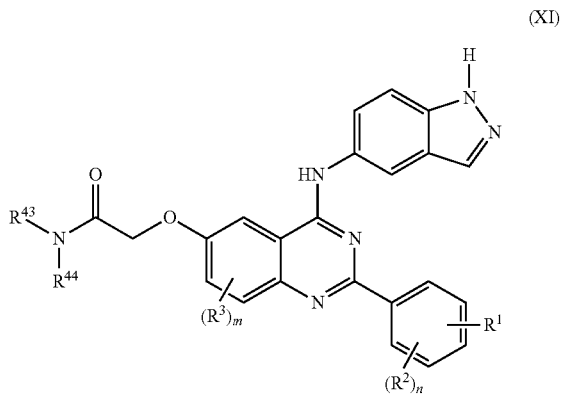

(XI)

or a pharmaceutically acceptable salt thereof, wherein:

$R^1$ is selected from the group consisting of aryl, —$(CH_2)_y$—$NR^{13}R^{14}$, —X—$R^{12}$, —O—$(CH_2)_y$—$CO_2R^{12}$, —O—$(CH_2)_y$—C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of H, aryl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^{43}$ and $R^{44}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{46}R^{47}$, —($C_1$-$C_6$ alkyl)-C(=O)$NR^{46}R^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{46}$ and $R^{47}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

n is selected from 0 to 4; and
m is selected from 0 to 3.

19. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound of formula XII:

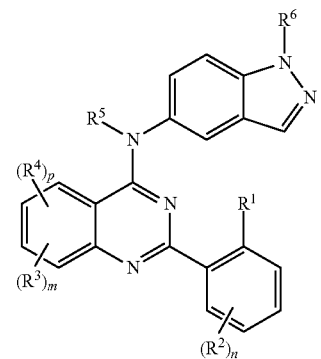

XII or a pharmaceutically acceptable salt thereof, wherein:

$R^1$ is selected from the group consisting of —O—$(CH_2)_y$, —$CO_2R^{12}$, —O—$(CH_2)_y$—C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-NR$^{16}$R$^{17}$, —CO$_2$R$^{18}$, —O—(CH$_2$)$_x$—CO$_2$R$^{18}$, and —C(=O)NR$^{16}$R$^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{16}$R$^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

$R^4$ is selected from H, —(CH$_2$)$_a$—NR$^{43}$R$^{44}$, —Y—R$^{42}$, —O—(CH$_2$)$_a$—CO$_2$R$^{42}$, —O—(CH$_2$)$_a$—C(=O)NR$^{43}$R$^{44}$, —O—(CH$_2$)$_a$-heteroaryl, —O—(CH$_2$)$_a$-cycloalkyl, —O—C(=O)—(CH$_2$)$_a$—NR$^{43}$R$^{44}$, —O—(CH$_2$)$_a$—NR$^{43}$R$^{44}$, —NH—C(=O)—(CH$_2$)$_a$—NR$^{43}$R$^{44}$, —NH—C(=O)—Y—R$^{45}$, —NH—C(=O)—(CH$_2$)$_a$—NR$^{43}$R$^{44}$;

$R^{42}$ is selected from the group consisting of $C_1$-$C_6$ alkyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-C(=O)NR$^{46}$R$^{47}$, —($C_1$-$C_6$ alkyl)-O—($C_1$-$C_6$ alkyl)-O—($C_1$-$C_6$ alkyl), each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{43}$ and $R^{44}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-C(=O)NR$^{46}$R$^{47}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{43}$ and $R^{44}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

Y is selected from a covalent bond, O, NH, and $C_1$-$C_6$ alkyl;

$R^{45}$ is selected from the group consisting of H, aryl, —($C_1$-$C_6$ alkyl)-O—($C_1$-$C_6$ alkyl), —($C_1$-$C_6$ alkyl)-NR$^{46}$R$^{47}$, —CO$_2$R$^{48}$, —O—(CH$_2$)$_b$—CO$_2$R$^{48}$, and —C(=O)NR$^{46}$R$^{47}$, $R^{46}$ and $R^{47}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{46}$ and $R^{47}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{48}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-NR$^{46}$R$^{47}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

a is selected from 0 to 6;
b is selected from 0 to 6;
c is selected from 2 to 6;

$R^5$ is selected from the group consisting of H, $C_1$-$C_6$ alkyl, —(CH$_2$)$_d$—C(=O)—NR$^{53}$R$^{54}$, —C(=O)—(CH$_2$)$_d$—NR$^{53}$R$^{54}$, —C(=O)—X—R$^{55}$, and —C(=O)—(CH$_2$)$_d$—NR$^{53}$R$^{54}$;

$R^{53}$ and $R^{54}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-NR$^{56}$R$^{57}$, —($C_1$-$C_6$ alkyl)-C(=O)NR$^{56}$R$^{57}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{53}$ and $R^{54}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{55}$ is selected from the group consisting of H, aryl, —($C_1$-$C_6$ alkyl)-O—($C_1$-$C_6$ alkyl), —($C_1$-$C_6$ alkyl)-$NR^{56}R^{57}$, —$CO_2R^{58}$, —O—$(CH_2)_e$—$CO_2R^{58}$, and —C(=O)$NR^{56}R^{57}$, $R^{56}$ and $R^{57}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{56}$ and $R^{57}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{58}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{56}R^{57}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

d is selected from 0 to 6;
e is selected from 0 to 6;

$R^6$ is selected from the group consisting of H, $C_1$-$C_6$ alkyl, —$(CH_2)_r$—C(=O)—$NR^{63}R^{64}$, —C(=O)—$(CH_2)_r$—$NR^{63}R^{64}$, —C(=O)—X—$R^{65}$, and —C(=O)—$(CH_2)_r$—$NR^{63}R^{64}$;

$R^{63}$ and $R^{64}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{66}R^{67}$, —($C_1$-$C_6$ alkyl)-C(=O)$NR^{66}R^{67}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{63}$ and $R^{64}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

$R^{65}$ is selected from the group consisting of H, aryl, —($C_1$-$C_6$ alkyl)-O—($C_1$-$C_6$ alkyl), —($C_1$-$C_6$ alkyl)-$NR^{66}R^{67}$, —$CO_2R^{68}$, —O—$(CH_2)_s$—$CO_2R^{68}$, and —C(=O)$NR^{66}R^{67}$, $R^{66}$ and $R^{67}$ independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{66}$ and $R^{67}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{68}$ is selected from the group consisting of H, aryl, aralkyl, heteroaryl, $C_1$-$C_6$ alkyl, —$C_1$-$C_6$ alkyl)-O—($C_1$-$C_6$ alkyl), —($C_1$-$C_6$ alkyl)-$NR^{66}R^{67}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

r is selected from 0 to 6;
s is selected from 0 to 6;
n is selected from 0 to 4;
m is selected from 0 to 3; and
p is selected from 0 and 1.

20. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound of formula $XII_a$:

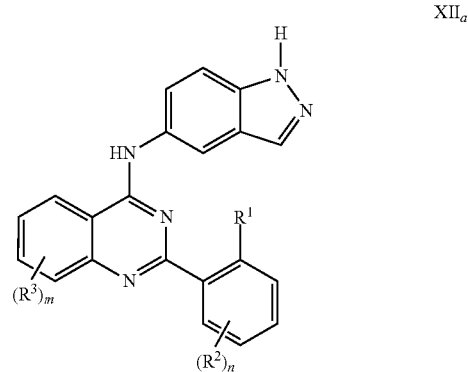

or a pharmaceutically acceptable salt thereof, wherein:
$R^1$ is selected from the group consisting of —O—$(CH_2)_y$—$CO_2R^{12}$, —O—$(CH_2)_y$—C(=O)$NR^{13}R^{14}$, —O—$(CH_2)_y$-heteroaryl, —O—$(CH_2)_y$-cycloalkyl, —O—C(=O)—$(CH_2)_y$—$NR^{13}R^{14}$, —O—$(CH_2)_z$—$NR^{13}R^{14}$, —NH—C(=O)—$(CH_2)_y$—$NR^{13}R^{14}$, —NH—C(=O)—X—$R^{15}$, —NH—$(CH_2)_y$—$NR^{13}R^{14}$;

$R^{12}$ is selected from the group consisting of $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, —($C_1$-$C_6$ alkyl)-O—($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted at one or more carbon atoms by from 1 to 3 substituents independently selected from halo, $C_1$-$C_6$ alkoxy, hydroxy, amino, cyano and $C_1$-$C_3$ perfluoro alkyl;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

$R^{18}$ is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;

y is selected from 0 to 6;

z is selected from 2 to 6;

each $R^2$ is independently selected from the group consisting of lower alkyl, CN, halo, hydroxy, lower alkoxy, amino, and perfluoro lower alkyl;

each $R^3$ is independently selected from the group consisting of lower alkyl, CN, halo, hydroxy, lower alkoxy, amino, and perfluoro lower alkyl;

n is selected from 0 to 4; and m is selected from 0 to 3.

21. The method of claim 20, wherein $R^1$ is selected from —NH—C(=O)—$(CH_2)_y$—$NR^{13}R^{14}$, —NH—C(=O)—X—$R^{15}$, and —NH—$(CH_2)_y$—$NR^{13}R^{14}$.

22. The method of claim 1, wherein the compound of formula I has the formula $XII_b$:

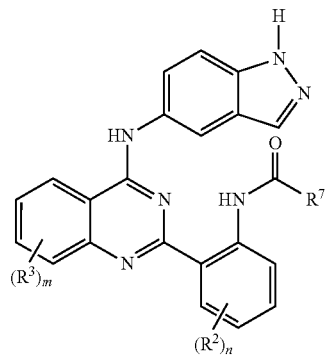

or a pharmaceutically acceptable salt thereof, wherein:

$R^7$ is selected from the group consisting of —$(CH_2)_y$—$NR^{13}R^{14}$, and X—$R^{15}$;

$R^{13}$ and $R^{14}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-C(=O)$NR^{16}R^{17}$, aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_3$-$C_7$ cycloalkyl, $C_1$-$C_6$ alkoxy, hydroxy, amino, cyano and $C_1$-$C_3$ perfluoro alkyl;

or $R^{13}$ and $R^{14}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, $C_3$-$C_7$ cycloalkyl, oxo, hydroxy, amino, cyano and $C_1$-$C_3$ perfluoro alkyl;

X is selected from a covalent bond, O, NH, and $C_1$-$C_6$ alkyl;

$R^{15}$ is selected from the group consisting of heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl, or $R^{15}$ is selected from —($C_1$-$C_6$ alkyl)-O—($C_1$-$C_6$ alkyl), —($C_1$-$C_6$ alkyl)-$NR^{16}R^{17}$, —$CO_2R^{18}$, —O—$(CH_2)_x$—$CO_2R^{18}$, and —C(=O)$NR^{16}R^{17}$;

$R^{16}$ and $R^{17}$ are independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), aryl, aralkyl, heteroaryl, $C_3$-$C_7$ cycloalkyl, a three to twelve membered heterocyclic ring containing up to 3 heteroatoms, each of which may be optionally substituted by from 1 to 3 substituents independently selected from halo, $C_1$-$C_6$ alkyl, $C_2$-$C_6$ alkenyl, $C_1$-$C_6$ alkoxy, hydroxy, amino, cyano and $C_1$-$C_3$ perfluoro alkyl;

or $R^{16}$ and $R^{17}$ may be taken together to form a three to twelve membered heterocyclic ring having up to 3 heteroatoms which is optionally substituted by from 1 to 3 substituents independently selected from halo, $C_1$-$C_6$ alkyl, $C_2$-$C_6$ alkenyl, $C_1$-$C_6$ alkoxy, oxo, hydroxy, amino, cyano and $C_1$-$C_3$ perfluoro alkyl;

R[18] is selected from the group consisting of H, aryl, aralkyl, heteroaryl, $C_1$-$C_6$ alkyl, —($C_1$-$C_6$ alkyl)-O—($C_1$-$C_6$ alkyl), —($C_1$-$C_6$ alkyl)-$NR^{16}R^{17}$, —($C_1$-$C_6$ alkyl)-O—($C_1$-$C_6$ alkyl)-O—($C_1$-$C_6$ alkyl), each of which may be optionally substituted by from 1 to 3 substituents independently selected from halo, $C_1$-$C_6$ alkoxy, hydroxy, amino, cyano and $C_1$-$C_3$ perfluoroalkyl;

x is selected from 0 to 6;
y is selected from 0 to 6;
each $R^2$ is independently selected from the group consisting of lower alkyl, CN, halo, hydroxy, lower alkoxy, amino, and perfluoro lower alkyl;
each $R^3$ is independently selected from the group consisting of lower alkyl, CN, halo, hydroxy, lower alkoxy, amino, and perfluoro lower alkyl;
n is selected from 0 to 4; and
m is selected from 0 to 3.

23. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound selected from the group consisting of:

2-(3-(4-(1H-indazol-5-ylamino)quinazolin-2-yl)phenoxy)-N-isopropylacetamide,
2-(3-(4-(1H-indazol-5-ylamino)quinazolin-2-yl)phenoxy)-N-(2-methoxyethyl)acetamide,
2-(3-(4-(1H-indazol-5-ylamino)quinazolin-2-yl)phenoxy)-N-(pyridin-3-yl)acetamide,
2-(3-(4-(1H-indazol-5-ylamino)quinazolin-2-yl)phenoxy)-1-(4-methylpiperazin-1-yl)ethanone,
2-(3-(4-(1H-indazol-5-ylamino)quinazolin-2-yl)phenoxy)-1-morpholinoethanone,
2-(3-(4-(1H-indazol-5-ylamino)quinazolin-2-yl)phenoxy)-N-methylacetamide,
2-(3-(4-(1H-indazol-5-ylamino)quinazolin-2-yl)phenoxy)-N—((R)-pyrrolidin-3-yl)acetamide,
2-(3-(4-(1H-indazol-5-ylamino)quinazolin-2-yl)phenoxy)-N—((S)-pyrrolidin-3-yl)acetamide,
2-(3-(4-(1H-indazol-5-ylamino)quinazolin-2-yl)phenoxy)-N—((R)-tetrahydrofuran-3-yl)acetamide,
2-(3-(4-(1H-indazol-5-ylamino)quinazolin-2-yl)phenoxy)-1-(piperidin-1-yl)ethanone,
2-(3-(4-(1H-indazol-5-ylamino)quinazolin-2-yl)phenoxy)-N-tert-butylacetamide,
2-(3-(4-(1H-indazol-5-ylamino)quinazolin-2-yl)phenoxy)-N-ethylacetamide,
2-(3-(4-(1H-indazol-5-ylamino)quinazolin-2-yl)phenoxy)-N-(cyanomethyl)acetamide,
2-(3-(4-(1H-indazol-5-ylamino)quinazolin-2-yl)phenoxy)-N-cyclobutylacetamide,
2-(3-(4-(1H-indazol-5-ylamino)quinazolin-2-yl)phenoxy)-N-isobutylacetamide,
2-(3-(4-(1H-indazol-5-ylamino)quinazolin-2-yl)phenoxy)-N-(2,2,2-trifluoroethyl)acetamide,
2-(3-(4-(1H-indazol-5-ylamino)quinazolin-2-yl)phenoxy)-N-cyclohexylacetamide,
2-(3-(4-(1H-indazol-5-ylamino)quinazolin-2-yl)phenoxy)-N-neopentylacetamide,
2-(3-(4-(1H-indazol-5-ylamino)quinazolin-2-yl)phenoxy)-N-(prop-2-ynyl)acetamide,
N-(3-(4-(1H-indazol-5-ylamino)quinazolin-2-yl)phenyl)-4-methylpiperazine-1-carboxamide,
3-(3-(4-(1H-indazol-5-ylamino)quinazolin-2-yl)phenyl)-1,1-dimethylurea,
N-(3-(4-(1H-indazol-5-ylamino)quinazolin-2-yl)phenyl)-2-methoxyacetamide,
methyl 2-(3-(4-(1H-indazol-5-ylamino)quinazolin-2-yl)phenylamino)-2-oxoacetate,
1-(3-(4-(1H-indazol-5-ylamino)quinazolin-2-yl)phenyl)-3-(2-(dimethylamino)ethyl)urea,
N-(3-(4-(1H-indazol-5-ylamino)quinazolin-2-yl)phenyl)-2-morpholinoacetamide,
N-(3-(4-(1H-indazol-5-ylamino)quinazolin-2-yl)phenyl)-3-(4-isopropylpiperazin-1-yl)propanamide, N-(3-(4-(1H-indazol-5-ylamino)quinazolin-2-yl)phenyl)piperidine-4-carboxamide, and N-(3-(4-(1H-indazol-5-ylamino)-6-(2-methoxyethoxy)quinazolin-2-yl)phenyl)butyramide.

24. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound having the formula:

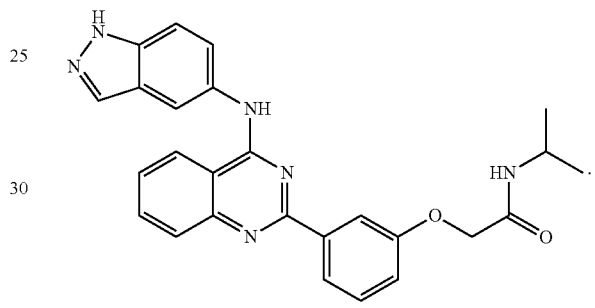

25. The method of claim 24, wherein the disease is liver fibrosis.
26. The method of claim 24, wherein the disease is asthma.
27. The method of claim 24, wherein the disease is atherosclerosis.

28. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound having the formula:

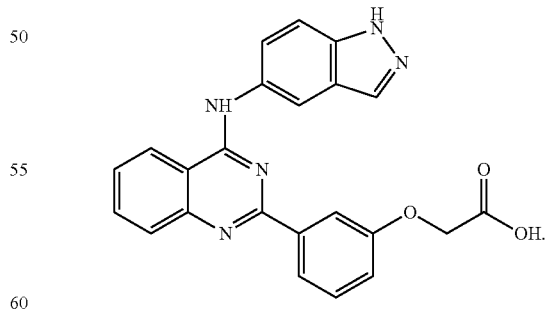

29. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound having the formula:

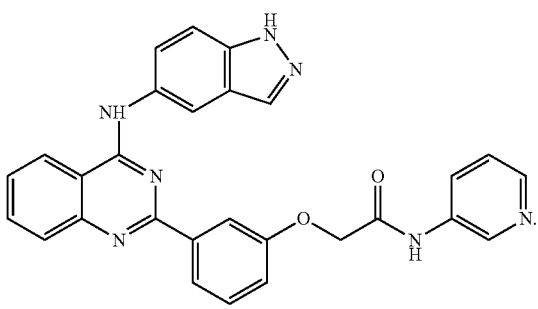 [SMILES: O=C(COc1cccc(-c2nc(Nc3ccc4[nH]ncc4c3)c3ccccc3n2)c1)Nc1cccnc1]

30. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound having the formula:

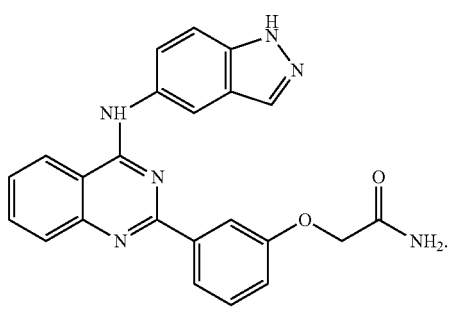 [SMILES: NC(=O)COc1cccc(-c2nc(Nc3ccc4[nH]ncc4c3)c3ccccc3n2)c1]

31. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound having the formula:

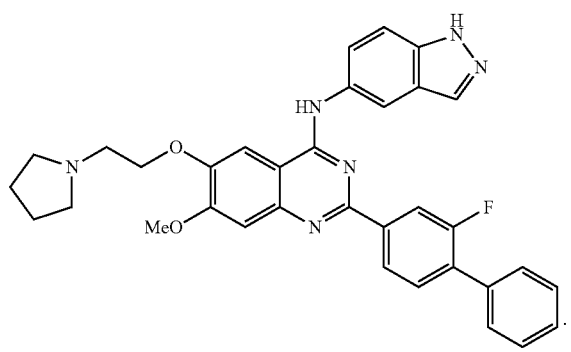 [SMILES: COc1cc2nc(-c3ccc(-c4ccccc4)c(F)c3)nc(Nc3ccc4[nH]ncc4c3)c2cc1OCCN1CCCC1]

32. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound having the formula:

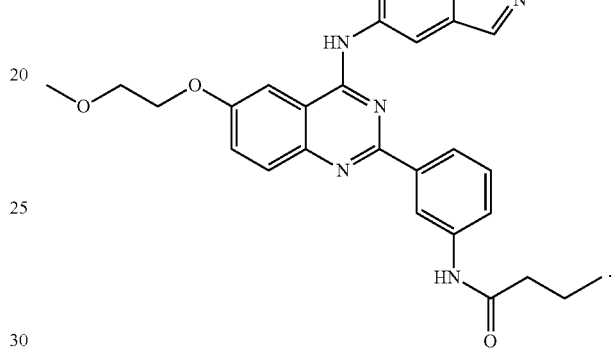

33. A method of treating a disease selected from the group consisting of hypertension, atherosclerosis, restenosis, cardiac hypertrophy, cerebral ischemia, cerebral vasospasm, glaucoma, ocular hypertension, liver fibrosis, and cardiac fibrosis, which comprises administering to a patient an effective amount of a compound having the formula:

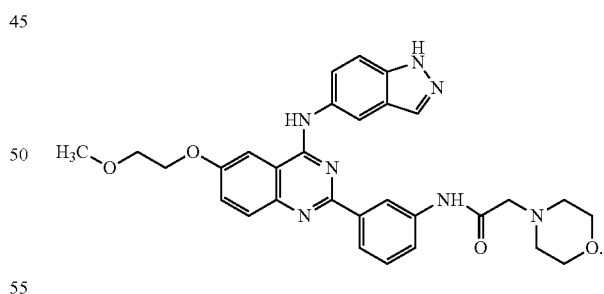

* * * * *